US012655436B2

(12) United States Patent
Romesberg et al.

(10) Patent No.: US 12,655,436 B2
(45) Date of Patent: Jun. 16, 2026

(54) IMPORT OF UNNATURAL OR MODIFIED NUCLEOSIDE TRIPHOSPHATES INTO CELLS VIA NUCLEIC ACID TRIPHOSPHATE TRANSPORTERS

(71) Applicant: The Scripps Research Institute, La Jolla, CA (US)

(72) Inventors: Floyd E. Romesberg, La Jolla, CA (US); Denis A. Malyshev, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 365 days.

(21) Appl. No.: 17/881,471

(22) Filed: Aug. 4, 2022

(65) Prior Publication Data

US 2023/0235339 A1 Jul. 27, 2023

Related U.S. Application Data

(62) Division of application No. 16/591,422, filed on Oct. 2, 2019, now Pat. No. 11,466,279, which is a division of application No. 15/302,874, filed as application No. PCT/US2015/025175 on Apr. 9, 2015, now Pat. No. 10,513,706.

(60) Provisional application No. 61/977,439, filed on Apr. 9, 2014, provisional application No. 61/977,430, filed on Apr. 9, 2014.

(51) Int. Cl.

| | |
|---|---|
| ***C12N 15/70*** | (2006.01) |
| ***C07K 14/295*** | (2006.01) |
| ***C07K 14/405*** | (2006.01) |
| ***C12N 15/82*** | (2006.01) |
| ***C12P 19/34*** | (2006.01) |

(52) U.S. Cl.

CPC ............ *C12N 15/70* (2013.01); *C07K 14/295* (2013.01); *C07K 14/405* (2013.01); *C12N 15/8243* (2013.01); *C12P 19/34* (2013.01)

(58) Field of Classification Search

CPC ...... C12N 15/70; C12N 15/8243; C12P 19/34
USPC ..................... 435/6.1, 91.1, 91.31, 455, 458; 514/44 R; 536/23.1, 24.5
See application file for complete search history.

(56) References Cited

U.S. PATENT DOCUMENTS

| | | | |
|---|---|---|---|
| 3,687,808 | A | 8/1972 | Merigan, Jr. et al. |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,667,025 | A | 5/1987 | Miyoshi et al. |
| 4,683,195 | A | 7/1987 | Mullis et al. |
| 4,683,202 | A | 7/1987 | Mullis |
| 4,762,779 | A | 8/1988 | Snitman |
| 4,766,106 | A | 8/1988 | Katre et al. |
| 4,789,737 | A | 12/1988 | Miyoshi et al. |
| 4,824,941 | A | 4/1989 | Gordon et al. |
| 4,828,979 | A | 5/1989 | Klevan et al. |
| 4,835,263 | A | 5/1989 | Nguyen et al. |
| 4,845,205 | A | 7/1989 | Huynh et al. |
| 4,849,513 | A | 7/1989 | Smith et al. |
| 4,876,335 | A | 10/1989 | Yamane et al. |
| 4,902,502 | A | 2/1990 | Nitecki et al. |
| 4,904,582 | A | 2/1990 | Tullis |
| 4,910,300 | A | 3/1990 | Urdea et al. |
| 4,931,544 | A | 6/1990 | Katre et al. |
| 4,948,882 | A | 8/1990 | Ruth |
| 4,958,013 | A | 9/1990 | Letsinger |
| 4,965,188 | A | 10/1990 | Mullis et al. |
| 4,981,957 | A | 1/1991 | Lebleu et al. |
| 5,015,733 | A | 5/1991 | Smith et al. |
| 5,023,243 | A | 6/1991 | Tullis |
| 5,034,506 | A | 7/1991 | Summerton et al. |
| 5,082,830 | A | 1/1992 | Brakel et al. |
| 5,089,261 | A | 2/1992 | Nitecki et al. |
| 5,093,232 | A | 3/1992 | Urdea et al. |
| 5,109,124 | A | 4/1992 | Ramachandran et al. |
| 5,112,963 | A | 5/1992 | Pieles et al. |
| 5,118,800 | A | 6/1992 | Smith et al. |

(Continued)

FOREIGN PATENT DOCUMENTS

| | | |
|---|---|---|
| EP | 0154316 B1 | 9/1989 |
| EP | 0614907 A1 | 9/1994 |

(Continued)

OTHER PUBLICATIONS

Acimovic et al. Molecular Evolution of the Equilibrative Nucleoside Transporter Family: Identification of Novel Family Members in Prokaryotes and Eukaryotes. Mol Biol Evol 12:2199-2210 (2002)
Acsadi et al. Human Dystrophin Expression in mdx Mice After Intramuscular Injection of DNA Constructs. Nature 352:815-818 (1991).
Adhikary et al. Adaptive Mutations Alter Antibody Structure and Dynamics During Affinity Maturation. Biochemistry 54(11):2085-93 (2015).
Akbergenov et al. ARC-1, a sequence element complementary to an internal 18S rRNA segment, enhances translation efficiency in plants when present in the leader or intercistronic region of mRNAs. Nucleic Acids Res 32(1):239-247 (2004). .

(Continued)

*Primary Examiner* — Jane J Zara
(74) *Attorney, Agent, or Firm* — Thomas Fitting

(57) ABSTRACT

A recombinantly expressed nucleotide triphosphate transporter efficiently imports the triphosphates of unnatural nucleotides into cells, and the endogenous cellular machinery incorporates those nucleotides into cellular nucleic acids. UBPs can therefore form within the cell's nucleic acids. Moreover, neither the presence of the unnatural triphosphates nor the replication of the UBP represents a significant growth burden. The UBP is not efficiently excised by nucleic acid repair pathways, and therefore can be retained as long as the unnatural triphosphates are available in the growth medium. Thus, the resulting cell is the first organism to stably propagate an expanded genetic alphabet.

40 Claims, 28 Drawing Sheets

Specification includes a Sequence Listing.

(56) References Cited

U.S. PATENT DOCUMENTS 5,118,802 A 6/1992 Smith et al.
5,130,302 A 7/1992 Spielvogel et al.
5,134,066 A 7/1992 Rogers et al.
5,138,045 A 8/1992 Cook et al.
5,166,315 A 11/1992 Summerton et al.
5,175,273 A 12/1992 Bischofberger et al.
5,177,196 A 1/1993 Meyer, Jr. et al.
5,185,444 A 2/1993 Summerton et al.
5,188,897 A 2/1993 Suhadolnik et al.
5,206,344 A 4/1993 Katre et al.
5,214,134 A 5/1993 Weis et al.
5,214,136 A 5/1993 Lin et al.
5,216,141 A 6/1993 Benner
5,218,105 A 6/1993 Cook et al.
5,229,109 A 7/1993 Grimm et al.
5,232,841 A 8/1993 Hashimoto et al.
5,235,033 A 8/1993 Summerton et al.
5,245,022 A 9/1993 Weis et al.
5,254,469 A 10/1993 Warren, III et al.
5,258,506 A 11/1993 Urdea et al.
5,262,536 A 11/1993 Hobbs, Jr.
5,264,423 A 11/1993 Cohen et al.
5,264,562 A 11/1993 Matteucci
5,264,564 A 11/1993 Matteucci
5,268,273 A 12/1993 Buckholz
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,317,098 A 5/1994 Shizuya et al.
5,319,080 A 6/1994 Leumann
5,321,131 A 6/1994 Agrawal et al.
5,359,044 A 10/1994 Cook et al.
5,367,066 A 11/1994 Urdea et al.
5,370,995 A 12/1994 Hennecke et al.
5,371,241 A 12/1994 Brush
5,389,529 A 2/1995 Panayotatos et al.
5,391,723 A 2/1995 Priest
5,393,878 A 2/1995 Leumann
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,446,137 A 8/1995 Maag et al.
5,451,463 A 9/1995 Nelson et al.
5,453,496 A 9/1995 Caruthers et al.
5,455,233 A 10/1995 Spielvogel et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,719 A 11/1995 Meng et al.
5,470,967 A 11/1995 Huie et al.
5,476,925 A 12/1995 Letsinger et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,510,475 A 4/1996 Agrawal et al.
5,512,439 A 4/1996 Hornes et al.
5,512,667 A 4/1996 Reed et al.
5,514,785 A 5/1996 Van Ness et al.
5,519,126 A 5/1996 Hecht
5,519,134 A 5/1996 Acevedo et al.
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,541,306 A 7/1996 Agrawal et al.
5,541,307 A 7/1996 Cook et al.
5,541,313 A 7/1996 Ruth
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,552 A 10/1996 Magda et al.
5,567,810 A 10/1996 Weis et al.
5,567,811 A 10/1996 Misiura et al.
5,571,799 A 11/1996 Tkachuk et al.
5,574,142 A 11/1996 Meyer, Jr. et al.
5,576,427 A 11/1996 Cook et al.
5,578,717 A 11/1996 Urdea et al.
5,578,718 A 11/1996 Cook et al.
5,580,731 A 12/1996 Chang et al.
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,591,722 A 1/1997 Montgomery et al.
5,594,121 A 1/1997 Froehler et al.
5,595,726 A 1/1997 Magda et al.
5,595,899 A 1/1997 Sato et al.
5,596,086 A 1/1997 Matteucci et al.
5,596,091 A 1/1997 Switzer
5,597,696 A 1/1997 Linn et al.
5,597,909 A 1/1997 Urdea et al.
5,599,923 A 2/1997 Sessler et al.
5,599,928 A 2/1997 Hemmi et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,612,199 A 3/1997 Western et al.
5,614,185 A 3/1997 Koths et al.
5,614,617 A 3/1997 Cook et al.
5,618,704 A 4/1997 Sanghvi et al.
5,623,070 A 4/1997 Cook et al.
5,625,050 A 4/1997 Beaton et al.
5,627,053 A 5/1997 Usman et al.
5,633,360 A 5/1997 Bischofberger et al.
5,639,873 A 6/1997 Barascut et al.
5,643,564 A 7/1997 Hamaguchi et al.
5,645,985 A 7/1997 Froehler et al.
5,646,265 A 7/1997 McGee
5,648,247 A 7/1997 Picataggio et al.
5,656,493 A 8/1997 Mullis et al.
5,658,873 A 8/1997 Bertsch-Frank et al.
5,663,312 A 9/1997 Chaturvedula
5,670,633 A 9/1997 Cook et al.
5,677,437 A 10/1997 Teng et al.
5,677,439 A 10/1997 Weis et al.
5,681,941 A 10/1997 Cook et al.
5,688,941 A 11/1997 Cook et al.
5,700,920 A 12/1997 Altmann et al.
5,712,114 A 1/1998 Mankovich et al.
5,714,331 A 2/1998 Buchardt et al.
5,719,262 A 2/1998 Buchardt et al.
5,747,646 A 5/1998 Hakimi et al.
5,750,692 A 5/1998 Cook et al.
5,763,588 A 6/1998 Matteucci et al.
5,830,653 A 11/1998 Froehler et al.
5,834,594 A 11/1998 Hakimi et al.
5,846,818 A 12/1998 Robinson et al.
5,888,732 A 3/1999 Hartley et al.
5,932,474 A 8/1999 Tsien et al.
6,005,096 A 12/1999 Matteucci et al.
6,008,378 A 12/1999 Tsien et al.
6,010,871 A 1/2000 Takahara et al.
6,013,526 A 1/2000 Takahara et al.
6,054,271 A 4/2000 Tsien et al.
6,124,090 A 9/2000 Rose et al.
6,143,557 A 11/2000 Hartley et al.
6,171,861 B1 1/2001 Hartley et al.
6,261,797 B1 7/2001 Sorge et al.
6,268,490 B1 7/2001 Imanishi et al.
6,270,969 B1 8/2001 Hartley et al.
6,277,608 B1 8/2001 Hartley et al.

(56) References Cited

U.S. PATENT DOCUMENTS

| | | | | |
|---|---|---|---|---|
| 6,288,302 | B1 | 9/2001 | Yu et al. | |
| 6,294,323 | B1 | 9/2001 | Ullman et al. | |
| 6,365,375 | B1 | 4/2002 | Dietmaier et al. | |
| 6,391,544 | B1 | 5/2002 | Salituro et al. | |
| 6,451,569 | B1 | 9/2002 | Tsien et al. | |
| 6,525,191 | B1 | 2/2003 | Ramasamy | |
| 6,670,461 | B1 | 12/2003 | Wengel et al. | |
| 6,720,140 | B1 | 4/2004 | Hartley et al. | |
| 6,770,748 | B2 | 8/2004 | Imanishi et al. | |
| 6,794,499 | B2 | 9/2004 | Wengel et al. | |
| 6,906,170 | B1 | 6/2005 | Lider et al. | |
| 6,955,807 | B1 | 10/2005 | Shanafelt et al. | |
| 7,034,133 | B2 | 4/2006 | Wengel et al. | |
| 7,053,207 | B2 | 5/2006 | Wengel | |
| 7,105,653 | B2 | 9/2006 | Shanafelt et al. | |
| 7,393,632 | B2 | 7/2008 | Cheo et al. | |
| 7,399,845 | B2 | 7/2008 | Seth et al. | |
| 7,427,672 | B2 | 9/2008 | Imanishi et al. | |
| 7,625,717 | B2 | 12/2009 | Chin et al. | |
| 7,670,823 | B1 | 3/2010 | Hartley et al. | |
| 8,252,743 | B2 | 8/2012 | Guyon et al. | |
| 8,420,792 | B2 | 4/2013 | Tian et al. | |
| 8,501,805 | B2 | 8/2013 | Seth et al. | |
| 8,546,556 | B2 | 10/2013 | Seth et al. | |
| 8,557,776 | B2 | 10/2013 | Lehmann et al. | |
| 8,609,383 | B2 | 12/2013 | Young et al. | |
| 9,682,934 | B2 | 6/2017 | Stafford et al. | |
| 9,840,493 | B2 | 12/2017 | Yang et al. | |
| 9,938,516 | B2 | 4/2018 | Zimmerman et al. | |
| 9,988,619 | B2 | 6/2018 | Zimmerman et al. | |
| 10,513,706 | B2 * | 12/2019 | Romesberg | C12N 15/70 |
| 10,626,138 | B2 | 4/2020 | Romesberg et al. | |
| 10,696,719 | B2 | 6/2020 | Romesberg et al. | |
| 10,696,720 | B2 | 6/2020 | Romesberg et al. | |
| 11,466,279 | B2 * | 10/2022 | Romesberg | C07K 14/295 |
| 11,834,689 | B2 * | 12/2023 | Ptacin | C12N 15/11 |
| 2002/0007051 | A1 | 1/2002 | Cheo et al. | |
| 2003/0083373 | A1 | 5/2003 | Tsien et al. | |
| 2004/0171570 | A1 | 9/2004 | Allerson et al. | |
| 2005/0112590 | A1 | 5/2005 | Boom et al. | |
| 2005/0130923 | A1 | 6/2005 | Bhat et al. | |
| 2006/0035254 | A1 | 2/2006 | Manoharan et al. | |
| 2006/0074035 | A1 | 4/2006 | Hong et al. | |
| 2006/0084136 | A1 | 4/2006 | Kudlicki et al. | |
| 2006/0263771 | A1 | 11/2006 | Hirao et al. | |
| 2007/0287831 | A1 | 12/2007 | Seth et al. | |
| 2008/0039618 | A1 | 2/2008 | Allerson et al. | |
| 2008/0300163 | A1 | 12/2008 | Cho et al. | |
| 2012/0022013 | A1 | 1/2012 | Sinclair et al. | |
| 2012/0077252 | A1 | 3/2012 | Picataggio et al. | |
| 2012/0244112 | A1 | 9/2012 | Ast et al. | |
| 2013/0333068 | A1 | 12/2013 | Coffin | |
| 2014/0255345 | A1 | 9/2014 | Grabstein et al. | |
| 2014/0328791 | A1 | 11/2014 | Bossard et al. | |
| 2017/0369871 | A1 | 12/2017 | Ptacin et al. | |
| 2018/0086734 | A1 | 3/2018 | Yang et al. | |
| 2019/0218257 | A1 | 7/2019 | Romesberg et al. | |
| 2019/0376054 | A1 | 12/2019 | Ptacin et al. | |
| 2020/0017540 | A1 | 1/2020 | Romesberg et al. | |
| 2020/0024597 | A1 | 1/2020 | Ptacin et al. | |
| 2020/0040027 | A1 | 2/2020 | Romesberg et al. | |
| 2020/0095591 | A1 | 3/2020 | Romesberg et al. | |
| 2020/0131555 | A1 | 4/2020 | Ptacin et al. | |
| 2020/0224234 | A1 | 7/2020 | Romesberg et al. | |
| 2020/0277342 | A1 | 9/2020 | Romesberg et al. | |
| 2020/0318122 | A1 | 10/2020 | Romesberg et al. | |
| 2020/0377877 | A1 | 12/2020 | Romesberg et al. | |
| 2020/0392550 | A1 | 12/2020 | Romesberg et al. | |
| 2021/0222147 | A1 | 7/2021 | Ptacin et al. | |
| 2022/0228148 | A1 | 7/2022 | Romesberg et al. | |
| 2022/0243244 | A1 | 8/2022 | Romesberg et al. | |

FOREIGN PATENT DOCUMENTS

| | | | |
|---|---|---|---|
| EP | 0629633 | A2 | 12/1994 |
| EP | 0811385 | B1 | 8/2003 |
| EP | 2581450 | B1 | 8/2018 |
| WO | WO-9213869 | A1 | 8/1992 |
| WO | WO-9422890 | A1 | 10/1994 |
| WO | WO-9735869 | A1 | 10/1997 |
| WO | WO-9914226 | A2 | 3/1999 |
| WO | WO-9921013 | A1 | 4/1999 |
| WO | WO-9962923 | A2 | 12/1999 |
| WO | WO-0074724 | A2 | 12/2000 |
| WO | WO-0105801 | A1 | 1/2001 |
| WO | WO-0132887 | A1 | 5/2001 |
| WO | WO-0236626 | A1 | 5/2002 |
| WO | WO-02070533 | A2 | 9/2002 |
| WO | WO-03031464 | A2 | 4/2003 |
| WO | WO-03070918 | A2 | 8/2003 |
| WO | WO-2004007713 | A1 | 1/2004 |
| WO | WO-2004060300 | A2 | 7/2004 |
| WO | WO-2004099231 | A2 | 11/2004 |
| WO | WO-2004106356 | A1 | 12/2004 |
| WO | WO-2005007121 | A2 | 1/2005 |
| WO | WO-2005021570 | A1 | 3/2005 |
| WO | WO-2005026187 | A1 | 3/2005 |
| WO | WO-2005045015 | A2 | 5/2005 |
| WO | WO-2005092928 | A1 | 10/2005 |
| WO | WO-2006049297 | A1 | 5/2006 |
| WO | WO-2006081510 | A2 | 8/2006 |
| WO | WO-2006082184 | A2 | 8/2006 |
| WO | WO-2007015557 | A1 | 2/2007 |
| WO | WO-2007066737 | A1 | 6/2007 |
| WO | WO-2007085485 | A2 | 8/2007 |
| WO | WO-2007090071 | A2 | 8/2007 |
| WO | WO-2007093599 | A1 | 8/2007 |
| WO | WO-2007134181 | A2 | 11/2007 |
| WO | WO-2008067825 | A1 | 6/2008 |
| WO | WO-2008101157 | A1 | 8/2008 |
| WO | WO-2008150729 | A2 | 12/2008 |
| WO | WO-2008154401 | A2 | 12/2008 |
| WO | WO-2009006478 | A2 | 1/2009 |
| WO | WO-2009123216 | A1 | 10/2009 |
| WO | WO-2009155102 | A2 | 12/2009 |
| WO | WO-2010023670 | A2 | 3/2010 |
| WO | WO-2010085495 | A1 | 7/2010 |
| WO | WO-2011043385 | A1 | 4/2011 |
| WO | WO-2011053065 | A2 | 5/2011 |
| WO | WO-2011139699 | A2 | 11/2011 |
| WO | WO-2012065086 | A1 | 5/2012 |
| WO | WO-2014160025 | A2 | 10/2014 |
| WO | WO-2015021432 | A1 | 2/2015 |
| WO | WO-2015086795 | A1 | 6/2015 |
| WO | WO-2015157555 | A2 | 10/2015 |
| WO | WO-2016025385 | A1 | 2/2016 |
| WO | WO-2016073433 | A1 | 5/2016 |
| WO | WO-2016094867 | A1 | 6/2016 |
| WO | WO-2016115168 | A1 | 7/2016 |
| WO | WO-2017106767 | A1 | 6/2017 |
| WO | WO-2017112825 | A2 | 6/2017 |
| WO | WO-2017223528 | A1 | 12/2017 |
| WO | WO-2019014262 | A1 | 1/2019 |
| WO | WO-2019014267 | A1 | 1/2019 |
| WO | WO-2019133883 | A1 | 7/2019 |
| WO | WO-2021067313 | A1 | 4/2021 |
| WO | WO-2022087475 | A1 | 4/2022 |

OTHER PUBLICATIONS

Allen et al. Roles of DNA polymerase I in leading and lagging-strand replication defined by a high-resolution mutation footprint of ColE1 plasmid replication. Nucleic Acids Res. 39:7020-7033 (2011).

Alpert et al. ABRF 2003: Precipitation of Large, High-Abundance Proteins from Serum With Organic Solvents. Poster No. P111-W (10 pgs) (2003).

Ambrogelly et al. Pyrrolysine is not hardwired for cotranslational insertion at UAG condons. PNAS 104(9):3141-3146 (2007).

Amiri et al. Deep origin of plastid/parasite ATP/ADP translocases. J. Mol. Evol. 56:137-150 (2003).

(56) References Cited

OTHER PUBLICATIONS

Arenas-Ramirez et al. Improved cancer immunotherapy by a CD25-mimobody conferring selectivity to human interleukin-2. Sci Transl Med 8:367ra166 (Nov. 30, 2016). 13 pages.
Arie et al. Phylogenetic identification of n-alkane assimilating Candida yeasts based on nucleotide divergence in the 59 end of LSU rDNA gene. J Gen Appl Microbiol. 46(5):257-262 (2000).
Asagarasu et al. Design and synthesis of piperazinylpyridine derivatives as novel 5-HT1A agonists/5-HT3 antagonists for the treatment of irritable bowel syndrome (IBS). Chem. Pharm. Bull. (Tokyo)57:34-42 (2009).
Ast et al. Diatom plastids depend on nucleotide import from the cytosol. PNAS USA 106:3621-3626 (2009).
Audia et al. Study of the five Rickettsia prowazekii proteins annotated as ATP/ADP translocases (Tlc): Only Tlc1 transports ATP/ADP, while Tlc4 and T1c5 transport other ribonucleotides. J. Bacteriol. 188:6261-6268 (2006).
Baba et al. Construction of *Escherichia coli* K-12 in-frame, single-gene knockout mutants: the Keio collection. Mol Syst Biol 2006. 0008 (2006).
Beigelman et al. Synthesis of 5'-C-Methyl-D-allo- & L-Talo-ribonucleoside 3'-O-Phosphoramidites & Their Incorporation into Hammerhead Ribozymes. Nucleosides and Nucleotides 14(3-5):901-905 (1995).
Bentebibel et al. The Novel IL-2 Cytokine Immune Agonist NKTR-214 Harnesses the Adaptive and Innate Immune System for the Treatment of Solid Cancers. Poster #P77. Society for Immunotherapy of Cancer 2017 Annual Meeting (SITC 2017).
Berger et al. Stability and selectivity of unnatural DNA with five-membered-ring nucleobase analogues. J Am Chem Soc 124(7):1222-6 (2002).
Berger et al. Stable and selective hybridization of oligonucleotides with unnatural hydrophobic bases. Angew Chem Int Ed Engl 39:2940-2942 (2000).
Berger et al. Universal bases for hybridization, replication and chain termination. Nucleic Acids Res 28(15):2911-2914 (2000).
Betz et al. KlenTaq polymerase replicates unnatural base pairs by inducing a Watson-Crick geometry. Nat Chem Biol 8:612-614 (2012).
Betz et al. Structural insights into DNA replication without hydrogen bonds. J Am Chem Soc 135:18637-18643 (2013).
Bhatt et al. Peripheral Blood Lymphocyte Responses in Patients with Renal Cell Carcinoma treated with High-Dose Interleukin-2. Poster (SITC 2018).
Biocentury Innovations publication Oct. 27, 2016 (26 pgs).
Bohringer et al. Synthesis of 5'-deoxy-5'-methylphosphonate linked thymidine oligonucleotides. Tet Lett 34:2723-2726 (1993).
Bordo et al. Suggestions for “safe” residue substitutions in site-directed mutagenesis. J Mol Biol 217:721-729 (1991).
Boyman et al. Selective Stimulation of T Cell subsets with Antibody-Cytokine Immune Complexes. Science 311:1924-1927 (2006).
Boyman et al. Selectively Expanding Subsets of T Cells in Mice by Injection of Interleukin-2/Antibody Complexes: Implications for Transplantation Tolerance. Transplantation Proceedings 44:1032-1034 (2012).
Boyman et al. The role of interleukin-2 during homeostatis and activation of the immune system. Nature 12:180-190 (2012).
Braasch et al. Locked nucleic acid (LNA): fine-tuning the recognition of DNA and RNA. Chem Bio 8:1-7 (2001).
Branca. Rekindling cancer vaccines. Nat Biotechnol 34(10):1019-1025 (2016).
Brauns et al. Studies On Lignin And Related Compounds: XII. Methanol Lignin. Canadian Journal of Research 13b(1):28-34 (1935).
Cameron et al. Tunable protein degradation in bacteria. Nature Biotechnology 32:1276-1281 (2014).
Cann et al. A heterodimeric DNA polymerase: Evidence that members of Euryarchaeota possess a distinct DNA polymerase. PNAS USA 95:14250 (1998).
Cantrell. Vectors for the expression of recombinant proteins in *E. coli*. Methods Mol Biol. 235:257-75 (2003).
Capone et al. Amber, ochre and opal suppressor tRNA genes derived from a human serine tRNA gene. EMBO J 4(1): 213-221 (1985).
Cariello et al. Fidelity of Thermococcus litoralis DNA polymerase (VentTM) in PCR determined by denaturing gradient gel electrophoresis Nucl Acid Res 19:4193-4198 (1991).
Charych et al. Combining Complementary Mechanisms of Immune Activation: NKTR-214, a biased IL-2 Pathway Agonist and Immune Checkpoint Antagonists. Poster Abstract 3018. ESMO Annual Meeting (Oct. 9, 2016, Copenhagen, Denmark).
Charych et al. Modeling the receptor pharmacology, pharmacokinetis, and pharmacodynamics of NKTR-214, a kinetically-controlled interleukin-2 (IL2) receptor agonist for cancer immunotherapy. PLoS One 12(7):e0179431 (2017).
Charych et al. NKTR-214, an Engineered Cytokine with Biased IL2 Receptor Binding, Increased Tumor Exposure, and Marked Efficacy in Mouse Tumor Models. Clin Cancer Res 22(3):680-690 (2016) (w/Supplemental Figures).
Chastgner et al. Lack of intermediate-affinity interleukin-2 receptor in mice leads to dependence on interkeukin-2 receptor α,β and γ chain expression for T cell growth. Eur J Immunol 26:201-206 (1996).
Chatterjee et al. A Versatile Platform for Single- and Multiple-Unnatural Amino Acid Mutagenesis in *Escherichia coli*. Biochemistry 52(10):1828-1837 (2013).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chatzkel et al. Coordinated pembrolizumab and high dose IL-2 (5-in-a-row schedule) for therapy of metastatic clear cell renal cancer: a single-center, single-arm trial. Poster Abstract No. 244333 (2010).
Chen et al. A novel human IL-2 mutein with minimal systemic toxicity exerts greater antitumor efficacy than wild-type IL-2. Cell Death& Disease 9:989 (2018).
Chen et al. Directed polymerase evolution. FEBS Lett. 588(2):219-229 (2014).
Chen et al. Phosphonate Analogues of Cytosine Arabinoside Monophosphate. Phosphorus, Sulfur and Silicon 177:1783-1786 (2002).
Chen et al. The expanding world of DNA and RNA. Curr Opin Chem Biol 34:80-87 (2016).
Chien et al. Deoxyribonucleic acid polymerase from the extreme thermophile Thermus aquaticus. J Bacteriol 127:1550-1557 (1976).
Cleary et al.: Production of complex nucleic acid libraries using highly parallel in situ oligonucleotide synthesis. Nat Methods. 1(3):241-248 (2004).
Collingwood et al. The Synthesis and Incorporation in Oligonucleotides of a Thymidine Dimer Containing an Internucleoside Phosphinate Linkage. Synlett 7:703-705 (1995).
Crooke et al. Pharmacokinetic properties of several novel oligonucleotide analogs in mice. J Pharmacol Exp Ther 277:923-937 (1996).
Database accession No. B7FWL8. Database UniProt [Online] Feb. 10, 2009 (Feb. 10, 2009), “RecName:Full=ADP,ATP carrier protein{ECO:0000256IRuleBase:RU363121};”, XP055864093, retrieved from EBI accession No. UNIPROT:B7FWL8.
Database UniParc [Online] May 31, 2010 (May 31, 2010), Database accession No. UPI0001D42ADE (2 pgs).
Datsenko et al. One-step inactivation of chromosomal genes in *Escherichia coli* K-12 using PCR products. PNAS USA 97(12):6640-6645 (2000).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11)1287-1290 (1997).
Deuschle et al. Promoters of *Escherichia coli*: a hierarchy of in vivo strength indicates alternate structures. EMBO J 5:2987-2994 (1986).
Dhami et al. Systematic exploration of a class of hydrophobic unnatural base pairs yields multiple new candidates for the expansion of the genetic alphabet. Nucleic Acids Res 42:10235-10244 (2014).

(56) References Cited

OTHER PUBLICATIONS

Diab et al. NKTR-214 (CD-122-biased agonist) plus nivolumab in patients with advanced solid tumors: Preliminary phase ½ results of PIVOT. Powerpoint presentation. ClinicalTrials.gov NCT02983045. 2018 ASCO Annual Meeting (2018).
Diab et al. Pivot-02: Preliminary safety, efficacy and biomarker results from dose escalation of the Phase ½ study of CD-122-biased agonist NKTR-214 plus nivolumab in patients with locally advanced/metastatic melanoma, renal cell carcinoma and non-small cell lung cancer. ClinicalTrials.gov Identifier: NCT02983045 PowerPoint presentation. SITC 2017 (Nov. 2017).
Diaz et al. Accuracy of replication in the polymerase chain reaction. Comparison between Thermotoga maritima DNA polymerase and Thermus aquaticus DNA polymerase. Braz J Med Res 31:1239-1242 (1998).
Dien et al. Eight-Letter DNA. Biochemistry 58:2581-2583 (2019).
Dien et al. Expansion of the genetic code via expansion of the genetic alphabet. Curr Opin Chem Biol 46:196-202 (2018).
Dien et al. Progress Toward a Semi-Synthetic Organism with an Unrestricted Expanded Genetic Alphabet. J Am Chem Soc. 140:16115-16123 (2018).
Doudna et al. Genome editing. The new frontier of genome engineering with CRISPR-Cas9. Science 346:1258096 (2014).
Dranoff. Cytokines in cancer pathogenesis and cancer therapy. Nature Reviews Cancer 4:11-22 (2004).
Dufour. THOR-707, an engineered not-alpha IL-2, for the treatment of solid tumors induces strong immunological responses in vivo. CSCO Immunotherapy Seminar Mar. 22-23, 2019 Shanghi, China (12 pgs).
Dumas et al. Designing logical codon reassignment—Expanding the chemistry in biology. Chem Sci 6:50-69 (2015).
Dupradeau et al. Differential solvation and tautomer stability of a model base pair within the minor and major grooves of DNA. J Am Chem Soc 127(44):15612-7 (2005).
Eggertsson et al. Transfer ribonucleic acid-mediated suppression of termination codons in *Escherichia coli*. Microbiol Rev 52(3):354-374 (1988).
Egholm et al. PNA hybridizes to complementary oligonucleotides obeying the Watson-Crick hydrogen-bonding rules. Nature 365(6446):566-568 (1993).
Elayadi et al. Application of PNA and LNA oligomers to chemotherapy. Curr Opinion Invens Drugs 2:558-561 (2001).
Ellington et al. In vitro selection of RNA molecules that bind specific ligands. Nature 346:818-822 (1990).
Engleerg-Kukla et al. Chapter 60: Suppression of Termination Codons. *Escherichia coli* and *Salmonella* Cellular and Molecular Biology (pp. 909-921) (1996).
Engler et al. A one pot, one step, precision cloning method with high throughput capability. PLoS One 3:e3647 (2008).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fa et al. Expanding the substrate repertoire of a DNA polymerase by directed evolution. J Am Chem Soc 126(6):1748-54 (2004).
Fairhurst et al. Synthesis and Hybridisation Properties of Phosphonamidate Ester Modified Nucleic Acid. Synlett 4:467-472 (2001).
Fan et al. Rationally evolving tRNAPyl for efficient incorporation of noncanonical amino acids. Nucleic Acids Res 43(22):e156 (2015).
Feldman et al. A Tool for the Import of Natural and Unnatural Nucleoside Triphosphates into Bacteria. J Am Chem Soc 140(4):1447-1454 (2018).
Feldman et al. Chemical Stabilization of Unnatural Nucleotide Triphosphates for the in Vivo Expansion of the Genetic Alphabet. J Am Chem Soc 139(6):2464-2467 (2017).
Feldman et al. In Vivo Structure-Activity Relationships and Optimization of an Unnatural Base Pair for Replication in a Semi-Synthetic Organism. J Am Chem Soc 139:11427-11433 (2017).
Feldman et al. Optimization of Replication, Transcription, and Translation in a Semi-Synthetic Organism. J Am Chem Soc 141:10644-10653 (2019).
Feldman. Expansion of the Genetic Alphabet: A Chemist's Approach to Synthetic Biology. Acc Chem Res 51(2):394-403 (2018).
Fersht. Enzyme Structure and Mechanism, 2nd ed., W. H. Freeman & Co., New York (pp. 350-351) (1985).
Fisher et al. Chlamydia trachomatis Transports NAD via the Npt1 ATP/ADP Translocase. Journal of Bacteriology 195(15):3381-3386 (2013).
Floros et al. Anticancer Cytokines: Biology and Clinical Effects of Interferon-α2, Interleukin (IL)-2, IL-15, IL-21, and IL-12. Semin Oncol 42(4):539-548 (2015).
Fluman et al. mRNA-programmed translation pauses in the targeting of *E. coli* membrane proteins. eLife 2014; 3:e03440.
Friedhoff et al. Quantitative polymerase chain reaction with oligodeoxynucleotide ligation assay/enzyme-linked immunosorbent assay detection. Anal Biochem 215(1):9-16 (1993).
Fu et al. Improving CRISPR-Cas nuclease specificity using truncated guide RNAs. Nat Biotechnol 32:279-284 (2014).
Gallie et al. The 5'-leader sequence of tobacco mosaic virus RNA enhances the expression of foreign gene transcripts in vitro and in vivo. Nucleic Acids Res. 15(8):3257-3273 (1987).
Gallie. The 5'-leader of tobacco mosaic virus promotes translation through enhanced recruitment of eIF4F. Nucleic Acids Res 30(15):3401-3411 (2002).
Gallier et al. Ex-Chiral-Pool Synthesis of β-Hydroxyphosphonate Nucleoside Analogues. Eur J Org Chem 6:925-933 (2007).
Gardner et al. Comparative Kinetics of Nucleotide Analog Incorporation by Vent DNA Polymerase. J Biol Chem 279(12):11834-11842 (2004).
Gardner et al. Determinants of nucleotide sugar recognition in an archaeon DNA polymerase. Nucleic Acids Research 27(12):2545-2553 (1999).
Geze et al. Synthesis of sinefungin and its C-6' epimer. J Am Chem Soc 105(26):7638-7640 (1983).
Gibson et al. Enzymatic assembly of DNA molecules up to several hundred kilobases. Nat Methods. 6(5):343-5 (2009).
Gietz et al. Improved method for high efficiency transformation of intact yeast cells. Nucleic Acids Res 20:1425 (1992).
Gillies et al. A Low-Toxicity IL-2-based Immunocytokine Retains Antitumor Activity Despite Its High Degree of IL-2 receptor Selectivity. Clin Cancer Res 17(11):3673-3686 (2011).
Goldberg et al. Re: Z. Ram et al. In situ retroviral-mediated gene transfer for the treatment of brain tumors in rats. Cancer Res. 53:83-88 (1993).
Goodman. Error-prone repair DNA polymerases in prokaryotes and eukaryotes. Annu. Rev. Biochem. 71:17-50 (2002).
Goodman et al. Causes and effects of N-terminal codon bias in bacterial genes. Science 342:475-479 (2013).
Guatelli et al. Isothermal, in vitro amplification of nucleic acids by a multienzyme reaction modeled after retroviral replication. PNAS USA 87(5):1874-1878 (1990).
Guo et al. Directed evolution of an enhanced and highly efficient Fokl cleavage domain for zinc finger nucleases. J Mot Biol 400:96-107 (2010).
Haferkamp et al. Functional expression and characterisation of membrane transport proteins. Plant Biol. 14:675-690 (2012).
Haferkamp et al. Tapping the nucleotide pool of the host: novel nucleotide carrier proteins of Protochlamydia amoebophila. Mol. Microbiol. 60:1534-1545 (2006).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).
Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and pyrophosphoryl anhydrides and studies of their interactions with adenine nucleotide utilizing enzymes. J Am Chem Soc 95(13):4404-4414 (1973).

(56) References Cited

OTHER PUBLICATIONS

Hancock et al. Expanding the Genetic Code of Yeast for Incorporation of Diverse Unnatural Amino Acids via a Pyrrolysyl-tRNA Synthetase/tRNA Pair. JACS 132:14819-14824 (2010).
Hari et al. Optimization of the pyridyl nucleobase scaffold for polymerase recognition and unnatural base pair replication. Chembiochem 9(17):2796-2799 (2008).
Hatch et al. Adenine nucleotide and lysine transport in Chlamydia psittaci. J. Bacteriol. 150:662-670 (1982).
Hayes et al. Combining computational and experimental screening for rapid optimization of protein properties. PNAS USA 99:15926-15931 (2002).
Heaton et al. Characterization of lymphokine-activated killing by human peripheral blood mononuclear cells stimulated with interleukin 2 (IL-2) analogs specific for the intermediate affinity IL-2 receptor. Cell Immunol 147:167-179 (1993).
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53:2597-2602 (1993).
Henry et al. Beyond A, C, G and T: augmenting nature's alphabet. Curr Opin Chem Biol 7(6):727-33 (2003).
Henry et al. Determinants of unnatural nucleobase stability and polymerase recognition. J Am Chem Soc 125(32):9638-9646 (2003).
Henry et al. Efforts to expand the genetic alphabet: identification of a replicable unnatural DNA self-pair. J Am Chem Soc 126(22):6923-31 (2004).
Hinnisdaels et al. Direct cloning of PCR products amplified with Pwo DNA polymerase. Biotechniques 20:186-188 (1996).
Hirao et al. An unnatural base pair between imidazolin-2-one and 2-amino-6-(2-thienyl)purine in replication and transcription. Nucleic Acids Res Suppl. 2(1):37-38 (2002).
Hirao et al., Unnatural base pair systems toward the expansion of the genetic alphabet in the central dogma.Proceedings of the Japan Academy, Series B, Phys Biol Sci. 88:345-367 (2012).
Horn et al. Bacterial endosymbionts of free-living amoebae. J. Eukaryot. Microbiol. 5:509-514 (2004).
Horvath et al. CRISPR/Cas, the Immune System of Bacteria and Archaea. Science 327:167-170 (2010).
Hsu et al.: Development and applications of CRISPR-Cas9 for genome engineering. Cell 157(6):1262-1278 (2014).
Hu et al. The Generation of Low Toxicity Interleukin-2 Fusion Proteins Devoid of Vasopermeability Activity. Blood 101(12):4853-61 (2003).
Hurwitz et al. A Novel Immune Agonist, NKTR-214, Increases the Number of Activity of CD8+ Tumor Infiltrating Lymphocytes in Patients with Advance Renal Cell Carcinoma. Poster Abstract #454. Poster Session C. ASCO Feb. 18, 2017 (ASCO 2017).
Hutter et al. From Phosphate to Bis(methylene) Sulfone: Non-Ionic Backbone Linkers in DNA. Helvetica Chimica Acta 85:2777-2806 (2002).
Hwang et al. Polymerase recognition and stability of fluoro-substituted pyridone nucleobase analogues. Chembiochem 8:1606-1611 (2007).
Hwang et al. Substituent effects on the pairing and polymerase recognition of simple unnatural base pairs. Nucleic Acids Res 34(7):2037-45 (2006).
Hwang et al. The effects of unnatural base pairs and mispairs on DNA duplex stability and solvation. Nucleic Acids Res 37(14):4757-4763 (2009).
Hwang et al. Unnatural substrate repertoire of A, B, and X family DNA polymerases. J Am Chem Soc 130(44):14872-14882 (2008).
INSIGHT-ESPRIT Study Group et al. Interleukin-2 Therapy in Patients with HIV Infection. N Engl J Med. 361(16):1548-59 (2009).
Jager et al. Oligonucleotide N-alkylphosphoramidates: synthesis and binding to polynucleotides. Biochemistry 27:7247-7246 (1988).
Jinek et al. A programmable dual-RNA-guided DNA endonuclease in adaptive bacterial immunity. Science 337:816-821 (2012).
Johansson et al. The solution structures of mutant calbindin D9k's, as determined by NMR, show that the calcium-binding site can adopt different folds. Biochemistry 35(25):8429-8438 (1996).
Jones et al. A Subset of Latency-Reversing Agents Expose HIV-Infected Resting CD4+ T-Cells to Recognition by Cytotoxic T-Lymphocytes. PLoS Pathogens 12(4):e1005545 (2016).
Joseph et al. THOR-707, A novel not-alpha IL-2, elicits durable pharmacodynamic responses in non-human primates and, efficacy as single agent and in combination with anti PD-1 in multiple syngeneic mouse models. American Association of Cancer Research (AACR) Annual Meeting 2019 Poster (Apr. 2, 2019).
Juncosa-Ginesta et al. Improved efficiency in site-directed mutagenesis by PCR using a *Pyrococcus* sp. GB-D polymerase. Biotechniques 16:820-823 (1994).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MDCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of rat methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Kaur et al. Thermodynamic, Counterion, and Hydration Effects for the Incorporation of Locked Nucleic Acid Nucleotides into DNA Duplexes. Biochemistry 45(23):7347-7344 (2006).
Khalili et al. Mechanistic modeling of a new kinetically-controlled CD122 agonist for cancer immunotherapy: NKTR-214 pharmacokinetics, pharmacodynamics, and receptor pharmacology. Poster Abstract 1614. AACR Annual Meeting, Apr. 2017 (AACR 2017).
Khlebnikov et al. Effect of lacY expression on homogeneity of induction from the P(tac) and P(trc) promoters by natural and synthetic inducers. Biotechnol Prog 18:672-674 (2002).
Kim et al. Stability and polymerase recognition of pyridine nucleobase analogues: role of minor-groove H-bond acceptors. Angew Chem Int Ed Engl 45(46):7809-12 (2006).
Kimoto et al. Creation of unnatural base pair systems toward new DNA/RNA biotechnologies. Chemical Biology of Nucleic Acids: Fundamentals and Clinical Applications (eds A. Volker Erdmann, T. Wojciech Markiewicz, & Jan Barciszewski) pp. 131-148 (Springer Berlin Heidelberg, 2014).
Kimoto et al. Generation of high-affinity DNA aptamers using an expanded genetic alphabet. Nat. Biotech. 31(5):453-458 (2013).
Kivimäe et al. Comprehensive Antitumor Immune Activation by a Novel TLR 7/8 Targeting Agent NKTR-262 Combined With CD122-Biased Immunostimulary Cytokine NKTR-214. Poster #3755 (AACR Apr. 14-18, 2018).
Kivimäe et al. Harnessing the innate and adaptive immune system to eradicate treated and distant untreated solid tumors. Poster #P275. Immunotherapy of Cancer 2017 Annual Meeting (2017).
Klein et al. Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines. Oncoimmunology 6(3):e1277306 (2017).
Knab et al. Nucleotide parasitism by Simkania negevensis (Chlamydiac). J. Bacteriol. 193:225-235 (2011).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Krieg et al. Improved IL-2 immunotherapy by selective stimulation of IL-2 receptors on lymphocytes and endothelial cells. PNAS USA 107(26):11906-11911 (Jun. 29, 2010).

(56) References Cited

OTHER PUBLICATIONS

Kroschwitz. The Concise Encyclopedia Of Polymer Science And Engineering. (pp. 858-859) (1990).
Kuhlman et al. Site-specific chromosomal integration of large synthetic constructs. Nucleic Acids Res 38:e92 (2010).
Kumar et al. The First Analogues of LNA (Locked Nucleic Acids): Phosphorothioate LNA and 2'-Thio-LNA. Bioorg Med Chem Lett 8:2219-2222 (1998).
Kutyavin. Use of base-modified duplex-stabilizing deoxynucleoside 5'-triphosphates to enhance the hybridization properties of primers and probes in detection polymerase chain reaction. Biochemistry 47(51):13666-13673 (2008).
Kwoh et al. Transcription-based amplification system and detection of amplified human immunodeficiency virus type 1 with a bead-based sandwich hybridization format. PNAS USA 86:1173-1177 (1989).
Landy. Mechanistic and structural complexity in the site-specific recombination pathways of Int and FLP. Curr Opin Genet Dev. 3(5):699-707 (1993).
Langowski et al. The CD122-biased immunostimulatory cytokine NKTR-214 combined with checkpoint blockade leads to mobilization of anti-tumor immunity and synergistic activity. Poster Abstract 311. 2016 CR-CIMT-EATIR-AACR Cancer Immunotherapy Conference (2016).
Lavergne et al. Expanding the scope of replicable unnatural DNA: Stepwise optimization of a predominantly hydrophobic base pair. JACS 135:5408-5419 (2013).
Lavergne et al. FRET Characterization of Complex Conformational Changes in a Large 16S Ribosomal RNA Fragment Site-Specifically Labeled Using Unnatural Base Pairs. ACS Chem Biol 11(5):1347-53 (2016).
Lavergne et al. Major groove substituents and polymerase recognition of a class of predominantly hydrophobic unnatural base pairs. Chem. Eur. J. 18:1231-1239 (2012).
Lazear et al. Targeting of IL-2 to cytotoxic lymphocytes as an improved method of cytokine-driven immunotherapy. Oncoimmunology 6(2):e1265721 (2017).
Lecomte et al. Selective Inactivation of the 3' to 5' exonuclease activity of *Escherichia coli* DNA polymerase I by heat. Nucl Acids Res 11:7505-7515 (1983).
Leconte et al. Amplify this! DNA and RNA get a third base pair. Nat Meth 3:667-668 (2006).
Leconte et al. An efficiently extended class of unnatural base pairs. J Am Chem Soc 128(21):6780-1 (2006).
Leconte et al. Chemical biology: a broader take on DNA. Nature 444:553-555 (2006).
Leconte et al. Directed Evolution of DNA Polymerases for Next-Generation Sequencing. Angew Chem Int Ed Engl 49(34):5921-5924 (2010).
Leconte et al. Discovery, characterization, and optimization of an unnatural base pair for expansion of the genetic alphabet. J Am Chem Soc 130(7):2336-2343 (2008).
Leconte et al. Efforts towards expansion of the genetic alphabet: pyridone and methyl pyridone nucleobases. Angew Chem Int Ed Engl 45(26):4326-9 (2006).
Leconte et al. Polymerase evolution: efforts toward expansion of the genetic code. J Am Chem Soc 127(36):12470-1 (2005).
Ledbetter et al. Editorial overview: Expanding the genetic alphabet and code. Curr Opin Chem Biol 46:A1-A2 (2018).
Ledbetter et al. Reprograming the Replisome of a Semisynthetic Organism for the Expansion of the Genetic Alphabet. J Am Chem Soc. 140:758-765 (2018).
Ledbetter et al. Site-Specific Labeling of DNA via PCR with an Expanded Genetic Alphabet. Methods Mol Biol 1973:193-212 (2019).
Letourneau et al. IL-2/anti-IL-2 antibody complexes show strong biological activity by avoiding interaction with IL-2 receptor alpha subunit CD25. PNAS USA 107:2171-2176 (2010).
Letsinger et al. Cholesteryl-conjugated oligonucleotides: Synthesis, properties, and activity as inhibitors of replication of human immunodeficiency virus in cell culture. PNAS 86:6553-6556 (1989).
Levin. It's prime time for reverse transcriptase. Cell 88:5-8 (1997).
Li et al. Improved Inhibition of Tumor Growth by Diabody-Drug Conjugates via Half-Life Extension. Bioconjugate Chem 30:1232-1243 (2019).
Li et al. Natural-like Replication of an Unnatural Base Pair for the Expansion of the Genetic Alphabet and Biotechnology Applications. J Am Chem Soc 136:826-829 (2014).
Li et al. Site-Specifically Arraying Small Molecules or Proteins on DNA Using An Expanded Genetic Alphabet. Chem Eur J 19:14205-14209 (2013).
Liu et al. Adding new chemistries to the genetic code. Annu Rev Biochem 79:413-444 (2010).
Lizardi et al. Exponential amplification of recombinant-RNA hybridization probes. Nature Biotechnology 6:1197-1202 (1988).
Lopes et al. Characterization of the Pharmacodynamic Immune Response to a Novel Immunotherapeutic Agent, ALKS 4230, in Mice and Non-Human Primates. Poster 22 (Abstract #2663) (AACR 2017).
Lopes et al. Ex Vivo Expansion and Activation of Human Lymphocytes With a Selective Activator of Effector Cells. Abstract #3158 Poster (AACR 2015).
Losey et al. Abstract #4280: Utilizing a Selective Agonist of the Intermediate-Affinity IL-2 Receptor With an Improved Pharmacokinetic Profile Leads to an Enhanced Immunostimulatory Response With Reduced Toxicity in Mice. Proceedings: AACR 106th Annual Meeting 2015 (Apr. 18-22, 2015, Philadelphia, PA).
Losey et al. Efficacy of ALKS 4230, a Novel Immunotherapeutic Agent, in Murine Syngeneic Tumor Models Alone and in Combination with Immune checkpoint Inhibitors. Poster 25 (Abstract #591) (AACR 2017).
Losey et al. Utilizing a Selective Agonist of the Intermediate-Affinity IL-2 Receptor With an Improved Pharmacokinetic Profile Leads to an Enhanced Immunostimulatory Response With Reduced Toxicity in Mice. Poster for Abstract #4280 (AACR 2015).
Lotze et al. In vivo administration of purified human interleukin 2. II. Half life, immunologic effects, and expansion of peripheral lymphoid cells in vivo with recombinant IL 2. J Immunol 135:2865-2875 (1985).
Lou et al. Fixing vascular leak in IL-2 immunotherapy. SciBX 3(27):2 pgs (2010).
Ludwig et al. Rapid and efficient synthesis of nucleoside 5'-0-(1-thiotriphosphates), 5'-triphosphates and 2',3'-cyclophosphorothioates using 2-chloro-4H-1,3,2-benzodioxaphosphorin-4-one. J. Org. Chem. 54:631-635 (1989).
Lundberg et al. High-fidelity amplification using a thermostable DNA polymerase isolated from Pyrococcus furiosus. Gene 108:1-6 (1991).
Malyshev et al. A semi-synthetic organism with an expanded genetic alphabet. Nature 509(7500):385-388 (2014).
Malyshev et al. Efficient and sequence-independent replication of DNA containing a third base pair establishes a functional six-letter genetic alphabet. PNAS USA 109:12005-12010 (2012).
Malyshev et al. PCR with an Expanded Genetic Alphabet. JACS 131(41):14620-14621 (2009).
Malyshev et al. Solution structure, mechanism of replication, and optimization of an unnatural base pair. Chem Eur J 16:12650-12659 (2010).
Malyshev et al. The expanded genetic alphabet. Angew Chem Int Ed Engl 54:11930-11944 (2015).
Manoharan et al. Chemical Modifications to Improve Uptake and Bioavailability of Antisense Oligonucleotides. Ann. N.Y. Acad. Scie 660:306-309 (1992).
Manoharan et al. Cholic Acid-Oligonucleotide Conjugates for Antisense Applications. Bioorg. Med. Chem. Let 4:1053-1060 (1994).
Manoharan et al. Introduction of a Lipophilic Thioether in the Minor Groove of Nucleic Acids for Antisense Applications. Bioorg. Med. Chem. Let 3:2765-2770 (1993).
Manoharan et al. Lipidic Nucleic Acids. Tetrahedron Lett 36:3651-3654 (1995).

(56) References Cited

OTHER PUBLICATIONS

Manoharan et al. Oligonucleotide Conjugates: Alteration of the Pharmacokinetic Properties of Antisense Agents. Nucleosides & Nucleotides 14:969-973 (1995).
Marraffini et al. CRISPR interference: RNA-directed adaptive immunity in bacteria and archaea. Nat Rev Genet. 11(3):181-90 (2010).
Marshall et al., A link between integral membrane protein expression and simulated integration efficiency. Cell Reports 16(8): 2169-2177 (2016).
Matsuda et al. Efforts toward expansion of the genetic alphabet: structure and replication of unnatural base pairs. J Am Chem Soc 129(34):10466-73 (2007).
Matsuda et al. Minor groove hydrogen bonds and the replication of unnatural base pairs. J Am Chem Soc 129(17):5551-7 (2007).
Matsuda et al. Optimization of interstrand hydrophobic packing interactions within unnatural DNA base pairs. J Am Chem Soc 126(44):14419-27 (2004).
Matsuda et al. Optimization of unnatural base pair packing for polymerase recognition. J Am Chem Soc 128(19):6369-75 (2006).
Matsuda et al. The effect of minor-groove hydrogen-bond acceptors and donors on the stability and replication of four unnatural base pairs. J Am Chem Soc 125(20):6134-9 (2003).
Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).
McMinn et al. Efforts toward Expansion of the Genetic Alphabet: DNA Polymerase Recognition of a Highly Stable, Self-Pairing Hydrophobic Base. J. Am. Chem. Soc. 121:11585-11586 (1999).
Meggers et al. A Novel Copper-Mediated DNA Base Pair. J. Am. Chem. Soc. 122:10714-10715 (2000).
Meghnem et al. Cutting Edge: Differential Fine-Tuning of IL-2- and IL-15-Dependent Functions by Targeting Their Common IL-2/15Rß/γc Receptor. J Immunol 198(12):4563-4568 (May 2017).
Melero et al. Clinical activity safety, and PK/PD from a Phase 1 study of RO6874281, a fibroblast activation protein (FAP) targeted interleukin-2 variant (IL-cv). ESMO 2018 Congress Poster (Oct. 20, 2018).
Merchant et al. Preclinical characterization of IL-2 Superkines engineered with biased CD8+ T cell stimulating properties. Poster (SITC 2018).
Meyers et al. Optimal alignments in linear space. CABIOS 4:11-17 (1989).
Mickefield. Backbone Modification of Nucleic Acids: Synthesis, Structure and Therapeutic Applications. Current Medicinal Chemistry 8:1157-1179 (2001).
Mignone et al. Untranslated regions of mRNAs. Genome Biol. 3(3):REVIEWS0004 (2002).
Mignone et al. UTRdb and UTRsite: a collection of sequences and regulatory motifs of the untranslated regions of eukaryotic mRNAs. Nucleic Acids Res 33(Database issue):D141-D146 (2005).
Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).
Milla et al. THOR-707: An engineered IL-2 for the treatment of solid tumors with superior pre-clinical efficacy and safety evidence. 2018 Society for Immunotherapy of Cancer (SITC) 33rd Annual Meeting Poster (Nov. 9, 2018).
Milla et al. THOR-707: Using Synthetic Biology to Reprogram the Therapeutic Activity of Interleukin-2 (IL-2). 2019 American Society of Clinical Oncology (ASCO) Annual Meeting Poster (May 15, 2019).
Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).
Miroux et al. Over-production of proteins in *Escherichia coli*: mutant hosts that allow synthesis of some membrane proteins and globular proteins at high levels. J Mol Biol 260:289-298 (1996).
Mishra et al. Improved leishmanicidal effect of phosphorotioate antisense oligonucleotides by LDL-mediated delivery. Biochem Biophys Acta 1264:229-237 (1995).
Morris et al. Synthetic Biology Parts for the Storage of Increased Genetic Information in Cells. ACS Synth Biol 6(10):1834-1840 (2017).
Mulligan et al. Expression of a bacterial gene in mammalian cells. Science 209:1422-1427 (1980).
Mullis et al. Specific enzymatic amplification of DNA in vitro the polymerase chain reaction. Cold Spring Harbor Symp. Quant. Biol. 51:263 (1986).
Mutalik, et al., Precise and reliable gene expression via standard transcription and translation initiation elements. Nature Methods 10:354-360 (2013).
Myers et al. Reverse transcription and DNA amplification by a Thermus thermophilus DNA polymerase. Biochemistry 30:7661-7666 (1991).
Nakazawa et al. UV and skin cancer: specific p53 gene mutation in normal skin as a biologically relevant exposure measurement. PNAS USA 91(1):360-364 (1994).
Nawrot et al. A novel class of DNA analogs bearing 5'-C-phosphonothymidine units: synthesis and physicochemical and biochemical properties. Oligonucleotides 16(1):68-82 (2006).
Needleman et al. A general method applicable to the search for similarities in the amino acid sequence of two proteins. J. Mol. Biol. 48:443-453 (1970).
Nektak Therapeutics Presents New Clinical Data from Ongoing Phase 1 Dose-Escalation Study of NKTR-214 at the Society for Immunotherapy of Cancer (SITC) 2016 Annual Meeting. PRNewswire Nov. 9, 2016.
Nektar Therapeutics. Investor Meeting presentation Jun. 3, 2017.
Nelson et al. N3'-->P5' Oligodeoxyribonucleotide Phosphoramidates: A New Method of Synthesis Based on a Phosphoramidite Amine-Exchange Reaction. J Org Chem 62:7278-7287 (1997).
New et al. The thieno[3,2-c]pyridine and furo[3,2-c]pyridine rings: new pharmacophores with potential antipsychotic activity. J. Med. Chem. 32:1147-1156 (1989).
Nguyen et al. Genetic Encoding and Labeling of Aliphatic Azides and Alkynes in Recombinant Proteins via a Pyrrolysyl-tRNA Synthetase/tRNACUA Pair and Click Chemistry. JACS 131:8720-8721 (2009).
Nicolini et al. The FAP-IL2v Immunocytokine is a Versatile Combination Partner for Cancer Immunotherapy. Poster (SITC 2018).
Nielsen et al. Sequence-selective recognition of DNA by strand displacement with a thymine-substituted polyamide. Science 254:1497-1500 (1991).
Nordstrom et al. Characterization of bacteriophage T7 DNA polymerase purified to homogeneity by antithioredoxin immunoadsorbent chromatography. J Biol Chem 256:3112-3117 (1981).
Oberhauser et al. Effective incorporation of 2'-O-methyl-oligoribonucleotides into liposomes and enhanced cell association through modification with thiocholesterol. Nucl. Acids Res. 20:533-538 (1992).
Obika et al. Synthesis of 2'-0,4'-C-methyleneuridine and -cytidine. Novel bicyclic nucleosides having a fixed C3'-endo sugar puckering. Tetrahedron Lett. 38(50):8735-8738 (1997).
Ogawa et al. Efforts toward the Expansion of the Genetic Alphabet: Information Storage and Replication with Unnatural Hydrophobic Base Pairs. J. Am. Chem. Soc. 122:3274-3278 (2000).
Ogawa et al. Rational Design of an Unnatural base Pair with Increased Kinetic Selectivity. J. Am. Chem. Soc. 122:8803-8804 (2000).
Ohtsuki et al. Unnatural base pairs for specific transcription. PNAS USA 98(9):4922-4925 (2001).
Okamoto. ECHO probes: a concept of fluorescence control for practical nucleic acid sensing. Chem. Soc. Rev. 40:5815-5828 (2011).
Oliphant et al. Defining the sequence specificity of DNA-binding proteins by selecting binding sites from random-sequence oligonucleotides: analysis of yeast GCN4 proteins. Mol. Cell Biol. 9:2944-2949 (1989).

(56) References Cited

OTHER PUBLICATIONS

Orum et al. Locked nucleic acids: a promising molecular family for gene-function analysis and antisense drug development. Curr Opinion Mol Ther 3:239-243 (2001).
Owczarzy et al. Stability and mismatch discrimination of locked nucleic acid-DNA duplexes. Biochem. 50(43):9352-9367 (2011).
Papanikolaou et al. Lipid production by Yarrowia lipolytica growing on industrial glycerol in a single-stage continuous culture. Bioresour Technol 82(1):43-9 (2002).
Parel et al. Triple-helix formation in the antiparallel binding motif of oligodeoxynucleotides containing N(9)- and N(7)-2-aminopurine deoxynucleosides. Nucleic Acids Res. 29(11):2260-2267 (2001).
Parisi et al. Enhanced expansion and tumor targeting of adoptively transferred T cells with NKTR-214. Poster Abstract #3566. (AACR Apr. 17, 2018).
Parrish et al. Functional anatomy of a dsRNA trigger: differential requirement for the two trigger strands in RNA interference. Mol Cell 6(5):1077-1087 (2000).
Paulous et al. Comparison of the capacity of different viral internal ribosome entry segments to direct translation initiation in poly(A)-dependent reticulocyte lysates. Nucleic Acids Res. 31(2):722-733 (2003).
PCT/US2014050423 International Preliminary Report on Patentability dated Feb. 18, 2016.
PCT/US2015/025175 International Report on Patentability dated Oct. 20, 2016.
PCT/US2015/025175 International Search Report and Written Opinion dated Oct. 13, 2015.
PCT/US2016/067353 International Preliminary Report on Patentability dated Jun. 28, 2018.
PCT/US2017/039133 International Preliminary Report on Patentability dated Jan. 3, 2019.
PCT/US2017/039133 International Search Report and Written Opinion dated Sep. 20, 2017.
PCT/US2018/041503 International Preliminary Report on Patentability dated Jan. 14, 2020.
PCT/US2018/041503 International Search Report and Written Opinion dated Nov. 7, 2018.
PCT/US2018/041509 International Preliminary Report on Patentability dated Jan. 14, 2020.
PCT/US2018/045257 International Search Report and Written Opinion dated Nov. 21, 2018.
PCT/US2020/037437 International Preliminary Report on Patentability dated Dec. 23, 2021.
Peyrottes et al. Oligodeoxynucleoside phosphoramidates (P-NH2): synthesis and thermal stability of duplexes with DNA and RNA targets. Nucleic Acids Res 24:1841-1848 (1996).
Pfannenstiel et al. A Novel, Individualized Xenograft Model of Cancer Immunotherapy and Tumor Growth Inhibition by ALKS 4230. Poster #P351 (SITC 2017).
Piccirilli et al. A C-nucleotide base pair: methylpseudouridine-directed incorporation of formycin triphosphate into RNA catalyzed by T7 RNA polymerase. Biochemistry 30(42):10350-10356 (1991).
Piccirilli et al. Enzymatic incorporation of a new base pair into DNA and RNA extends the genetic alphabet. Nature 343:33-37 (1990).
Pieper et al. NKTR-214 in combination with radiation produces a potent in situ vaccine in the syngeneic B78 melanoma model. Poster (STIC 2018).
Plieth. Cytokine therapy focus—interleukin-2 claims the early lead. EP Vantage. Evaluate Feb. 27, 2018 (Available at https://www.evaluate.com/vantage/articles/analysis/cytokine-therapy-focus-interleukin-2-claims-early-lead).
Quan et al. Circular polymerase extension cloning for high-throughput cloning of complex and combinatorial DNA libraries. Nat Protoc 6(2):242-251 (2011).
Rath et al. The CRISPR-Cas immune system: biology, mechanisms and applications. Biochimie 117:119-128 (2015).
Roessler et al. Cooperative interactions between the interleukin 2 receptor α and β chains later the interleukin 2-binding affinity of the receptor subunits. PNAS USA 91:3344-3347 (1994).
Romesberg et al. Development of a universal nucleobase and modified nucleobases for expanding the genetic code. Curr Prot Nucleic Acid Chem Chapter 1:Unit 1.5 (2002).
Rosentrater et al. Determination of the Relative potency of a Selective Agonist of the Intermediate-Affinity IL-2 Receptor on Lymphocytes from Human, Cynomolgus Monkey and Mouse. Poster for Abstract #4281 (No date available).
Sabri et al. Knock-in/Knock-out (KIKO) vectors for rapid integration of large DNA sequences, including whole metabolic pathways, onto the *Escherichia coli* chromosome at well-characterised loci. Microb Cell Fact 12:60 (2013).
Saha et al. 5'-Methyl-DNA—A New Oligonucleotide Analog: Synthesis and Biochemical Properties J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sakaguchi et al. Immunologic self-tolerance maintained by activated T cells expressing IL-2 receptor alpha-chains (CD25). Breakdown of a single mechanism of self-tolerance causes various autoimmune diseases. J Immunol 155(3):1151-64 1995).
Sanghvi. Chapter 15: Heterocyclic Base Modifications In Nucleic Acids And Their Applications In Antisense Oligonucleotides. Antisense Research and Applications, Crookeand Lebleu Eds., CRC Press (pp. 273-288) (1993).
Sauer. Site-specific recombination: developments and applications. Curr Opin Biotechnol 5(5):521-527 (1994).
Schlegel et al. De-convoluting the genetic adaptations of *E. coli* C41(DE3) in real time reveals how alleviating protein production stress improves yields. Cell Rep 10:1758-1766 (2015).
Schmied et al. Efficient Multisite Unnatural Amino Acid Incorporation in Mammalian Cells via Optimized Pyrrolysyl tRNA Synthetase/tRNA Expression and Engineered eRF1. JACS 136:15577-15583 (2014).
Schneider et al. NIH Image to ImageJ: 25 years of image analysis. Nat Methods 9:671-675 (2012).
Schultz et al. Oligo-2'-fluoro-2'-deoxynucleotide N3'-->P5' phosphoramidates: synthesis and properties. Nucleic Acids Res 24:2966-2973 (1996).
Seo et al. Major groove derivatization of an unnatural base pair. Chembiochem 10(14):2394-2400 (2009).
Seo et al. Optimization of an unnatural base pair toward natural-like replication. J Am Chem Soc 131:3246-3252 (2009).
Seo et al. Site-specific labeling of DNA and RNA using an efficiently replicated and transcribed class of unnatural base pairs. J Am Chem Soc 133:19878-19888 (2011).
Seo et al. Transcription of an Expanded Genetic Alphabet. JACS 131(14):5046-5047 (2009).
Shaloiko et al. Effective non-viral leader for cap-independent translation in a eukaryotic cell-free system. Biotechnology and Bioengineering 88(6):730-739 (2004).
Sharma et al. NKTR-214 enhances anti-tumor T cell immune responses induced by checkpoint blockade or vaccination. Poster (SITC 2017).
Shea et al. Synthesis, hybridization properties and antiviral activity of lipid-oligodeoxynucleotide conjugates. Nucl. Acids Res 18:3777-3783 (1990).
Siegel et al. Interleukin-2 Toxicity. J Clin Oncol 9(4):694-704 (1991).
Sikorski et al. A system of shuttle vectors and yeast host strains designed for efficient manipulation of DNA in *Saccharomyces cerevisiae*. Genetics 122:19-27 (1989).
Sim et al. IL2 Variant Circumvents ICOS+ Regulatory T-cell Expansion and Promotes NK Cell Activation. Cancer Immunol Res. 4(11):983-995 (Nov. 2016).
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Sivakumar et al. Comparison of Vascular Leak Syndrome in Mice treated with IL21 or IL2. Comparative Medicine 63(1):13-21 (2013).

(56) References Cited

OTHER PUBLICATIONS

Southern et al. Transformation of mammalian cells to antibiotic resistance with a bacterial gene under control of the SV40 early region promoter. J Mol Appl Genet 1:327-341 (1982).
Spangler et al. Antibodies to Interleukin-2 Elicit Selective T Cell Subset Potentiation through Distinct Conformational Mechanism. Immunity 42:815-825 (2015).
Srivastava et al. Five- and six-membered conformationally locked 2',4'-carbocyclic ribo-thymidines: synthesis, structure, and biochemical studies. J Am Chem Soc 129(26):8362-8379 (2007).
Stauber et al. Crystal Structure of the IL-2 signaling complex: Paradigm for a heterotrimeric cytokine receptor. PNAS 103(8):2788-2793 (2006).
Stenesh et al. DNA polymerase from mesophilic and thermophilic bacteria. III. Lack of fidelity in the replication of synthetic polydeoxyribonucleotides by DNA polymerase from Bacillus licheniformis and Bacillus stearothermophilus. Biochim Biophys Acta 475:32-41 (1977).
Sugden et al. A vector that replicates as a plasmid and can be efficiently selected in B-lymphoblasts transformed by Epstein-Barr virus. Mol. Cell. Biol. 5:410-413 (1985).
Sun et al. First-In-Human dose Selection of ALKS 4230, an Investigational Immunotherapeutic Agent. Poster 4088 (AACR 2017).
Sun et al. Pharmacokinetics and Pharmacodynamic Effects of ALKS 4230, an Investigational Immunotherapeutic Agent, in Cynomolgus Monkeys After Intravenous and Subcutaneous Administration. Poster (SITC 2018).
Svinarchuk et al. Inhibition of HIV proliferation in MT-4 cells by antisense oligonucleotide conjugated to lipophilic groups. Biochimie 75:49-54 (1993).
Switzer et al. Enzymatic recognition of the base pair between isocytidine and isoguanosine. Biochemistry 32(39):10489-10496 (1993).
Synthorx, Inc. Commission File No. 001-38756. Form 10-K Annual Report Pursuant to Section 13 or 15(d) of the Securities Exchange Act of 1934 for Fiscal Year End dated Dec. 31, 2018 (144 pgs).
Synthorx, Inc. Commission File No. 001-38756. Form 10-Q Quarterly Report Pursuant to Section 13 or 15(d) of the Securities Exchange Act of 1934 for Quarterly Period Ended Mar. 31, 2019.
Synthorx, Inc. Commission File No. 001-38756. Form 8-K Current Report Pursuant to Section 13 or 15(d) of the Securities Exchange Act of 1934 dated Apr. 2, 2019 (8 pgs).
Synthorx, Inc. Commission File No. 001-38756. Form 8-K Current Report Pursuant to Section 13 or 15(d) of the Securities Exchange Act of 1934 dated May 31, 2019 (15 pgs).
Synthorx, Inc. Registration No. 333-228355. Amendment No. 1 to Form S-1 Registration Statement Under The Securities Act of 1933 filed Nov. 27, 2018 (355 pgs.).
Tae et al. Efforts toward expansion of the genetic alphabet: replication of DNA with three base pairs. J. Am. Chem. Soc. 123:7439-7440 (2001).
Takagi et al. Characterization of DNA polymerase from *Pyrococcus* sp. strain KOD1 and its application to PCR. Appl Environ Microbiol 63(11):4504-4510 (1997).
Takeshita et al. High-copy-number and low-copy-number plasmid vectors for lacZ alpha-complementation and chloramphenicol- or kanamycin-resistance selection. Gene 61, 63-74 (1987).
Tapp et al. Homogeneous scoring of single-nucleotide polymorphisms: comparison of the 5'-nuclease TaqMan assay and Molecular Beacon probes. Biotechniques 28(4):732-738 (2000).
The Concise Encyclopedia of Polymer Science and Engineering, Kroschwitz, J.I., Ed., John Wiley & Sons pp. 858-859 (1990).
Tjalsma et al. Signal peptide-dependent protein transport in Bacillus subtilis: a genome-based survey of the secretome. Microbiol Mol Biol Rev 64(3):515-547 (2000).
Tomizawa et al. Initiation of DNA synthesis in *Escherichia coli*. Annu. Rev. Biochem. 48:999-1034 (1979).
Tuerk. Systematic evolution of ligands by exponential enrichment: RNA ligands to bacteriophage T4 Dna polymerase. Science 249:505-510 (1990).
Tyagi et al. Molecular Beacons: Probes that Fluoresce Upon Hybridization. Nature Biotechnology 14(3):303-308 (Mar. 1996).
U.S. Appl. No. 15/302,874 Office Action dated Jan. 28, 2019.
U.S. Appl. No. 15/302,874 Office Action dated Jul. 27, 2018.
U.S. Appl. No. 15/302,874 Office Action dated Jun. 19, 2019.
U.S. Appl. No. 15/302,874 Office Action dated Mar. 13, 2018.
U.S. Appl. No. 15/543,217 Office Action dated Apr. 3, 2020.
U.S. Appl. No. 15/543,217 Office Action dated Aug. 7, 2019.
U.S. Appl. No. 15/543,217 Office Action dated Feb. 7, 2019.
U.S. Appl. No. 15/543,217 Office Action dated Nov. 18, 2019.
U.S. Appl. No. 15/543,217 Office Action dated Sep. 24, 2018.
U.S. Appl. No. 16/413,209, filed May 15, 2019.
U.S. Appl. No. 16/413,219, filed May 15, 2019.
U.S. Appl. No. 16/434,999, filed Jun. 7, 2019.
U.S. Appl. No. 16/518,715, filed Jul. 22, 2019.
U.S. Appl. No. 16/518,715 Office Action dated May 7, 2021.
U.S. Appl. No. 16/530,742, filed Aug. 2, 2019.
U.S. Appl. No. 16/535,992, filed Aug. 8, 2019.
U.S. Appl. No. 16/546,097, filed Aug. 20, 2019.
U.S. Appl. No. 16/546,097 Office Action dated Feb. 7, 2020.
U.S. Appl. No. 16/546,097 Office Action dated Nov. 21, 2019.
U.S. Appl. No. 16/546,100, filed Aug. 20, 2019.
U.S. Appl. No. 16/546,100 Office Action dated Feb. 7, 2020.
U.S. Appl. No. 16/546,100 Office Action dated Nov. 27, 2019.
U.S. Appl. No. 16/577,347, filed Sep. 9, 2020.
U.S. Appl. No. 16/591,422, filed Oct. 2, 2019.
U.S. Appl. No. 16/839,741, filed Apr. 3, 2020.
U.S. Appl. No. 16/900,154, filed Jun. 12, 2020.
U.S. Appl. No. 16/591,422 Office Action dated Dec. 2, 2021.
U.S. Appl. No. 16/591,422 Office Action dated Jun. 28, 2021.
Vaishampayan et al. A Phase 1 Trial of ALKS 4230, an Engineered Cytokine Activator of NK and Effector T Cells, in Patients with Advanced Solid Tumors. Poster for Abstract #TPS3111 (ASCO 2017).
Vaishampayan et al. Safety, pharmacokinetics and pharmacodynamic effects of ALKS 4230 in patients with advanced solid tumors from the ongoing dose escalation portion of a first in human (FIH) study. Poster (SITC 2018).
Van Gool et al. Interleukin-5-producing group 2 innate lymphoid cells control eosinophilia induced by interleukin-2 therapy. Blood 124(24):3572-3576 (2014).
Van Haelst Pinsani et al. Administration of Interleukin-2 (IL-2) Results in Increased Plasma Concentrations of IL-5 and Eosinophilia in Patients with Cancer. Blood 78:1538-1544 (1991).
Vanbrunt et al. Genetically Encoded Azide Containing Amino Acid in Mammalian Cells Enables Site-Specific Antibody—Drug Conjugates Using Click Cycloaddition Chemistry. Bioconjug Chem. 26(11):2249-60 (2015).
Vazquez-Lombardi et al. Potent antitumour activity of the interleukin-2-Fc fusion proteins requires Fc-mediated depletion of regulatory T-cells. Nat Comm 8:15373 (2017).
Verma. Retroviral vectors for gene transfer. In: Microbiology (Leive L et al., eds., Ann. Soc. Microbiol) American Society of Microbiology, Washington, DC, p. 229-232 (1985).
Verma. The reverse transcriptase. Biochim Biophys Acta. 473:1-38 (1977).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Waldmann et al. The Shared and Contrasting Roles of IL2 and IL15 in the Life and Death of Normal and Neoplastic Lymphocytes: Implications for Cancer Therapy. Cancer Immunol Res 3(3):219-227 (2015).
Walker et al. Combination of NKTR-214 and Radiotherapy (RT) to reverse anergy and expand specific CD8 T cells. Poster (SITC 2017).

(56) References Cited

OTHER PUBLICATIONS

Wan et al. Pyrrolysyl-tRNAPyrrolysyl-tRNA synthetase: an ordinary enzyme but an outstanding genetic code expansion tool. Biocheim Biophys Aceta 1844(6):1059-1070 (2014).
Wandry et al. Probing unnatural amino acid integration into enhanced green fluorescent protein by genetic code expansion with a high-throughput screening platform. J Biol Eng. 10:11 (2016).
Wang et al. An engineered rare codon device for optimization of metabolic pathways. Scientific Reports 6:20608 (2016).
Wang et al. Biophysical and biochemical properties of oligodeoxy-nucleotides containing 4'-C- and 5'-C-substituted thymidines. Bioorg Med Chem Lett 9:885-890 (1999).
Wang et al. Enhanced Anti-tumor Activity of the Combination of Entinostat and NKTR-214 in Renal and Colon Cancer Tumor Models. Poster. AACR Annual Meeting 2018 (AACR 2018).
Wang et al. Structure of the Quaternary Complex of Interleukin-2 with Its α, ß, and γc Receptors. Science 310:1159-63 (2005).
Wang et al. Synthesis of Azole Nucleoside 5'-Monophosphate Mimics (P1Ms) and Their Inhibitory Properties of IMP Dehydrogenases. Nucleosides Nucleotides & Nucleic Acids 23(1 & 2):317-337 (2004).
Webster et al. In vivo expansion of T reg cells with IL-2-mAb complexes: induction of resistance to EAE and long-term acceptance of islet allografts without immunosuppression. J Med Chem 206(4):751-760 (2009).
Winkler et al. Non-mitochondrial ATP transport. Trends Biochem. Sci. 24:64-68 (1999).
Winkler. Rickettsial permeability: an ADP-ATP transport system. J Biol Chem 251:389-396 (1976).
Wolff et al. Direct gene transfer into mouse muscle in vivo. Science 247:1465-1468 (1990).
Wu et al. Efforts toward expansion of the genetic alphabet: Optimization of interbase hydrophobic interactions. J Am Chem Soc 122:7621-7632 (2000).
Wu et al. Enzymatic phosphorylation of unnatural nucleosides. J Am Chem Soc 124:14626-14630 (2002).
Wu et al. Functionalization of the sugar moiety of oligoribonucleotides on solid support. Bioconjugate Chem 10:921-924 (1999).
Wu et al. Reverse transcriptase. CRC Crit Rev Biochem 3:289-347 (1975).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wu et al. Synthesis of Site-Specific Radiolabeled Antibodies for Radioimmunotherapy via Genetic Code Expansion. Bioconjugate Chem. 27:2460-2468 (2016).
Xia et al. Directed evolution of novel polymerase activities: mutation of a DNA polymerase into an efficient RNA polymerase. PNAS USA 99(10):6597-602 (2002).
Yamaguchi et al. Role of IL-5 in IL-2-induced eosinophilia. In vivo and in vitro expression of IL-5 mRNA by IL-2. J Immunol 145:873-877 (1990).
Yan et al. Nucleoside monophosphate kinases: structure, mechanism, and substrate specificity. Adv. Enzymol. Relat. Areas Mol. Biol. 73:103-134 (1999).
Yu et al. Polymerase recognition of unnatural base pairs. Angew Chem Int Ed Engl 41(20):3841-4 (2002).
Zalevsky. Jefferies 2016 Global Healthcare Conference. PowerPoint presentation (Nov. 16, 2016).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zhang et al. Evolution of functional six-nucleotide DNA. J Am Chem Soc 137:6734-6737 (2015).
Zhang et al. Semisynthetic Organisms with Expanded Genetic Codes. Biochemistry 57:2177-2178 (20180.
Zhang et al. Studies of nucleoside transporters using novel autofluorescent nucleoside probes. Biochemistry 45(4): 1087-1098 (2006).
Zhou et al. Fine tuning of electrostatics around the internucleotidic phosphate through incorporation of modified 2',4'-carbocyclic-LNAs and -ENAs leads to significant modulation of antisense properties. J Org Chem 74:118-134 (2009).
Zon. Chapter 8: Oligonucleotide Phosphorothioates in Protocols for Oligonucleotides and Analogs, Synthesis and Properties. Humana Press (pp. 165-190) (1993).

* cited by examiner d5SICS dNaM dC dG (Part of SEQ ID NOS: 26 and 27)

15(h)

24(h)

32(h)

43(h)

53(h)

77(h)

146(h)

IMPORT OF UNNATURAL OR MODIFIED NUCLEOSIDE TRIPHOSPHATES INTO CELLS VIA NUCLEIC ACID TRIPHOSPHATE TRANSPORTERS

CROSS-REFERENCE

This application is a divisional of U.S. application Ser. No. 16/591,422, filed Oct. 2, 2019, which is a divisional of U.S. application Ser. No. 15/302,874, filed on Oct. 7, 2016, now U.S. Pat. No. 10,513,706, which is the U.S. National Stage entry of International Application No. PCT/US2015/025175, filed on Apr. 9, 2015, which claims the benefit of U.S. provisional Application No. 61/977,439, filed Apr. 9, 2014, and U.S. provisional Application No. 61/977,430, filed Apr. 9, 2014, all of which are incorporated herein by reference in their entireties.

STATEMENT AS TO FEDERALLY SPONSORED RESEARCH

This invention was made with government support under GM060005 awarded by National Institutes of Health. The government has certain rights in the invention.

SEQUENCE LISTING

Sequence Listing

The instant application contains a Sequence Listing which has been submitted in XML format via EFS-Web and is hereby incorporated by reference in its entirety. Said XML copy, created on Mar. 1, 2023, is named 36271-801_402_SL. xml and is 48,665 bytes in size.

BACKGROUND OF THE INVENTION

Large amounts of genetic information essential for vital activities of living organisms are recorded as sequences comprised of nucleic acid nucleobases. Unlike proteins which are composed of 20 types of amino acids, the chemical and physical diversity of nucleic acids is limited by only 4 bases (2 base pairs) in natural nucleic acids. Such nucleic acids allow self-replication using itself as a template and transmission of genetic information from DNA to DNA, from DNA to RNA, and/or from RNA to protein. Natural nucleotides pair through two or three hydrogen bonds (A:T/U, G:C) and this pairing enables replication and transmission of the genetic information. In vitro, the natural two-letter genetic alphabet has been expanded with chemically synthetized unnatural nucleotides that form unnatural base pairs (UBPs).

To create an organism with an expanded genetic alphabet, the unnatural nucleoside triphosphates must first be available inside the cell. It has been suggested that this might be accomplished by passive diffusion of free nucleosides into the cytoplasm followed by their conversion to the corresponding triphosphate via the nucleoside salvage pathway. Some unnatural nucleic acids are phosphorylated by the nucleoside kinase from *D. melanogaster*, and monophosphate kinases appear to be more specific. However, *E. coli* over-expression of endogenous nucleoside diphosphate kinase results in poor cellular growth.

Benner et al. have designed novel base pairs based on different hydrogen-bonding combinations from natural base pairs, e.g., isoG:isoC and κ:X base pairs (Piccirilli et al., 1990; Piccirilli et al., 1991; Switzer et al., 1993). However, isoG forms a base pair with T through keto-enol tautomerism between 1- and 2-positions; isoC and K are not substrates of polymerases due to an amino group substitution at the 2-position; and nucleoside derivatives of isoC are chemically unstable.

Base pairs that have hydrogen-bonding patterns different from those of natural base pairing and that are capable of eliminating base pairing with natural bases by steric hindrance have also been developed. For example, Ohtsuki et al. (2001) and Hirao et al. (2002) designed 2-amino-6-dimethylaminopurine (X), 2-amino-6-thienylpurine (S), and pyridin-2-one (Y). However, the incorporation of Y opposite X showed low selectivity.

Kool et al. synthesized A and T derivatives (4-methylbenzimidazole (Z) and 9-methyl-1-H-imidazo[(4,5)-b]pyridine (Q), respectively) lacking hydrogen bonding. These base pairs were found to be incorporated into DNA in a complementary manner by the Klenow fragment of *E. coli*-derived DNA polymerase I. Other base pairs including A:F, Q:T and Z:T are also shown to be incorporated [Morales & Kool, 1999]. Other examples include 7-(2-thienyl)-imidazo[4,5-b]pyridine (Ds) and pyrrole-2-carbaldehyde (Pa).

In an effort to develop an orthogonal third base pair, over 100 hydrophobic bases have been designed, synthesized as the triphosphate and phosphoramidite, and characterized in Floyd Romesberg's laboratory. A large number of hydrophobic base pairs have also been generated, including pyrrolopyridine (PP) and C3-methylisocarbostyryl (MICS) (Wu et al., 2000). However, these bases paired with each other independently of shape fitting, resulting in PP:PP and MICS:MICS incorporation into DNA; and elongation did not substantially proceed after incorporation of such base combinations formed without any shape fitting. Neither H-bonding nor a large aromatic surface area was found to be required for base pair stability in duplex DNA or polymerase mediated replication for some UBPs, e.g., a 3-fluorobenzene (3FB) self-pair.

The development of a third, unnatural DNA base pair, and an expanded genetic alphabet, is a central goal of synthetic and chemical biology and would increase the functional diversity of nucleic acids, provide tools for their site-specific labeling, increase the information potential of DNA, and lay the foundation of a semi-synthetic organism. Described herein is a newly developed class of UBPs that is formed between nucleotides bearing hydrophobic nucleobases (exemplified by the pair formed between d5SICS and dNaM (d5SICS-dNaM)), which is efficiently PCR amplified and transcribed, and whose unique mechanism of replication has been thoroughly characterized through kinetic (Lavergne et al., Chem. Eur. J. (2012) 18:1231-1239; Seo et al., J. Am. Chem. Soc. (2009) 131:3246-3252) and structural studies (Betz et al., J. Am. Chem. Soc. (2013) 135:18637-18643; Malyshev et al., Proc. Natl. Acad. Sci. USA (2012) 109:12005-12010). Until now, no living organisms capable of incorporation and propagation of unnatural information existed.

The limitation of having only four different base components (nucleotides) in standard nucleic acids restricts their functions and potential, as compared to the 20 different amino acids in natural proteins. The UBPs and cells stably incorporating the UBPs described herein offer numerous advantages and can be applied to a broad range of biotechnologies. Having a third base pair that replicates in the ranges of natural ones could significantly increase the information density in the same length of DNA and make DNA a more attractive alternative for information storage. More importantly, a third UBP could expand coding of DNA for unnatural amino acids, providing access to proteins (including protein therapeutics) with unique properties not available using the 20 natural ones.

SUMMARY OF THE INVENTION

Provided herein, is a cell comprising a first unnatural nucleic acid, wherein the first unnatural nucleic acid is an imported unnatural nucleic acid.

In some embodiments, the cell further comprises an unnatural base pair (UBP), wherein the UBP is formed within the cell.

In some embodiments, the UBP comprises the first unnatural nucleic acid.

In some embodiments, the cell comprises an expanded genetic alphabet.

In some embodiments, the expanded genetic alphabet comprises the UBP.

In some embodiments, the UBP is incorporated into a nucleic acid of the cell.

In some embodiments, the UBP is stably incorporated into a nucleic acid of the cell.

In some embodiments, the UBP is not efficiently recognized by a DNA repair pathway of the cell.

In some embodiments, the UBP comprises the first unnatural nucleic acid.

In some embodiments, the cell further comprises a heterologous nucleic acid.

In some embodiments, the heterologous nucleic acid encodes for a nucleotide triphosphate transporter (NTT), a polymerase, or a combination thereof.

In some embodiments, the heterologous nucleic acid encodes for an NTT.

In some embodiments, the cell further comprises at least one template UBP comprising a first unnatural template nucleic acid.

In some embodiments, the first unnatural template nucleic acid is capable of base pairing with the first unnatural nucleic acid.

In some embodiments, the base pairing comprises hydrophobic base pairing.

In some embodiments, the base pairing does not comprise hydrogen bonding.

In some embodiments, the cell imports the first unnatural nucleic acid.

In some embodiments, the heterologous NTT transports the first unnatural nucleic acid into the cell.

In some embodiments, the cell comprises enhanced import of an unnatural nucleotide, enhanced incorporation of an unnatural nucleotide into a nucleic acid of the cell, or decreased degradation of an unnatural nucleic acid in comparison to a respective wild type cell.

In some embodiments, the cell comprises enhanced import of the first unnatural nucleic acid in comparison to a cell without the heterologous NTT.

In some embodiments, the heterologous NTT is bound to the first unnatural nucleic acid In some embodiments, the cell further comprises a second unnatural nucleic acid.

In some embodiments, the cell imports the second unnatural nucleic acid.

In some embodiments, the heterologous NTT transports the second unnatural nucleic acid into the cell.

In some embodiments, the at least one template UBP further comprises a second unnatural template nucleic acid.

In some embodiments, the second unnatural template nucleic acid is capable of base pairing with the second unnatural nucleic acid.

In some embodiments, the first unnatural template nucleic acid is capable of base pairing with the second unnatural template nucleic acid.

In some embodiments, the first unnatural nucleic acid is capable of base pairing with the second unnatural nucleic acid.

In some embodiments, the first unnatural nucleic acid is different from the second unnatural nucleic acid.

In some embodiments, the first unnatural nucleic acid is the same as the second unnatural nucleic acid.

In some embodiments, the at least one template UBP comprises at least about 2, 3, 4, 5, 6, 7, 8, 9, 10, 20, 30, 40, 50, 60, 70, 80, 90, 100, 200, 300, 400, 500, 600, 700, 800, 900, or 1000 template UBPs.

In some embodiments, the at least one template UBP is present in at least one heterologous nucleic acid.

In some embodiments, the at least one heterologous nucleic acid comprises at least about 2, 3, 4, 5, 6, 7, 8, 9, 10, 20, 30, 40, 50, 60, 70, 80, 90, 100, 200, 300, 400, 500, 600, 700, 800, 900, or 1000 heterologous nucleic acids.

In some embodiments, the at least one template UBP is introduced into the cell by transfection, lipofection, injection, viral vector, or electroporation.

In some embodiments, the UBP comprises the first unnatural template nucleic acid.

In some embodiments, the UBP comprises the second unnatural nucleic acid.

In some embodiments, the UBP comprising the second unnatural nucleic acid comprises the second unnatural template nucleic acid.

In some embodiments, the UBP comprises at least 2 UBPs.

In some embodiments, the at least 2 UBPs comprise at least 3, 4, 5, 6, 7, 8, 9, 10, 20, 30, 40, 50, 60, 70, 80, 90, 100, 200, 300, 400, 500, 600, 700, 800, 900, or 1000 UBPs.

In some embodiments, the at least 2 UBPs comprise a first UBP and a second UBP, wherein the first UBP comprises: the first unnatural nucleic acid and the first unnatural template nucleic acid or the first unnatural nucleic acid and the second unnatural template nucleic acid; and wherein the second UBP comprises: the second unnatural nucleic acid and the second unnatural template nucleic acid, or the second unnatural nucleic acid and the first unnatural template nucleic acid; or any combination thereof.

In some embodiments, the at least one template UBP is formed outside of the cell.

In some embodiments, the first or second unnatural nucleic acid is a deoxyribonucleoside.

In some embodiments, the first or second unnatural nucleic acid is a ribonucleoside.

In some embodiments, the first or second unnatural nucleic acid is a nucleoside triphosphate.

In some embodiments, the first or second unnatural nucleic acid comprises a modified sugar group In some embodiments, the first or second unnatural nucleic acid is selected from the group consisting of any one of those listed in Appendix A, and any combination thereof.

In some embodiments, the cell comprises at least one genetic modification.

In some embodiments, the at least one genetic modification comprises a heterologous polymerase, a mutant polymerase, a disruption in a nucleotidase of the cell, a disruption of a phosphatase of the cell, or a combination thereof.

In some embodiments, the cell is incontact with a phosphatase inhibitor or a nucleotidase inhibitor.

In some embodiments, the cell is a prokaryotic cell.

In some embodiments, the cell is from *Phaeodactylum tricornutum, Thalassiosira pseudonana* or *Protochlamydia amoebophila.*

In some embodiments, the cell is a eukaryotic cell.

In some embodiments, the cell is *E. coli.*

In some embodiments, the heterologous NTT is from *Phaeodactylum tricornutum* (Pt) NTT2, *Thalassiosira pseudonana* (Tp) NTT2, *Protochlamydia amoebophila* (Pam) NTT2, *Protochlamydia amoebophila* (Pam) NTT5, or a combination thereof.

In some embodiments, the heterologous NTT is a nucleotide transporter 1 (NTT1), nucleotide transporter 2 (NTT2), nucleotide transporter 3 (NTT3), nucleotide transporter 4 (NTT4), nucleotide transporter 5 (NTT5), nucleotide transporter 6 (NTT6), nucleotide transporter 7 (NTT7), nucleotide transporter 8 (NTT8), or a combination thereof.

In some embodiments, the UBP is not efficiently removed by the cell.

In some embodiments, the removal comprises 3'-5' nuclease activity.

In some embodiments, the removal comprises nucleotide excision by the cell.

In some embodiments, the UBP is not efficiently removed from the cell after growth for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications.

In some embodiments, the UBP is not efficiently removed from the cell afer growth for about 1, 2, 3, 4, 5, 6, 7, 8, 9, 10, 11, 12, 13, 14, 15, 16, 17, 18, 19, 20, 21, 22, 23, or 24 hours; 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days; 2, 3, 4, 5, 6, 7, 8, 9, 10, 11, or 12 months; or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

In some embodiments, the first or second unnatural nucleic acid comprises an unnatural base.

In some embodiments, the unnatural base is selected from the group consisting of 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifluoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, 0-6 substituted purines, those that increase the stability of duplex formation, universal nucleic acids, hydrophobic nucleic acids, promiscuous nucleic acids, size-expanded nucleic acids, fluorinated nucleic acids, tricyclic pyrimidines, phenoxazine cytidine([5,4-b][1,4]benzoxazin-2(3H)-one), phenothiazine cytidine (1H-pyrimido [5,4-b][1,4]benzothiazin-2(3H)-one), G-clamps, phenoxazine cytidine (9-(2-aminoethoxy)-H-pyrimido[5,4-b][1,4]benzoxazin-2(3H)-one), carbazole cytidine (2H-pyrimido [4,5-b]indol-2-one), pyridoindole cytidine (H-pyrido[3',2':4,5]pyrrolo[2,3-d]pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine and those in which the purine or pyrimidine base is replaced with a heterocycle.

In some embodiments, the unnatural base is selected from the group consisting of

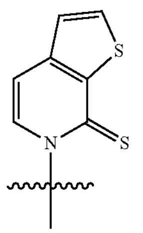

(d)TPT3

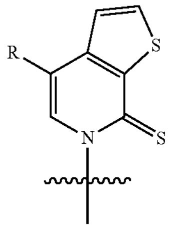

(d)TPT3pa

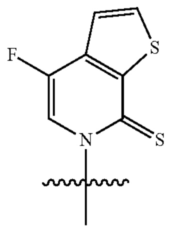

(d)FTPT3

-continued

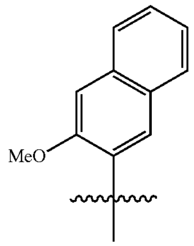

(d)NaM

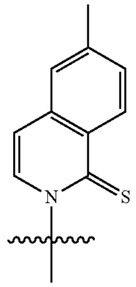

(d)SSICS

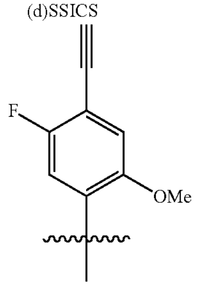

(d)FEMO

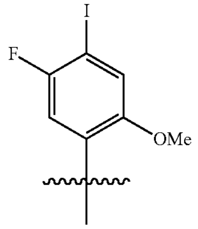

(d)FIMO

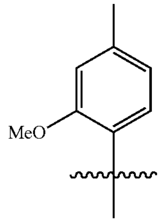

(d)MMO2 wherein R is a functional group.

In some embodiments, the functional group is selected from the group consisting of an affinity tag such as biotin, flourophore, alkyl, alkenyl, alkynyl, phenyl, benyl, halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocasrbonate ester, carboxamide, primary amine, secondary amine, tertiary amine, primary ketamine, secondary ketamine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfino, sulfo, thiocyanate, isothiocyanante, carbonothioyl, phoshino, phosphono, phosphate, borono, boronate, borino, borinate, and combinations thereof.

In some embodiments, the first or second unnatural nucleic acid comprises an unnatural sugar moeity.

In some embodiments, the unnatural sugar moeity is selected from the group consisting of a modification at the 2' position: OH; substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-$OCH_3$, 2'—$O(CH_2)_2OCH_3$ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, —$O[(CH_2)n\ O]mCH_3$, —$O(CH_2)nOCH_3$, —$O(CH_2)n\ NH_2$, —$O(CH_2)n\ CH_3$, —$O(CH_2)n$-$ONH_2$, and —$O(CH_2)nON[(CH_2)n\ CH_3)]_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

In some embodiments, the unnatural nucleic acid comprises an unnatural backbone.

In some embodiments, the unnatural backbone is selected from the group consisting of a phosphorothioate, chiral phosphorothioate, phosphorodithioate, phosphotriester, aminoalkylphosphotriester, $C_1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates.

In some embodiments, the cell is in contact with a natural nucleic acid.

In some embodiments, the natural nucleic acid is selected from the group consisting of ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, dGMP, dATP, dTTP, dCTP, dGTP, dADP, dTDP, dCDP, dGDP, dAMP, dTMP, dCMP, dGMP, and any combination thereof.

In some embodiments, the natural nucleic acid is selected from the group consisting of ATP, UTP, CTP, GTP, and any combination thereof.

In some embodiments, the NTT is from a bacterium.

In some embodiments, the bacterium is *Phaeodactylum tricornutum, Thalassiosira pseudonana*, or *Protochlamydia amoebophila*.

In some embodiments, the NTT comprises an amino acid sequence with at least about 60% identity to any one of SEQ ID NOs: 1, 3, 5, 7, 9, 11, 13, 14, 16, 18, 19, 20, 22, or 24.

In some embodiments, the NTT is encoded by a nucleic acid encoding an amino acid sequence with at least about 60% identity to any one of SEQ ID NOs: 1, 3, 5, 7, 9, 11, 13, 14, 16, 18, 19, 20, 22, or 24.

In some embodiments, the NTT is encoded by a nucleic acid sequence with at least about 60% identical to any one of SEQ ID NOs: 2, 4, 6, 8, 10, 12, 15, 17, 19, 21, 23, 25, or 28.

In some embodiments, the cell comprises a vector comprising the heterologous nucleic acid.

In some embodiments, the heterologous nucleic acid is incorporated into the genome of the cell.

In some embodiments, the heterologous nucleic acid encodes for a polymerase.

In some embodiments, the polymerase is a mesophilic polymerase or a thermophilic polymerase.

In some embodiments, the polymerase is altered.

In some embodiments, the polymerase is 3'-5' exonuclease-deficient.

In some embodiments, the polymerase is selected from the group consisting DNA polymerase, RNA polymerase, and reverse transcriptase.

In some embodiments, the polymerase is selected from the group consisting of Φ29, B103, GA-1, PZA, Φ15, BS32, M2Y, Nf, GI, Cp-1, PRD1, PZE, SF5, Cp-5, Cp-7, PR4, PR5, PR722, L17, ThermoSequenase®, 9° Nm™, Therminator™, Tne, Tma, TfI, Tth, TIi, Stoffel fragment, Vent™ and Deep Vent™ DNA polymerase, KOD DNA polymerase, Tgo, JDF-3, Pfu, Taq, T7 DNA polymerase, PGB-D, UlTma DNA polymerase, *E. coli* DNA polymerase I, archaeal DP1I/DP2 DNA polymerase II, 9° N DNA Polymerase, Taq DNA polymerase, Phusion® DNA polymerase, Pfu DNA polymerase, and RB69 DNA polymerase.

In some embodiments, the polymerase is a reverse transcriptase from a retrovirus.

In some embodiments, the retrovirus is from HIV, HTLV-I, HTLV-II, FeLV, FIV, SIV, AMV, MMTV, or MoMuLV.

In some embodiments, the alteration comprises an alteration arising from directed evolution.

In some embodiments, the cell further comprises an alteration in a homologous nucleic acid.

In some embodiments, the homologous nucleic acid encodes for a nucleotidase, a nucleotide phosphatase, or a combination thereof.

In some embodiments, the homologous nucleic acid comprises a gene that encodes for a nucleotide phosphatase, and wherein the nucleotide phosphatase is selected from the group consisting of: polynucleotide phosphatase; nucleotide phosphatase activity, acting on free nucleotides; nucleotide triphosphatase apyrase; ATP-diphosphatase; adenosine diphosphatase; ADPase; ATP diphosphohydrolase nucleoside diphosphate phosphatase; nucleoside-diphosphatase; thiaminpyrophosphatase; UDPase; inosine diphosphatase; adenosine diphosphatase; IDPase; ADPase; adenosinepyrophosphatase; guanosine diphosphatase; guanosine 5'-diphosphatase; inosine 5'-diphosphatase; uridine diphosphatase; uridine 5'-diphosphatase; type B nucleoside diphosphatase; GDPase; CDPase; nucleoside 5'-diphosphatase; type L nucleoside diphosphatase; NDPase; nucleoside diphosphate phosphohydrolase; and any combination thereof.

In some embodiments, the homologous nucleic acid encodes for a nucleotide phosphatase, and wherein the nucleotide phosphatase is selected from the group consisting of any of those listed in Table 4 or 5.

In some embodiments, the homologous nucleic acid encodes for a nucleotidase, and wherein the nucleotidase, is selected from the group consisting of a 5'-nucleotidase, 3'-nucleotidase, or a combination thereof.

In some embodiments, the homologous nucleic acid encodes for a nucleotidase, and wherein the nucleotidase, is selected from the group consisting of any of those listed in Table 2 or 3.

In some embodiments, the alteration comprises a loss or decrease of function of a gene encoded by the homologous nucleic acid.

In some embodiments, the alteration comprises an alteration arising from directed evolution.

In some embodiments, the cell is in contact with a phosphatase or a nucleotidase inhibitor.

In some embodiments, the phosphatase or nucleotidase inhibitor is selected from the group consisting of Sodium Fluoride, Sodium Orthovanadate, beta-Glycerophosphate, pyrophosphate and salts thereof, potassium phosphate (KPi), Phosphate (Pi), Oligomycin, pyrophosphate (PPi) anions, ammonium ions inositol hexaphosphate, and combinations thereof.

In some embodiments, the phosphatase or nucleotidase inhibitor is present at a concentration of from 0.1 μM to 500 mM, 0.1 mM to 500 mM, 0.2 mM to 250 mM, 0.25 mM to 200 mM, 1.0 mM to 150 mM, 2.5 mM to 125 mM, 5 mM to 100 mM, 25 mM to 75 mM, or 40 mM to 60 mM.

In some aspects, provided herein is a method for producing a genetically modified cell comprising: providing a cell exhibiting a wild type level of import of a first unnatural nucleotide; and introducing a heterologous NTT into the cell, thereby enhancing the level of import of the first unnatural nucleotide in comparison the level of import of the first unnatural nucleotide into the cell that exhibits a wild type level of import of the first unnatural nucleotide.

In some embodiments, the cell that exhibits a wild type level of import of the first unnatural nucleotide does not comprise the heterologous NTT.

In some embodiments, the method further comprises contacting the cell comprising a heterologous NTT with the first unnatural nucleotide.

In some aspects, provided herein is a method incorporating an unnatural nucleic acid into a cell, comprising contacting a cell comprising a heterologous NTT with a first unnatural nucleic acid; and cultivating the cell for a period of time; wherein the heterologous NTT transports the first unnatural nucleic acid into the cell In some aspects, provided herein is a method for genetically engineering a cell comprising: contacting a cell comprising a heterologous NTT with a liquid, the liquid comprising a concentration of an unnatural nucleic acid, and a concentration of a natural nucleic acid; cultivating the cell for a period of time; increasing the ratio of the concentration of the unnatural nucleic acid to the concentration of the natural nucleic acid; and repeating (b) and (c) one or more times.

In some embodiments, after one or more repeats of (b) and (c), the cell comprises enhanced import of an unnatural nucleotide, enhanced incorporation of an unnatural nucleotide into a nucleic acid of the cell, or decreased degradation of an unnatural nucleic acid in comparison to the respective wild type cell.

In some embodiments, the cell comprising the heterologous NTT further comprises at least one template UBP comprising a first unnatural template nucleic acid.

In some embodiments, the first unnatural template nucleic acid is capable of base pairing with the first unnatural nucleic acid.

In some aspects, provided herein is a method of making a cell with an expanded genetic alphabet, comprising: contacting a first unnatural nucleic acid to a cell, the cell comprising a heterologous NTT, and at least one template UBP comprising an unnatural template nucleic acid; and cultivating the cell for a period of time, wherein the unnatural template nucleic acid base is capable of base pairing with the first unnatural nucleic acid.

In some embodiments, the cell comprising the heterologous NTT comprises enhanced import of the first unnatural nucleic acid in comparison to a cell without the heterologous NTT.

In some embodiments, a UBP is formed within the cell comprising the heterologous NTT.

In some embodiments, the UBP formed within the cell comprises the imported first unnatural nucleic acid.

In some embodiments, the method further comprises determining the presence of the UBP comprising the imported first unnatural nucleic acid.

In some embodiments, the method further comprises isolating the UBP comprising the first unnatural nucleic acid from the cell.

In some embodiments, the method further comprises determining the amount of the first unnatural nucleic acid present inside the cell.

In some embodiments, the method further comprises comparing the amount of the first unnatural nucleic acid present inside the cell to the amount of the first unnatural nucleic acid present inside a corresponding wild type cell.

In some embodiments, the contacting comprises contacting a liquid containing the first unnatural nucleic acid to the cell and wherein the method further comprises determining the amount of the first unnatural nucleic acid present in the liquid after the period of time in comparison to the respective wild type.

In some embodiments, the period of time is 1 hour or more.

In some embodiments, the cell comprises at least one genetic modification.

In some embodiments, the at least one genetic modification comprises a heterologous polymerase, a mutant polymerase, a disruption in a nucleotidase of the cell, a disruption of a phosphatase of the cell, or a combination thereof.

In some embodiments, the method further comprises adding a phosphatase or a nucleotidase inhibitor.

In some embodiments, the cell is a prokaryotic cell.

In some embodiments, the cell is from *Phaeodactylum tricornutum, Thalassiosira pseudonana* or *Protochlamydia amoebophila.*

In some embodiments, the cell is a eukaryotic cell.

In some embodiments, the cell is *E. coli.*

In some embodiments, the heterologous NTT is from *Phaeodactylum tricornutum* (Pt) NTT2, *Thalassiosira pseudonana* (Tp) NTT2, *Protochlamydia amoebophila* (Pam) NTT2, *Protochlamydia amoebophila* (Pam) NTT5, or a combination thereof.

In some embodiments, the heterologous NTT is a nucleotide transporter 1 (NTT1), nucleotide transporter 2 (NTT2), nucleotide transporter 3 (NTT3), nucleotide transporter 4 (NTT4), nucleotide transporter 5 (NTT5), nucleotide transporter 6 (NTT6), nucleotide transporter 7 (NTT7), nucleotide transporter 8 (NTT8), or a combination thereof.

In some embodiments, the method further comprises contacting the cell with a second unnatural nucleic acid.

In some embodiments, the heterologous NTT transports the second unnatural nucleic acid into the cell.

In some embodiments, the at least one template UBP further comprises a second unnatural template nucleic acid.

In some embodiments, the first unnatural template nucleic acid is capable of base pairing with the second unnatural template nucleic acid.

In some embodiments, the second unnatural template nucleic acid is capable of base pairing with the second unnatural nucleic acid.

In some embodiments, the first unnatural nucleic acid is capable of base pairing with the second unnatural nucleic acid.

In some embodiments, the first unnatural nucleic acid is different from the second unnatural nucleic acid.

In some embodiments, the first unnatural nucleic acid is the same as the second unnatural nucleic acid.

In some embodiments, the at least one template UBP comprises at least 2, 3, 4, 5, 6, 7, 8, 9, 10, 20, 30, 40, 50, 60, 70, 80, 90, 100, 200, 300, 400, 500, 600, 700, 800, 900, or 1000 template UBPs.

In some embodiments, the at least one template UBP is present in the cell prior to the contacting with the first or second unnatural nucleic acid.

In some embodiments, the at least one template UBP is present in at least one heterologous nucleic acid.

In some embodiments, the at least one heterologous nucleic acid comprises at least 2, 3, 4, 5, 6, 7, 8, 9, 10, 20, 30, 40, 50, 60, 70, 80, 90, 100, 200, 300, 400, 500, 600, 700, 800, 900, or 1000 heterologous nucleic acids.

In some embodiments, the at least one template UBP is introduced into the cell by transfection, lipofection, injection, viral vector, or electroporation.

In some embodiments, the cell forms a UBP comprising the imported first unnatural nucleic acid.

In some embodiments, the UBP comprising the imported second unnatural nucleic acid further comprises the first unnatural template nucleic acid.

In some embodiments, the cell forms a UBP comprising the imported second unnatural nucleic acid.

In some embodiments, the UBP comprising the imported second unnatural nucleic acid further comprises the second unnatural template nucleic acid.

In some embodiments, the cell forms a UBP comprising the imported first unnatural nucleic acid and the imported second unnatural nucleic acid.

In some embodiments, the UBP is formed within the cell.

In some embodiments, the first or second unnatural nucleic acid is a deoxyribonucleoside.

In some embodiments, the first or second unnatural nucleic acid is a ribonucleoside.

In some embodiments, the first or second unnatural nucleic acid is a nucleoside triphosphate.

In some embodiments, the first or second unnatural nucleic acid comprises a modified sugar group.

In some embodiments, the unnatural sugar moeity is selected from the group consisting of a modification at the 2' position: OH; substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2F$; O-alkyl, S-alkyl, N-alkyl; O-alkenyl, S-alkenyl, N-alkenyl; O-alkynyl, S-alkynyl, N-alkynyl; O-alkyl-O-alkyl, 2'-F, 2'-$OCH_3$, 2'—$O(CH_2)_2OCH_3$ wherein the alkyl, alkenyl and alkynyl may be substituted or unsubstituted $C_1$-$C_{10}$, alkyl, $C_2$-$C_{10}$ alkenyl, $C_2$-$C_{10}$ alkynyl, —$O[(CH_2)n\ O]mCH_3$, —$O(CH_2)nOCH_3$, —$O(CH_2)n\ NH_2$, —$O(CH_2)n\ CH_3$, —$O(CH_2)n$-$ONH_2$, and —$O(CH_2)nON[(CH_2)n\ CH_3)]_2$, where n and m are from 1 to about 10; and/or a modification at the 5' position: 5'-vinyl, 5'-methyl (R or S), a modification at the 4' position, 4'-S, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and any combination thereof.

In some embodiments, the first or second unnatural nucleic acid comprises a modified base group.

In some embodiments, the modified base group is selected from the group consisting of

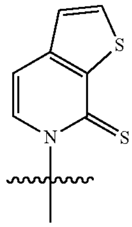

(d)TPT3

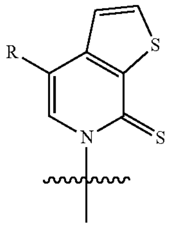

(d)TPT3pa

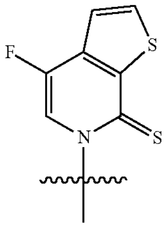

(d)FTPT3

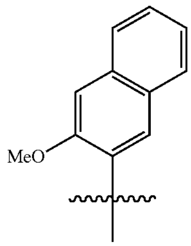

(d)NaM

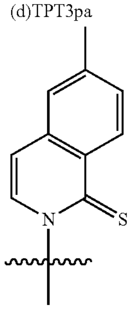

(d)5SICS

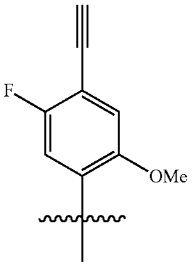

(d)FEMO

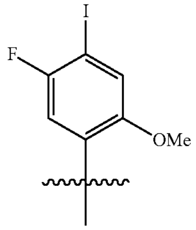

(d)FIMO

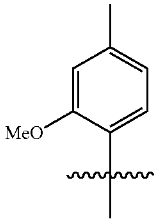

(d)MMO2 wherein R is a functional group.

In some embodiments, the functional group is selected from the group consisting of an affinity tag such as biotin, flourophore, alkyl, alkenyl, alkynyl, phenyl, benyl, halo, hydroxyl, carbonyl, aldehyde, haloformyl, carbonate ester, carboxylate, carboxyl, ester, methoxy, hydroperoxy, peroxy, ether, hemiacetal, hemiketal, acetal, ketal, orthoester, methylenedioxy, orthocasrbonate ester, carboxamide, primary amine, secondary amine, tertiary amine, primary ketamine, secondary ketamine, primary aldimine, secondary aldimine, imide, azide, azo, cyanate, isocyanate, nitrate, nitrile, isonitrile, nitrosooxy, nitro, nitroso, pyridyl, sulfhydryl, sulfide, disulfide, sulfinyl, sulfino, sulfo, thiocyanate, isothiocyanante, carbonothioyl, phoshino, phosphono, phosphate, borono, boronate, borino, borinate, and combinations thereof.

In some embodiments, the first or second unnatural nucleic acid comprises an unnatural backbone.

In some embodiments, the unnatural backbone is selected from the group consisting of a phosphorothioate, chiral phosphorothioate, phosphorodithioate, phosphotriester, aminoalkylphosphotriester, $C_1$-$C_{10}$ phosphonates, 3'-alkylene phosphonate, chiral phosphonates, phosphinates, phosphoramidates, 3'-amino phosphoramidate, aminoalkylphosphoramidates, thionophosphoramidates, thionoalkylphosphonates, thionoalkylphosphotriesters, and boranophosphates.

In some embodiments, the method further comprises contacting the cell with one or more natural nucleotide triphosphates.

In some embodiments, the one or more natural nucleotide triphosphates comprise dATP, dTTP, ATP, TTP, UTP, or any mixture thereof.

In some embodiments, the first or second unnatural nucleic acid is selected from the group consisting of any one of those listed in Appendix A, and any combination thereof.

In some aspects, provided herein is an isolated nucleic acid comprising a UBP, wherein the UBP was formed within a cell.

In some embodiments, the UBP is selected from the group consisting of any one of those listed in Appendix A, and any combination thereof.

In some aspects, provided herein is an isolated heterologous NTT protein comprising an unnatural nucleic acid bound thereto.

In some embodiments, the unnatural nucleic acid bound thereto is selected from the group consisting of any one of those listed in Appendix A.

The details of one or more inventive embodiments are set forth in the accompanying drawings, the claims, and in the description herein. Other features, objects, and advantages of inventive embodiments disclosed and contemplated herein will be apparent from the description and drawings, and from the claims.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

Figure 1:
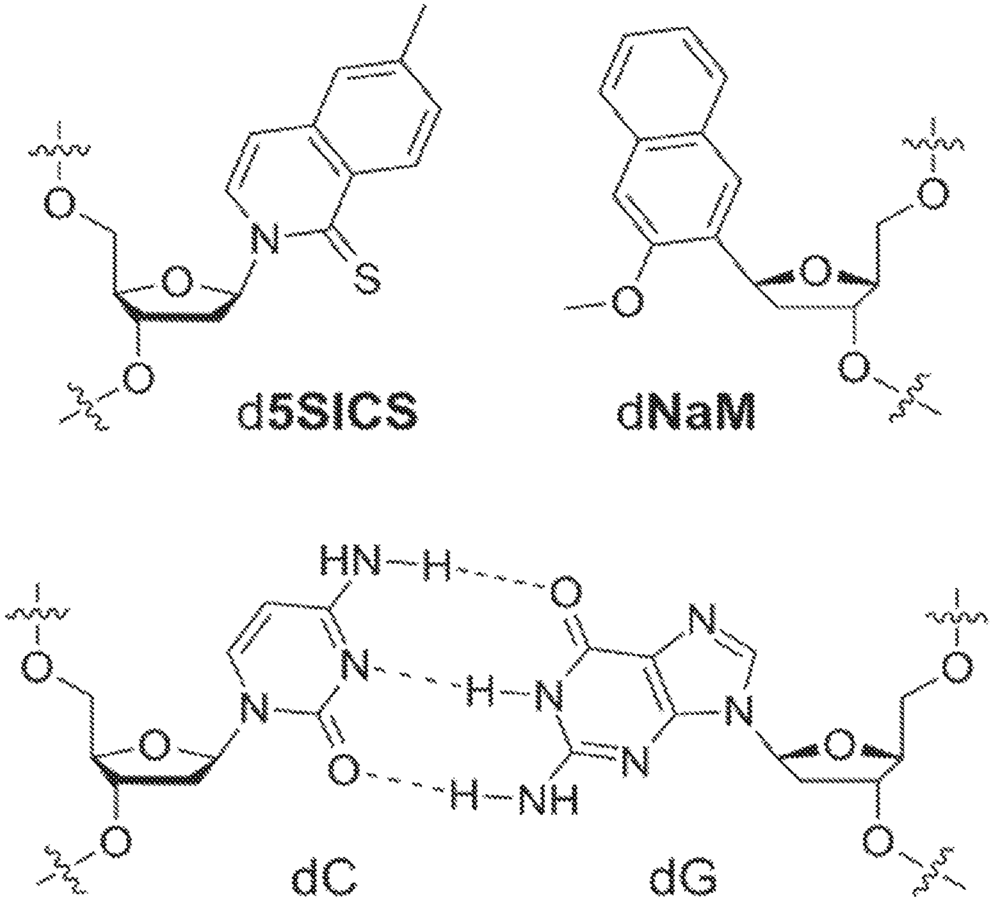
FIG. 1 shows the structure of d5SICS-dNaM with a natural (dC-dG) base pair shown for comparison.
Figure 2:
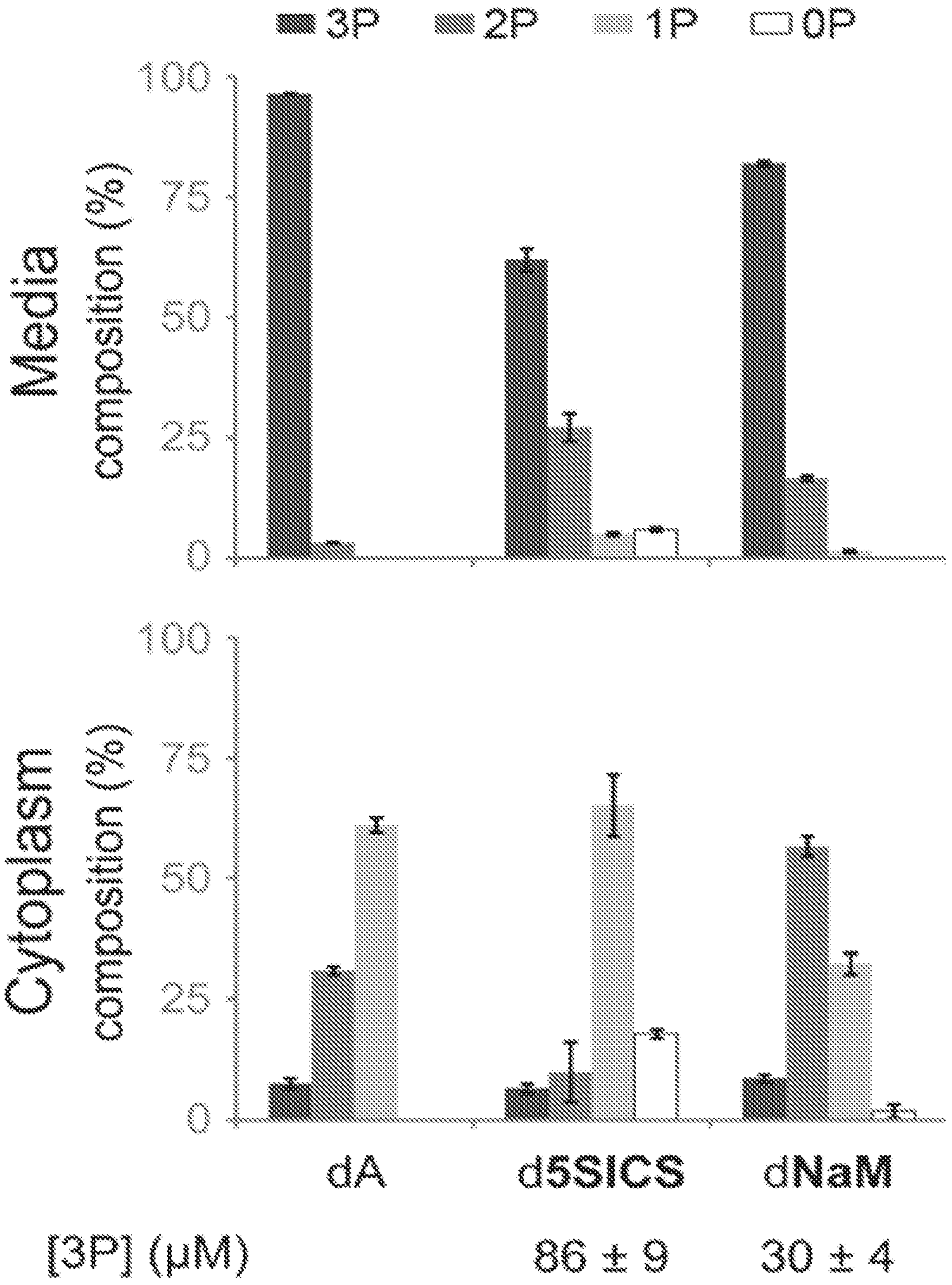
FIG. 2 depicts data relating to nucleoside triphosphate stability and import; and a composition analysis of d5SICS, and dNaM nucleotides in the media and cytoplasmic fractions of cells expressing PtNTT2. 3P, 2P, 1P and 0P correspond to triphosphate, diphosphate, monophosphate and nucleoside, respectively. [3P]=the total intracellular concentration of triphosphate.

As illustrated herein, d5SICSTP and dNaMTP can be efficiently imported into *E. coli* by the transporter 2 from *Phaeodactylum tricornutum* (PtNTT2), and *E. coli* replication machinery can efficiently incorporate these unnatural triphosphates into DNA within the cellular environment to form unnatural DNA base pairs.

The present invention is based, in part, on the discovery that particular unnatural base bairs (UBPs) including but not limited to (d)5SICS-(d)NaM and (d)TPT3-(d)NaM can be amplified with natural base pair-like efficiency and fidelity (Malyshev et al., Proc. Natl. Acad. Sci. USA (2012) 109: 12005-12010; Li et al., J. Am. Chem. Soc. (2014) 136:826-829). Thus, provided herein are methods, compositions, and kits, for increasing the genetic alphabet of cell or an organism. Also, provided herein are compositions, e.g., cells, comprising an expanded genetic alphabet, e.g., cells that stably propagate an expanded genetic alphabet. Also, provided herein are compositions, e.g., cells, comprising an expanded genetic alphabet, wherein neither the presence of unnatural triphosphates nor the replication of the UBP represents a significant growth burden on the cells.

In addition, the present invention relates to genetic constructs, modified cells and methods of importing and incorporating natural and unnatural nucleotides into nucleic acids of a living cell. Aspects of the invention facilitate labeling and modification of living cells. Unnatural nucleotides imported into cells by the modified cells and methods described herein can form UBPs in vivo and these UBPs can be replicated through one or more replication cycles of the cell. For the first time, a cell that stably incorporates within its cellular nucleic acids, nucleotides other than A, G, T, and C, e.g., (d)5SICS and (d)NaM, is described. Also provided herein are methods of incorporating an unnatural nucleotide into a nucleic acid by using, as a template, a nucleic acid containing a first unnatural nucleotide so that a second unnatural nucleic acid is incorporated at a site complementary to the first unnatural nucleotide. For example, such methods of incorporating an unnatural nucleotide into a nucleic acid can comprise effecting transcription, replication, reverse transcription or translation of unnatural nucleotides into unnatural amino acids.

Also, provided herein are compositions, e.g., cells, that retain a UBP, e.g., when unnatural triphosphates are available in a growth medium of the cells. The methods, compositions, and kits, can utilize enhanced cellular uptake of nucleic acids, e.g., via enhanced cellular import of nucleic acids. The nucleic acids undergoing enhanced cellular uptake can be one or more unnatural nucleotides. In some embodiments, nucleic acids undergoing enhanced cellular uptake can be one or more unnatural nucleotides, and not a natural nucleic acid. In some embodiments, nucleic acids undergoing enhanced cellular uptake can be one or more unnatural nucleotide and one or more natural nucleotides. In some embodiments, nucleic acids undergoing enhanced cellular uptake can be one or more unnatural nucleotide and one or more first natural nucleotides, but not one or more second natural nucleotides. In some embodiments, nucleic acids undergoing enhanced cellular uptake can be one or more first unnatural nucleotide and one or more natural nucleotides, but not one or more second unnatural nucleotides.

The methods, compositions, and kits, can utilize one or more endogenous or exognenous enzymes to stably integrate unnatural nucleic acids, e.g., unnatural nucleoside triphosphates. The methods, compositions, and kits, can utilize one or more endogenous or exognenous enzymes to copy a homologous nucleic acid to form a nucleic acid comprising an unnatural nucleic acid. For example, endogenous or exognenous enzymes, e.g., endogenous or exognenous polymerases, can be utilized to replicate genomic DNA to form a containing a UBP within a cell. The methods, compositions, and kits, can utilize one or more endogenous or exognenous enzymes to copy a cellular nucleic acid comprising a UBP to form a nucleic acid copy comprising an unnatural nucleic acid. For example, endogenous or exognenous polymerases can be utilized to replicate genomic DNA containing a UBP within a cell. The methods, compositions, and kits, can also utilize a UBP that is not efficiently excised by DNA repair pathways.

Nucleic Acids

A nucleic acid (e.g., also referred to herein as target nucleic acid, target nucleotide sequence, nucleic acid sequence of interest or nucleic acid region of interest) can be from any source or composition, such as DNA, cDNA, gDNA (genomic DNA), RNA, siRNA (short inhibitory RNA), RNAi, tRNA or mRNA, for example, and can be in any form (e.g., linear, circular, supercoiled, single-stranded, double-stranded, and the like). Nucleic acids can comprise nucleotides, nucleosides, or polynucleotides. Nucleic acids can comprise natural and unnatural nucleic acids. A nucleic acid can also comprise unnatural nucleic acids, such as DNA or RNA analogs (e.g., containing base analogs, sugar analogs and/or a non-native backbone and the like). It is understood that the term "nucleic acid" does not refer to or infer a specific length of the polynucleotide chain, thus polynucleotides and oligonucleotides are also included in the definition. Exemplary natural nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Exemplary natural deoxyribonucleotides include dATP, dTTP, dCTP, dGTP, dADP, dTDP, dCDP, dGDP, dAMP, dTMP, dCMP, and dGMP. Exemplary natural ribonucleotides include ATP, UTP, CTP, GTP, ADP, UDP, CDP, GDP, AMP, UMP, CMP, and GMP. For RNA, the uracil base is uridine. A nucleic acid sometimes is a vector, plasmid, phage, autonomously replicating sequence (ARS), centromere, artificial chromosome, yeast artificial chromosome (e.g., YAC) or other nucleic acid able to replicate or be replicated in a host cell. An unnatural nucleic acid can be a nucleic acid analogue. An unnatural nucleic acid can be from an extracellular source. An unnatural nucleic acid can be available to the intracellular space of an organism provided herein, e.g., a genetically modified organism.

Unnatural Nucleic Acids

A nucleotide analog, or unnatural nucleotide, comprises a nucleotide which contains some type of modification to either the base, sugar, or phosphate moieties. A modification can comprise a chemical modification. Modifications may be, for example, of the 3'OH or 5'OH group, of the backbone, of the sugar component, or of the nucleotide base. Modifications may include addition of non-naturally occurring linker molecules and/or of interstrand or intrastrand cross links. In one aspect, the modified nucleic acid comprises modification of one or more of the 3'OH or 5'OH group, the backbone, the sugar component, or the nucleotide base, and/or addition of non-naturally occurring linker molecules. In one aspect a modified backbone comprises a backbone other than a phosphodiester backbone. In one aspect a modified sugar comprises a sugar other than deoxyribose (in modified DNA) or other than ribose (modified RNA). In one aspect a modified base comprises a base other than adenine, guanine, cytosine or thymine (in modified DNA) or a base other than adenine, guanine, cytosine or uracil (in modified RNA).

The nucleic acid may comprise at least one modified base. Modifications to the base moiety would include natural and synthetic modifications of A, C, G, and T/U as well as different purine or pyrimidine bases. In some embodiments, a modification is to a modified form of adenine, guanine cytosine or thymine (in modified DNA) or a modified form of adenine, guanine cytosine or uracil (modified RNA).

A modified base of a unnatural nucleic acid includes but is not limited to uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, 0-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C-CI1/4) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-aminoadenine, 8-azaguanine, 8-azaadenine, 7-deazaguanine, 7-deazaadenine, 3-deazaguanine, 3-deazaadenine, tricyclic pyrimidines, phenoxazine cytidine([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thioguanine, 2-thio-thymine, 4-thio-thymine, 5-propynyl-uracil, 4-thio-uracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acid can include one or several heterocyclic bases other than the principal five base components of naturally-occurring nucleic acids. For example, the heterocyclic base may include uracil-5-yl, cytosin-5-yl, adenin-7-yl, adenin-8-yl, guanin-7-yl, guanin-8-yl, 4-aminopyrrolo[2.3-d]pyrimidin-5-yl, 2-amino-4-oxopyrolo[2, 3-d]pyrimidin-5-yl, 2-amino-4-oxopyrrolo[2.3-d]pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Unnatural nucleic acids can include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

Unnatural nucleic acids can include modifications at the 5'-position and the 2'-position of the sugar ring (PCT/US94/02993), such as 5'-$CH_2$-substituted 2'-O-protected nucleosides (Wu et al., Helvetica Chimica Acta, 2000, 83, 1127-1143 and Wu et al., Bioconjugate Chem. 1999, 10, 921-924). Unnatural nucleic acids can include amide linked nucleoside dimers have been prepared for incorporation into oligonucleotides wherein the 3' linked nucleoside in the dimer (5' to 3') comprises a 2'-$OCH_3$ and a 5'-(S)—$CH_3$ (Mesmaeker et al., Synlett, 1997, 1287-1290). Unnatural nucleic acids can include 2'-substituted 5'-$CH_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group ($SC(CH_3)_3$) (and analogs thereof); a methyleneamino group ($CH_2NH_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

Unnatural nucleic acids can also include modifications of the sugar moiety. Nucleic acids of the invention can optionally contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substitutent groups (including 5' and/or 2' substituent groups; bridging of two ring atoms to form bicyclic nucleic acids (BNA); replacement of the ribosyl ring oxygen atom with S, N(R), or C(Ri)($R_2$) (R=H, $C_1$-$C_{12}$ alkyl or a protecting group); and combinations thereof. Examples of chemically modified sugars can be found in WO2008/101157, US2005/0130923, and WO2007/134181.

A modified nucleic acid may comprise modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to $—O[(CH_2)_nO]_m CH_3$, $—O(CH_2)_nOCH_3$, $—O(CH_2)_nNH_2$, $—O(CH_2)_nCH_3$, $—O(CH_2)_nONH_2$, and $—O(CH_2)_nON[(CH_2)_n CH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl, O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as $CH_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-$OCH_3$, and 2'-$O(CH_2)_2OCH_3$ substituent groups. The substituent at the 2' position can also be selected from allyl, amino, azido, thio, O-allyl, O—($C_1$-$C_{10}$ alkyl), $OCF_3$, $O(CH_2)_2SCH_3$, $O(CH_2)_2—O—N(R_m)(R_n)$, and $O—CH_2—C(=O)—N(R_m)(R_n)$, where each $R_m$ and $R_n$ is, independently, H or substituted or unsubstituted $C_1$-$C_{10}$ alkyl.

In certain embodiments, nucleic acids of the present invention include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-$(CH_2)$—O-2' (LNA); 4'-$(CH_2)$—S-2'; 4'-$(CH_2)_2$—O-2' (ENA); 4'-$CH(CH_3)$—O-2' and 4'-$CH(CH_2OCH_3)$—O-2', and analogs thereof (see, U.S. Pat. No. 7,399,845); 4'-$C(CH_3)(CH_3)$—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A, 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids can comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but are not limited to, methylenemethylimino ($—CH_2—N(CH_3)—O—CH_2—$), thiodiester (—O—C(O)—S—), thionocarbamate (—O—C(O)(NH)—

S—); siloxane (—O—$Si(H)_2$—O—); and N,N*-dimethylhydrazine (—$CH_2$—$N(CH_3)$—$N(CH_3)$). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

A phosphorous derivative (or modified phosphate group) can be attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, N.Y.; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

Backbone modification may comprise replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene(methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1-di-O-hexadecyl-rac-glycero-S—H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Nucleic Acids for Cellular Import

In some embodiments, the nucleic acids undergoing enhanced cellular uptake comprise nucleotide triphosphates. In some embodiments, the nucleic acids undergoing enhanced cellular uptake comprise nucleotide diphosphates. In some embodiments, the nucleic acids undergoing enhanced cellular uptake comprise nucleotide monophosphates. In some embodiments, the nucleic acids undergoing enhanced cellular uptake comprise nucleosides. In some embodiments, the nucleic acids undergoing enhanced cellular uptake do not comprise nucleotide diphosphates. In some embodiments, the nucleic acids undergoing enhanced cellular uptake do not comprise nucleotide monophosphates. In some embodiments, the nucleic acids undergoing enhanced cellular uptake do not comprise nucleosides.

In some embodiments, the nucleic acids undergoing enhanced cellular uptake comprise nucleic acid analogs e.g., unnatural nucleic acids. In some embodiments enhanced uptake of active transport of nucleic acids utilizes nucleotide triphosphate transporters (NTTs), e.g., from obligate intracellular bacteria or algal plastids. In some embodiments, the methods, compositions, and kits incorporate natural and/or unnatural nucleotides into an organism or cell.

A variety of natural and unnatural nucleotides can be imported into cells. One example of a pair of unnatural nucleotide triphosphates that can be transported into cells and that can base pair to form an UBP when incorporated into nucleic acids with the cells, includes a triphosphate of (d)5SICS ((d)5SICSTP) and a triphosphate of (d)NaM ((d) NaMTP). One example of a pair of unnatural nucleotide triphosphates that can be transported into cells and that can base pair to form an UBP when incorporated into nucleic acids with the cells, includes a triphosphate of (d)TPT3 ((d)TPT3TP) and a triphosphate of (d)NaM ((d)NaMTP), which can be PCR amplified with a natural base pair-like efficiency and fidelity. In some embodiments, (d)TPT3 comprises a propargyl amine linker (TPT3$^{PA}$). One example of a pair of unnatural nucleotide triphosphates that can be transported into cells and that can base pair to form an UBP when incorporated into nucleic acids with the cells, includes a triphosphate of (d)TPT3$^{PA}$ and a triphosphate of NaM$^{A}$-dNaM pair which can be PCR amplified with a natural base pair-like efficiency and fidelity. Such unnatural nucleotides can have a ribose or deoxyribose sugar moiety. The structures of 5SICS, d5SICS, NAM, and dNaM, unnatural nucleotides are shown below.

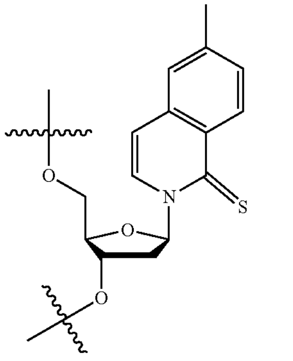

d5SICS

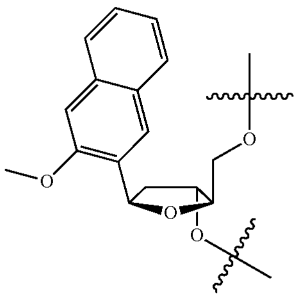

dNAM

-continued

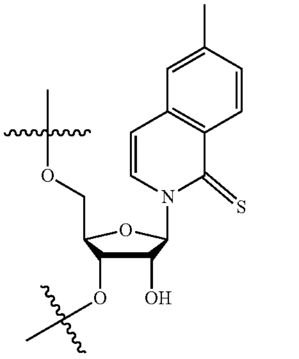

5SICS

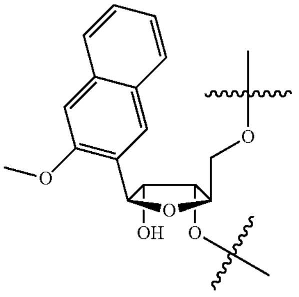

NAM

Other types of unnatural nucleotides can be imported into the cells by the nucleotide triphosphate transporter, such as (d)TPT3, (d)TPT3PA, (d)FTPT3, (d)NaM, (d)5SICS, (d)FEMO, (d)FIMO, (d)MMO2 and combinations thereof, wherein (d) means that the nucleobase can be attached to a deoxyribose or a ribose. The structures of the nucleobases of these unnatural nucleotide triphosphates are shown below.

wherein the wavy line identifies a point of attachment to the (deoxy)ribose or ribose sugar and R

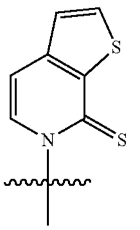

(d)TPT3

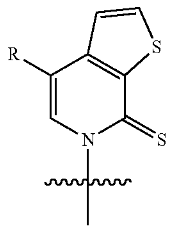

(d)TPT3pa

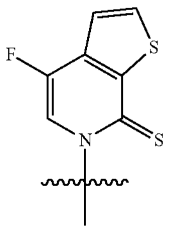

(d)FTPT3

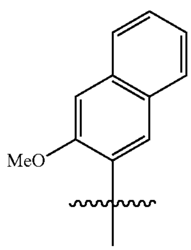

(d)NaM

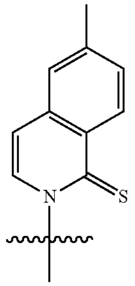

(d)5SICS

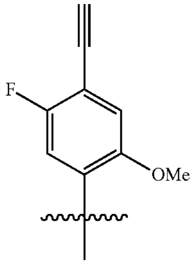

(d)FEMO

-continued

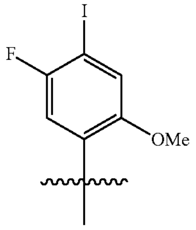

(d)FIMO

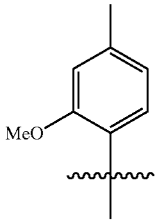

(d)MMO2 indicates a propargyl amine linker. The sugar can be phosphorylated (i.e., to form a nucleotide triphosphate).

A variety of naturally-occurring nucleotide triphosphates can also be transported by the methods described herein. Naturally-occurring nucleotide triphosphates include the ribose or deoxyribose nucleotide triphosphates having adenosine, guanine, cytosine, thymine or uracil.

Examples of other types of modified or unnatural nucleotide triphosphates that can also be transported into cells include those with 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, (acp3)w, and 2,6-diaminopurine.

The structures of TPT3, dTPT3, NAM, and dNaM, unnatural nucleotides are shown below.

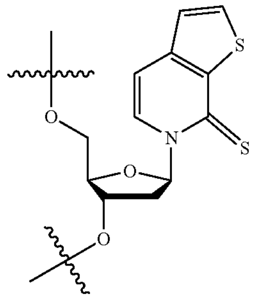

dTPT3

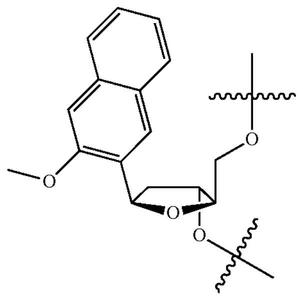

dNAM

-continued

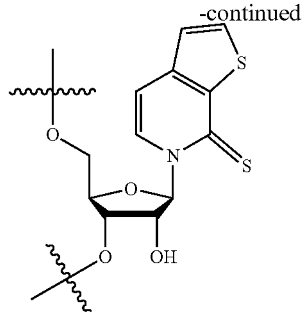

TPT3

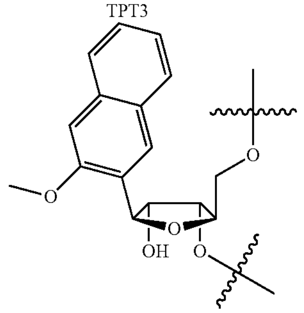

NAM

Exemplary nucleic acids (or UDPs) that can be used, e.g., for importation into cells, can also include any one or more of the nucleic acid structures depicted in Appendix A, wherein the wavy line identifies a point of attachment to the sugar moeity, such as a (deoxy)ribose or ribose.

A variety of naturally-occurring nucleotides as well other modified or unnatural nucleotides can also be transported into cells via the methods described herein.

In some embodiments, the imported nucleic acids may locate within a region of a cell or a cellular compartment. In some embodiments, the region or compartment of a cell may include a membrane, an organelle and/or the cytosol. For example, the membranes may include, but are not limited to, nuclear membrane, plasma membrane, endoplasmic reticulum membrane, cell wall, cell membrane and/or mitochondrial membrane. In some embodiments, the membranes may include a complete membrane or a fragment of a membrane. For example, the organelles may include, but are not limited to, the nucleolus, nucleus, chloroplast, plastid, endoplasmic reticulum, rough endoplasmic reticulum, smooth endoplasmic reticulum, centrosome, golgi apparatus, mitochondria, vacuole, acrosome, autophagosome, centriole, cilium, eyespot apparatus, glycosome, glyoxysome, hydrogenosome, lysosome, melanosome, mitosome, myofibril, parenthesome, peroxisome, proteasome, ribosome, vesicle, carboxysome, chlorosome, flagellum, magenetosome, nucleoid, plasmid, thylakoid, mesosomes, cytoskeleton, and/or vesicles. In some embodiments, the organelles may include a complete membrane or a fragment of a membrane. For example, the cytosol may be encapsulated by the plasma membrane, cell membrane and/or the cell wall.

Nucleic Acid Base Pairing Properties

An unnatural nucleic acid can form a base pair with another nucleic acid. In some embodiments, a stably integrated unnatural nucleic acid is an unnatural nucleic acid that can form a base pair with another nucleic acid, e.g., a natural or unnatural nucleic acid. In some embodiments, a stably integrated unnatural nucleic acid is an unnatural nucleic acid that can form a base pair with another unnatural nucleic acid (unnatural nucleic acid base pair (UBP)). For example, a first unnatural nucleic acid can form a base pair with a second unnatural nucleic acid. For example, one pair of unnatural nucleotide triphosphates that can base pair when incorporated into nucleic acids include a triphosphate of (d)5SICS ((d)5SICSTP) and a triphosphate of (d)NaM ((d)NaMTP). For example, one pair of unnatural nucleotide triphosphates that can base pair when incorporated into nucleic acids include a triphosphate of (d)TPT3 ((d)TPT3TP) and a triphosphate of (d)NaM ((d)NaMTP). Such unnatural nucleotides can have a ribose or deoxyribose sugar moiety. In some embodiments, an unnatural nucleic acid does not substantially form a base pair with a natural nucleic acid (A, T, G, C). In some embodiments, a stably integrated unnatural nucleic acid can form a base pair with a natural nucleic acid.

In some embodiments, a stably integrated unnatural nucleic acid is an unnatural nucleic acid that can form a UBP, but does not substantially form a base pair with each of the four natural nucleic acids. In some embodiments, a stably integrated unnatural nucleic acid is an unnatural nucleic acid that can form a UBP, but does not substantially form a base pair with one or more natural nucleic acids. For example, a stably integrated unnatural nucleic acid may not substantially form a base pair with A, T, and, C, but can form a base pair with G. For example, a stably integrated unnatural nucleic acid may not substantially form a base pair with A, T, and, G, but can form a base pair with C. For example, a stably integrated unnatural nucleic acid may not substantially form a base pair with C, G, and, A, but can form a base pair with T. For example, a stably integrated unnatural nucleic acid may not substantially form a base pair with C, G, and, T, but can form a base pair with A. For example, a stably integrated unnatural nucleic acid may not substantially form a base pair with A and T, but can form a base pair with C and G. For example, a stably integrated unnatural nucleic acid may not substantially form a base pair with A and C, but can form a base pair with T and G. For example, a stably integrated unnatural nucleic acid may not substantially form a base pair with A and G, but can form a base pair with C and T. For example, a stably integrated unnatural nucleic acid may not substantially form a base pair with C and T, but can form a base pair with A and G. For example, a stably integrated unnatural nucleic acid may not substantially form a base pair with C and G, but can form a base pair with T and G. For example, a stably integrated unnatural nucleic acid may not substantially form a base pair with T and G, but can form a base pair with A and G. For example, a stably integrated unnatural nucleic acid may not substantially form a base pair with, G, but can form a base pair with A, T, and, C. For example, a stably integrated unnatural nucleic acid may not substantially form a base pair with, A, but can form a base pair with G, T, and, C. For example, a stably integrated unnatural nucleic acid may not substantially form a base pair with, T, but can form a base pair with G, A, and, C. For example, a stably integrated unnatural nucleic acid may not substantially form a base pair with, C, but can form a base pair with G, T, and, A.

Exemplary, unnatural nucleotides capable of forming an unnatural DNA or RNA base pair (UBP) under conditions in vivo can include 5SICS, d5SICS, NAM, dNaM, and combinations thereof.

Target Sequences/Activities

A nucleotide reagent sometimes can comprise a target nucleotide sequence. A "target nucleic acid" sequence as used herein encodes a nucleic acid, peptide, polypeptide or protein of interest, and may be a ribonucleotide sequence or a deoxyribonucleotide sequence. A target nucleic acid sometimes is an untranslated ribonucleic acid and sometimes is a translated ribonucleic acid. An untranslated ribonucleic acid may include, but is not limited to, a small interfering ribonucleic acid (siRNA), a short hairpin ribonucleic acid (shRNA), other ribonucleic acid capable of RNA interference (RNAi), an antisense ribonucleic acid, or a ribozyme. A translatable target nucleotide sequence (e.g., a target ribonucleotide sequence) sometimes encodes a peptide, polypeptide or protein, which are sometimes referred to herein as "target peptides," "target polypeptides" or "target proteins."

A translatable nucleotide sequence generally is located between a start codon (AUG in ribonucleic acids and ATG in deoxyribonucleic acids) and a stop codon (e.g., UAA (ochre), UAG (amber) or UGA (opal) in ribonucleic acids and TAA, TAG or TGA in deoxyribonucleic acids), and sometimes is referred to herein as an "open reading frame" (ORF). A translatable nucleotide sequence (e.g., ORF) sometimes is encoded differently in one organism (e.g., most organisms encode CTG as leucine) than in another organism (e.g., *C. tropicalis* encodes CTG as serine). In some embodiments, a translatable nucleotide sequence is altered to correct alternate genetic code (e.g., codon usage) differences between a nucleotide donor organism and a nucleotide recipient organism (e.g., engineered organism). In certain embodiments, a translatable nucleotide sequence is altered to improve; (i) codon usage, (ii) transcriptional efficiency, (iii) translational efficiency, (iv) the like, and combinations thereof.

Any peptides, polypeptides or proteins, or an activity catalyzed by one or more peptides, polypeptides or proteins may be encoded by a target nucleotide sequence and may be selected by a user. Representative proteins include transporters (e.g., nucleotide triphosphate transporters), enzymes (e.g., polymerases, replication machinery, and the like, for example) and membrane bound proteins, and include both naturally occurring and exogenously expressed polypeptides.

Representative activities (e.g., enzymes or combinations of enzymes which are functionally associated to provide an activity) include nucleotide triphosphate transporter activity and polymerase activity, Specific polypeptides (e.g., enzymes) useful for embodiments described herein are listed herein. A protein or polypeptide sometimes is of intracellular origin (e.g., located in the nucleus, cytosol, or interstitial space of host cells in vivo) and sometimes is a cell membrane protein in vivo. In some embodiments (described above, and in further detail hereafter), a genetic modification can result in a modification (e.g., increase, substantially increase, decrease or substantially decrease) of a target activity.

Nucleotide Triphosphate Transporter Activity

Chloroplasts are characteristic organelles of plants, possess an envelope of two membranes and arose by a primary endosymbiosis between a protozoan host and a cyanobacterium (higher plant, green algae, red algae and glaucophyta). However, the engulfment of a red or a green alga by a non-photosynthetic host through a process called secondary endosymbiosis gave rise to further groups of complex chimeric eukaryotes (chloraracheans, chromalveolates). The resulting photosynthetic organelle accordingly exhibits four bounding membranes. Until now the knowledge on metabolic fluxes across the membranes of complex plastids is limited. Biochemical characterization of plastidial carrier proteins involved in energy provision (nucleotide transporters, NTTs) and in the transport of intermediates of starch metabolism provided insights into the cellular communication across the envelope membranes of primary and complex plastids.

Apart from plastidial nucleotide transporters (NTTs), which mediate the transport of ATP in counter exchange with ADP and other deoxyribonucleotides and ribonucleotides, structurally related proteins are also present in some intracellular living bacterial species. The different biochemical characteristics of specialized NTTs enable these intracellular bacteria to exploit metabolic intermediates of the host cell. The endosymbiotic bacterium *Protochlamydia amoebophila* for example possesses five NTTs essential not only for energy provision by ATP/ADP counter exchange, but also for uptake of DNA and RNA components and nucleotide derivatives from the host cell. Furthermore, in *Protochlamydia amoebophila* corresponding biosynthetic pathways were eliminated during evolution.

A cell can contain, or can be modified to contain, a nucleotide triphosphate transporter that facilitates transport of the unnatural nucleotides through cellular and other membranes so that the unnatural nucleotides are available to the cellular machinery for incorporation into the cell's nucleic acids. UBPs can therefore form within the cell's nucleic acids. Moreover, neither the presence of the unnatural triphosphates nor the replication of the UBP represents a significant growth burden. The UBPs are not efficiently excised by nucleic acid repair pathways, and therefore can be retained as long as the unnatural triphosphates are available in the growth medium. Thus, the resulting cell is the first organism to stably propagate an expanded genetic alphabet.

Certain types of nucleotide triphosphate transporters are more effective than others. For example, nucleotide triphosphate transporters from some types or diatoms or algae are useful for transporting natural and/or unnatural nucleotide triphosphates into cells without degradation or loss of the nucleotide triphosphates, particularly when the cells and nucleotide triphosphates are maintained in the presence of potassium phosphate.

The unnatural nucleotides are transported into cells by a nucleotide triphosphate transporter. As illustrated herein, a variety of nucleotide triphosphate transporters can be employed to transport the unnatural nucleotides into cells. Examples of nucleotide triphosphate transporters that can be employed include those from diatoms such as *Phaeodactylum tricornutum, Thalassiosira pseudonana* and/or *Protochlamydia amoebophila.*

Diatom plastids rely on nucleotide uptake by a specialized import system in their membranes that interconnects cytosolic nucleotide formation and nucleotide consumption in the organelle. Because diatom plastids are surrounded by four membranes, whereas primary plastids possess only two, diatoms have extra transporters in the additional membranes.

Examples of nucleotide triphosphate transporters that can be employed include those from *Phaeodactylum tricornutum* with NCBI accession numbers EEC44449.1 (GI:217404502, protein NTT1, PHATRDRAFT_49533); EEC49227.1 (GI:217409295, protein NTT2, PHATRDRAFT_45145); EEC43534.1 (GI:217403582, protein NTT3, PHATRDRAFT_50189); AC165362.1 (GI:209582741, protein NTT4, PHATR_46794); EEC50831.1 (GI:217410902, protein NTT5, PHATRDRAFT_54110); XP_002182967.1 (GI:219125393, protein NTT6, PHATRDRAFT_54907).

A nucleotide triphosphate transporter 2 from *Phaeodactylum tricornutum* (PtNTT2; EEC49227.1, GI:217409295) that has the following sequence SEQ ID NO: 1

```
  1 MRPYPTIALI SVFLSAATRI SATSSHQASA LPVKKGTHVP
 41 DSPKLSKLYI MAKTKSVSSS FDPPRGGSTV APTTPLATGG
 81 ALRKVRQAVF PIYGNQEVTK FLLIGSIKFF IILALTLTRD
121 TKDTLIVTQC GAEAIAFLKI YGVLPAATAF IALYSKMSNA
161 MGKKMLFYST CIPFFTFFGL FDVFIYPNAE RLHPSLEAVQ
201 AILPGGAASG GMAVLAKIAT HWTSALFYVM AEIYSSVSVG
241 LLFWQFANDV VNVDQAKRFY PLFAQMSGLA PVLAGQYVVR
281 FASKAVNFEA SMHRLTAAVT FAGIMICIFY QLSSSYVERT
321 ESAKPAADNE QSIKPKKKKP KMSMVESGKF LASSQYLRLI
361 AMLVLGYGLS INFTEIMWKS LVKKQYPDPL DYQRFMGNFS
401 SAVGLSTCIV IFFGVHVIRL LGWKVGALAT PGIMAILALP
441 FFACILLGLD SPARLEIAVI FGTIQSLLSK TSKYALFDPT
481 TQMAYIPLDD ESKVKGKAAI DVLGSRIGKS GGSLIQQGLV
521 FVFGNIINAA PVVGVVYYSV LVAWMSAAGR LSGLFQAQTE
561 MDKADKMEAK TNKEK
```

A nucleotide triphosphate transporter 2 from *Phaeodactylum tricornutum* with SEQ ID NO:1 is encoded by a nucleic acid with the following cDNA sequence SEQ ID NO:2

```
  1 ATGAGACCAT ATCCGACGAT TGCCTTGATT TCGGTTTTTC
 41 TTTCGGCGGC GACTCGTATT TCGGCCACTT CCTCTCATCA
 81 AGCAAGTGCA CTTCCTGTCA AAAAGGGAAC GCATGTCCCG
121 GACTCTCCGA AGTTGTCAAA GCTATATATC ATGGCCAAAA
161 CCAAGAGTGT ATCCTCGTCC TTCGACCCCC CTCGGGGAGG
201 CAGTACTGTT GCGCCAACTA CACCGTTGGC AACCGGCGGT
241 GCGCTCCGCA AAGTGCGACA AGCCGTCTTT CCCATCTACG
281 GAAACCAAGA AGTCACCAAA TTTCTGCTCA TCGGATCCAT
321 TAAATTCTTT ATAATCTTGG CACTCACGCT CACGCGTGAT
361 ACCAAGGACA CGTTGATTGT CACGCAATGT GGTGCCGAAG
401 CGATTGCCTT TCTCAAAATA TACGGGGTGC TACCCGCAGC
441 GACCGCATTT ATCGCGCTCT ATTCCAAAAT GTCCAACGCC
481 ATGGGCAAAA AAATGCTATT TTATTCCACT TGCATTCCTT
521 TCTTTACCTT TTTCGGGCTG TTTGATGTTT TCATTTACCC
561 GAACGCGGAG CGACTGCACC CTAGTTTGGA AGCCGTGCAG
601 GCAATTCTCC CGGGCGGTGC CGCATCTGGC GGCATGGCGG
641 TTCTGGCCAA GATTGCGACA CACTGGACAT CCGCCTTATT
681 TTACGTCATG GCGGAAATAT ATTCTTCCGT ATCGGTGGGG
721 CTATTGTTTT GGCAGTTTGC GAACGACGTC GTCAACGTGG
761 ATCAGGCCAA GCGCTTTTAT CCATTATTTG CTCAAATGAG
```

-continued

```
 801 TGGCCTCGCT CCAGTTTTAG CGGGCCAGTA TGTGGTACGG
 841 TTTGCCAGCA AAGCGGTCAA CTTTGAGGCA TCCATGCATC
 881 GACTCACGGC GGCCGTAACA TTTGCTGGTA TTATGATTTG
 921 CATCTTTTAC CAACTCAGTT CGTCATATGT GGAGCGAACG
 961 GAATCAGCAA AGCCAGCGGC AGATAACGAG CAGTCTATCA
1001 AACCGAAAAA GAAGAAACCC AAAATGTCCA TGGTTGAATC
1041 GGGGAAATTT CTCGCGTCAA GTCAGTACCT GCGTCTAATT
1081 GCCATGCTGG TGCTGGGATA CGGCCTCAGT ATTAACTTTA
1121 CCGAAATCAT GTGGAAAAGC TTGGTGAAGA AACAATATCC
1161 AGACCCGCTA GATTATCAAC GATTTATGGG TAACTTCTCG
1201 TCAGCGGTTG GTTTGAGCAC ATGCATTGTT ATTTTCTTCG
1241 GTGTGCACGT GATCCGTTTG TTGGGGTGGA AAGTCGGAGC
1281 GTTGGCTACA CCTGGGATCA TGGCCATTCT AGCGTTACCC
1321 TTTTTTGCTT GCATTTTGTT GGGTTTGGAT AGTCCAGCAC
1361 GATTGGAGAT CGCCGTAATC TTTGGAACAA TTCAGAGTTT
1401 GCTGAGCAAA ACCTCCAAGT ATGCCCTTTT CGACCCTACC
1441 ACACAAATGG CTTATATTCC TCTGGACGAC GAATCAAAGG
1481 TCAAAGGAAA AGCGGCAATT GATGTTTTGG GATCGCGGAT
1521 TGGAAAGAGT GGAGGCTCAC TGATCCAGCA GGGCTTGGTC
1561 TTTGTTTTTG GAAATATCAT TAATGCCGCA CCTGTAGTAG
1601 GGGTTGTCTA CTACAGTGTC CTTGTTGCGT GGATGAGCGC
1641 AGCTGGCCGA CTAAGTGGGC TTTTTCAAGC ACAAACAGAA
1681 ATGGATAAGG CCGACAAAAT GGAGGCAAAG ACCAACAAAG
1721 AAAAGTAG
```

A nucleotide triphosphate transporter 2 from *Protochlamydia amoebophila* (strain UWE25), is referred to as PamTTT2, and has the following sequence SEQ ID NO:3

```
  1 MSQQESEFGK LRAFFWPIHG HEVKKVLPMM LMLFLICFNY
 41 SILRNVKDAI VVTAKASGAE VIPFIKVWVL LPTAVLFTLI
 81 FTKLSNRFSQ EKVFYIVIST FLLFFGSFTY IFYPLRDVLH
121 PHQLCDYLET ILPAGFKGLI AMFRNWSFTL FYVICELWGS
161 IVLTVLFWGF ANEITKMTEA RRFYSMLGVI ASFAATIAGI
201 IANLLSNDQS WEQTLNILMV AVIVSGTIAM VIFRWMNKNV
241 NGPEFQEFH EAKRIQKMKK RLSIRESFTY LANSKYLICI
281 AVLVISYNLV INLVEIVWKD QLRQLYSSAL DYNRYMNNMT
321 SAVGIIATIT SLFMSTMITR FGWTRTALVT PTIMLVTSVG
361 FFAFMLFRND LADPVYILTG TTPLTIAVFF GAAQVCMSKA
401 CKYSVFDSTK EMAFIPLDYE SKLKGKAAID GVGSRLGKSG
441 GSLIHQSLLM IFATVSSSAP YVAVILIGVI IVWMLCVRSL
481 GKQFAAIIGE KAREDIGEST PRTSEEQVLH PLKAAS
```

An example of a nucleotide sequence for the above PamTTT2 protein is provided below as SEQ ID NO:4

```
   1 ATGTCTCAAC AAGAATCAGA GTTTGGTAAA TTGAGGGCAT
  41 TTTTTTGGCC TATTCACGGC CATGAAGTCA AAAAAGTGCT
  81 GCCGATGATG TTGATGCTAT TTTTGATTTG TTTCAACTAT
 121 AGTATTTTAC GCAATGTTAA AGATGCTATT GTTGTGACTG
 161 CTAAGGCTTC AGGGGCTGAA GTTATTCCAT TTATTAAAGT
 201 ATGGGTGCTG TTACCCACGG CAGTCTTATT TACTTTAATT
 241 TTTACTAAGT TGTCTAACCG TTTTAGCCAA GAAAAAGTTT
 281 TTTATATTGT CATTTCTACA TTTTTGCTAT TTTTTGGTTC
 321 GTTTACTTAT ATTTTTTATC CTTTACGTGA CGTACTACAT
 361 CCTCATCAAC TATGCGATTA CTTAGAAACG ATTTTACCAG
 401 CGGGATTTAA AGGATTAATT GCCATGTTCC GTAATTGGTC
 441 ATTTACTTTG TTTTATGTAA TTTGTGAACT TTGGGGCAGT
 481 ATTGTTTTAA CTGTCCTTTT TTGGGGATTT GCGAATGAAA
 521 TCACAAAAAT GACTGAAGCT CGTCGTTTTT ATAGTATGCT
 561 TGGTGTCATT GCAAGTTTTG CCGCGACGAT AGCAGGAATC
 601 ATAGCCAATC TTCTTTCTAA TGATCAAAGT TGGGAACAGA
 641 CTTTAAATAT TCTCATGGTT GCTGTAATTG TAAGTGGAAC
 681 GATAGCCATG GTTATTTTTC GTTGGATGAA TAAAAATGTA
 721 CTCAATGGCC CAGAATTCCA AGAATTCCAT GAAGCAAAAC
 761 GCATTCAAAA AATGAAAAAA AGATTATCGA TCCGAGAAAG
 801 TTTTACCTAT CTCGCTAATT CTAAATATCT TATTTGTATT
 841 GCAGTTTTAG TTATTTCTTA TAATCTTGTC ATTAACTTAG
 881 TTGAAATTGT ATGGAAAGAC CAGCTTCGCC AACTTTATTC
 921 GTCAGCCCTT GATTATAATC GCTATATGAA TAACATGACA
 961 TCAGCAGTCG GAATTATTGC CACAATCACA TCCTTATTTA
1001 TGTCTACAAT GATTACTCGG TTTGGATGGA CACGGACAGC
1041 TCTAGTAACA CCGACTATTA TGCTTGTCAC AAGTGTGGGA
1081 TTTTTTGCTT TTATGCTATT TCGAAATGAT TTGGCTGATC
1121 CTGTTTATAT ATTAACAGGA ACGACACCTT TAACTATAGC
1161 CGTCTTTTTT GGTGCAGCTC AAGTCTGCAT GAGTAAAGCC
1201 TGTAAGTATT CTGTTTTTGA TTCTACAAAA GAAATGGCTT
1241 TTATCCCTCT GGATTATGAA AGTAAATTGA AAGGAAAAGC
1281 TGCGATTGAT GGTGTGGGTT CTCGTCTTGG TAAATCGGGC
1321 GGTTCCTTAA TTCATCAAAG TTTATTGATG ATTTTTGCAA
1361 CTGTTAGCTC CAGCGCTCCT TATGTAGCTG TGATCTTAAT
1401 TGGCGTTATC ATTGTTTGGA TGCTCTGCGT ACGTTCATTA
1441 GGTAAGCAAT TTGCTGCTAT TATTGGGGAA AAGGCTCGAG
1481 AAGATATTGG TGAATCTACT CCAAGAACGA GTGAAGAGCA
1521 AGTTTTACAT CCCTTAAAAG CTGCATCTTAA
```

An example of a nucleotide triphosphate transporter 3 from *Protochlamydia amoebophila* (strain UWE25), is referred to as PamTTT3, and has the following sequence SEQ ID NO:5

```
  1 MSQTPTGSRE FSPWRSNLWP VHRYELKKLI PMLLIFFFIS
 41 FDYNILRTLK DSLLITAKSS GAEVIPFVKV WAMFPGAILM
 81 TLLFTWLSNR LSREIVFYLI TSLFLSYFFI FTFILYPIRD
121 IIHPHATADY LETILPIGFK GLVAMFRYWT FTIFYVMSEL
161 WGSTVLFVLF WGFANQVTKI SEAKRFYGLF GVGANLSGIF
201 AGQASVYCCQ FNKQNDLGIL GSDPWYQSLV MMVSLILLSG
241 ALVLALFRWM NVEVLTDKRF YDPSSVKTEG EAKGKLSLKQ
281 SFSYLLRSNY LLCIALIVIS YNLVINLTEV LWKHQVRELY
321 PDPNDYTLYM NHIVSIIGVV ATLSSLFVSG NAIRKFGWTT
361 TALITPIILA VTSLGFFSFF FLKKASPEIF LSFSGVTPLV
401 LVVFFGTAQN ILSRGAKYSV FDATKEMSFV PLNPESKLVG
441 KAAIDGVCSR LGKSGGSVVH QSLLLLFSTI NASAPYVAIV
481 LFAVILVWAM AIRVLGKQFN ELTSQVENNE TSGTLMTPIR
521 AVNILSDTIL KEQKAV
```

An example of a nucleotide sequence or the above PamTTT3 protein is provided below as SEQ ID NO:6

```
   1 ATGTCACAGA CACCAACAGG GTCCCGTGAA TTTAGTCCAT
  41 GGCGGAGCAA TCTTTGGCCC GTTCATCGCT ATGAGCTTAA
  81 AAAACTCATC CCAATGTTGT TAATATTCTT TTTTATTTCT
 121 TTTGATTACA ACATATTACG TACTTTAAAA GACTCACTAC
 161 TTATAACTGC AAAATCTTCA GGTGCTGAGG TCATTCCTTT
 201 TGTAAAGGTT TGGGCTATGT TCCCTGGAGC TATTTTAATG
 241 ACCCTTTTGT TCACTTGGTT GTCTAATCGC CTGTCAAGAG
 281 AAATCGTTTT TTACCTTATC ACTTCTCTTT TTTTATCTTA
 321 TTTTTTTATT TTCACTTTTA TTCTCTATCC TATTCGAGAT
 361 ATTATCCATC CTCACGCAAC TGCTGACTAT CTTGAAACAA
 401 TTTTACCGAT TGGATTTAAA GGGCTAGTTG CGATGTTTCG
 441 TTACTGGACT TTTACTATTT TCTATGTGAT GTCAGAACTT
 481 TGGGGAAGTA CTGTTTTATT TGTCTTATTT TGGGGTTTTG
 521 CTAATCAAGT GACTAAAATT AGTGAGGCAA AAAGATTTTA
 561 CGGTCTGTTT GGGGTAGGTG CTAATCTTTC GGGTATTTTC
 601 GCAGGACAAG CTTCTGTGTA CTGTTGTCAA TTTAATAAGC
 641 AGAACGATTT GGGAATCCTT GGTAGTGATC CATGGTATCA
 681 ATCATTAGTG ATGATGGTTT CTTTAATTTT ATTATCGGGT
 721 GCTTTAGTTT TAGCTTTATT TCGTTGGATG AATGTAGAAG
 761 TCTTAACCGA TAAACGTTTT TATGATCCTT CTTCGGTTAA
 801 AACAGAAGGA GAAGCTAAAG GTAAGCTTTC TCTAAAGCAA
```

-continued

```
 841 AGCTTTTCCT ATCTTCTTCG CTCTAATTAC TTACTTTGTA
 881 TTGCTCTTAT TGTTATTTCT TATAACCTAG TTATTAACCT
 921 CACAGAAGTT TTATGGAAAC ATCAAGTCCG AGAGCTATAT
 961 CCTGATCCTA ATGATTATAC TTTATATATG AATCATATCG
1001 TATCCATTAT TGGGGTAGTA GCGACCTTAA GTTCCCTTTT
1041 CGTATCAGGA AATGCGATTC GCAAATTTGG GTGGACCACT
1081 ACTGCTTTAA TTACACCTAT CATTTTAGCT GTAACAAGTT
1121 TGGGCTTTTT CTCCTTTTTC TTCCTTAAAA AGGCATCTCC
1161 CGAAATTTTC TTATCTTTTT CCGGAGTAAC TCCTTTGGTT
1201 TTAGTGGTTT TCTTTGGAAC TGCTCAAAAC ATATTGAGTC
1241 GAGGAGCTAA ATACTCTGTA TTTGATGCCA CTAAAGAAAT
1281 GAGTTTTGTT CCTTTAAATC CTGAATCCAA ACTCGTTGGA
1321 AAAGCGGCGA TTGATGGAGT TTGTTCTCGC CTCGGAAAAT
1361 CGGGTGGATC TGTGGTTCAT CAGAGCCTTC TACTTTTGTT
1401 TTCTACAATT AATGCAAGTG CCCCTTATGT AGCTATCGTC
1441 TTGTTCGCCG TAATTCTAGT CTGGGCAATG GCAATTCGCG
1481 TTTTAGGTAA ACAATTTAAT GAATTGACAA GTCAGGTAGA
1521 AAACAATGAA ACTTCTGGGA CATTGATGAC TCCTATTCGA
1561 GCTGTTAATA TTCTTTCAGA CACAATTTTG AAAGAACAGA
1601 AAGCTGTATA A
```

An example of a nucleotide triphosphate transporter 5 from *Protochlamydia amoebophila* (strain UWE25), is referred to as PamTTT5, and has the following sequence SEQ ID NO:7

```
  1 MKNQQNSVSS TLLILKKRSL ILFQFFLIII VYHTLKDLKD
 41 TIVITASDAG AEIIPFIKIW GMLPLAICAS YFFAKFYNKF
 81 GREKTFYIFS SFLLVNYLFF AFVLYPFRKF FYLENVADYL
121 HMILPVGAKG FVAMVSYWHY TLFYLTAELW SMLILSILFW
161 GYVSDTTSLV EAKKFYPLCM FVGNMAGIIS GQLSHFLCQH
201 LSDFMSWERT LQWMIGIVCV CGLLIMIINR RLALTTDFSA
241 IKQKVKKQIA PSSFKDNVMD VLRTGPLLCI AVLVVGFGLT
281 TNLIEVIWKE NIRQLHPTPQ AYNAYINQLT SLIGTGAVCI
321 ALLSSWIFRK FTWTQIALTT PLCLLITSSA FFSSLLMPKE
361 LLAEIASFFQ FSPTQLIVTL GSICYVFSMS AKYTIFDTSK
401 EIAFLSIETE KRTYAKSVID SIGSRLGKSG ASCFYQFLLI
441 AFGIASEHIL LIGVVSIIMI GISIFATKKL GGQLSGKNEN
481 HRFIEASHG
```

An example of a nucleotide sequence for the above PamTTT5 protein is provided below as SEQ ID NO:8

```
 1 ATGAAAAATC AACAAAATTC TGTATCTTCT ACCTTACTAA
41 TCTTAAAAAA GCGTAGCTTG ATCCTATTTC AATTTTTTCT
```

-continued

```
  81 AATTATCATT GTTTATCATA CATTAAAAGA CCTCAAAGAT
 121 ACGATTGTTA TCACAGCAAG TGATGCAGGT GCAGAGATCA
 161 TTCCTTTTAT TAAAATTTGG GGAATGCTTC CTCTTGCCAT
 201 TTGTGCTAGT TATTTTTTTG CTAAATTTTA TAATAAATTT
 241 GGAAGAGAAA AAACATTTTA TATTTTTAGC TCTTTCTTAC
 281 TAGTTAACTA TCTTTTCTTT GCTTTTGTAT TATATCCATT
 321 CCGCAAGTTT TTTTATTTAG AAAATGTTGC AGATTATTTA
 361 CATATGATTT TACCTGTTGG AGCGAAAGGG TTTGTTGCCA
 401 TGGTAAGCTA TTGGCATTAC ACTCTATTTT ATTTAACGGC
 441 AGAATTATGG TCGATGCTCA TTCTATCTAT CCTTTTTTGG
 481 GGTTATGTGA GTGATACGAC TTCTTTAGTA GAAGCCAAAA
 521 AATTTTACCC CCTCTGTATG TTCGTTGGAA ATATGGCAGG
 561 AATTATTTCT GGTCAGCTCT CTCATTTCTT ATGTCAACAT
 601 TTGTCTGATT TCATGTCATG GGAAAGAACC CTGCAATGGA
 641 TGATTGGTAT TGTCTGTGTT TGCGGCCTTT TAATTATGAT
 681 TATTAATAGA CGGCTGGCTC TTACAACTGA TTTTTCGGCA
 721 ATTAAACAAA AAGTAAAAAA ACAAATAGCT CCCTCTTCTT
 761 TCAAAGATAA TGTTATGGAT GTTTTAAGAA CAGGTCCCTT
 801 ACTTTGTATA GCTGTATTGG TAGTGGGGTT TGGACTGACA
 841 ACGAATCTAA TTGAAGTTAT TTGGAAAGAA AATATTAGGC
 881 AACTACACCC GACACCTCAA GCCTACAATG CTTATATTAA
 921 TCAATTGACT TCTTTAATTG GGACTGGTGC TGTTTGTATA
 961 GCCTTGTTAT CAAGCTGGAT TTTTAGAAAG TTTACTTGGA
1001 CGCAAATTGC CCTCACAACC CCTTTATGTT TATTAATCAC
1041 AAGCTCTGCT TTTTTTTCAT CGCTTCTTAT GCCTAAAGAG
1081 CTGTTAGCGG AAATTGCTTC TTTTTTTCAG TTTTCCCCAA
1121 CTCAATTGAT AGTGACACTA GGATCTATTT GCTATGTTTT
1161 TAGCATGTCT GCGAAGTACA CAATTTTTGA TACTAGTAAA
1201 GAAATAGCTT TTCTTTCTAT TGAAACAGAA AAAAGAACGT
1241 ATGCTAAATC TGTAATTGAT AGCATTGGCT CTCGTTTGGG
1281 AAAATCTGGC GCTTCTTGTT TTTATCAATT TCTTCTTATT
1321 GCCTTTGGAA TTGCTTCCGA ACATATTTTA TTAATTGGAG
1361 TTGTATCCAT TATAATGATT GGAATTTCGA TTTTTGCTAC
1401 GAAAAAATTG GGTGGGCAGC TGTCTGGTAA AAATGAAAAC
1441 CATCGCTTTA TAGAAGCTTC CCATGGATAA
```

An example of a nucleotide triphosphate transporter 2 from *Thalassiosira pseudonana*, is referred to as TpTTT2, and has the following sequence SEQ ID NO:9

```
  1 MKTSCTIQRR VKSISSKHSI IDTHHSTSRR LSVILLFFLL
 41 HSSAEMLFAS ATGNHNANTS PPPANIPMIS TNNKSCMMRR
```

-continued

```
 81 TRSQSRRDSS RSPDSVASAN VVGRGGDGGT IMGAKSVFQT
121 ASKALPPNTV SSTASGSVSK ASRLRTVLFP IQNDEMKKFL
161 LIGSIKFFVI LALTLTRDNK DTMVVTECGA EAIAFLKIYG
201 VLPSATLFIA LYSKMATIFD KKTLFYATCI PFFAFFFLFD
241 AIIYPNRNVI QPSLESVQRV MRITADSSGA MSIFAKLFAN
281 WTSALFYIVA EVYSSVSVGI LFWQYANDVV SVSQAKRFYP
321 LFAQMSGLAP IVAGQYVVRY ASRANDFEES LHRLTWMVSF
361 SGVMICLFYK WSNEYNDQTS GGLNGGIEDG VKETKVVKKK
401 KAKMSMRDSA KFLASSEYLR LIAALVVGYG LSINFTDIMW
441 KSIVKRQYPD PLDYQRFMGN FSSVVGLSTC IVIFLGVHAI
481 RILGWRMGAL ATPAVMAILA FPYFSSILVG LDSPGSLRIA
521 VIFGTIQCLL SKTAKYALFD PTTQMAYIPL DDESKIKGKA
561 AIEVLGSRIG KSGGSLIQQG LVLVFGNIIN AAPALVVLYY
601 SVLAWWVYSA NRLGSLFLAK TAMQEETKEH QK
```

An example of a nucleotide sequence for the above TpTTT2 protein is provided below as SEQ ID NO:10

```
  1 ATGAAAACAT CTTGTACAAT CCAACGTCGT GTCAAATCCA
 41 TCTCATCCAA ACACAGTATC ATCGACACAC ACCACTCTAC
 81 TTCTCGCCGT TTAAGTGTCA TCCTACTCTT CTTTCTACTA
121 CACTCCTCGG CAGAGATGCT ATTTGCTTCC GCCACGGGCA
161 ATCACAACGC CAATACATCA CCACCACCTG CGAATATTCC
201 CATGATTAGC ACTAACAACA AATCATGTAT GATGCGACGA
241 ACCAGGAGTC AATCACGACG AGATAGCAGC CGTTCGCCTG
281 ATTCGGTGGC CTCGGCCAAT GTTGTTGGGA GGGGCGGCGA
321 TGGGGGTACC ATTATGGGTG CCAAGAGTGT CTTCCAGACT
361 GCTTCGAAAG CATTACCTCC CAACACTGTG TCGTCCACAG
401 CAAGCGGCAG TGTATCCAAA GCATCGCGCC TACGAACGGT
441 CCTCTTCCCC ATTCAAAATG ACGAGATGAA GAAGTTTCTC
481 TTGATTGGAA GTATCAAGTT CTTTGTAATT CTAGCGTTGA
521 CACTCACGAG AGATAATAAG GATACAATGG TGGTTACCGA
561 GTGTGGAGCT GAGGCCATCG CTTTTCTAAA GATCTACGGA
601 GTACTACCAT CCGCCACACT CTTCATAGCA CTCTACTCGA
641 AAATGGCCAC TATCTTTGAC AAAAAGACCT TATTCTACGC
681 CACGTGCATT CCATTCTTTG CATTCTTCTT CTTATTCGAT
721 GCAATCATCT ATCCTAACCG GAATGTCATT CAGCCTTCCT
761 TAGAGAGTGT TCAGCGTGTC ATGAGAATCA CAGCCGATTC
801 ATCGGGTGCC ATGTCCATCT TTGCAAAGTT GTTCGCCAAT
841 TGGACGTCGG CCTTGTTTTA TATTGTAGCA GAGGTATACT
881 CGTCTGTTTC AGTGGGGATA TTGTTCTGGC AGTATGCCAA
921 TGATGTGGTG TCTGTCTCGC AAGCAAAACG ATTTTACCCA
```

-continued

```
 961 CTCTTTGCAC AGATGAGTGG ACTTGCCCCC ATTGTGGCTG
1001 GACAGTATGT GGTACGATAT GCTAGTAGAG CCAATGACTT
1041 TGAAGAATCA TTGCATAGGT TGACGTGGAT GGTATCCTTT
1081 TCGGGAGTGA TGATTTGTCT GTTTTACAAG TGGAGCAATG
1121 AGTACAATGA TCAGACGTCT GGAGGGTTAA ATGGGGGAAT
1161 TGAGGATGGA GTAAAAGAGA CGAAGGTGGT GAAGAAAAAG
1201 AAAGCCAAAA TGTCAATGAG GGATTCAGCC AAGTTTTTGG
1241 CTTCATCCGA GTATTTGAGA CTGATTGCTG CTTTGGTTGT
1281 GGGATATGGT CTGTCGATCA ACTTTACAGA TATAATGTGG
1321 AAATCAATCG TCAAGAGACA ATATCCCGAT CCTCTCGACT
1361 ATCAACGTTT CATGGGGAAC TTTTCATCAG TAGTTGGATT
1401 GTCTACGTGC ATCGTTATCT TTCTCGGTGT ACATGCTATT
1441 CGTATACTAG GCTGGCGAAT GGGTGCCCTA GCGACTCCAG
1481 CCGTCATGGC AATCTTGGCA TTCCCTTACT TCTCGAGCAT
1521 TCTCGTTGGG TTGGACAGTC CAGGTAGTTT ACGAATTGCA
1561 GTGATCTTTG GTACTATTCA ATGCCTGCTT AGTAAGACAG
1601 CAAAGTATGC CCTGTTCGAT CCGACAACTC AAATGGCCTA
1641 CATTCCTTTG GATGACGAAT CAAAGATCAA GGGAAAGGCA
1681 GCAATAGAAG TACTTGGTTC TCGGATTGGA AAAAGTGGTG
1721 GTTCGTTGAT ACAACAAGGT CTTGTGTTGG TGTTTGGGAA
1761 CATTATCAAT GCTGCTCCCG CGTTGGTTGT TCTTTACTAC
1801 TCAGTGTTGG CGTGGTGGGT GTACTCAGCA AATCGGCTCG
1841 GATCATTGTT CTTGGCAAAG ACAGCTATGC AAGAGGAAAC
1881 AAAAGAGCAC CAGAAGTAG
```

An example of a nucleotide triphosphate transporter 3 from *Simkania negevensis*, is referred to as SnTTT3 and has the following sequence SE ID NO:11

```
  1 MSSTEYEKST WTQKIWPIRR FELKKVLPLL ILKFLVSMVY
 41 ATLTLIKDPL VVTAKHSGAE VIPVLKGWIV FPLSILCAIG
 81 YSKLSNHFKR STLFYGIITA FLAIVLIYGF VLYPNMGILT
121 PSDSANLLTA KFGEKYTHWI AVYRNWIHSL FFVTTELWGQ
161 VVIFLLYWGF ANHICQVKEA KRSYTLFIAA GDLATILAGP
201 LTYYYGKKFL GQSYALTLQS LLGYVLVCGL LIMAVYWWMN
241 RYVLTDKRYY DPSVTKQTVN QKTKLSLRDS IRHIFSSKYL
281 LAIAVLVVGC ALTINMVEVT WKAHLKMQYP TTADYQMFMG
321 RVTTIVGVVA LITVFFLGGN FLRRFGWHFS AQITPWAIGI
361 TGGVFFLLCL LKPYLGSFAH YVGLTPLMMI VIFGAFQNIT
401 SKVVKYSFFD STKEMAYIPL DPESKVKGKA AIDMVGSRLG
441 KSSSSWLQIG LIELVGTGSV ISITPYLLPI VLGAALYWSY
481 SVRYLNKELS VREETLLEEE EAKKRAGELQ PEPEPAT
```

An example of a nucleotide sequence for the above *Simkania negevensis* SnTTT3 protein is provided below as SEQ ID NO:12

```
   1 ATGAGTAGTA CCGAATATGA GAAGTCCACA TGGACTCAAA
  41 AAATCTGGCC AATAAGGCGC TTTGAACTTA AGAAAGTCCT
  81 TCCTCTTTTA ATCCTTAAAT TTCTAGTCTC TATGGTTTAT
 121 GCCACTCTCA CCTTAATCAA GGATCCCCTT GTGGTGACGG
 161 CAAAACATTC TGGAGCAGAA GTCATTCCAG TTCTAAAAGG
 201 TTGGATTGTT TTCCCCTTAT CGATTCTTTG TGCTATTGGT
 241 TACTCAAAGT TAAGCAACCA CTTCAAACGT TCCACCCTCT
 281 TTTACGGAAT CATTACAGCT TTCCTAGCTA TTGTTCTTAT
 321 CTACGGCTTC GTTTTGTATC CCAATATGGG AATTCTCACA
 361 CCAAGCGACT CTGCAAACTT GTTAACAGCT AAATTTGGGG
 401 AAAAATACAC ACACTGGATT GCAGTTTATC GGAATTGGAT
 441 CCATTCTCTC TTTTTCGTCA CCACAGAGCT TTGGGGGCAA
 481 GTTGTCATTT TCCTCCTCTA CTGGGGATTT GCCAACCACA
 521 TTTGCCAAGT GAAAGAAGCT AAAAGATCTT ACACTCTTTT
 561 CATCGCTGCA GGCGATTTAG CAACGATCTT GGCTGGTCCA
 601 CTTACCTATT ACTACGGAAA AAAGTTTCTA GGACAAAGCT
 641 ATGCTCTCAC TCTTCAATCC CTACTAGGAT ATGTCTTAGT
 681 CTGCGGGCTA CTCATCATGG CAGTCTATTG GTGGATGAAT
 721 CGATATGTCC TAACAGACAA ACGGTACTAC GATCCATCAG
 761 TGACGAAGCA AACAGTCAAC CAAAAGACCA AACTCTCTCT
 801 GCGTGATAGT ATCCGGCATA TCTTTTCATC AAAGTATCTC
 841 CTTGCTATTG CGGTCCTCGT TGTCGGTTGC GCTCTCACCA
 881 TCAACATGGT AGAAGTCACC TGGAAAGCTC ACTTAAAGAT
 921 GCAATACCCA ACAACTGCTG ATTACCAAAT GTTCATGGGG
 961 CGAGTCACAA CTATTGTTGG AGTTGTTGCC CTCATCACTG
1001 TATTCTTCTT AGGAGGAAAC TTCCTGAGAC GGTTTGGATG
1041 GCACTTCAGT GCTCAAATCA CCCCATGGGC GATTGGAATC
1081 ACAGGTGGTG TTTTCTTTTT ACTCTGCCTT TTGAAGCCCT
1121 ATCTCGGGTC TTTCGCTCAT TATGTTGGAC TCACCCCTCT
1161 TATGATGATT GTCATCTTTG GAGCCTTCCA AAATATCACT
1201 AGTAAAGTCG TCAAATACTC GTTCTTTGAT TCGACGAAAG
1241 AAATGGCTTA TATTCCACTA GACCCTGAAT CTAAAGTGAA
1281 AGGAAAAGCA GCCATCGACA TGGTCGGTTC AAGATTGGGT
1321 AAGTCGAGCT CCTCCTGGCT ACAAATTGGC TTGATTGAAC
1361 TAGTTGGGAC TGGTTCGGTG ATCTCAATCA CTCCTTATCT
1401 ACTGCCTATC GTTCTAGGTG CCGCCCTCTA TTGGAGCTAC
```

-continued

1441 TCTGTACGCT ACCTCAATAA AGAGCTTTCT GTGCGTGAAG

1481 AAACACTCCT CGAGGAAGAA GAAGCTAAGA AAAGAGCGGG

1521 AGAGCTTCAG CCTGAACCTG AGCCTGCCAC TTGA

A single nucleotide mismatch resulted in an amino acid substitution at position 248 of the SEQ ID NO:11 sequence where arginine (R), which is a basic amino acid, is replaced with a tryptophan (W), which is a nonpolar/hydrophobic amino acid. This mutant nucleotide triphosphate transporter 3 from *Simkania negevensis* has the following sequence SEQ ID NO:13

1 MSSTEYEKST WTQKIWPIRR FELKKVLPLL ILKFLVSMVY

41 ATLTLIKDPL VVTAKHSGAE VIPVLKGWIV FPLSILCAIG

81 YSKLSNHFKR STLFYGIITA FLAIVLIYGF VLYPNMGILT

121 PSDSANLLTA KFGEKYTHWI AVYRNWIHSL FFVTTELWGQ

161 VVIFLLYWGF ANHICQVKEA KRSYTLFIAA GDLATILAGP

201 LTYYYGKKFL GQSYALTLQS LLGYVLVCGL LIMAVYWWMN

241 RYVLTDKWYY DPSVTKQTVN QKTKLSLRDS IRHIFSSKYL

281 LAIAVLVVGC ALTINMVEVT WKAHLKMQYP TTADYQMFMG

321 RVTTIVGVVA LITVFFLGGN FLRRFGWHFS AQITPWAIGI

361 TGGVFFLLCL LKPYLGSFAH YVGLTPLMMI VIFGAFQNIT

401 SKVVKYSFFD STKEMAYIPL DPESKVKGKA AIDMVGSRLG

441 KSSSSWLQIG LIELVGTGSV ISITPYLLPI VLGAALYWSY

481 SVRYLNKELS VREETLLEEE EAKKRAGELQ PEPEPAT

An example of a nucleotide triphosphate transporter 2 from *Simkania negevensis*, is referred to as SnTTT2, and has the following sequence SEQ ID NO:14

1 MSTQTDVSFS KWRSFLWPIQ GREIKKFLPL LLIYALICLN

41 YSVLKVAKDT LVITAPGSGA EAIPFIKVWV ILPMALLVTY

81 LFTRLFNRFS QEQVFYIMIG SFISFFALFA FVLYPLRDFL

121 HPHDTADKLQ AMLPQGFQGL IAIFRNWSYT LFYVMSELWG

161 TAIMSVLFWG FTNEIISVGE AKRYYGILSV GANIATIFSG

201 YITTFLSLQV IDMSFIFGPD RWGQSLGLVT CVVVAAGLLI

241 MALFRWYNKR VINRDAVLLK MKQDHTETKK TMKMGMRKNF

281 AYLAKSKYLI CIAVLVVAFN VGINMVEIIW KDQIKELYPN

321 PNDFIVYMGK VMSAIGWVAT FVGLFLSSNL IRRLGWTVSA

361 LITPVALLVT GVFFFGFILF KNNPTLVGWT AAIGFTPLAL

401 GVLFGTIQNV MSRACKYTLF DSTKEIAFIP LSPESKLKGK

441 AAIDGVGSRV GKSGGSIVHG GLLMLFGSVS LSAPYVGLIL

481 LAVVFGWIGA ARSLGRQFNL LTTHHEKLEI NEEAQPSEKK

521 PLLESV

An example of a nucleotide sequence for the above *Simkania negevensis* SnTTT2 protein with SEQ ID NO:13 is provided below as SEQ ID NO:15.

1 ATGTCAACAC AGACTGATGT GAGTTTCAGT AAATGGCGCT

41 CATTTTTGTG GCCAATTCAA GGAAGAGAAA TTAAAAAATT

81 TCTTCCTCTT CTCCTGATTT ACGCTCTCAT TTGTCTTAAC

121 TATAGCGTCT TAAAAGTCGC AAAAGACACA CTTGTCATTA

161 CAGCCCCTGG ATCAGGCGCA GAAGCAATCC CGTTTATCAA

201 GGTCTGGGTC ATTCTCCCCA TGGCACTCCT CGTAACTTAT

241 CTCTTTACTC GCCTCTTCAA TCGATTTAGC CAAGAACAAG

281 TGTTTTACAT CATGATCGGG AGCTTCATTT CGTTTTTCGC

321 TCTATTTGCA TTTGTCCTCT ACCCCTTGCG AGATTTTCTT

361 CATCCTCATG ACACAGCTGA TAAATTACAA GCCATGCTTC

401 CACAGGGATT CCAAGGGCTC ATAGCCATTT TCCGTAACTG

441 GTCCTATACC CTCTTTTATG TGATGTCTGA GCTATGGGGA

481 ACCGCTATTA TGTCTGTCCT CTTTTGGGGA TTCACAAATG

521 AAATTATTTC TGTAGGTGAG GCCAAAAGGT ATTATGGAAT

561 TCTCAGTGTA GGGGCCAATA TTGCAACTAT TTTTTCAGGG

601 TACATCACCA CCTTTCTCTC TTTGCAAGTG ATTGACATGT

641 CATTCATTTT TGGACCTGAC CGCTGGGGAC AATCATTAGG

681 TCTTGTGACA TGTGTTGTTG TTGCAGCAGG TCTCCTTATT

721 ATGGCCCTTT TCAGATGGTA CAACAAGCGA GTCATTAATC

761 GTGATGCAGT ACTATTAAAA ATGAAACAAG ACCACACAGA

801 AACGAAGAAG ACCATGAAAA TGGGAATGCG TAAGAATTTT

841 GCTTACCTTG CAAAATCAAA GTATTTAATT TGCATTGCAG

881 TTCTGGTTGT TGCATTCAAT GTTGGAATCA ACATGGTCGA

921 AATTATCTGG AAAGATCAAA TCAAAGAACT GTATCCCAAT

961 CCCAACGATT TTATTGTTTA TATGGGGAAG GTCATGAGTG

1001 CAATTGGTTG GGTTGCAACA TTTGTCGGAC TATTTCTCAG

1041 TAGTAATTTA ATCAGGCGCT TAGGATGGAC TGTCAGCGCC

1081 TTAATCACTC CTGTTGCTCT CCTCGTAACA GGTGTTTTCT

1121 TTTTCGGATT CATTCTCTTT AAAAACAACC CTACATTAGT

1161 GGGTTGGACA GCCGCCATAG GATTTACACC TCTTGCACTA

1201 GGGGTTCTCT TTGGGACAAT CCAAAATGTG ATGTCTCGAG

1241 CATGTAAATA CACCTTATTT GACTCTACAA AAGAAATAGC

1281 GTTTATCCCC CTTAGCCCTG AGTCCAAGCT AAAAGGAAAA

1321 GCTGCAATTG ATGGAGTAGG CTCTCGCGTT GGAAAGTCCG

1361 GAGGGTCGAT TGTTCATGGT GGACTACTGA TGCTCTTCGG

1401 CTCCGTTTCT CTCAGCGCAC CTTACGTCGG CTTGATCTTA

1441 CTCGCCGTTG TTTTCGGTTG GATTGGTGCA GCTCGTTCAC

1481 TCGGGAGACA ATTTAATCTC CTTACGACGC ATCATGAAAA

1521 ACTCGAGATT AACGAGGAGG CACAGCCCTC CGAAAAAAAG

1561 CCCTTACTTG AATCCGTTTA A

An example of a nucleotide triphosphate transporter from *Rickettsia prowazekii*, is referred to as RPTlc1, and has the following sequence SEQ ID NO:16

```
  1 MSTSKSENYL SELRKIIWPI EQYENKKFLP LAFMMFCILL
 41 NYSTLRSIKD GFVVTDIGTE SISFLKTYIV LPSAVIAMII
 81 YVKLCDILKQ ENVFYVITSF FLGYFALFAF VLYPYPDLVH
121 PDHKTIESLS LAYPNFKWFI KIVGKWSFAS FYTIAELWGT
161 MMLSLLFWQF ANQITKIAEA KRFYSMFGLL ANLALPVTSV
201 VIGYFLHEKT QIVAEHLKFV PLFVIMITSS FLIILTYRWM
241 NKNVLTDPRL YDPALVKEKK TKAKLSFIES LKMIFTSKYV
281 GYIALLIIAY GVSVNLVEGV WKSKVKELYP TKEAYTIYMG
321 QFQFYQGWVA IAFMLIGSNI LRKVSWLTAA MITPLMMFIT
361 GAAFFSFIFF DSVIAMNLTG ILASSPLTLA VMIGMIQNVL
401 SKGVKYSLFD ATKNMAYIPL DKDLRVKGQA AVEVIGGRLG
441 KSGGAIIQST FFILFPVFGF IEATPYFASI FFIIVILWIF
481 AVKGLNKEYQ VLVNKNEK
```

An example of a nucleotide sequence for the above *Rickettsia prowazekii* RPTlc1 protein is provided below as SEQ ID NO:17

```
   1 ATGAGTACTT CCAAAAGTGA AAATTATCTT TCAGAACTAA
  41 GAAAGATAAT TTGGCCTATA GAACAATATG AAAATAAGAA
  81 GTTTTTGCCA CTTGCATTTA TGATGTTCTG TATTTTATTA
 121 AACTACTCAA CTCTTCGTTC AATTAAAGAC GGTTTTGTAG
 161 TAACAGATAT AGGTACAGAA TCGATAAGTT TTTTAAAAAC
 201 ATATATAGTA CTACCTTCTG CTGTAATTGC TATGATAATT
 241 TATGTTAAGC TATGTGATAT TTTAAAGCAA GAAAACGTAT
 281 TTTATGTTAT TACTTCATTT TTTTTAGGGT ATTTTGCATT
 321 ATTTGCCTTT GTTCTTTACC CATATCCTGA TTTAGTCCAC
 361 CCTGATCATA AAACTATAGA ATCTTTAAGT TTAGCTTATC
 401 CTAATTTCAA ATGGTTTATA AAAATAGTTG GTAAATGGAG
 441 TTTTGCATCT TTTTATACTA TTGCCGAGCT TTGGGGAACA
 481 ATGATGCTTA GTTTATTATT TTGGCAATTT GCTAATCAAA
 521 TTACTAAAAT CGCTGAAGCT AAACGTTTCT ACTCAATGTT
 561 TGGTTTACTT GCGAATTTAG CATTGCCTGT AACATCAGTG
 601 GTTATTGGAT ATTTTCTACA CGAAAAAACT CAAATAGTTG
 641 CAGAACATTT AAAATTTGTA CCTTTATTTG TTATAATGAT
 681 AACAAGTAGT TTCTTAATAA TATTAACATA TAGATGGATG
 721 AATAAAAATG TTCTAACTGA TCCTAGACTA TATGATCCAG
 761 CATTAGTAAA AGAAAAAAAA ACTAAAGCTA AATTGTCGTT
 801 CATAGAAAGT TTAAAAATGA TCTTTACTTC GAAATATGTA
 841 GGTTATATTG CATTATTAAT TATTGCTTAT GGTGTTTCAG
```

-continued

```
 881 TAAATTTAGT TGAAGGTGTT TGGAAATCCA AAGTAAAAGA
 921 ATTATATCCG ACAAAGGAGG CTTATACCAT ATATATGGGT
 961 CAGTTCCAAT TTTATCAGGG TTGGGTTGCA ATTGCTTTTA
1001 TGCTGATAGG TAGTAATATT TTAAGAAAAG TATCATGGCT
1041 AACTGCAGCT ATGATCACTC CATTAATGAT GTTCATAACA
1081 GGTGCGGCAT TTTTTTCATT TATATTTTTT GATAGCGTTA
1121 TTGCAATGAA TTTAACCGGC ATCCTTGCTT CAAGTCCTTT
1161 AACACTTGCT GTTATGATCG GTATGATTCA AAATGTTTTA
1201 AGTAAAGGTG TGAAATATTC TTTATTTGAT GCAACTAAAA
1241 ATATGGCGTA TATTCCACTT GATAAGGATT TACGAGTCAA
1281 AGGGCAAGCT GCCGTTGAAG TTATCGGAGG AAGGCTCGGT
1321 AAATCAGGCG GTGCTATTAT TCAATCTACA TTCTTTATTT
1361 TATTTCCTGT ATTTGGTTTT ATAGAGGCGA CTCCTTATTT
1401 TGCTTCTATA TTCTTTATAA TAGTAATATT ATGGATATTT
1441 GCAGTTAAAG GTTTAAATAA AGAGTATCAA GTTTTGGTAA
1481 ATAAAAATGA AAAATAG
```

Another example of a nucleotide triphosphate transporter from *Rickettsia prowazekii*, is referred to as RPTlc2, and has the following sequence SEQ ID NO:18

```
  1 MNIVDSNCTI WHKARNSKFR HIVWPIRSYE LTKFIPMTLL
 41 MFFILLNQNL VRSIKDSFVV TLISSEVLSF IKLWGEMPMG
 81 VLFVILYSKL CNIMTTEQVF RIITSTFLFF FAIFGFILFP
121 YKEFFHPNPE LINQYIIVLP HLKWFLIIWG QWSLVLFYIM
161 GELWPVIVFT LLYWQLANKI TKVEEAPRFY SFFTLFGQTN
201 LLFSGTVIIY FAKSEHFLLP LFAHLNDTNE ILLKSFITVI
241 LISGLICLAL HKLIDKSVVE ADKNIKFKNQ RTDILKLSLL
281 ESAKIILTSR YLGFICLLVM SYSMSINLIE GLWMSKVKQL
321 YPATKDFISY HGEVLFWTGV LTLVSAFLGS SLIRIYGWFW
361 GAIITPIMMF VAGVMFFSFT IFEQHLGNIV NTLGYSSPLV
401 IIVFIGGLWH VFAKSVKYSL FDATKEMVYI PLDNEIKTKG
441 KAAVDVMGAK IGKSIGAIIQ FISFSIFPNA VHNDIAGLLM
481 VTFIIVCILW LYGVKVLSQN YNKMIKR
```

An example of a nucleotide sequence for the above *Rickettsia prowazekii* RPTlc2 protein is provided below as SEQ ID NO:19

```
  1 ATGAATATAG TAGATTCTAA CTGTACAATT TGGCATAAAG
 41 CAAGAAATAG TAAATTTAGG CATATAGTAT GGCCAATTAG
 81 ATCGTATGAA TTAACAAAAT TCATCCCGAT GACTTTATTA
121 ATGTTTTTTA TTTTACTTAA TCAAAATTTA GTGCGTAGTA
161 TTAAAGATAG TTTTGTTGTT ACATTAATTA GTTCAGAAGT
201 ATTAAGTTTT ATAAAACTTT GGGGTGAAAT GCCGATGGGG
```

-continued

241 GTTTTATTTG TTATTCTTTA TTCTAAACTC TGTAATATTA

281 TGACCACAGA GCAAGTTTTT AGGATAATTA CCAGTACCTT

321 TTTATTTTTC TTTGCAATTT TTGGTTTTAT TTTATTCCCA

361 TACAAAGAGT TTTTTCATCC TAACCCTGAA TTAATTAATC

401 AATATATCAT TGTTCTGCCT CACTTAAAGT GGTTTTTAAT

441 AATTTGGGGA CAATGGAGTT TAGTATTATT TTATATAATG

481 GGTGAGTTAT GGCCTGTTAT AGTTTTTACT CTTTTATATT

521 GGCAGCTTGC AAATAAAATC ACCAAAGTCG AAGAAGCACC

561 AAGATTTTAC TCATTTTTTA CTTTATTTGG ACAAACTAAT

601 TTGCTCTTCT CAGGCACTGT AATTATTTAT TTTGCTAAGA

641 GCGAACATTT TTTATTACCT TTATTTGCTC ATTTAAATGA

681 CACAAATGAA ATTCTTTTAA AATCATTCAT CACAGTTATT

721 TTAATATCAG GATTAATTTG TTTAGCTCTC CATAAGCTAA

761 TTGATAAATC AGTTGTAGAA GCTGATAAAA ATATAAAATT

801 TAAAAACCAA AGAACAGATA TATTAAAATT AAGCTTGCTC

841 GAAAGTGCAA AAATAATCTT AACGTCTAGA TATCTTGGTT

881 TTATTTGTCT TCTCGTAATG TCTTATTCTA TGAGTATTAA

921 CCTAATAGAA GGATTGTGGA TGTCAAAAGT AAAACAACTC

961 TATCCTGCTA CAAAGGATTT TATATCATAT CACGGTGAAG

1001 TATTGTTTTG GACTGGAGTG TTAACTTTAG TTAGTGCATT

1041 TTTAGGCAGT AGTTTAATTA GAATTTATGG CTGGTTTTGG

1081 GGGGCTATTA TAACACCGAT TATGATGTTT GTAGCAGGGG

1121 TTATGTTTTT TTCATTCACA ATTTTTGAAC AACACTTAGG

1161 AAATATAGTA AATACTCTTG GCTATAGTTC TCCACTTGTC

1201 ATTATAGTTT TTATTGGTGG ACTTTGGCAT GTATTTGCTA

1241 AATCTGTAAA GTATTCCCTT TTCGATGCTA CTAAAGAAAT

1281 GGTGTATATT CCACTAGATA ATGAAATTAA GACTAAAGGT

1321 AAAGCAGCAG TTGATGTTAT GGGTGCTAAA ATTGGTAAGT

1361 CAATAGGTGC TATTATTCAA TTCATATCCT TTAGTATCTT

1401 TCCAAATGCT GTACATAACG ACATAGCAGG CTTATTGATG

1441 GTTACTTTTA TTATCGTATG TATATTATGG CTATATGGAG

1481 TGAAAGTTTT ATCACAAAAT TATAATAAAA TGATAAAACG

1501 TTAA

Another example of a nucleotide triphosphate transporter from *Rickettsia prowazekii*, is referred to as RPTlc3, and has the following sequence SEQ ID NO:20

1 MLPPKIFFEK VKEIIWPIER KELKLFIPMA LMMLCILFNF

41 GALRSIKDSL VVPSMGAEII SFLKLWLVLP SCVIFTILYV

81 KLSNKLNFEY IFYSIVGTFL LFFLLFAYII YPNQDIYHPN

121 DAMINNLIAS YPNLKWFIKI GSKWSYALMY IFSELWSAVV

-continued

161 INLMFWQFAN HIFDTAKAKR FYPVLGMVGN IGLIIAGSVL

201 VFFSSGQYII DSELLTDSYN SSSNNSIMLQ PIISIIVTAG

241 IIAMFLFRII NKFILTNSIN VLDVKKVAAK TKTKLALIES

281 IKLIIHSKYI GRIALLIICY GLLINIVEGP WKAKIKELHP

321 NTVDYVNFMG MFNIWMGISC VTFMIIGSNI LRRLGWLISA

361 LLTPIMLSIT GFMFFIFIIF IEEIGTCFGD FNLLYVAIIV

401 GAIQNILSKS SKYSLFDSTK EMAYIPLSLE LRTKGKAAVE

441 VIGTKFGKSL GAFIQSLIFI IIPTATFDSI IIYLLVIFIV

481 MMNLWIWNII KLNKEYIKLC Q

An example of a nucleotide sequence for the above *Rickettsia prowazekii* RPTlc3 protein is provided below as SEQ ID NO:21

1 ATGTTACCGC CTAAAATTTT CTTTGAAAAA GTTAAAGAAA

41 TAATTTGGCC TATAGAAAGG AAAGAATTAA AGCTATTTAT

81 ACCAATGGCT TTAATGATGT TATGTATCCT GTTTAATTTT

121 GGGGCTTTAA GATCTATTAA AGATAGTTTA GTAGTACCCT

161 CTATGGGGGC TGAAATTATT AGTTTCTTAA AATTATGGTT

201 AGTGCTACCC TCGTGCGTAA TTTTTACGAT ACTTTACGTT

241 AAACTTAGTA ATAAATTAAA TTTTGAATAT ATTTTCTATA

281 GTATAGTCGG TACTTTTTTA CTATTTTTCT TATTATTTGC

321 CTATATTATT TATCCAAATC AAGATATTTA TCATCCTAAT

361 GATGCAATGA TAAATAATTT AATTGCTTCA TACCCTAATT

401 TAAAGTGGTT TATTAAAATA GGTAGTAAAT GGAGTTATGC

441 GCTAATGTAT ATTTTCTCAG AATTATGGAG TGCAGTAGTT

481 ATAAACTTAA TGTTTTGGCA ATTTGCTAAT CACATTTTTG

521 ATACTGCTAA AGCTAAACGA TTTTATCCTG TTCTTGGGAT

561 GGTTGGTAAT ATCGGTCTTA TAATAGCAGG CAGCGTACTT

601 GTTTTTTTTT CAAGTGGGCA GTACATCATT GATTCAGAAT

641 TATTAACGGA TTCTTATAAT TCATCTTCTA ACAATTCTAT

681 CATGCTTCAG CCAATCATAT CAATTATTGT TACTGCAGGA

721 ATAATTGCTA TGTTTTTATT TAGAATAATA AATAAATTTA

761 TTTTAACTAA TTCTATAAAT GTTTTAGATG TAAAAAAAGT

801 TGCTGCTAAA ACAAAAACAA AACTTGCATT AATTGAAAGT

841 ATAAAATTAA TAATTCATTC AAAATATATA GGTCGTATTG

881 CATTATTAAT AATCTGTTAT GGATTACTAA TAAATATAGT

921 TGAAGGACCT TGGAAAGCGA AAATAAAAGA ATTACATCCA

961 AATACTGTAG ATTATGTTAA TTTTATGGGC ATGTTTAATA

1001 TTTGGATGGG GATCTCATGT GTTACTTTCA TGATAATAGG

1041 TAGTAATATT CTTAGAAGGC TTGGTTGGCT CATTTCTGCA

1081 TTATTAACTC CTATTATGTT ATCTATTACA GGCTTCATGT

1121 TTTTTATCTT TATAATTTTT ATTGAAGAAA TAGGTACATG

-continued

```
1161  TTTTGGTGAT TTTAATCTTC TATATGTAGC GATTATTGTC
1201  GGAGCAATTC AGAATATACT TAGTAAATCG TCTAAATATT
1241  CATTATTCGA TTCAACAAAA GAAATGGCAT ATATTCCTTT
1281  ATCTTTAGAA CTGAGAACTA AGGGAAAAGC CGCTGTAGAG
1321  GTAATAGGAA CGAAATTTGG TAAATCACTT GGAGCATTTA
1361  TCCAGTCTTT GATATTTATT ATTATTCCAA CGGCTACCTT
1401  TGATTCTATT ATAATATATT TACTAGTAAT TTTTATAGTG
1441  ATGATGAATT TATGGATTTG GAATATTATA AAATTAAATA
1481  AGGAATATAT AAAGCTGTGT CAATAA
```

Another example of a nucleotide triphosphate transporter from *Rickettsia prowazekii*, is referred to as RPTlc4, and has the following sequence SEQ ID NO:22

```
  1 MTINASNIEN SFSKINSHFS KLTDYIWPIK RHEISKFLFI
 41 TLLMFCILFI QNLIRALKDS IVTTMIGAET ISFLKFWGVM
 81 PSAFLITVIY VKLVNRMKAE NIFYLIISIF LTFFALFAYV
121 IFPNHEMLHL RPVTVHNLTA SLPNLKWFIL LLSKWSFSLF
161 YIIAELWPNV VFALLFWQFV NNITTVEESK RFYPLFGLLS
201 QTGIYLAGHF LENLSNINYY VTNKFALQSS FHTLSIQIIL
241 TIVLILGIVS IKTFWLLNHK VLDKKHMALL RFKTKNKSIT
281 IAKSFQMILS SRHIRLIATL LICYGIAINL VEGPWKAAAT
321 KIYKTPTEYA AFIGSYLSYT GVFTIFFVLL GSNIVRRMGW
361 FTSAVITPSI VFITGILFFA VNNFEGFAGL IIANFILTDP
401 ALVAITIGAI QNVLSKSSKY TLFDSTKEMA YVPLEPEIKI
441 SGKAAADVIG TKLGKSGSAF LQSLIFIILP SASYQSISIC
481 LMIIFILTCV TWIWATKELN KEYKNSIKFS QK
```

An example of a nucleotide sequence for the above *Rickettsia prowazekii* RPTlc4 protein is provided below as SEQ ID NO:23

```
  1  ATGACGATTA ACGCCAGTAA TATAGAAAAT TCTTTTTCTA
 41  AAATCAATAG CCATTTTTCT AAGCTTACAG ATTATATCTG
 81  GCCTATAAAA CGCCACGAAA TTTCTAAGTT TTTATTCATT
121  ACATTATTAA TGTTCTGTAT TTTATTTATT CAAAATCTCA
161  TCAGAGCTTT AAAAGATAGT ATTGTTACTA CTATGATAGG
201  TGCTGAGACT ATATCATTTT TGAAATTTTG GGGCGTGATG
241  CCGTCAGCAT TCTTAATAAC TGTTATATAT GTTAAACTTG
281  TCAATAGGAT GAAAGCAGAA AATATATTTT ATCTTATTAT
321  ATCAATTTTT TTAACATTCT TTGCTTTGTT TGCATACGTT
361  ATTTTCCCAA ATCATGAAAT GCTGCATTTA AGGCCTGTAA
401  CCGTGCATAA TTTAACGGCA AGTTTACCGA ATTTAAAATG
441  GTTTATACTT CTTTTATCAA AATGGAGTTT TTCACTATTT
```

-continued

```
 481  TATATAATAG CCGAATTATG GCCAAATGTA GTTTTTGCAT
 521  TACTGTTTTG GCAGTTTGTG AATAATATTA CTACAGTAGA
 561  AGAATCGAAA AGATTTTATC CATTATTTGG TTTACTTAGT
 601  CAAACAGGTA TTTATTTAGC AGGACATTTT TTAGAAAATC
 641  TAAGTAATAT AAATTATTAT GTCACTAATA AATTTGCATT
 681  GCAATCGTCT TTTCATACAC TTTCTATACA AATTATACTA
 721  ACTATAGTAT TAATTTTAGG CATAGTATCG ATAAAAACTT
 761  TTTGGTTACT TAATCATAAA GTACTAGACA AAAAGCATAT
 801  GGCATTACTC AGGTTCAAAA CAAAAAATAA ATCTATTACT
 841  ATTGCTAAAA GTTTTCAGAT GATTCTATCG TCAAGACACA
 881  TTAGATTAAT TGCAACTTTG CTTATCTGCT ATGGCATTGC
 921  AATTAATTTA GTAGAAGGCC CTTGGAAAGC AGCAGCAACT
 961  AAAATTTATA AAACTCCAAC CGAATATGCA GCTTTTATAG
1001  GAAGTTATTT AAGCTACACT GGAGTATTTA CTATTTTCTT
1041  TGTTCTACTT GGTTCCAATA TAGTTAGAAG AATGGGCTGG
1081  TTTACTTCAG CTGTGATCAC ACCTTCAATA GTTTTTATTA
1121  CCGGTATATT ATTTTTTGCT GTTAATAATT TTGAAGGCTT
1201  TGCTGGCTTA ATAATAGCAA ATTTTATTTT GACCGATCCT
1241  GCTTTAGTTG CTATAACAAT AGGTGCTATT CAAAATGTAC
1281  TTAGTAAATC AAGCAAATAT ACTTTATTTG ATTCTACAAA
1321  AGAAATGGCT TATGTTCCTT TAGAACCAGA AATCAAAATA
1361  AGTGGTAAGG CTGCTGCCGA CGTTATAGGT ACAAAACTCG
1401  GTAAATCCGG TAGTGCATTT TTACAATCAT TAATATTTAT
1441  AATATTACCT TCTGCTAGTT ATCAATCTAT TTCAATCTGT
1481  TTAATGATTA TATTTATCCT CACTTGCGTA ACTTGGATTT
1521  GGGCTACTAA AGAACTAAAT AAAGAATATA AAAATTCTAT
1561  TAAATTTTCT CAAAAATAA
```

Another example of a nucleotide triphosphate transporter from *Rickettsia prowazekii*, is referred to as RPTlc5, and has the following sequence SEQ ID NO:24

```
  1 MLSTSPSRSF KNKFRAAFWP VHNYELGKFI PISALMFCIL
 41 FNQNILRILK DSILISEISA EIAGFAKVYC VTPVAALFVI
 81 IYAKMINHLT FEKIFYYLSA FFISCFILFA FVIYPNIHIF
121 HVHPDTLSDW MNKYPHFKWY ISLVGNWGYI VYYSLAELWP
161 NIFYVLLFWQ FTNELTTTEE AKRFYTLFSL FGNSSLILVG
201 FLMMNLSSED TIIKKFISIS DSKITLVQVS TTIIAIVAII
241 CCLLVRFISK YIFTNPLFYH KTKSSRSTAQ RMGLIKSFKY
281 IVKSKYLWLL LICSAAFGFA INLVEAVWKA KIKELYPTVN
321 TYAEFNSLYI LWTGVAIIVM TIIGNNVMRM HNWFVAAVIS
361 PVIIMVTGVL FFGLIVFDQQ ILSLFDGAIL MSPLALAVSI
401 GGIQNILAKG TKYSIWDTSR EMLYIPLDDE LKTKGKAAVD
```

-continued

```
441 VISAKVGKSS SGLVQSIIFT LVPNATFTSI SPILMVVFTF

481 VCFAWIYAVR KIYFEYQKIA
```

An example of a nucleotide sequence for the above *Rickettsia prowazekii* RPTlc5 protein is provided below as SEQ ID NO:25

```
   1 ATGCTAAGTA CCTCACCGTC ACGATCGTTT AAAAACAAAT
  41 TTAGAGCAGC ATTTTGGCCT GTGCATAATT ATGAACTTGG
  81 GAAATTTATT CCGATCAGCG CCTTAATGTT TTGTATTTTA
 121 TTTAATCAAA ATATTTTGCG AATCTTAAAG GATAGTATTT
 161 TAATCTCTGA GATTAGTGCA GAAATAGCAG GATTTGCTAA
 201 AGTTTACTGC GTTACACCTG TAGCTGCTTT GTTTGTTATT
 241 ATTTATGCTA AAATGATCAA TCATTTGACA TTTGAAAAAA
 281 TCTTTTATTA TTTAAGTGCA TTTTTTATAA GCTGTTTTAT
 321 TTTATTTGCC TTTGTGATTT ATCCTAATAT TCATATTTTT
 361 CATGTACATC CTGATACACT ATCAGACTGG ATGAACAAAT
 401 ATCCTCATTT TAAGTGGTAT ATCTCATTAG TAGGTAATTG
 441 GGGTTATATA GTATATTATA GTCTTGCCGA GCTTTGGCCT
 481 AATATTTTTT ACGTATTATT ATTTTGGCAG TTTACTAATG
 521 AACTTACTAC TACCGAAGAA GCAAAAAGAT TTTATACTCT
 561 CTTTTCGCTA TTCGGTAATT CTTCCTTAAT ATTAGTCGGC
 601 TTTTTAATGA TGAATTTATC ATCGGAAGAT ACTATTATTA
 641 AGAAATTTAT AAGTATTTCA GATAGTAAAA TCACTTTAGT
 681 TCAAGTATCA ACGACGATTA TAGCAATTGT TGCAATCATT
 721 TGTTGTTTGT TAGTTAGGTT TATTAGCAAG TACATTTTTA
 761 CTAATCCATT ATTTTATCAT AAAACAAAAA GCAGTAGATC
 801 AACTGCACAA CGGATGGGAC TAATTAAAAG CTTTAAATAT
```

-continued

```
 841 ATTGTGAAAT CAAAATATTT ATGGCTACTT TTAATTTGTT
 881 CTGCAGCTTT CGGATTTGCT ATAAACTTAG TCGAAGCAGT
 921 ATGGAAAGCA AAAATTAAGG AATTATATCC GACTGTAAAT
 961 ACCTACGCTG AATTCAATAG TCTGTATATA CTTTGGACAG
1001 GCGTTGCGAT AATTGTTATG ACAATTATCG GTAATAACGT
1041 CATGCGTATG CATAATTGGT TTGTAGCCGC AGTTATTTCC
1081 CCAGTGATAA TAATGGTGAC AGGTGTTTTG TTCTTTGGAC
1121 TAATTGTATT TGATCAACAA ATTTTATCAT TATTTGATGG
1161 CGCGATTTTA ATGTCACCTC TTGCACTTGC TGTTTCTATT
1201 GGCGGTATTC AGAATATTTT AGCCAAAGGC ACTAAATATT
1241 CTATATGGGA TACTTCAAGA GAAATGTTAT ATATACCACT
1281 TGATGATGAA CTTAAAACAA AGGGTAAAGC AGCAGTTGAT
1321 GTTATAAGTG CAAAAGTTGG AAAATCCTCT AGTGGTCTTG
1361 TACAATCCAT TATTTTTACT TTAGTGCCAA ATGCGACCTT
1401 TACCTCAATC TCGCCGATTT TAATGGTAGT ATTTACGTTC
1441 GTATGCTTTG CTTGGATTTA TGCAGTAAGA AAAATATATT
1481 TTGAATATCA AAAAATAGCC TGA
```

Examples of nucleotide triphosphate transporters that can be employed include those in Table 1:

TABLE 1

Exemplary nucleotide triphosphate transporters

| Host Organism | NTT | Amino Acid Seq ID | Nucleic Seq ID |
|---|---|---|---|
| *Phaeodactylum tricornutum* | nucleotide triphosphate transporter 2 PtNTT2 EEC49227.1 GI: 217409295 | SEQ ID NO: 1 | SEQ ID NO: 2 |
| *Protochlamydia amoebophila* (strain UWE25) | nucleotide triphosphate transporter 2 PamTTT2 | SEQ ID NO: 3 | SEQ ID NO: 4 |
| *Protochlamydia amoebophila* (strain UWE25) | nucleotide triphosphate transporter 3 PamTTT3 | SEQ ID NO: 5 | SEQ ID NO: 6 |
| *Protochlamydia amoebophila* (strain UWE25) | nucleotide triphosphate transporter 5 PamTTT5 | SEQ ID NO: 7 | SEQ ID NO: 8 |
| *Thalassiosira pseudonana* | nucleotide triphosphate transporter 2 TpTTT2 | SEQ ID NO: 9 | SEQ ID NO: 10 |
| *Simkania negevensis* | nucleotide triphosphate transporter 3 SnTTT3 | SEQ ID NO: 11 | SEQ ID NO: 12 |
| *Simkania negevensis* | nucleotide triphosphate transporter 3 SnTTT3(R248W) | SEQ ID NO: 13 | SEQ ID NO: 15 |

TABLE 1-continued

| Exemplary nucleotide triphosphate transporters | | | |
|---|---|---|---|
| Host Organism | NTT | Amino Acid Seq ID | Nucleic Seq ID |
| *Simkania negevensis* | nucleotide triphosphate transporter 3 SnTTT3 | SEQ ID NO: 14 | |
| *Rickettsia prowazekii* | nucleotide triphosphate transporter 1 RPTlc1 | SEQ ID NO: 16 | SEQ ID NO: 17 |
| *Rickettsia prowazekii* | nucleotide triphosphate transporter 2 RPTlc2 | SEQ ID NO: 18 | SEQ ID NO: 19 |
| *Rickettsia prowazekii* | nucleotide triphosphate transporter 3 RPTlc3 | SEQ ID NO: 20 | SEQ ID NO: 21 |
| *Rickettsia prowazekii* | nucleotide triphosphate transporter 3 RPTlc4 | SEQ ID NO: 22 | SEQ ID NO: 23 |
| *Rickettsia prowazekii* | nucleotide triphosphate transporter 3 RPTlc5 | SEQ ID NO: 24 | SEQ ID NO: 25 |

A sequence of a pACS plasmid with a PtNTT2 gene sequence (pACS_PtNTT2) corresponds to SEQ ID NO: 28.

```
ggggaattgtgagcggataacaattcccctgtagaaataattttgtttaa

ctttaataaggagatataccATGAGACCATTTCCGACGATTGCCTTGATT

TCGGTTTTTCTTTCGGCGGCGACTCGCATTTCGGCAACTTCCTCTCATCA

AGCAAGTGCACTTCCTCTCAAAAAGGGAACGCATGTCCCGGACTCTCCGA

AGTTGTCAAAGCTATATATCATGGCCAAAACCAAGAGTGTATCCTCGTCC

TTCGACCCCCCTCGGGGAGGCAGTACTGTTGCACCAACTACACCGTTGGC

AACCGGCGGTGCGCTCCGCAAAGTGCGACAAGCCGTCTTTCCCATCTACG

GAAACCAAGAAGTCACCAAATTTCTGCTCATCGGATCCATTAAATTCTTT

ATAATCTTGGCACTCACGCTCACGCGTGATACCAAGGACACGTTGATTGT

CACGCAATGTGGTGCCGAAGCGATTGCCTTTCTCAAAATATACGGGGTGC

TACCCGCAGCGACCGCATTTATCGCGCTCTATTCCAAAATGTCCAACGCC

ATGGGCAAAAAAATGCTATTTTATTCCACTTGCATTCCTTTCTTTACCTT

TTTCGGGCTGTTTGATGTTTTCATTTACCCGAACGCGGAGCGACTGCACC

CTAGTTTGGAAGCCGTGCAGGCAATTCTCCCGGGCGGTGCCGCATCTGGC

GGCATGGCGGTTCTGGCCAAGATTGCGACACACTGGACATCGGCCTTATT

TTACGTCATGGCGGAAATATATTCTTCCGTATCGGTGGGGCTATTGTTTT

GGCAGTTTGCGAACGACGTCGTCAACGTGGATCAGGCCAAGCGCTTTTAT

CCATTATTTGCTCAAATGAGTGGCCTCGCTCCAGTTTTAGCGGGCCAGTA

TGTGGTACGGTTTGCCAGCAAAGCGGTCAACTTTGAGGCATCCATGCATC

GACTCACGGCGGCCGTAACATTTGCTGGTATTATGATTTGCATCTTTTAC

CAACTCAGTTCGTCATATGTGGAGCGAACGGAATCAGCAAAGCCAGCGGC

AGATAACGAGCAGTCTATCAAACCGAAAAAGAAGAAACCCAAAATGTCCA

TGGTTGAATCGGGGAAATTTCTCGCGTCAAGTCAGTACCTGCGTCTAATT

GCCATGCTGGTGCTGGGATACGGCCTCAGTATTAACTTTACCGAAATCAT

GTGGAAAAGCTTGGTGAAGAAACAATATCCAGACCCGCTAGATTATCAAC

GATTTATGGGTAACTTCTCGTCAGCGGTTGGTTTGAGCACATGCATTGTT

ATTTTCTTCGGTGTGCACGTGATCCGTTTGTTGGGGTGGAAAGTCGGAGC

GTTGGCTACACCTGGGATCATGGCCATTCTAGCGTTACCCTTTTTTGCTT
```

-continued

```
GCATTTTGTTGGGTTTGGATAGTCCAGCACGATTGGAGATCGCCGTAATC

TTTGGAACAATTCAGAGTTTGCTGAGCAAAACCTCCAAGTATGCCCTTTT

CGACCCTACCACACAAATGGCTTATATTCCTCTGGACGACGAATCAAAGG

TCAAAGGAAAAGCGGCAATTGATGTTTTGGGATCGCGGATTGGCAAGAGT

GGAGGCTCACTGATCCAGCAGGGCTTGGTCTTTGTTTTTGGAAATATCAT

TAATGCCGCACCTGTAGTAGGGGTTGTCTACTACAGTGTCCTTGTTGCGT

GGATGAGCGCAGCTGGCCGACTAAGTGGGCTTTTTCAAGCACAAACAGAA

ATGGATAAGGCCGACAAAATGGAGGCAAAGACCAACAAAGAAAAGTAGtt

aacctaggctgctgccaccgctgagcaataactagcataaccccttgggg

cctctaaacgggtcttgaggggttttttgctgaaacctcaggcatttgag

aagcacacggtcacactgcttccggtagtcaataaaccggtaaaccagca

atagacataagcggctatttaacgaccctgccctgaaccgacgaccgggt

catcgtggccggatcttgcggcccctcggcttgaacgaattgttagacat

tatttgccgactaccttggtgatctcgcctttcacgtagtggacaaattc

ttccaactgatctgcgcgcgaggccaagcgatcttcttcttgtccaagat

aagcctgtctagcttcaagtatgacgggctgatactgggccggcaggcgc

tccattgcccagtcggcagcgacatccttcggcgcgattttgccggttac

tgcgctgtaccaaatgcgggacaacgtaagcactacatttcgctcatcgc

cagcccagtcgggcggcgagttccatagcgttaaggtttcatttagcgcc

tcaaatagatcctgttcaggaaccggatcaaagagttcctccgccgctgg

acctaccaaggcaacgctatgttctcttgcttttgtcagcaagatagcca

gatcaatgtcgatcgtggctggctcgaagatacctgcaagaatgtcattg

cgctgccattctccaaattgcagttcgcgcttagctggataacgccacgg

aatgatgtcgtcgtgcacaacaatggtgacttctacagcgcggagaatct

cgctctctccaggggaagccgaagtttccaaaaggtcgttgatcaaagct

cgccgcgttgtttcatcaagccttacggtcaccgtaaccagcaaatcaat

atcactgtgtggcttcaggccgccatccactgcggagccgtacaaatgta

cggccagcaacgtcggttcgagatggcgctcgatgacgccaactacctct

gatagttgagtcgatacttcggcgatcaccgcttccctcatactcttcct

ttttcaatattattgaagcatttatcagggttattgtctcatgagcggat
```

-continued acatatttgaatgtatttagaaaaataaacaaatagctagctcactcggt cgctacgctccgggcgtgagactgcggcgggcgctgcggacacatacaaa gttacccacagattccgtggataagcaggggactaacatgtgaggcaaaa cagcagggccgcgccggtggcgtttttccataggctccgccctcctgcca gagttcacataaacagacgcttttccggtgcatctgtgggagccgtgagg ctcaaccatgaatctgacagtacgggcgaaacccgacaggacttaaagat ccccaccgtttccggcgggtcgctccctcttgcgctctcctgttccgacc ctgccgtttaccggatacctgttccgcctttctcccttacgggaagtgtg gcgctttctcatagctcacacactggtatctcggctcggtgtaggtcgtt cgctccaagctgggctgtaagcaagaactccccgttcagcccgactgctg cgccttatccggtaactgttcacttgagtccaacccggaaaagcacggta aaacgccactggcagcagccattggtaactgggagttcgcagaggatttg tttagctaaacacgcggttgctcttgaagtgtgcgccaaagtccggctac actggaaggacagatttggttgctgtgctctgcgaaagccagttaccacg gttaagcagttccccaactgacttaaccttcgatcaaaccacctccccag gtggtttttttcgtttacagggcaaaagattacgcgcagaaaaaaaggatc tcaagaagatcctttgatcttttctactgaaccgctctagatttcagtgc aatttatctcttcaaatgtagcacctgaagtcagccccatacgatataag ttgtaattctcatgttagtcatgccccgcgcccaccggaaggagctgact gggttgaaggctctcaagggcatcggtcgagatcccggtgcctaatgagt gagctaacttacattaattgcgttgcgctcactgcccgctttccagtcgg gaaacctgtcgtgccagctgcattaatgaatcggccaacgcgcggggaga ggcggtttgcgtattgggcgccagggtggtttttcttttcaccagtgaga cgggcaacagctgattgcccttcaccgcctggccctgagagagttgcagc aagcggtccacgctggtttgccccagcaggcgaaaatcctgtttgatggt ggttaacggcgggatataacatgagctgtcttcggtatcgtcgtatccca ctaccgagatgtccgcaccaacgcgcagcccggactcggtaatggcgcgc attgcgcccagcgccatctgatcgttggcaaccagcatcgcagtgggaac gatgccctcattcagcatttgcatggtttgttgaaaaccggacatggcac tccagtcgccttcccgttccgctatcggctgaatttgattgcgagtgaga tatttatgccagccagccagacgcagacgcgccgagacagaacttaatgg gcccgctaacagcgcgatttgctggtgacccaatgcgaccagatgctcca cgcccagtcgcgtaccgtcttcatgggagaaaataatactgttgatgggt gtctggtcagagacatcaagaaataacgccggaacattagtgcaggcagc ttccacagcaatggcatcctggtcatccagcggatagttaatgatcagcc cactgacgcgttgcgcgagaagattgtgcaccgccgctttacaggcttcg acgccgcttcgttctaccatcgacaccaccacgctggcacccagttgatc ggcgcgagatttaatcgccgcgacaatttgcgacggcgcgtgcagggcca gactggaggtggcaacgccaatcagcaacgactgtttgcccgccagttgt tgtgccacgcggttgggaatgtaattcagctccgccatcgccgcttccac -continued tttttcccgcgttttcgcagaaacgtggctggcctggttcaccacgcggg aaacggtctgataagagacaccggcatactctgcgacatcgtataacgtt actggtttcacattcaccaccctgaattgactctcttccgggcgctatca tgccataccgcgaaaggttttgcgccattcgatggtgtccgggatctcga cgctctcccttatgcgactcctgcattaggaaattaatacgactcactat a In some embodiments, a nucleotide triphosphate transporter is from bacteria, plant, or algae. In some embodiments, a nucleotide triphosphate transporter is TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTT1, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*).

As used herein, the term "transporter" refers to a large group of membrane transport proteins which transport nucleotides (and particularly unnatural or modified nucleotides) across the membranes of cells and/or vesicle. Nucleoside transporters can encompass, but are not limited to, equilibrate nucleoside transporters (ENT) and concentrate nucleoside transporters (CNT). According to the invention, the term also encompasses the organic anion transporters (OAT) and the organic cation transporters (OCT). According to the invention, the nucleoside transporter may for example be selected in the group comprising, but not limited to, CNT1, CNT2, CNT3, ENT1, ENT2, OAT1, OAT3 and OCT1.

A nucleotide triphosphate transporter can have at least 40%, 50%, 60%, 70%, 75%, 80%, 85%, 90%, 95%, 97%, 98%, 99%, 99.5%, 99.9% sequence identity to any one of amino acid sequences SEQ ID NOs:1, 3, 5, 7, 9, 11, 13, 14, 16, 18, 19, 20, 22, or 24, or fragments thereof. A nucleotide triphosphate transporter can also have one or more amino acid substitutions, so that they are not identical to those with any of amino acid sequence SEQ ID NOs:1, 3, 5, 7, 9, 11, 13, 14, 16, 18, 19, 20, 22, or 24.

One or more nucleic acids can encode for one or more nucleotide triphosphate transporters having at least about 40, 50%, 60%, 70%, 75%, 80%, 85%, 90%, 95%, 97%, 98%, 99%, 99.5%, 99.9% sequence identity to any of nucleic acid sequence SEQ ID NOs: 1, 3, 5, 7, 9, 11, 13, 14, 16, 18, 19, 20, 22, or 24. The One or more nucleic acids that encode for the one or more nucleotide triphosphate transporters can also have one or more nucleotide substitutions, so that they are not identical to those with any of nucleotide sequence SEQ ID NOs: 1, 3, 5, 7, 9, 11, 13, 14, 16, 18, 19, 20, 22, or 24. Despite such nucleotide substitutions, the nucleotide triphosphate transporters can encode any of the nucleotide triphosphate transporter proteins described herein.

One or more nucleic acids encoding one or more nucleotide triphosphate transporter can have at least 40%, 50%, 60%, 70%, 75%, 80%, 85%, 90%, 95%, 97%, 98%, 99%, 99.5%, 99.9% sequence identity to any of nucleic acid sequence SEQ ID NOs:2, 4, 6, 8, 10, 12, 15, 17, 19, 21, 23, 25, or 28. The nucleotide triphosphate transporters can also have one or more nucleotide substitutions, so that they are not identical to those with any of nucleotide sequence SEQ ID NOs: 2, 4, 6, 8, 10, 12, 15, 17, 19, 21, 23, 25, or 28. Despite such nucleotide substitutions, the nucleotide triphosphate transporters can encode any of the nucleotide triphosphate transporter proteins described herein.

The invention includes NTTs that import unnatural nucleic acids into cell. In some embodiments, NTTs can be modified such that the nucleotide biding site of the NTT is modified to reduce steric entry inhibition of the unnatural nucleic acid into the nucleotide biding site. In some embodiments, NTTs can be modified to provide increased interaction with one or more unnatural features of the unnatural nucleic acids. Such NTTs can be expressed or engineered in cells for stably importing a UBP into the cells. Accordingly, the invention includes compositions that include a heterologous or recombinant NTT and methods of use thereof.

NTTs can be modified using methods pertaining to protein engineering. For example, molecular modeling can be carried out based on crystal structures to identify the locations of the NTTs where mutations can be made to modify a target activity or binding site. A residue identified as a target for replacement can be replaced with a residue selected using energy minimization modeling, homology modeling, and/or conservative amino acid substitutions, such as described in Bordo et al., J. Mol. Biol. 217: 721-729 (1991) and Hayes et al., Proc Natl Acad Sci, USA 99: 15926-15931 (2002).

Any of a variety of NTTs can be used in a method or composition set forth herein including, for example, protein-based enzymes isolated from biological systems and functional variants thereof. Reference to a particular NTT, such as those exemplified below, will be understood to include functional variants thereof unless indicated otherwise. In some embodiments, a NTT is a wild type NTT. In some embodiments, a NTT is a modified, or mutant, NTT.

NTTs, with features for improving entry of unnatural nucleic acids into cells and for coordinating with unnatural nucleotides in the nucleotide biding region, can also be used. In some embodiments, a modified NTT has a modified nucleotide binding site. In some embodiments, a modified or wild type NTT has a relaxed specificity for an unnatural nucleic acid.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified NTT has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid. In some embodiments, a modified or wild type NTT has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified sugar. In some embodiments, a modified or wild type NTT has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type NTT toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward a nucleic acid comprising a triphosphate and/or the unnatural nucleic acid without the triphosphate. For example, a modified or wild type NTT can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type NTT toward the unnatural nucleic acid with a diphosphate or monophosphate, or no phosphate, or a combination thereof.

In some embodiments, a modified or wild type NTT has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid. In some embodiments, a modified or wild type NTT has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type NTT toward the natural nucleic acid.

NTTs can be characterized according to their rate of dissociation from nucleic acids. In some embodiments a NTT has a relatively low dissociation rate for one or more natural and unnatural nucleic acids. In some embodiments a NTT has a relatively high dissociation rate for one or more natural and unnatural nucleic acids. The dissociation rate is an activity of a NTT that can be adjusted to tune reaction rates in methods set forth herein.

NTTs from native sources or variants thereof can be screened using an assay that detects importation of an unnatural nucleic acid having a particular structure. For example, NTTs can be screened for the ability to import an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP. A NTT, e.g., a heterologous NTT, can be used that displays a modified property for the unnatural nucleic acid as compared to the wild-type NTT. For example, the modified property can be, e.g., $K_m$, $k_{cat}$, $V_{max}$, NTT importation in the presence of an unnatural nucleic acid (or of a naturally occurring nucleotide), average template read-length by a cell with the NTT in the presence of an unnatural nucleic acid, specificity of the NTT for an unnatural nucleic acid, rate of binding of an unnatural nucleic acid, or rate of product release, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the NTT optionally has an increased rate of binding of an unnatural nucleic acid, an increased rate of product release, and/or an increased cell importation rate, as compared to a wild-type NTT.

At the same time, a NTT can import natural nucleic acids, e.g., A, C, G, and T, into cell. For example, a NTT optionally displays a specific importation activity for a natural nucleic acid that is at least about 5% as high (e.g., 5%, 10%, 25%, 50%, 75%, 100% or higher), as a corresponding wild-type NTT. Optionally, the NTT displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type NTT.

NTTs used herein that can have the ability to import an unnatural nucleic acid of a particular structure can also be produced using a directed evolution approach. A nucleic acid synthesis assay can be used to screen for NTT variants having specificity for any of a variety of unnatural nucleic acids. For example, NTT variants can be screened for the ability to import an unnatural nucleic acid or UBP; e.g., (d)5SICSTP, (d)NaMTP, (d)TPT3TP, (d)TPT3TP-(d) NaMTP UBP, or (d)5SICSTP-(d)NaMTP UBP into nucleic acids. In some embodiments, such an assay is an in vitro assay, e.g., using a recombinant NTT variant. In some embodiments, such an assay is an in vivo assay, e.g., expressing a NTT variant in a cell. Such directed evolution techniques can be used to screen variants of any suitable NTT for activity toward any of the unnatural nucleic acids set forth herein.

Polymerase Activity

A particularly useful function of a polymerase is to catalyze the polymerization of a nucleic acid strand using an existing nucleic acid as a template. Other functions that are useful are described elsewhere herein. Examples of useful polymerases include DNA polymerases and RNA polymerases.

The ability to improve specificity, processivity, or other features of polymerases unnatural nucleic acids would be highly desirable in a variety of contexts where, e.g., unnatural nucleic acid incorporation is desired, including amplification, sequencing, labeling, detection, cloning, and many others. The present invention provides polymerases with modified properties for unnatural nucleic acids, methods of making such polymerases, methods of using such polymerases, and many other features that will become apparent upon a complete review of the following.

The invention includes polymerases that incorporate unnatural nucleic acids into a growing template copy, e.g., during DNA amplification. In some embodiments, polymerases can be modified such that the active site of the polymerase is modified to reduce steric entry inhibition of the unnatural nucleic acid into the active site. In some embodiments, polymerases can be modified to provide complementarity with one or more unnatural features of the unnatural nucleic acids. Such polymerases can be expressed or engineered in cells for stably incorporating a UBP into the cells. Accordingly, the invention includes compositions that include a heterologous or recombinant polymerase and methods of use thereof.

Polymerases can be modified using methods pertaining to protein engineering. For example, molecular modeling can be carried out based on crystal structures to identify the locations of the polymerases where mutations can be made to modify a target activity. A residue identified as a target for replacement can be replaced with a residue selected using energy minimization modeling, homology modeling, and/or conservative amino acid substitutions, such as described in Bordo et al., J. Mol. Biol. 217: 721-729 (1991) and Hayes et al., Proc Natl Acad Sci, USA 99: 15926-15931 (2002).

Any of a variety of polymerases can be used in a method or composition set forth herein including, for example, protein-based enzymes isolated from biological systems and functional variants thereof. Reference to a particular polymerase, such as those exemplified below, will be understood to include functional variants thereof unless indicated otherwise. In some embodiments, a polymerase is a wild type polymerase. In some embodiments, a polymerase is a modified, or mutant, polymerase.

Polymerases, with features for improving entry of unnatural nucleic acids into active site regions and for coordinating with unnatural nucleotides in the active site region, can also be used. In some embodiments, a modified polymerase has a modified nucleotide binding site.

In some embodiments, a modified polymerase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid. In some embodiments, a modified or wild type polymerase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified sugar. In some embodiments, a modified or wild type polymerase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type polymerase toward a natural nucleic acid and/or the unnatural nucleic acid without the modified base. In some embodiments, a modified or wild type polymerase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward a nucleic acid comprising a triphosphate and/or the unnatural nucleic acid without the triphosphate. For example, a modified or wild type polymerase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type polymerase toward the unnatural nucleic acid with a diphosphate or monophosphate, or no phosphate, or a combination thereof.

In some embodiments, a modified or wild type polymerase has a relaxed specificity for an unnatural nucleic acid. In some embodiments, a modified or wild type polymerase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid. In some embodiments, a modified or wild type polymerase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type polymerase toward the natural nucleic acid.

Absence of exonuclease activity can be a wild type characteristic or a characteristic imparted by a variant or engineered polymerase. For example, an exo minus Klenow fragment is a mutated version of Klenow fragment that lacks 3' to 5' proofreading exonuclease activity.

The method of the invention may be used to expand the substrate range of any DNA polymerase which lacks an intrinsic 3' to 5' exonuclease proofreading activity or where a 3' to 5' exonuclease proofreading activity has been disabled, e.g. through mutation. Examples of DNA polymerases include polA, polB (see e.g. Parrel & Loeb, Nat. Struc. Biol. 2001) polC, polD, polY, polX and reverse transcriptases (RT) but preferably are processive, high-fidelity polymerases (PCT/GB2004/004643). In some embodiments a modified or wild type polymerase substantially lacks 3' to 5' proofreading exonuclease activity. In some embodiments a modified or wild type polymerase substantially lacks 3' to 5' proofreading exonuclease activity for an unnatural nucleic acid. In some embodiments, a modified or wild type polymerase has a 3' to 5' proofreading exonuclease activity. In some embodiments, a modified or wild type polymerase has a 3' to 5' proofreading exonuclease activity for a natural nucleic acid and substantially lacks 3' to 5' proofreading exonuclease activity for an unnatural nucleic acid.

In some embodiments, a modified polymerase has a 3' to 5' proofreading exonuclease activity that is at least about 60%, 70%, 80%, 90%, 95%, 97%, 98%, 99%, 99.5%, 99.99% the proofreading exonuclease activity of the wild type polymerase. In some embodiments, a modified polymerase has a 3' to 5' proofreading exonuclease activity for an unnatural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for an unnatural nucleic acid and a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to a natural nucleic acid. In some embodiments, a modified polymerase has a 3' to 5' proofreading exonuclease activity for a natural nucleic acid that is at least about 60%, 70%, 80%, 90%, 95%, 97%, 98%, 99%, 99.5%, 99.99% the proofreading exonuclease activity of the wild type polymerase to the natural nucleic acid.

In a related aspect, the invention provides methods of making a modified polymerase that include structurally modeling a parental polymerase, e.g., a DNA polymerase, identifying one or more complex stability or nucleotide interaction feature affecting complex stability or nucleotide access or binding in the active site or a complementarity feature for a nucleotide analog at the active site, and mutating the parental polymerase to include or remove these features. For example, the polymerase can be mutated to improve steric access of the unnatural nucleotide to the active site or to improve charge-charge or hydrophobic interactions between the unnatural nucleotide and the polymerase. The methods also include determining whether the resulting modified polymerase displays an increased incorporation of a nucleotide or unnatural nucleotide into a growing nucleic acid copy as compared to the parental polymerase.

Polymerases can be characterized according to their rate of dissociation from nucleic acids. In some embodiments a polymerase has a relatively low dissociation rate for one or more natural and unnatural nucleic acids. In some embodiments a polymerase has a relatively high dissociation rate for one or more natural and unnatural nucleic acids. The dissociation rate is an activity of a polymerase that can be adjusted to tune reaction rates in methods set forth herein.

Polymerases can be characterized according to their fidelity when used with a particular natural and/or unnatural nucleic acid or collections of natural and/or unnatural nucleic acid. Fidelity generally refers to the accuracy with which a polymerase incorporates correct nucleic acids into a growing nucleic acid chain when making a copy of a nucleic acid template. DNA polymerase fidelity can be measured as the ratio of correct to incorrect natural and unnatural nucleic acid incorporations when the natural and unnatural nucleic acid are present, e.g., at equal concentrations, to compete for strand synthesis at the same site in the polymerase-strand-template nucleic acid binary complex. DNA polymerase fidelity can be calculated as the ratio of ($k_{cat}/K_m$) for the natural and unnatural nucleic acid and ($k_{cat}/K_m$) for the incorrect natural and unnatural nucleic acid; where $k_{cat}$ and $K_m$ are Michaelis-Menten parameters in steady state enzyme kinetics (Fersht, (1985) Enzyme Structure and Mechanism, 2nd ed., p 350, W. H. Freeman & Co., New York., incorporated herein by reference). In some embodiments, a polymerase has a fidelity value of at least about 100, 1000, 10,000, 100,000, or $1\times10^6$, with or without a proofreading activity.

Polymerases from native sources or variants thereof can be screened using an assay that detects incorporation of an unnatural nucleic acid having a particular structure. In one example, polymerases can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP. A polymerase, e.g., a heterologous polymerase, can be used that displays a modified property for the unnatural nucleic acid as compared to the wild-type polymerase. For example, the modified property can be, e.g., $K_m$, $k_{cat}$, $V_{max}$, polymerase processivity in the presence of an unnatural nucleic acid (or of a naturally occurring nucleotide), average template read-length by the polymerase in the presence of an unnatural nucleic acid, specificity of the polymerase for an unnatural nucleic acid, rate of binding of an unnatural nucleic acid, rate of product (pyrophosphate, triphosphate, etc.) release, branching rate, or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the polymerase optionally has an increased rate of binding of an unnatural nucleic acid, an increased rate of product release, and/or a decreased branching rate, as compared to a wild-type polymerase.

At the same time, a polymerase can incorporate natural nucleic acids, e.g., A, C, G, and T, into a growing nucleic acid copy. For example, a polymerase optionally displays a specific activity for a natural nucleic acid that is at least about 5% as high (e.g., 5%, 10%, 25%, 50%, 75%, 100% or higher), as a corresponding wild-type polymerase and a processivity with natural nucleic acids in the presence of a template that is at least 5% as high (e.g., 5%, 10%, 25%, 50%, 75%, 100% or higher) as the wild-type polymerase in the presence of the natural nucleic acid. Optionally, the polymerase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type polymerase.

Polymerases used herein that can have the ability to incorporate an unnatural nucleic acid of a particular structure can also be produced using a directed evolution approach. A nucleic acid synthesis assay can be used to screen for polymerase variants having specificity for any of a variety of unnatural nucleic acids. For example, polymerase variants can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP into nucleic acids. In some embodiments, such an assay is an in vitro assay, e.g., using a recombinant polymerase variant. In some embodiments, such an assay is an in vivo assay, e.g., expressing a polymerase variant in a cell. Such directed evolution techniques can be used to screen variants of any suitable polymerase for activity toward any of the unnatural nucleic acids set forth herein.

Modified polymerases of the compositions described can optionally be a modified and/or recombinant Φ29-type DNA polymerase. Optionally, the polymerase can be a modified and/or recombinant Φ29, B103, GA-1, PZA, Φ15, BS32, M2Y, Nf, GI, Cp-1, PRD1, PZE, SF5, Cp-5, Cp-7, PR4, PR5, PR722, or L17 polymerase.

Nucleic acid polymerases generally useful in the invention include DNA polymerases, RNA polymerases, reverse transcriptases, and mutant or altered forms thereof. DNA polymerases and their properties are described in detail in, among other places, DNA Replication $2^{nd}$ edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9° Nm™ DNA polymerase (New England Biolabs), Stoffel fragment, Thermo Sequenase® (Amersham Pharmacia Biotech UK), Therminator™ (New England Biolabs), *Thermotoga maritima* (Tma) DNA polymerase (Diaz and Sabino, 1998 Braz J Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO/0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), UlTma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al., 1998, Proc. Natl. Acad. Sci. USA 95:14250). Both mesophilic polymerases and thermophilic polymerases are contemplated. Thermophilic DNA polymerases include, but are not limited to, ThermoSequenase®, 9° Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A polymerase that is a 3' exonuclease-deficient mutant is also contemplated. Reverse transcriptases useful in the invention include, but are not limited to, reverse transcriptases from HIV, HTLV-I, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit Rev Biochem. 3:289-347(1975)). Further examples of polymerases include, but are not limited to 9° N DNA Polymerase, Taq DNA polymerase, Phusion® DNA polymerase, Pfu DNA polymerase, RB69 DNA polymerase, KOD DNA polymerase, and VentR® DNA polymerase (Gardner et al. (2004) "Comparative Kinetics of Nucleotide Analog Incorporation by Vent DNA Polymerase, J. Biol. Chem., 279(12), 11834-11842; Gardner and Jack "Determinants of nucleotide sugar recognition in an archaeon DNA polymerase" Nucleic Acids Research, 27(12) 2545-2553). Polymerases isolated from non-thermophilic organisms can be heat inactivatable. Examples are DNA polymerases from phage. It will be understood that polymerases from any of a variety of sources can be modified to increase or decrease their tolerance to high temperature conditions. In some embodiments, a polymerase can be thermophilic. In some embodiments, a thermophilic polymerase can be heat inactivatable. Thermophilic polymerases are typically useful for high temperature conditions or in thermocycling conditions such as those employed for polymerase chain reaction (PCR) techniques.

Additionally, such polymerases can be used for DNA amplification and/or sequencing applications, including real-time applications, e.g., in the context of amplification or sequencing that include incorporation of unnatural nucleic acid residues into DNA by the polymerase. In other embodiments, the unnatural nucleic acid that is incorporated can be the same as a natural residue, e.g., where a label or other moiety of the unnatural nucleic acid is removed by action of the polymerase during incorporation, or the unnatural nucleic acid can have one or more feature that distinguishes it from a natural nucleic acid.

Ribonucleotide Reductase Activity

A particularly useful function of a ribonucleotide reductase (RNR), also known as (ribonucleoside diphosphate reductase) is to catalyze the formation of deoxyribonucleotides from ribonucleotides. Deoxyribonucleotides can then be, e.g., used in the synthesis of DNA polymerization of a nucleic acid strand using an existing nucleic acid as a template. Other functions that are useful are described elsewhere herein. Natural substrates for RNR can include ADP, GDP, CDP and UDP. The natural activity catalyzes the conversion of 2'-deoxyribonucleoside diphosphate to ribonucleoside diphosphate.

Examples of useful ribonucleotide reductases include CDP reductase; ribonucleoside diphosphate reductase; UDP reductase; ADP reductase; nucleoside diphosphate reductase; ribonucleoside 5'-diphosphate reductase; ribonucleotide diphosphate reductase; and 2'-deoxyribonucleoside-diphosphate:oxidized-thioredoxin 2'-oxidoreductase.

The ability to improve specificity, processivity, or other features of ribonucleotide reductases unnatural nucleic acids would be highly desirable in a variety of contexts where, e.g., unnatural nucleic acid incorporation is desired, including amplification, sequencing, labeling, detection, cloning, and many others. The present invention provides ribonucleotide reductases with modified properties for unnatural nucleic acids, methods of making such ribonucleotide reductases, methods of using such ribonucleotide reductases, and many other features that will become apparent upon a complete review of the following.

The invention includes ribonucleotide reductases that catalyze the formation of deoxyribonucleotides from ribonucleotides, e.g., for use during DNA synthesis or amplification. In some embodiments, ribonucleotide reductases can be modified such that the active site of the ribonucleotide reductases is modified to reduce steric entry inhibition of the unnatural nucleic acid into the active site. In some embodiments, ribonucleotide reductases can be modified to provide complementarity with one or more unnatural features of an unnatural nucleic acid. In some embodiments, ribonucleotide reductases can be modified to provide complementarity with one or more natural features of an unnatural nucleic acid. Such ribonucleotide reductases can be expressed or engineered in cells for stably incorporating a UBP into the cells. Accordingly, the invention includes compositions that include a heterologous or recombinant ribonucleotide reductases and methods of use thereof.

Ribonucleotide reductases can be modified using methods pertaining to protein engineering. For example, molecular modeling can be carried out based on crystal structures to identify the locations of the ribonucleotide reductases where mutations can be made to modify a target activity. A residue identified as a target for replacement can be replaced with a residue selected using energy minimization modeling, homology modeling, and/or conservative amino acid substitutions, such as described in Bordo et al., J Mol Biol 217: 721-729 (1991) and Hayes et al., Proc Natl Acad Sci, USA 99: 15926-15931 (2002).

Any of a variety of ribonucleotide reductases can be used in a method or composition set forth herein including, for example, protein-based enzymes isolated from biological systems and functional variants thereof. Reference to a particular ribonucleotide reductase, such as those exemplified below, will be understood to include functional variants thereof unless indicated otherwise. In some embodiments, a ribonucleotide reductase is a wild type polymerase. In some embodiments, a ribonucleotide reductase is a modified, or mutant, ribonucleotide reductase.

Ribonucleotide reductases, with features for improving conversion of natural and/or unnatural deoxyribonucleotide triphosphate nucleic acids to natural and/or unnatural ribonucleotide triphosphates. Ribonucleotide reductases, with features for coordinating with unnatural nucleotides in the active site region, can also be used. In some embodiments, a modified ribonucleotide reductase has a modified nucleotide binding site. In some embodiments, a modified or wild type ribonucleotide reductase has a relaxed specificity for an unnatural nucleic acid.

In some embodiments, a modified ribonucleotide reductase has a specificity for an unnatural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the unnatural nucleic acid. In some embodiments, a modified or wild type ribonucleotide reductase has a specificity for an unnatural nucleic acid comprising a modified sugar that is at least about 10%, 20%, 30%, 40%, 50%, 60%, 70%, 80%, 90%, 95%, 97%, 98%, 99%, 99.5%, 99.99% the specificity of the wild type ribonucleotide reductase toward a natural nucleic acid and/or the unnatural nucleic acid without the modified sugar. In some embodiments, a modified or wild type ribonucleotide reductase has a specificity for an unnatural nucleic acid comprising a modified base that is at least about 10%, 20%, 30%, 40%, 50%, 60%, 70%, 80%, 90%, 95%, 97%, 98%, 99%, 99.5%, 99.99% the specificity of the wild type ribonucleotide reductase toward a natural nucleic acid and/or the unnatural nucleic acid without the modified base. In some embodiments, a modified or wild type ribonucleotide reductase has a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type ribonucleotide reductase toward a nucleic acid comprising a triphosphate and/or the unnatural nucleic acid without the triphosphate. For example, a modified or wild type ribonucleotide reductase can have a specificity for an unnatural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the unnatural nucleic acid with a diphosphate or monophosphate, or no phosphate, or a combination thereof In some embodiments, a modified or wild type ribonucleotide reductase has a specificity for an unnatural nucleic acid and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid. In some embodiments, a modified or wild type ribonucleotide reductase has a specificity for an unnatural nucleic acid comprising a modified sugar and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid. In some embodiments, a modified or wild type ribonucleotide reductase has a specificity for an unnatural nucleic acid comprising a modified base and a specificity to a natural nucleic acid that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid. In some embodiments, a modified or wild type ribonucleotide reductase has a specificity for an unnatural nucleic acid comprising a triphosphate and a specificity to a natural nucleic acid comprising a triphosphate that is at least about 10%, 20%, 30%, 40%, 50%, 60%, 70%, 80%, 90%, 95%, 97%, 98%, 99%, 99.5%, 99.99% the specificity of the wild type ribonucleotide reductase toward the natural nucleic acid triphosphate.

In a related aspect, the invention provides methods of making a modified ribonucleotide reductase that include structurally modeling a parental ribonucleotide reductase, e.g., a DNA ribonucleotide reductase, identifying one or more complex stability or nucleotide interaction feature affecting complex stability or nucleotide access or binding in the active site or a complementarity feature for a nucleotide analog at the active site, and mutating the parental ribonucleotide reductase to include or remove these features. For example, the ribonucleotide reductase can be mutated to improve steric access of the unnatural nucleotide to the active site or to improve charge-charge or hydrophobic interactions between the unnatural nucleotide and the ribonucleotide reductase. The methods also include determining whether the resulting modified ribonucleotide reductase displays an increased incorporation of a nucleotide or unnatural nucleotide into a growing nucleic acid copy as compared to the parental ribonucleotide reductase.

Ribonucleotide reductases can be characterized according to their rate of dissociation from nucleic acids. In some embodiments a ribonucleotide reductase has a relatively low dissociation rate for one or more natural and unnatural nucleic acids. In some embodiments a ribonucleotide reductase has a relatively high dissociation rate for one or more natural and unnatural nucleic acids. The dissociation rate is an activity of a ribonucleotide reductase that can be adjusted to tune reaction rates in methods set forth herein.

Ribonucleotide reductases from native sources or variants thereof can be screened using an assay that detects incorporation of an unnatural nucleic acid having a particular structure. In one example, ribonucleotide reductases can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP. A ribonucleotide reductase, e.g., a heterologous ribonucleotide reductase, can be used that displays a modified property for the unnatural nucleic acid as compared to the wild-type ribonucleotide reductase. For example, the modified property can be, e.g., $K_m$, $k_{cat}$, $V_{max}$, ribonucleotide reductase processivity in the presence of an unnatural nucleic acid (or of a naturally occurring nucleotide), turnover rate by the ribonucleotide reductase in the presence of an unnatural nucleic acid, specificity of the ribonucleotide reductase for an unnatural nucleic acid, rate of binding of an unnatural nucleic acid, rate of product (pyrophosphate, triphosphate, etc.), or any combination thereof. In one embodiment, the modified property is a reduced $K_m$ for an unnatural nucleic acid and/or an increased $k_{cat}/K_m$ or $V_{max}/K_m$ for an unnatural nucleic acid. Similarly, the ribonucleotide reductase optionally has an increased rate of binding of an unnatural nucleic acid and/or an increased rate of product release, as compared to a wild-type ribonucleotide reductase.

At the same time, a ribonucleotide reductase can process natural deoxyribonucleic acids, e.g., dA, dC, and dG, into natural deoxyribonucleic acids. For example, a ribonucleotide reductase optionally displays a specific activity for a natural nucleic acid that is at least about 5% as high (e.g., 5%, 10%, 25%, 50%, 75%, 100% or higher), as a corresponding wild-type ribonucleotide reductase and a $k_{cat}$ that is at least 5% as high (e.g., 5%, 10%, 25%, 50%, 75%, 100% or higher) as the wild-type ribonucleotide reductase in the presence of the natural nucleic acid. Optionally, the ribonucleotide reductase displays a $k_{cat}/K_m$ or $V_{max}/K_m$ for a naturally occurring nucleotide that is at least about 5% as high (e.g., about 5%, 10%, 25%, 50%, 75% or 100% or higher) as the wild-type ribonucleotide reductase.

Ribonucleotide reductases used herein that can have the ability to incorporate an unnatural nucleic acid of a particular structure can also be produced using a directed evolution approach. A nucleic acid synthesis assay can be used to screen for ribonucleotide reductase variants having specificity for any of a variety of unnatural nucleic acids. For example, ribonucleotide reductase variants can be screened for the ability to incorporate an unnatural nucleic acid or UBP; e.g., (d)5SICSTP, (d)NaMTP, (d)TPT3TP, (d)TPT3TP-(d)NaMTP UBP, or (d)5SICSTP-(d)NaMTP UBP into nucleic acids. In some embodiments, such an assay is an in vitro assay, e.g., using a recombinant ribonucleotide reductase variant. In some embodiments, such an assay is an in vivo assay, e.g., expressing a ribonucleotide reductase variant in a cell. Such directed evolution techniques can be used to screen variants of any suitable ribonucleotide reductase for activity toward any of the unnatural nucleic acids set forth herein.

Engineered Cells

Methods and compositions (e.g., nucleic acids and reagents) described herein can be used to generate engineered microorganisms, e.g., a living cell that incorporates and replicates at least one unnatural nucleotide or at least one UBP within its cellular environment. The cell employed can be genetically transformed with an expression cassette encoding a heterologous protein, e.g., a nucleotide triphosphate transporter capable of transporting unnatural nucleotide triphosphates into the cell and/or a polymerase with high fidelity for an unnatural nucleic acid, so that the unnatural nucleotides can be incorporated into cellular nucleic acids and can, e.g., form UBPs under in vivo conditions. Cells can comprise enhanced activity for unnatural nucleic acid uptake. Cells can comprise enhanced activity for unnatural nucleic acid import. Cells can comprise enhanced polymerase activity for unnatural nucleic acids.

Accordingly, by practice of a method of the invention, a living cell is generated that incorporates within its nucleic acids at least one unnatural nucleotide and/or at least one UBP. The UBP can include a pair of unnatural mutually base-pairing nucleotides capable of forming the UBP under in vivo conditions, when the unnatural mutually base-pairing nucleotides, as their respective triphosphates, are taken up into the cell by action of a nucleotide triphosphate transporter. The cell can be genetically transformed by an expression cassette encoding a nucleotide triphosphate transporter so that the nucleotide triphosphate transporter is expressed and is available to transport the unnatural nucleotides into the cell. The cell can be genetically transformed by an expression cassette encoding a polymerase so that the polymerase is expressed and is available to incorporate unnatural nucleotides into the cell's nucleic acids. The cell can be a prokaryotic or eukaryotic cell. The pair of unnatural mutually base-pairing nucleotides, as their respective triphosphates, can be a triphosphate of (d)5SICS ((d)5SICSTP) and a triphosphate of (d)NaM ((d)NaMTP). The pair of unnatural mutually base-pairing nucleotides, as their respective triphosphates, can be a triphosphate of (d)TPT3 ((d)TPT3TP) and a triphosphate of (d)NaM ((d)NaMTP).

The cell can comprise a template UBP. A template UBP can be a UBP present on a nucleic acid inside the cell that comprises a first and a second unnatural template nucleic acid. The unnatural template nucleic acids can base pair with the imported unnatural nucleic acids. For example, an imported nucleic acid can form a UBP by base pairing with an unnatural template nucleic acid present in the cell. In some embodiments, the template UBP is formed outside of the cell. In some embodiments, the template UBP is introduced into the cell, such as by transfection, electroporation, or the like.

Cells can be genetically transformed cells with a nucleic acid, e.g., an expression cassette encoding a nucleotide triphosphate transporter capable of transporting such unnatural nucleotides into the cell. A cell can comprise a heterologous nucleotide triphosphate transporter, where the heterologous nucleotide triphosphate transporter can transport natural and unnatural nucleotide triphosphates into the cell. A cell can comprise a heterologous polymerase, where the heterologous polymerase has activity for an unnatural nucleic acid.

A method can also include contacting a genetically transformed cell with the respective triphosphate forms unnatural nucleotides, in the presence of potassium phosphate and/or an inhibitor of phosphatases or nucleotidases. During or after such contact, the cell can be placed within a life-supporting medium suitable for growth and replication of the cell. The cell can be maintained in the life-supporting medium so that the respective triphosphate forms of unnatural nucleotides are incorporated into nucleic acids within the cells, and through at least one replication cycle of the cell. The pair of unnatural mutually base-pairing nucleotides as a respective triphosphate, can comprise a triphosphate of (d)5SICS ((d)5SICSTP) and a triphosphate of (d)NaM ((d)NaMTP). The pair of unnatural mutually base-pairing nucleotides as a respective triphosphate, can comprise a triphosphate of (d)TPT3 ((d)TPT3TP) and a triphosphate of (d)NaM ((d)NaMTP). The cell can be *E. coli*, and the (d)5SICSTP and (d)NaMTP or (d)TPT3TP and (d)NaMTP can be efficiently imported into *E. coli* by, for example, the transporter PtNTT2, wherein an *E. coli* polymerase, such as Pol I, can efficiently use the unnatural triphosphates to replicate DNA, thereby incorporating unnatural nucleotides and/or UBPs into cellular nucleic acids within the cellular environment.

By practice of a method of the invention, the person of ordinary skill can obtain a population of a living and propagating cells that has at least one unnatural nucleotide and/or at least one UBP within at least one nucleic acid maintained within at least some of the individual cells, wherein the at least one nucleic acid is stably propagated within the cell, and wherein the cell expresses a nucleotide triphosphate transporter suitable for providing cellular uptake of triphosphate forms of one or more unnatural nucleotides when contacted with (e.g., grown in the presence of) the unnatural nucleotide(s) in a life-supporting medium suitable for growth and replication of the organism.

After transport into the cell by the nucleotide triphosphate transporter, the unnatural base-pairing nucleotides are incorporated into nucleic acids within the cell by cellular machinery, e.g., the cell's own DNA and/or RNA polymerases, a heterologous polymerase, or a polymerase that has been evolved using directed evolution (Chen and Romesberg, FEBS Lett. (2014) 588(2):219-29). The unnatural nucleotides can be incorporated into cellular nucleic acids such as genomic DNA, genomic RNA, mRNA, structural RNA, microRNA, and autonomously replicating nucleic acids (e.g., plasmids, viruses, or vectors).

Genetically engineered cells can be generated by introduction of nucleic acids, e.g., heterologous nucleic acids, into cells. Any cell described herein can be a host cell and can comprise an expression vector. In one embodiment, the host cell is a prokaryotic cell. In another embodiment, the host cell is *E. coli*. In some embodiments, a cell comprises one or more heterologous polynucleotides. Nucleic acid reagents can be introduced into microorganisms using various techniques. Non-limiting examples of methods used to introduce heterologous nucleic acids into various organisms include; transformation, transfection, transduction, electroporation, ultrasound-mediated transformation, particle bombardment and the like. In some instances the addition of carrier molecules (e.g., bis-benzimdazolyl compounds, for example, see U.S. Pat. No. 5,595,899) can increase the uptake of DNA in cells typically though to be difficult to transform by conventional methods. Conventional methods of transformation are readily available to the artisan and can be found in Maniatis et al., (1982) Molecular Cloning: a Laboratory Manual; Cold Spring Harbor Laboratory, Cold Spring Harbor, N.Y.

Genetic transformation can be obtained using direct transfer of an expression cassette, in but not limited to, plasmids, viral vectors, viral nucleic acids, phage nucleic acids, phages, cosmids, and artificial chromosomes, or via transfer of genetic material in cells or carriers such as cationic liposomes. Such methods are available in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)). Appropriate means for transfection, including viral vectors, chemical transfectants, or physico-mechanical methods such as electroporation and direct diffusion of DNA, are described by, for example, Wolff et al., Science, 247, 1465-1468, (1990); and Wolff, Nature, 352, 815-818, (1991).

For example, a nucleotide triphosphate transporter or polymerase nucleic acid molecule, expression cassette and/or vector can be introduced to a cell by any method including, but not limited to, calcium-mediated transformation, electroporation, microinjection, lipofection, particle bombardment and the like.

A cell can comprise unnatural nucleotide triphosphates incorporated into one or more nucleic acids within the cell. For example, the cell can be a living cell capable of incorporating at least one unnatural nucleotide within DNA or RNA maintained within the cell. The cell can also incorporate at least one UBP comprising a pair of unnatural mutually base-pairing nucleotides into nucleic acids within the cell under in vivo conditions, wherein the unnatural mutually base-pairing nucleotides, e.g., their respective triphosphates, are taken up into the cell by action of a nucleotide triphosphate transporter, the gene for which is present (e.g., was introduced) into the cell by genetic transformation. For example, upon incorporation into the nucleic acid maintained within a cell, (d)5SICS and (d)NaM can form a stable UBP that can be stably propagated by the DNA replication machinery of an organism, e.g., when grown in a life-supporting medium comprising (d)5SICS and (d)NaM. For example, upon incorporation into the nucleic acid maintained within a cell, (d)TPT3 and (d)NaM can form a stable UBP that can be stably propagated by the DNA replication machinery of an organism, e.g., when grown in a life-supporting medium comprising (d)TPT3 and (d)NaM.

Cells can be capable of replicating an unnatural nucleic acid. Provided herein, is a method of generating a living cell with nucleic acids that incorporate and/or replicate at least one unnatural nucleotide and/or at least one UBP comprising a pair of unnatural mutually base-pairing nucleotides, into the cell's nucleic acids under in vivo conditions. Such methods can include genetically transforming the cell with an expression cassette encoding a nucleotide triphosphate transporter capable of transporting into the cell, as a respective triphosphate, one or more unnatural nucleotides under in vivo conditions. Alternatively, a cell can be employed that has previously been genetically transformed with an expression cassette that can express an encoded nucleotide triphosphate transporter. The method can also include contacting or exposing the genetically transformed cell to potassium phosphate and the respective triphosphate forms of at least one unnatural nucleotide (e.g., two mutually base-pairing nucleotides capable of forming the UBP) in a life-supporting medium suitable for growth and replication of the cell, and maintaining the transformed cell in the life-supporting medium in the presence of the respective triphosphate forms of at least one unnatural nucleotide (e.g., two mutually base-pairing nucleotides capable of forming the UBP) under in vivo conditions, through at least one replication cycle of the cell.

Cells can comprise a stably propagated unnatural nucleic acid. Provided herein is a population of a living and propagating cells, comprising within the nucleic acids of at least some of the individual cells of the population at least one unnatural nucleotide (e.g., two mutually base-pairing nucleotides capable of forming the UBP) or at least one UBP, as a stably propagated component of the DNA of the cell, wherein the cell is genetically transformed with a nucleotide triphosphate transporter suitable for providing cellular uptake of triphosphate forms of the pair of unnatural nucleotides. The population of cells can be grown in the presence of the respective triphosphate forms of the pair of unnatural nucleotides, in a life-supporting medium suitable for growth and replication of the organism.

A cell can comprise a stably incorporated unnatural nucleic acid. Some embodiments comprise a cell (e.g., as *E. coli*) that stably incorporates nucleotides other than A, G, T, and C within nucleic acids maintained within the cell. For example, the nucleotides other than A, G, T, and C can be (d)5SICS, (d)TPT3 and (d)NaM, which upon incorporation into nucleic acids of the cell, can form a stable UBP within the nucleic acids. In one aspect, unnatural nucleotides and UBPs can be stably propagated by the replication apparatus of the organism, when an organism transformed with the gene for the triphosphate transporter, is grown in a life-supporting medium that includes potassium phosphate and the triphosphate forms of (d)5SICS, (d)TPT3 and (d)NaM.

A cell can comprise an expanded genetic alphabet. A cell can comprise a stably incorporated unnatural nucleic acid. In some embodiments, a cell with an expanded genetic alphabet comprises an unnatural nucleic acid that can form a base pair (bp) with another nucleic acid, e.g., a natural or unnatural nucleic acid. In some embodiments, a cell with an expanded genetic alphabet comprises an unnatural nucleic acid that is hydrogen bonded to another nucleic acid. In some embodiments, a cell with an expanded genetic alphabet comprises an unnatural nucleic acid that is not hydrogen bonded to another nucleic acid to which it is base paired. In some embodiments, a cell with an expanded genetic alphabet comprises an unnatural nucleic acid that base pairs to another nucleic acid via hydrophobic interactions. In some embodiments, a cell with an expanded genetic alphabet comprises an unnatural nucleic acid that base pairs to another nucleic acid via non-hydrogen bonding interactions. A cell with an expanded genetic alphabet can be a cell that can copy a homologous nucleic acid to form a nucleic acid comprising an unnatural nucleic acid. A cell with an expanded genetic alphabet can be a cell comprising an unnatural nucleic acid base paired with another unnatural nucleic acid (UBP).

Cells can form UBPs from the imported unnatural nucleotides under in vivo conditions. In some embodiments potassium phosphate and/or inhibitors of phosphatase and/or nucleotidase activities can facilitate transport of unnatural nucleic acids. The methods include use of a cell that expresses a heterologous nucleotide triphosphate transporter. When such a cell is contacted with one or more nucleotide triphosphates, the nucleotide triphosphates are transported into the cell. The cell can be in the presence of potassium phosphate and/or inhibitors of phosphatase and nucleotidase. Unnatural nucleotide triphosphates can be incorporated into nucleic acids within the cell by the cell's natural machinery and, for example, can mutually base-pair to form UBPs within the nucleic acids of the cell.

In some embodiments a UBP can be incorporated into a cell or population of cells when exposed to unnatural triphosphates. In some embodiments a UBP can be incorporated into a cell or population of cells when substantially consistently exposed to unnatural triphosphates. In some embodiments, replication of a UBP does not result in a substantially reduced growth rate. In some embodiments, replication expression of a heterologous protein, e.g., a nucleotide triphosphate transport does not result in a substantially reduced growth rate.

In some embodiments, induction of expression of a heterologous gene, e.g., an NTT, in a cell can result in slower cell growth and increased natural and/or unnatural nucleic acid uptake compared to the growth and uptake of a cell without induction of expression of the heterologous gene. In some embodiments, induction of expression of a heterologous gene, e.g., an NTT, in a cell can result in increased cell growth and increased natural and/or unnatural nucleic acid uptake compared to the growth and uptake of a cell without induction of expression of the heterologous gene.

In some embodiments, induction of expression of a heterologous gene, e.g., an NTT, in a cell treated with a first concentration of an induction reagent can result in slower cell growth and increased natural and/or unnatural nucleic acid uptake compared to the growth and uptake of a cell without induction of expression of the heterologous gene. In some embodiments, induction of expression of a heterologous gene, e.g., an NTT, can result in increased cell growth and increased natural and/or unnatural nucleic acid uptake compared to the growth and uptake of a cell treated with a first concentration of an induction reagent.

In some embodiments, a UBP is incorporated during a log growth phase. In some embodiments, a UBP is incorporated during a non-log growth phase. In some embodiments, a UBP is incorporated during a substantially linear growth phase. In some embodiments a UBP is stably incorporated into a cell or population of cells after growth for a time period. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP can be stably incorporated into a cell or population of cells after growth for at least about 1, 2, 3, 4, 5, 6, 7, 8, 9, 10, 11, or 12 months of growth. For example, a UBP can be stably incorporated into a cell or population of cells after growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

In some embodiments a UBP is not efficiently recognized by DNA repair pathways of a cell. In some embodiments a UBP is not efficiently removed by a cell. In some embodiments a UBP is not efficiently excised by a cell. In some embodiments a UBP is not efficiently removed from a cell or population of cells after a time period. For example, a UBP cannot be efficiently removed from a cell or population of cells afer growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 50 or more duplications. For example, a UBP cannot be efficiently removed from a cell or population of cells afer growth for at least about 1, 2, 3, 4, 5, 6, 7, 8, 9, 10, 11, 12, 13, 14, 15, 16, 17, 18, 19, 20, 21, 22, 23, or 24 hours of growth. For example, a UBP cannot be efficiently removed from a cell or population of cells afer growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days of growth. For example, a UBP cannot be efficiently removed from a cell or population of cells afer growth for at least about 1, 2, 3, 4, 5, 6, 7, 8, 9, 10, 11, or 12 months of growth. For example, a UBP cannot be efficiently removed from a cell or population of cells afer growth for at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 50 years of growth.

Thus an organism can be generated that stably harbors an expanded genetic alphabet.

Cell Types

Many types of cells/microorganisms can be used, e.g., for transforming or genetically engineering. A cell can be a prokaryotic or eukaryotic cell. For example, the cell can be a microorganism such as a bacterial cell, fungal cell, yeast, or unicellular protozoan. Alternatively, the cell can be a eukaryotic cell, such as a cultured animal, plant, or human cell. The cell can be present in an organism such as a plant or animal.

In some embodiments an engineered microorganism is a single cell organism, often capable of dividing and proliferating. A microorganism can include one or more of the following features: aerobe, anaerobe, filamentous, non-filamentous, monoploid, dipoid, auxotrophic and/or non-auxotrophic. In certain embodiments, an engineered microorganism is a prokaryotic microorganism (e.g., bacterium), and in certain embodiments, an engineered microorganism is a non-prokaryotic microorganism. In some embodiments, an engineered microorganism is a eukaryotic microorganism (e.g., yeast, fungi, amoeba). In some embodiments, an engineered microorganism is a fungus. In some embodiments, an engineered organism is yeast.

Any suitable yeast may be selected as a host microorganism, engineered microorganism, genetically modified organism or source for a heterologous or modified polynucleotide. Yeast include, but are not limited to, *Yarrowia* yeast (e.g., *Y. lipolytica* (formerly classified as *Candida lipolytica*)), *Candida* yeast (e.g., *C. revkaufi, C. viswanathii, C. pulcherrima, C. tropicalis, C. utilis*), *Rhodotorula* yeast (e.g., *R. glutinus, R. graminis*), *Rhodosporidium* yeast (e.g., *R. toruloides*), *Saccharomyces* yeast (e.g., *S. cerevisiae, S. bayanus, S. pastorianus, S. carlsbergensis*), *Cryptococcus* yeast, *Trichosporon* yeast (e.g., *T. pullans, T. cutaneum*), *Pichia* yeast (e.g., *P. pastoris*) and Lipomyces yeast (e.g., *L. starkeyii, L. lipoferus*). In some embodiments, a suitable yeast is of the genus *Arachniotus, Aspergillus, Aureobasidium, Auxarthron, Blastomyces, Candida, Chrysosporuim, Chrysosporuim Debaryomyces, Coccidiodes, Cryptococcus, Gymnoascus, Hansenula, Histoplasma, Issatchenkia, Kluyveromyces, Lipomyces, Lssatchenkia, Microsporum, Myxotrichum, Myxozyma, Oidiodendron, Pachysolen, Penicillium, Pichia, Rhodosporidium, Rhodotorula, Rhodotorula, Saccharomyces, Schizosaccharomyces, Scopulariopsis, Sepedonium, Trichosporon*, or *Yarrowia*. In some embodiments, a suitable yeast is of the species *Arachniotus flavoluteus, Aspergillus flavus, Aspergillus fumigatus, Aspergillus niger, Aureobasidium pullulans, Auxarthron thaxteri, Blastomyces dermatitidis, Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida xestobii, Chrysosporuim keratinophilum, Coccidiodes immitis, Cryptococcus albidus* var. diffluens, *Cryptococcus laurentii, Cryptococcus* neofomans, Debaryomyces *hansenii, Gymnoascus dugwayensis, Hansenula anomala, Histoplasma capsulatum, Issatchenkia occidentalis, Isstachenkia orientalis, Kluyveromyces lactis, Kluyveromyces marxianus, Kluyveromyces thermotolerans, Kluyveromyces waltii*, Lipomyces lipoferus, Lipomyces starkeyii, *Microsporum gypseum*, Myxotrichum deflexum, Oidiodendron echinulatum, *Pachysolen* tannophilis, *Penicillium notatum, Pichia anomala, Pichia pastoris, Pichia stipitis, Rhodosporidium toruloides, Rhodotorula glutinus, Rhodotorula graminis, Saccharomyces cerevisiae, Saccharomyces kluyveri, Schizosaccharomyces pombe, Scopulariopsis acremonium, Sepedonium chrysospermum, Trichosporon cutaneum, Trichosporon pullans, Yarrowia lipolytica*, or *Yarrowia lipolytica* (formerly classified as *Candida lipolytica*). In some embodiments, a yeast is a *Y. lipolytica* strain that includes, but is not limited to, ATCC20362, ATCC8862, ATCC18944, ATCC20228, ATCC76982 and LGAM S(7)1 strains (Papanikolaou S., and Aggelis G., Bioresour. Technol. 82(1):43-9 (2002)). In certain embodiments, a yeast is a *Candida* species (i.e., *Candida* spp.) yeast. Any suitable *Candida* species can be used and/or genetically modified for production of a fatty dicarboxylic acid (e.g., octanedioic acid, decanedioic acid, dodecanedioic acid, tetradecanedioic acid, hexadecanedioic acid, octadecanedioic acid, eicosanedioic acid). In some embodiments, suitable *Candida* species include, but are not limited to *Candida albicans, Candida dubliniensis, Candida famata, Candida glabrata, Candida guilliermondii, Candida kefyr, Candida krusei, Candida lambica, Candida lipolytica, Candida lustitaniae, Candida parapsilosis, Candida pulcherrima, Candida revkaufi, Candida rugosa, Candida tropicalis, Candida utilis, Candida viswanathii, Candida* xestobii and any other *Candida* spp. yeast described herein. Non-limiting examples of *Candida* spp. strains include, but are not limited to, sAA001 (ATCC20336), sAA002 (ATCC20913), sAA003 (ATCC20962), sAA496 (US2012/0077252), sAA106 (US2012/0077252), SU-2 (ura3-/ura3-), H5343 (beta oxidation blocked; U.S. Pat. No. 5,648,247) strains. Any suitable strains from *Candida* spp. yeast may be utilized as parental strains for genetic modification.

Yeast genera, species and strains are often so closely related in genetic content that they can be difficult to distinguish, classify and/or name. In some cases strains of *C. lipolytica* and *Y. lipolytica* can be difficult to distinguish, classify and/or name and can be, in some cases, considered the same organism. In some cases, various strains of *C. tropicalis* and *C. viswanathii* can be difficult to distinguish, classify and/or name (for example see Arie et al., J. Gen. Appl. Microbiol., 46, 257-262 (2000). Some *C. tropicalis* and *C. viswanathii* strains obtained from ATCC as well as from other commercial or academic sources can be considered equivalent and equally suitable for the embodiments described herein. In some embodiments, some parental strains of *C. tropicalis* and *C. viswanathii* are considered to differ in name only.

Any suitable fungus may be selected as a host microorganism, engineered microorganism or source for a heterologous polynucleotide. Non-limiting examples of fungi include, but are not limited to, *Aspergillus* fungi (e.g., *A. parasiticus, A. nidulans*), Thraustochytrium fungi, Schizochytrium fungi and *Rhizopus* fungi (e.g., *R. arrhizus, R. oryzae, R. nigricans*). In some embodiments, a fungus is an *A. parasiticus* strain that includes, but is not limited to, strain ATCC24690, and in certain embodiments, a fungus is an *A. nidulans* strain that includes, but is not limited to, strain ATCC38163.

Any suitable prokaryote may be selected as a host microorganism, engineered microorganism or source for a heterologous polynucleotide. A Gram negative or Gram positive bacteria may be selected. Examples of bacteria include, but are not limited to, *Bacillus* bacteria (e.g., *B. subtilis, B. megaterium*), *Acinetobacter* bacteria, *Norcardia* baceteria, *Xanthobacter* bacteria, *Escherichia* bacteria (e.g., *E. coli* (e.g., strains DH10B, Stbl2, DH5-alpha, DB3, DB3.1), DB4, DB5, JDP682 and ccdA-over (e.g., U.S. application Ser. No. 09/518,188))), *Streptomyces* bacteria, *Erwinia* bacteria, *Klebsiella* bacteria, *Serratia* bacteria (e.g., *S. marcessans*), *Pseudomonas* bacteria (e.g., *P. aeruginosa*), *Salmonella* bacteria (e.g., *S. typhimurium, S. typhi*), Megasphaera bacteria (e.g., Megasphaera elsdenii). Bacteria also include, but are not limited to, photosynthetic bacteria (e.g., green non-sulfur bacteria (e.g., *Choroflexus* bacteria (e.g., *C. aurantiacus*), *Chloronema* bacteria (e.g., *C. gigateum*)), green sulfur bacteria (e.g., *Chlorobium* bacteria (e.g., *C. limicola*), *Pelodictyon* bacteria (e.g., *P. luteolum*), purple sulfur bacteria (e.g., *Chromatium* bacteria (e.g., *C. okenii*)), and purple non-sulfur bacteria (e.g., *Rhodospirillum* bacteria (e.g., *R. rubrum*), *Rhodobacter* bacteria (e.g., R. *sphaeroides, R. capsulatus*), and *Rhodomicrobium* bacteria (e.g., *R. vanellii*).

Cells from non-microbial organisms can be utilized as a host microorganism, engineered microorganism or source for a heterologous polynucleotide. Examples of such cells, include, but are not limited to, insect cells (e.g., *Drosophila* (e.g., *D. melanogaster*), *Spodoptera* (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; mammalian cells (e.g., NIH3T3, 293, CHO, COS, VERO, C127, BHK, Per-$C_6$, Bowes melanoma and HeLa cells); and plant cells (e.g., *Arabidopsis thaliana, Nicotania tabacum, Cuphea acinifolia, Cuphea aequipetala, Cuphea angustifolia, Cuphea appendiculata, Cuphea avigera, Cuphea* avigera var. *pulcherrima, Cuphea axilliflora, Cuphea bahiensis, Cuphea baillonis, Cuphea brachypoda, Cuphea bustamanta, Cuphea calcarata, Cuphea calophylla, Cuphea calophylla* subsp. mesostemon, *Cuphea* carthagenensis, *Cuphea* circaeoides, *Cuphea confertiflora, Cuphea cordata, Cuphea crassiflora, Cuphea cyanea, Cuphea decandra, Cuphea denticulata, Cuphea disperma, Cuphea epilobifolia, Cuphea ericoides, Cuphea flava, Cuphea flavisetula, Cuphea fuchsiifolia, Cuphea gaumeri, Cuphea glutinosa, Cuphea heterophylla, Cuphea hookeriana, Cuphea hyssopifolia* (Mexican-heather), *Cuphea* hyssopoides, *Cuphea* ignea, *Cuphea* ingrata, *Cuphea jorullensis, Cuphea lanceolata, Cuphea linarioides, Cuphea llavea, Cuphea lophostoma, Cuphea lutea, Cuphea lutescens, Cuphea melanium, Cuphea melvilla, Cuphea micrantha, Cuphea micropetala, Cuphea mimuloides, Cuphea nitidula, Cuphea palustris, Cuphea parsonsia, Cuphea pascuorum, Cuphea paucipetala, Cuphea procumbens, Cuphea pseudosilene, Cuphea pseudovaccinium, Cuphea pulchra, Cuphea racemosa, Cuphea repens, Cuphea salicifolia, Cuphea salvadorensis, Cuphea schumannii, Cuphea sessiliflora, Cuphea sessilifolia, Cuphea setosa, Cuphea spectabilis, Cuphea spermacoce, Cuphea splendida, Cuphea* splendida var. *viridiflava, Cuphea strigulosa, Cuphea subuligera, Cuphea teleandra, Cuphea thymoides, Cuphea tolucana, Cuphea urens, Cuphea utriculosa, Cuphea viscosissima, Cuphea watsoniana, Cuphea wrightii*, and *Cuphea lanceolata*).

Microorganisms or cells used as host organisms or source for a heterologous polynucleotide are commercially available. Microorganisms and cells described herein, and other suitable microorganisms and cells are available, for example, from Invitrogen Corporation, (Carlsbad, Calif.), American Type Culture Collection (Manassas, Va.), and Agricultural Research Culture Collection (NRRL; Peoria, Ill.). Host microorganisms and engineered microorganisms may be provided in any suitable form. For example, such microorganisms may be provided in liquid culture or solid culture (e.g., agar-based medium), which may be a primary culture or may have been passaged (e.g., diluted and cultured) one or more times. Microorganisms also may be provided in frozen form or dry form (e.g., lyophilized). Microorganisms may be provided at any suitable concentration.

Stabilization of Nucleic Acids for Cellular Import

Figure 6A:
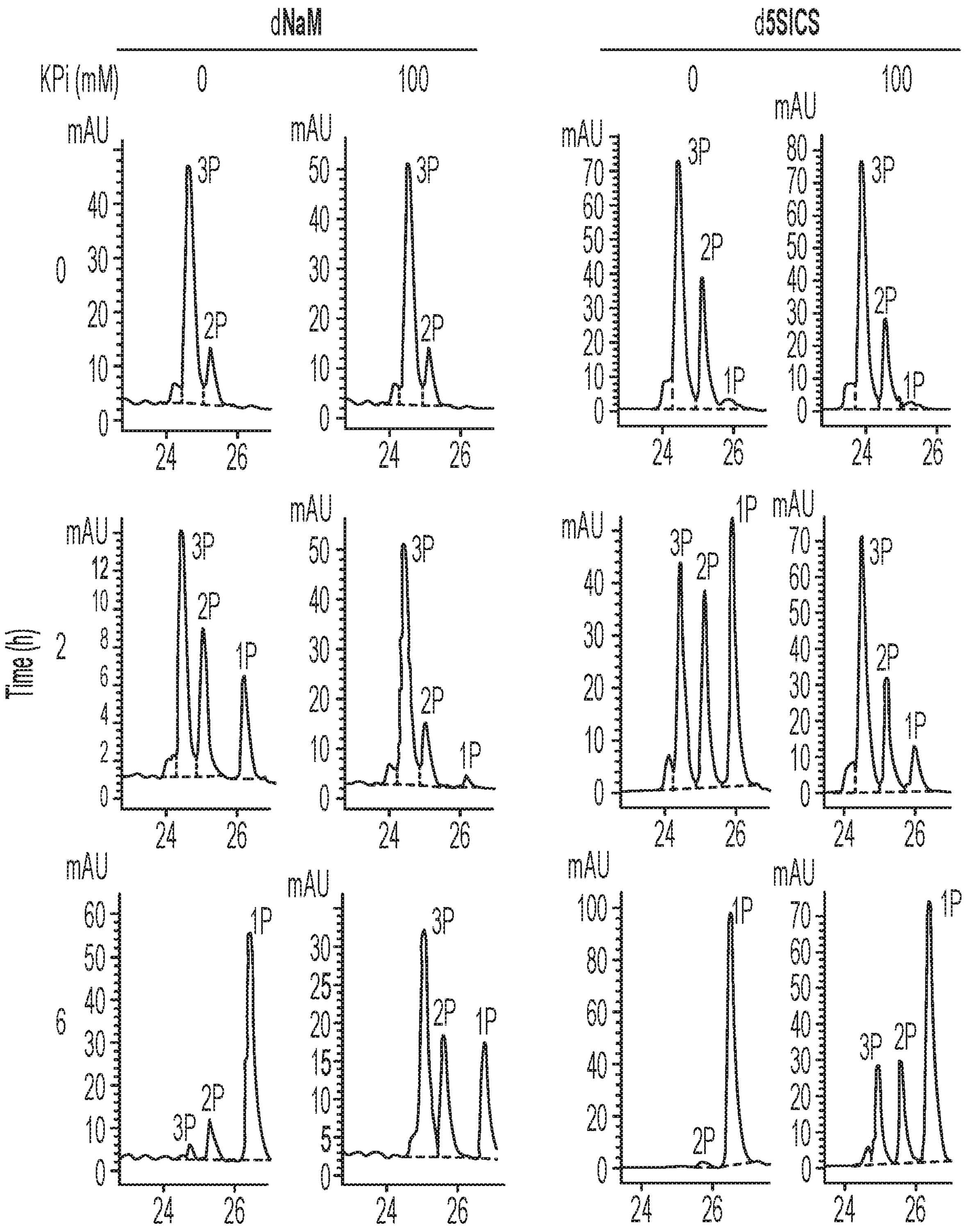
FIG. 6A depicts HPLC of unnatural triphosphates (3P) of dNaM and d5SICS from growing bacterial culture in the presence or absence of potassium phosphate (KPi).
Figure 6B:
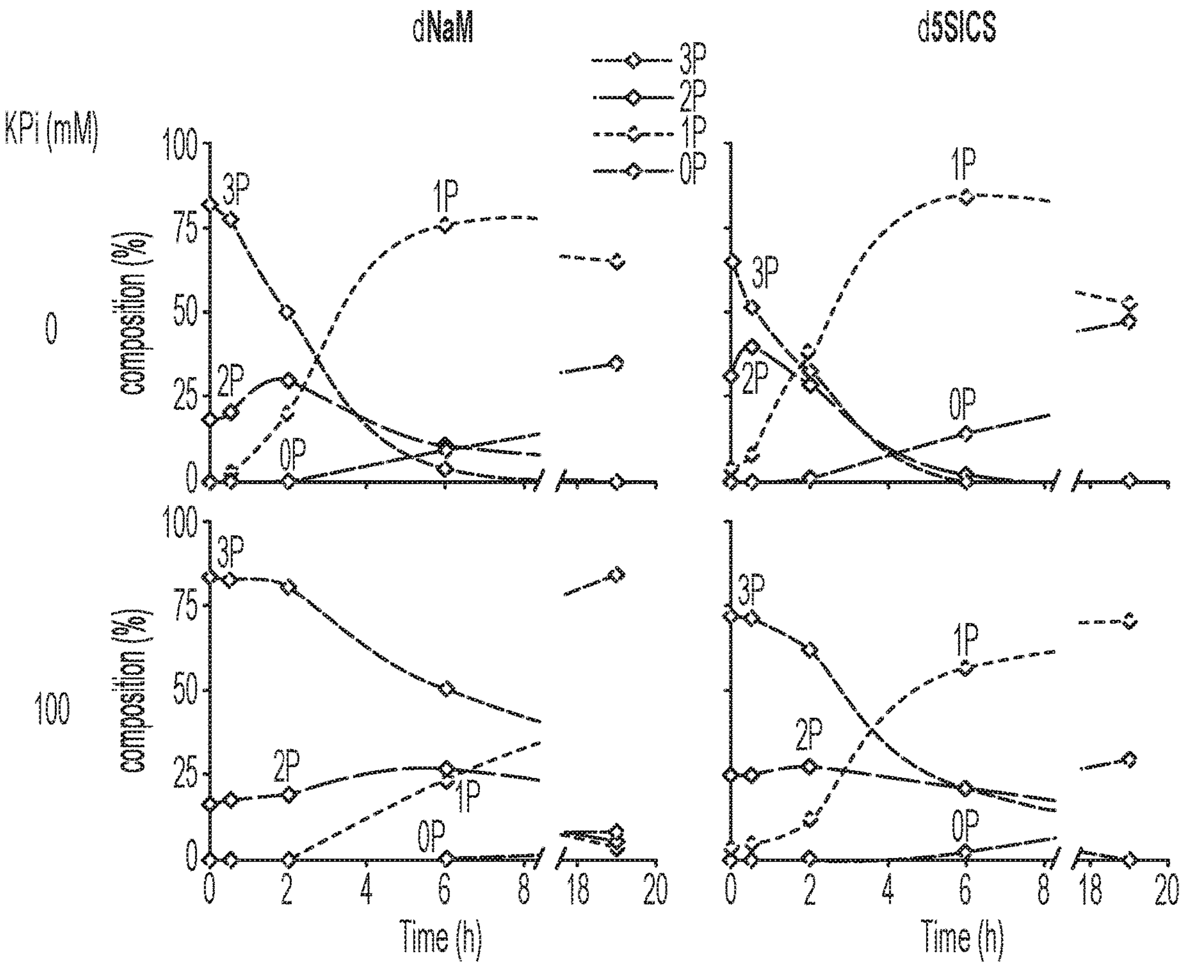
FIG. 6B depicts composition profiles of unnatural triphosphates of dNaM and d5SICS from growing bacterial culture in the presence or absence of KPi.

Active transport via a nucleotide triphosphate transporter has been discovered to be optimal when the transported unnatural nucleotide triphosphates are sufficiently stable, e.g., stable in culture media. Preliminary characterization of unnatural nucleic acids, e.g., d5SICSTP and dNaMTP, indicated that they are degraded in the presence of actively growing *E. coli* (FIG. 6B). Similar behavior was observed with [α-$^{32}$P]-dATP, and the dephosphorylation products detected by thin layer chromatography for [α-$^{32}$P]-dATP or by HPLC and MALDI for d5SICSTP and dNaMTP (FIG. 6A), suggested that decomposition was mediated by phosphatases. Minimal to negligent degradation was observed in spent media, suggesting that decomposition may occur within the periplasm. No improvement in stability was observed in cultures of single-gene deletion mutants of *E. coli* BW25113 lacking a specific periplasmic phosphatase (as identified by the presence of a Sec-type N-terminal leader sequence), including phoA, ushA, appA, aphA, yjjX, surE, yjbR, yjjG, yfaO, mutT, nagD, yggV, yrfG, or ymjB, suggesting that decomposition may occur as a result of the activity of multiple phosphatases.

The cells that express the nucleotide triphosphate transporter can be modified in a variety of other ways to facilitate nucleotide triphosphate importation and/or improve the stability of nucleotide triphosphates. For example, the cells can be modified by deletion or disruption, e.g., mutation, of one or more genes that encode a phosphatase or a nucleotidase. Such modifications can increase the stability of nucleotide triphosphates that can be imported by the nucleotide triphosphate transporter. Cells can be modified by deletion of one or more genes that encode phosphatases such as a 5' or 3' nucleotidase.

A nucleotidase is a hydrolytic enzyme that catalyzes the hydrolysis of a nucleotide into a nucleoside and a phosphate. For example, it converts adenosine monophosphate to adenosine, and guanosine monophosphate to guanosine. The nucleotidase that is modified or deleted from the cell can be a 5'-nucleotidase (such as EC 3.1.3.5) or a 3'-nucleotidase (such as EC 3.1.3.6). In some embodiments, it can be more useful to modify or eliminate a gene encoding a 5'-nucleotidase to improve the stability of nucleotide triphosphates that can be imported by the nucleotide triphosphate transporter.

Cells can also be modified by deletion of one or more genes that encode a 5'-nucleotidase (ENZYME entry: EC 3.1.3.5), such as one or more genes in Table 2.

TABLE 2

| 5'-Nucleotidases | | |
|---|---|---|
| Q7ZWS2, 5N3BA_XENLA; | Q7ZWS2, 5N3BA_XENLA; | Q7ZWS2, 5N3BA_XENLA; |
| Q2TAG6, 5N3BB_XENLA; | Q2TAG6, 5N3BB_XENLA; | Q2TAG6, 5N3BB_XENLA; |
| Q9BXI3, 5NT1A_HUMAN; | Q9BXI3, 5NT1A_HUMAN; | Q9BXI3, 5NT1A_HUMAN; |
| A3KFX0, 5NT1A_MOUSE; | A3KFX0, 5NT1A_MOUSE; | A3KFX0, 5NT1A_MOUSE; |
| Q96P26, 5NT1B_HUMAN; | Q96P26, 5NT1B_HUMAN; | Q96P26, 5NT1B_HUMAN; |

TABLE 2-continued

| 5'-Nucleotidases | | |
|---|---|---|
| Q91YE9, 5NT1B_MOUSE; | Q91YE9, 5NT1B_MOUSE; | Q91YE9, 5NT1B_MOUSE; |
| Q5ZID6, 5NT3A_CHICK; | Q5ZID6, 5NT3A_CHICK; | Q5ZID6, 5NT3A_CHICK; |
| Q9H0P0, 5NT3A_HUMAN; | Q9H0P0, 5NT3A_HUMAN; | Q9H0P0, 5NT3A_HUMAN; |
| Q9D020, 5NT3A_MOUSE; | Q9D020, 5NT3A_MOUSE; | Q9D020, 5NT3A_MOUSE; |
| Q5ZKF6, 5NT3B_CHICK; | Q5ZKF6, 5NT3B_CHICK; | Q5ZKF6, 5NT3B_CHICK; |
| Q9W197, 5NT3B_DROME; | Q9W197, 5NT3B_DROME; | Q9W197, 5NT3B_DROME; |
| Q969T7, 5NT3B_HUMAN; | Q969T7, 5NT3B_HUMAN; | Q969T7, 5NT3B_HUMAN; |
| Q3UFY7, 5NT3B_MOUSE; | Q3UFY7, 5NT3B_MOUSE; | Q3UFY7, 5NT3B_MOUSE; |
| Q6AYP7, 5NT3B_RAT; | Q6AYP7, 5NT3B_RAT; | Q6AYP7, 5NT3B_RAT; |
| Q09315, 5NT3_CAEEL; | Q09315, 5NT3_CAEEL; | Q09315, 5NT3_CAEEL; |
| Q7SYN4, 5NT3_DANRE; | Q7SYN4, 5NT3_DANRE; | Q7SYN4, 5NT3_DANRE; |
| O46411, 5NTC_BOVIN; | O46411, 5NTC_BOVIN; | O46411, 5NTC_BOVIN; |
| Q5ZIZ4, 5NTC_CHICK; | Q5ZIZ4, 5NTC_CHICK; | Q5ZIZ4, 5NTC_CHICK; |
| Q54XC1, 5NTC_DICDI; | Q54XC1, 5NTC_DICDI; | Q54XC1, 5NTC_DICDI; |
| P49902, 5NTC_HUMAN; | P49902, 5NTC_HUMAN; | P49902, 5NTC_HUMAN; |
| Q3V1L4, 5NTC_MOUSE; | Q3V1L4, 5NTC_MOUSE; | Q3V1L4, 5NTC_MOUSE; |
| Q5RA22, 5NTC_PONAB; | Q5RA22, 5NTC_PONAB; | Q5RA22, 5NTC_PONAB; |
| Q6DKB0, 5NTC_XENLA; | Q6DKB0, 5NTC_XENLA; | Q6DKB0, 5NTC_XENLA; |
| Q5EBF1, 5NTC_XENTR; | Q5EBF1, 5NTC_XENTR; | Q5EBF1, 5NTC_XENTR; |
| Q05927, 5NTD_BOVIN; | Q05927, 5NTD_BOVIN; | Q05927, 5NTD_BOVIN; |
| P29240, 5NTD_DIPOM; | P29240, 5NTD_DIPOM; | P29240, 5NTD_DIPOM; |
| P44569, 5NTD_HAEIN; | P44569, 5NTD_HAEIN; | P44569, 5NTD_HAEIN; |
| P21589, 5NTD_HUMAN; | P21589, 5NTD_HUMAN; | P21589, 5NTD_HUMAN; |
| Q9XZ43, 5NTD_LUTLO; | Q9XZ43, 5NTD_LUTLO; | Q9XZ43, 5NTD_LUTLO; |
| Q61503, 5NTD_MOUSE; | Q61503, 5NTD_MOUSE; | Q61503, 5NTD_MOUSE; |
| Q9I767, 5NTD_PSEAE; | Q9I767, 5NTD_PSEAE; | Q9I767, 5NTD_PSEAE; |
| P21588, 5NTD_RAT; | P21588, 5NTD_RAT; | P21588, 5NTD_RAT; |
| P52307, 5NTD_RHIMP; | P52307, 5NTD_RHIMP; | P52307, 5NTD_RHIMP; |
| O83142, 5NTD_TREPA; | O83142, 5NTD_TREPA; | O83142, 5NTD_TREPA; |
| Q9KQ30, 5NTD_VIBCH; | Q9KQ30, 5NTD_VIBCH; | Q9KQ30, 5NTD_VIBCH; |
| P22848, 5NTD_VIBPA; | P22848, 5NTD_VIBPA; | P22848, 5NTD_VIBPA; |
| Q8DFG4, 5NTD_VIBVU; | Q8DFG4, 5NTD_VIBVU; | Q8DFG4, 5NTD_VIBVU; |
| P0AF25, NAGD_ECO57; | P0AF25, NAGD_ECO57; | P0AF25, NAGD_ECO57; |
| P0AF24, NAGD_ECOLI; | P0AF24, NAGD_ECOLI; | P0AF24, NAGD_ECOLI; |
| O34313, NTPES_BACSU; | O34313, NTPES_BACSU; | O34313, NTPES_BACSU; |
| P15309, PPAP_HUMAN; | P15309, PPAP_HUMAN; | P15309, PPAP_HUMAN; |
| Q8CE08, PPAP_MOUSE; | Q8CE08, PPAP_MOUSE; | Q8CE08, PPAP_MOUSE; |
| P20646, PPAP_RAT; | P20646, PPAP_RAT; | P20646, PPAP_RAT; |
| Q390V3, SURE1_BURS3; | Q390V3, SURE1_BURS3; | Q390V3, SURE1_BURS3; |
| Q823A6, SURE1_CHLCV; | Q823A6, SURE1_CHLCV; | Q823A6, SURE1_CHLCV; |
| Q8ZU79, SURE1_PYRAE; | Q8ZU79, SURE1_PYRAE; | Q8ZU79, SURE1_PYRAE; |
| Q72H70, SURE1_THET2; | Q72H70, SURE1_THET2; | Q72H70, SURE1_THET2; |
| Q39FP8, SURE2_BURS3; | Q39FP8, SURE2_BURS3; | Q39FP8, SURE2_BURS3; |
| Q823A7, SURE2_CHLCV; | Q823A7, SURE2_CHLCV; | Q823A7, SURE2_CHLCV; |
| Q8ZSY4, SURE2_PYRAE; | Q8ZSY4, SURE2_PYRAE; | Q8ZSY4, SURE2_PYRAE; |
| Q746M5, SURE2_THET2; | Q746M5, SURE2_THET2; | Q746M5, SURE2_THET2; |
| B0C6V3, SURE_ACAM1; | B0C6V3, SURE_ACAM1; | B0C6V3, SURE_ACAM1; |
| Q6FCV6, SURE_ACIAD; | Q6FCV6, SURE_ACIAD; | Q6FCV6, SURE_ACIAD; |
| B7GZ27, SURE_ACIB3; | B7GZ27, SURE_ACIB3; | B7GZ27, SURE_ACIB3; |
| B7I4K2, SURE_ACIB5; | B7I4K2, SURE_ACIB5; | B7I4K2, SURE_ACIB5; |
| B2HVM9, SURE_ACIBC; | B2HVM9, SURE_ACIBC; | B2HVM9, SURE_ACIBC; |
| B0VUE2, SURE_ACIBS; | B0VUE2, SURE_ACIBS; | B0VUE2, SURE_ACIBS; |
| A3M7F7, SURE_ACIBT; | A3M7F7, SURE_ACIBT; | A3M7F7, SURE_ACIBT; |
| B0VBZ1, SURE_ACIBY; | B0VBZ1, SURE_ACIBY; | B0VBZ1, SURE_ACIBY; |
| B9MFW6, SURE_ACIET; | B9MFW6, SURE_ACIET; | B9MFW6, SURE_ACIET; |
| A3N3M1, SURE_ACTP2; | A3N3M1, SURE_ACTP2; | A3N3M1, SURE_ACTP2; |
| B3H2Z8, SURE_ACTP7; | B3H2Z8, SURE_ACTP7; | B3H2Z8, SURE_ACTP7; |
| B0BTK8, SURE_ACTPJ; | B0BTK8, SURE_ACTPJ; | B0BTK8, SURE_ACTPJ; |
| A6VLU0, SURE_ACTSZ; | A6VLU0, SURE_ACTSZ; | A6VLU0, SURE_ACTSZ; |
| A0KGH8, SURE_AERHH; | A0KGH8, SURE_AERHH; | A0KGH8, SURE_AERHH; |
| Q9YDW8, SURE_AERPE; | Q9YDW8, SURE_AERPE; | Q9YDW8, SURE_AERPE; |
| A4SRB6, SURE_AERS4; | A4SRB6, SURE_AERS4; | A4SRB6, SURE_AERS4; |
| B9JEH2, SURE_AGRRK; | B9JEH2, SURE_AGRRK; | B9JEH2, SURE_AGRRK; |
| Q8UEQ3, SURE_AGRT5; | Q8UEQ3, SURE_AGRT5; | Q8UEQ3, SURE_AGRT5; |
| B9JXD7, SURE_AGRVS; | B9JXD7, SURE_AGRVS; | B9JXD7, SURE_AGRVS; |
| Q0A7L4, SURE_ALKEH; | Q0A7L4, SURE_ALKEH; | Q0A7L4, SURE_ALKEH; |
| A6TRH0, SURE_ALKMQ; | A6TRH0, SURE_ALKMQ; | A6TRH0, SURE_ALKMQ; |
| B8JDR1, SURE_ANAD2; | B8JDR1, SURE_ANAD2; | B8JDR1, SURE_ANAD2; |
| Q2INZ4, SURE_ANADE; | Q2INZ4, SURE_ANADE; | Q2INZ4, SURE_ANADE; |
| A7H8F6, SURE_ANADF; | A7H8F6, SURE_ANADF; | A7H8F6, SURE_ANADF; |
| B9KI89, SURE_ANAMF; | B9KI89, SURE_ANAMF; | B9KI89, SURE_ANAMF; |
| Q5PB34, SURE_ANAMM; | Q5PB34, SURE_ANAMM; | Q5PB34, SURE_ANAMM; |

TABLE 2-continued

| 5'-Nucleotidases | | |
|---|---|---|
| B4UE89, SURE_ANASK; | B4UE89, SURE_ANASK; | B4UE89, SURE_ANASK; |
| Q3MB98, SURE_ANAVT; | Q3MB98, SURE_ANAVT; | Q3MB98, SURE_ANAVT; |
| O67004, SURE_AQUAE; | O67004, SURE_AQUAE; | O67004, SURE_AQUAE; |
| A8EX03, SURE_ARCB4; | A8EX03, SURE_ARCB4; | A8EX03, SURE_ARCB4; |
| O29320, SURE_ARCFU; | O29320, SURE_ARCFU; | O29320, SURE_ARCFU; |
| Q5P832, SURE_AROAE; | Q5P832, SURE_AROAE; | Q5P832, SURE_AROAE; |
| A8I066, SURE_AZOC5; | A8I066, SURE_AZOC5; | A8I066, SURE_AZOC5; |
| A1K4E9, SURE_AZOSB; | A1K4E9, SURE_AZOSB; | A1K4E9, SURE_AZOSB; |
| C1DSR8, SURE_AZOVD; | C1DSR8, SURE_AZOVD; | C1DSR8, SURE_AZOVD; |
| Q5LHD7, SURE_BACFN; | Q5LHD7, SURE_BACFN; | Q5LHD7, SURE_BACFN; |
| Q64YA5, SURE_BACFR; | Q64YA5, SURE_BACFR; | Q64YA5, SURE_BACFR; |
| Q8A0L8, SURE_BACTN; | Q8A0L8, SURE_BACTN; | Q8A0L8, SURE_BACTN; |
| A6L1M6, SURE_BACV8; | A6L1M6, SURE_BACV8; | A6L1M6, SURE_BACV8; |
| B2IJG0, SURE_BEII9; | B2IJG0, SURE_BEII9; | B2IJG0, SURE_BEII9; |
| Q2L006, SURE_BORA1; | Q2L006, SURE_BORA1; | Q2L006, SURE_BORA1; |
| Q7WI36, SURE_BORBR; | Q7WI36, SURE_BORBR; | Q7WI36, SURE_BORBR; |
| Q7W670, SURE_BORPA; | Q7W670, SURE_BORPA; | Q7W670, SURE_BORPA; |
| A9IP06, SURE_BORPD; | A9IP06, SURE_BORPD; | A9IP06, SURE_BORPD; |
| Q7VXN2, SURE_BORPE; | Q7VXN2, SURE_BORPE; | Q7VXN2, SURE_BORPE; |
| Q89L02, SURE_BRADU; | Q89L02, SURE_BRADU; | Q89L02, SURE_BRADU; |
| A5EJV7, SURE_BRASB; | A5EJV7, SURE_BRASB; | A5EJV7, SURE_BRASB; |
| A4YV68, SURE_BRASO; | A4YV68, SURE_BRASO; | A4YV68, SURE_BRASO; |
| C0ZGV3, SURE_BREBN; | C0ZGV3, SURE_BREBN; | C0ZGV3, SURE_BREBN; |
| B2S5B9, SURE_BRUA1; | B2S5B9, SURE_BRUA1; | B2S5B9, SURE_BRUA1; |
| Q2YNM5, SURE_BRUA2; | Q2YNM5, SURE_BRUA2; | Q2YNM5, SURE_BRUA2; |
| Q57DM1, SURE_BRUAB; | Q57DM1, SURE_BRUAB; | Q57DM1, SURE_BRUAB; |
| A9MAQ9, SURE_BRUC2; | A9MAQ9, SURE_BRUC2; | A9MAQ9, SURE_BRUC2; |
| C0RIL9, SURE_BRUMB; | C0RIL9, SURE_BRUMB; | C0RIL9, SURE_BRUMB; |
| P66879, SURE_BRUME; | P66879, SURE_BRUME; | P66879, SURE_BRUME; |
| A5VQ63, SURE_BRUO2; | A5VQ63, SURE_BRUO2; | A5VQ63, SURE_BRUO2; |
| B0CLL1, SURE_BRUSI; | B0CLL1, SURE_BRUSI; | B0CLL1, SURE_BRUSI; |
| P66880, SURE_BRUSU; | P66880, SURE_BRUSU; | P66880, SURE_BRUSU; |
| A3MK87, SURE_BURM7; | A3MK87, SURE_BURM7; | A3MK87, SURE_BURM7; |
| A2S290, SURE_BURM9; | A25290, SURE_BURM9; | A2S290, SURE_BURM9; |
| Q62JV2, SURE_BURMA; | Q62JV2, SURE_BURMA; | Q62JV2, SURE_BURMA; |
| A1V4L3, SURE_BURMS; | A1V4L3, SURE_BURMS; | A1V4L3, SURE_BURMS; |
| A3NVY2, SURE_BURP0; | A3NVY2, SURE_BURP0; | A3NVY2, SURE_BURP0; |
| Q3JRP0, SURE_BURP1; | Q3JRP0, SURE_BURP1; | Q3JRP0, SURE_BURP1; |
| A3NA65, SURE_BURP6; | A3NA65, SURE_BURP6; | A3NA65, SURE_BURP6; |
| Q63UU4, SURE_BURPS; | Q63UU4, SURE_BURPS; | Q63UU4, SURE_BURPS; |
| Q2SWF5, SURE_BURTA; | Q2SWF5, SURE_BURTA; | Q2SWF5, SURE_BURTA; |
| A4JEQ1, SURE_BURVG; | A4JEQ1, SURE_BURVG; | A4JEQ1, SURE_BURVG; |
| Q13Z72, SURE_BURXL; | Q13Z72, SURE_BURXL; | Q13Z72, SURE_BURXL; |
| A8MBQ3, SURE_CALMQ; | A8MBQ3, SURE_CALMQ; | A8MBQ3, SURE_CALMQ; |
| A7ZCD9, SURE_CAMC1; | A7ZCD9, SURE_CAMC1; | A7ZCD9, SURE_CAMC1; |
| A7H0A1, SURE_CAMC5; | A7H0A1, SURE_CAMC5; | A7H0A1, SURE_CAMC5; |
| A0RMU4, SURE_CAMFF; | A0RMU4, SURE_CAMFF; | A0RMU4, SURE_CAMFF; |
| A7I2X3, SURE_CAMHC; | A7I2X3, SURE_CAMHC; | A7I2X3, SURE_CAMHC; |
| A8FK82, SURE_CAMJ8; | A8FK82, SURE_CAMJ8; | A8FK82, SURE_CAMJ8; |
| A7H578, SURE_CAMJD; | A7H578, SURE_CAMJD; | A7H578, SURE_CAMJD; |
| Q9PIK6, SURE_CAMJE; | Q9PIK6, SURE_CAMJE; | Q9PIK6, SURE_CAMJE; |
| A1VY14, SURE_CAMJJ; | A1VY14, SURE_CAMJJ; | A1VY14, SURE_CAMJJ; |
| Q5HWH7, SURE_CAMJR; | Q5HWH7, SURE_CAMJR; | Q5HWH7, SURE_CAMJR; |
| B9KDQ8, SURE_CAMLR; | B9KDQ8, SURE_CAMLR; | B9KDQ8, SURE_CAMLR; |
| Q3ADI0, SURE_CARHZ; | Q3ADI0, SURE_CARHZ; | Q3ADI0, SURE_CARHZ; |
| B8GX52, SURE_CAUCN; | B8GX52, SURE_CAUCN; | B8GX52, SURE_CAUCN; |
| Q9A6T5, SURE_CAUCR; | Q9A6T5, SURE_CAUCR; | Q9A6T5, SURE_CAUCR; |
| B0T1Q2, SURE_CAUSK; | B0T1Q2, SURE_CAUSK; | B0T1Q2, SURE_CAUSK; |
| Q5L5X3, SURE_CHLAB; | Q5L5X3, SURE_CHLAB; | Q5L5X3, SURE_CHLAB; |
| B8G513, SURE_CHLAD; | B8G513, SURE_CHLAD; | B8G513, SURE_CHLAD; |
| Q3ATV8, SURE_CHLCH; | Q3ATV8, SURE_CHLCH; | Q3ATV8, SURE_CHLCH; |
| Q254M8, SURE_CHLFF; | Q254M8, SURE_CHLFF; | Q254M8, SURE_CHLFF; |
| B3EFW1, SURE_CHLL2; | B3EFW1, SURE_CHLL2; | B3EFW1, SURE_CHLL2; |
| Q9PKH4, SURE_CHLMU; | Q9PKH4, SURE_CHLMU; | Q9PKH4, SURE_CHLMU; |
| A1BI19, SURE_CHLPD; | A1BI19, SURE_CHLPD; | A1BI19, SURE_CHLPD; |
| Q9Z8S6, SURE_CHLPN; | Q9Z8S6, SURE_CHLPN; | Q9Z8S6, SURE_CHLPN; |
| B0B9W8, SURE_CHLT2; | B0B9W8, SURE_CHLT2; | B0B9W8, SURE_CHLT2; |
| Q3KME4, SURE_CHLTA; | Q3KME4, SURE_CHLTA; | Q3KME4, SURE_CHLTA; |
| B0BBJ8, SURE_CHLTB; | B0BBJ8, SURE_CHLTB; | B0BBJ8, SURE_CHLTB; |
| Q8KC69, SURE_CHLTE; | Q8KC69, SURE_CHLTE; | Q8KC69, SURE_CHLTE; |
| O84220, SURE_CHLTR; | O84220, SURE_CHLTR; | O84220, SURE_CHLTR; |
| Q1QU76, SURE_CHRSD; | Q1QU76, SURE_CHRSD; | Q1QU76, SURE_CHRSD; |
| Q7NRV1, SURE_CHRVO; | Q7NRV1, SURE_CHRVO; | Q7NRV1, SURE_CHRVO; |
| A8ANV8, SURE_CITK8; | A8ANV8, SURE_CITK8; | A8ANV8, SURE_CITK8; |
| A7FQP3, SURE_CLOB1; | A7FQP3, SURE_CLOB1; | A7FQP3, SURE_CLOB1; |
| C3KZ52, SURE_CLOB6; | C3KZ52, SURE_CLOB6; | C3KZ52, SURE_CLOB6; |
| A6LS61, SURE_CLOB8; | A6LS61, SURE_CLOB8; | A6LS61, SURE_CLOB8; |
| B2UXL6, SURE_CLOBA; | B2UXL6, SURE_CLOBA; | B2UXL6, SURE_CLOBA; |

TABLE 2-continued

| 5'-Nucleotidases | | |
|---|---|---|
| B2TPM3, SURE_CLOBB; | B2TPM3, SURE_CLOBB; | B2TPM3, SURE_CLOBB; |
| A5HYC6, SURE_CLOBH; | A5HYC6, SURE_CLOBH; | A5HYC6, SURE_CLOBH; |
| C1FQW9, SURE_CLOBJ; | C1FQW9, SURE_CLOBJ; | C1FQW9, SURE_CLOBJ; |
| B1IDC2, SURE_CLOBK; | B1IDC2, SURE_CLOBK; | B1IDC2, SURE_CLOBK; |
| A7G9Y6, SURE_CLOBL; | A7G9Y6, SURE_CLOBL; | A7G9Y6, SURE_CLOBL; |
| B1KTK1, SURE_CLOBM; | B1KTK1, SURE_CLOBM; | B1KTK1, SURE_CLOBM; |
| B9E0C7, SURE_CLOK1; | B9E0C7, SURE_CLOK1; | B9E0C7, SURE_CLOK1; |
| A5N6V8, SURE_CLOK5; | A5N6V8, SURE_CLOK5; | A5N6V8, SURE_CLOK5; |
| Q899M5, SURE_CLOTE; | Q899M5, SURE_CLOTE; | Q899M5, SURE_CLOTE; |
| Q487E6, SURE_COLP3; | Q487E6, SURE_COLP3; | Q487E6, SURE_COLP3; |
| B6J4X6, SURE_COXB1; | B6J4X6, SURE_COXB1; | B6J4X6, SURE_COXB1; |
| B6J3X6, SURE_COXB2; | B6J3X6, SURE_COXB2; | B6J3X6, SURE_COXB2; |
| A9KDH9, SURE_COXBN; | A9KDH9, SURE_COXBN; | A9KDH9, SURE_COXBN; |
| A9N9U7, SURE_COXBR; | A9N9U7, SURE_COXBR; | A9N9U7, SURE_COXBR; |
| Q9KI21, SURE_COXBU; | Q9KI21, SURE_COXBU; | Q9KI21, SURE_COXBU; |
| A7MJ60, SURE_CROS8; | A7MJ60, SURE_CROS8; | A7MJ60, SURE_CROS8; |
| Q0K950, SURE_CUPNH; | Q0K950, SURE_CUPNH; | Q0K950, SURE_CUPNH; |
| Q46ZH1, SURE_CUPPJ; | Q46ZH1, SURE_CUPPJ; | Q46ZH1, SURE_CUPPJ; |
| B3R1L4, SURE_CUPTR; | B3R1L4, SURE_CUPTR; | B3R1L4, SURE_CUPTR; |
| B1WXT3, SURE_CYAA5; | B1WXT3, SURE_CYAA5; | B1WXT3, SURE_CYAA5; |
| B8HSQ9, SURE_CYAP4; | B8HSQ9, SURE_CYAP4; | B8HSQ9, SURE_CYAP4; |
| B7KB74, SURE_CYAP7; | B7KB74, SURE_CYAP7; | B7KB74, SURE_CYAP7; |
| Q11WK5, SURE_CYTH3; | Q11WK5, SURE_CYTH3; | Q11WK5, SURE_CYTH3; |
| Q47D24, SURE_DECAR; | Q47D24, SURE_DECAR; | Q47D24, SURE_DECAR; |
| Q3Z8C0, SURE_DEHE1; | Q3Z8C0, SURE_DEHE1; | Q3Z8C0, SURE_DEHE1; |
| A5FR64, SURE_DEHSB; | A5FR64, SURE_DEHSB; | A5FR64, SURE_DEHSB; |
| Q3ZXG5, SURE_DEHSC; | Q3ZXG5, SURE_DEHSC; | Q3ZXG5, SURE_DEHSC; |
| Q1J2E1, SURE_DEIGD; | Q1J2E1, SURE_DEIGD; | Q1J2E1, SURE_DEIGD; |
| Q9RRT8, SURE_DEIRA; | Q9RRT8, SURE_DEIRA; | Q9RRT8, SURE_DEIRA; |
| B8FC91, SURE_DESAA; | B8FC91, SURE_DESAA; | B8FC91, SURE_DESAA; |
| C6BUG4, SURE_DESAD; | C6BUG4, SURE_DESAD; | C6BUG4, SURE_DESAD; |
| B1I3V7, SURE_DESAP; | B1I3V7, SURE_DESAP; | B1I3V7, SURE_DESAP; |

Cells can also be modified by deletion of one or more genes that encode a 3'-nucleotidase, such as one or more genes in Table 3.

TABLE 3

| 3'-Nucleotidases | | |
|---|---|---|
| P08331, CPDB_ECOLI; | P08331, CPDB_ECOLI; | P08331, CPDB_ECOLI; |
| P44764, CPDB_HAEIN; | P44764, CPDB_HAEIN; | P44764, CPDB_HAEIN; |
| P26265, CPDB_SALTY; | P26265, CPDB_SALTY; | P26265, CPDB_SALTY; |
| P53052, CPDB_YEREN; | P53052, CPDB_YEREN; | P53052, CPDB_YEREN; |
| O34313, NTPES_BACSU; | O34313, NTPES_BACSU; | O34313, NTPES_BACSU; |
| P24504, NUP3_PENSQ; | P24504, NUP3_PENSQ; | P24504, NUP3_PENSQ; |
| A8ANV8, SURE_CITK8; | A8ANV8, SURE_CITK8; | A8ANV8, SURE_CITK8; |
| A7MJ60, SURE_CROS8; | A7MJ60, SURE_CROS8; | A7MJ60, SURE_CROS8; |
| A7ZQI8, SURE_ECO24; | A7ZQI8, SURE_ECO24; | A7ZQI8, SURE_ECO24; |
| B7UHG3, SURE_ECO27; | B7UHG3, SURE_ECO27; | B7UHG3, SURE_ECO27; |
| B7MKL8, SURE_ECO45; | B7MKL8, SURE_ECO45; | B7MKL8, SURE_ECO45; |
| B7LEG2, SURE_ECO55; | B7LEG2, SURE_ECO55; | B7LEG2, SURE_ECO55; |
| P0A842, SURE_ECO57; | P0A842, SURE_ECO57; | P0A842, SURE_ECO57; |
| B5Z3A6, SURE_ECO5E; | B5Z3A6, SURE_ECO5E; | B5Z3A6, SURE_ECO5E; |
| B7NT88, SURE_ECO7I; | B7NT88, SURE_ECO7I; | B7NT88, SURE_ECO7I; |
| B7MZ45, SURE_ECO81; | B7MZ45, SURE_ECO81; | B7MZ45, SURE_ECO81; |
| B7LXF6, SURE_ECO8A; | B7LXF6, SURE_ECO8A; | B7LXF6, SURE_ECO8A; |
| C4ZZP8, SURE_ECOBW; | C4ZZP8, SURE_ECOBW; | C4ZZP8, SURE_ECOBW; |
| B1XCS0, SURE_ECODH; | B1XCS0, SURE_ECODH; | B1XCS0, SURE_ECODH; |
| A8A3M3, SURE_ECOHS; | A8A3M3, SURE_ECOHS; | A8A3M3, SURE_ECOHS; |
| A1AET8, SURE_ECOK1; | A1AET8, SURE_ECOK1; | A1AET8, SURE_ECOK1; |
| Q0TEB4, SURE_ECOL5; | Q0TEB4, SURE_ECOL5; | Q0TEB4, SURE_ECOL5; |

A cell expressing a nucleotide triphosphate transporter can be modified to reduce or eliminate the activity of one or more phosphatases. Cells can also be modified by deletion of one or more genes that encode phosphatases such as alkaline phosphatase. Other examples of genes that can be modified to have loss of function include phoA, ushA, appA, aphA, yjjX, surE, yjbR, yjjG, yfaO, mutT, nagD, yggV, yrfG, ymjB, or combinations thereof. In some embodiments, the cells have loss of function mutations in more than one phosphatase gene.

Cells can also be modified by deletion of one or more genes that encode a polynucleotide phosphatase activity. Cells can also be modified by deletion of one or more genes that encode a Nucleotide phosphatase activity, acting on free nucleotides. Cells can also be modified by deletion of one or more genes that encode a nucleotide triphosphatase (NTPases), apyrase; ATP-diphosphatase; adenosine diphosphatase; ADPase; ATP diphosphohydrolase, or any combination thereof, such as one more genes in Table 4.

TABLE 4

Polynucleotide phosphatases

| | | | |
|---|---|---|---|
| ZMA: | 100273224(TIDP3667) 100273583 100281594(pco140907) 100381419 | HSA: | 377841(ENTPD8) 953(ENTPD1) 956(ENTPD3) |
| SITA: | 101757382 101764324 101769705 101772875 101775667 101786001 | PTR: | 100614135(ENTPD1) 460286(ENTPD3) 736974(ENTPD8) |
| SMO: | SELMODRAFT_233281(APY-1) SELMODRAFT_94922 | PPS: | 100971059(ENTPD1) 100983594(ENTPD3) 100995976(ENTPD8) |
| PPP: | PHYPADRAFT_175090 PHYPADRAFT_201168 PHYPADRAFT_31384 | GGO: | 101132716(ENTPD1) 101132747(ENTPD3) |
| CRE: | CHLREDRAFT_167044 CHLREDRAFT_170567 | PON: | 100442938(ENTPD8) 100447406(ENTPD3) 100453241(ENTPD1) |
| VCN: | VOLCADRAFT_120373 VOLCADRAFT_78871 VOLCADRAFT_91259 | MCC: | 703591(ENTPD1) 704424(ENTPD8) 718311(ENTPD3) |
| OLU: | OSTLU_36812 | MCF: | 102134382(ENTPD8) 102138702(ENTPD3) |
| OTA: | Ot04g01290 | MMU: | 12495(Entpd1) 215446(Entpd3) 72090(Entpd8) |
| MIS: | MICPUN_84198 MICPUN_87507 | RNO: | 316077(Entpd3) 613267(Entpd8) 64519(Entpd1) |
| MPP: | MICPUCDRAFT_32900 | CGE: | 100751964(Entpd8) 100762593 100772668 |
| CSL: | COCSUDRAFT_28740 | HGL: | 101696417(Entpd3) 101708535(Entpd8) 101715301(Entpd1) |
| SCE: | YER005W(YND1) | CFA: | 100688937(ENTPD8) 485604(ENTPD3) 486810(ENTPD1) |
| AGO: | AGOS_ADR006W | AML: | 100468369 100473727(ENTPD3) 100474255 |
| ERC: | Ecym_4478 | FCA: | 101085582(ENTPD8) 101096356(ENTPD1) 101098083(ENTPD3) |
| KLA: | KLLA0D13662g | BTA: | 282223(ENTPD1) 506087(ENTPD3) 515532(ENTPD8) |
| LTH: | KLTH0F13178g | BOM: | 102269229(ENTPD8) 102270483(ENTPD1) 102273587(ENTPD3) |
| PPA: | PAS_chr1-1_0063 | PHD: | 102321352(ENTPD1) 102338946(ENTPD3) |
| VPO: | Kpol_312p10 | CHX: | 102189182(ENTPD1) 102190080(ENTPD3) |
| ZRO: | ZYRO0D09570g | SSC: | 100516719(ENTPD8) 100623360(ENTPD3) 397298(ENTPD1) |
| CGR: | CAGL0H09746g | ECB: | 100058558(ENTPD8) 100068004(ENTPD3) 100070956(ENTPD1) |
| NCS: | NCAS_0I00760(NCAS0I00760) | MYB: | 102255350(ENTPD3) 102256383(ENTPD1) |
| NDI: | NDAI_0A08280(NDAI0A08280) | MDO: | 100022843(ENTPD8) 100022899(ENTPD1) 100023686 100025436(ENTPD3) |
| TPF: | TPHA_0L00770(TPHA0L00770) | SHR: | 100914154(ENTPD1) 100919726 100926510(ENTPD3) 100932670(ENTPD8) |
| TBL: | TBLA_0A01060(TBLA0A01060) | OAA: | 100078824(ENTPD3) |
| TDL: | TDEL_0H03120(TDEL0H03120) | GGA: | 374095(ENTPD8) 417281(ENTPD8L) 423826(ENTPD1) 427778(ENTPD1) 428447(ENTPD3) |
| KAF: | KAFR_0L00600(KAFR0L00600) | MGP: | 100543984(ENTPD1) 100546469 100547592 100550087 |
| DHA: | DEHA2D16764g | TGU: | 100218994(ENTPD1) 100221575(ENTPD3) 100229162 |
| PIC: | PICST_75213(YND1) | FAB: | 101806865(ENTPD3) 101809481 101809685 101817605(ENTPD1) |
| PGU: | PGUG_00627 | PHI: | 102099317(ENTPD3) 102105445 102107727(ENTPD8) 102110072(ENTPD1) |
| LEL: | LELG_04414 | APLA: | 101795263 101795762(ENTPD8) 101796222 101801191(ENTPD1) 101804288(ENTPD3) |
| CAL: | CaO19.10432(YND1) CaO19.2915(YND1) | FPG: | 101912881(ENTPD3) 101915751(ENTPD1) 101918437 |
| CTP: | CTRG_04045 | FCH: | 102048208 102054936(ENTPD3) |
| CDU: | CD36_45750 | CLV: | 102083509 102083693 102095399(ENTPD1) 102096210 102097422(ENTPD3) |
| COT: | CORT_0E01960 | ACS: | 100553564 100561052(entpd3) |
| YLI: | YALI0C19712g | ASN: | 102373368(ENTPD1) 102373540(ENTPD3) 102380815 102381055 102381801 |
| CLU: | CLUG_01050 | XLA: | 444164(entpd1) |
| MBR: | MONBRDRAFT_28117 | XTR: | 100125010(entpd3) 448501(entpd1) 733458(entpd8) |
| PFA: | PF14_0297 | DRE: | 100005551(entpd3) 436652(entpd8) 445151(entpd1) |
| TET: | TTHERM_00684480 TTHERM_01256510 | TRU: | 101068571 101070429 |
| PTM: | GSPATT00035597001 GSPATT00037111001 | MZE: | 101473382 101487105 |
| EHX: | EMIHUDRAFT_52732 EMIHUDRAFT_52751 | OLA: | 101165837 101166588 |
| GTT: | GUITHDRAFT_95407 | XMA: | 102217482 102226175 |
| TVA: | TVAG_167570 | LCM: | 102348651(ENTPD3) 102360392(ENTPD8) |
| LPN: | lpg0971 | BFO: | BRAFLDRAFT_124940 |
| LPU: | LPE509_02235 | TSP: | Tsp_07798 |
| LPH: | LPV_1110 | SMM: | Smp_042020.1 |
| LPO: | LPO_1060 | HMG: | 100199550 |
| LPM: | LP6_0959 | AQU: | 100640703 |
| LPF: | lpl1000 | ATH: | AT1G14230 AT1G14240 AT1G14250 AT2G02970 AT3G04080(APY1) AT5G18280(APY2) |

TABLE 4-continued

| Polynucleotide phosphatases | | | |
|---|---|---|---|
| LPP: | lpp1033 | ALY: | ARALYDRAFT_471586 ARALYDRAFT_477668 ARALYDRAFT_679147 ARALYDRAFT_904563 ARALYDRAFT_909838 |
| LPC: | LPC_2316 | GMX: | 100780748 100781628 100786073 100807287 |
| LPA: | lpa_01464 | MTR: | MTR_5g040710 MTR_7g085090 |
| LPE: | lp12_0993 | CAM: | 101497346 101498578 |
| SLY: | 101250072 101252471 101258050 101262543 101268182 | FVE: | 101293262 101304566 |
| OSA: | 4332967 4344315 4345665 4351367 | CSV: | 101203551 101224969 |
| DOSA | Os03t0378000-01(Os03g0378000) Os07t0682800-01(Os07g0682800) Os08t0436100-01(Os08g0436100) Os12t0123500-01(Os12g0123500) | RCU: | RCOM_0836420 RCOM_1122480 |
| BDI | 100825383 100833921 100834806 100834835 100838315 | POP: | POPTR_573883 POPTR_729947 POPTR_765739 POPTR_833712 |
| SBI: | SORBI_01g034030(SORBIDRAFT_01g034030) SORBI_01g036510(SORBIDRAFT_01g036510) SORBI_07g021350(SORBIDRAFT_07g021350) | VVI: | 100244785 100267968 |

Cells can also be modified by deletion of one or more genes that encode a nucleoside diphosphate phosphatase; nucleoside-diphosphatase; thiaminpyrophosphatase; UDPase; inosine diphosphatase; adenosine diphosphatase; IDPase; ADPase; adenosinepyrophosphatase; guanosine diphosphatase; guanosine 5'-diphosphatase; inosine 5'-diphosphatase; uridine diphosphatase; uridine 5'-diphosphatase; type B nucleoside diphosphatase; GDPase; CDPase; nucleoside 5'-diphosphatase; type L nucleoside diphosphatase; NDPase; nucleoside diphosphate phosphohydrolase, or any combination thereof, such as one or more of the genes listed in Table 5.

TABLE 5

| Nucleoside diphosphate phosphatases | | | |
|---|---|---|---|
| HSA: | 124583(CANT1) 955(ENTPD6) 957(ENTPD5) 9583(ENTPD4) | XTR: | 394537(cant1) 677731(entpd4) 677734(entpd5) 677735(entpd6) |
| PTR | 453027(ENTPD5) 458146(ENTPD6) 464056(ENTPD4) 468345(CANT1) | DRE: | 406558(cant1a) 436692(entpd4) 445201(cant1b) 550560(entpd6) 556849 |
| PPS: | 100969324(ENTPD4) 100971740 100974659(CANT1) 100975707(ENTPD5) 100985458(ENTPD6) | TRU: | 101065382 101070342 101075790 101076188 |
| GGO: | 101126430(ENTPD6) 101142724(ENTPD5) 101148282(CANT1) 101148704(ENTPD4) | MZE: | 101466916 101470512 101474178 101481315 101483235 |
| PON: | 100433776(ENTPD4) 100449249(ENTPD6) 100453014(ENTPD5) 100454763(CANT1) | OLA: | 101158069 101165115 101171168 101172088 101173329 |
| MCC: | 698503(ENTPD5) 705663(ENTPD6) 710935(CANT1) 717197(ENTPD4) | XMA: | 102222595 102222865 102222913 102236347 |
| MCF: | 102118635(ENTPD5) 102127579(CANT1) 102133506(ENTPD6) 102139183(ENTPD4) | LCM: | 102345277(CANT1) 102354256(ENTPD6) 102364599(ENTPD4) 102364924(ENTPD5) |
| MMU: | 100862375(Gm21685) 12497(Entpd6) 12499(Entpd5) 67464(Entpd4) 76025(Cant1) | BFO: | BRAFLDRAFT_57510 BRAFLDRAFT_79389 |
| RNO: | 246272(Cant1) 314312(Entpd5) 361063(Entpd4) 85260(Entpd6) | CIN: | 100181442 100181727 |
| CGE: | 100751454(Entpd5) 100765414 100767250(Cant1) 100771637(Entpd4) | SPU: | 576801 580175(entpd4) 587808 |
| HGL: | 101700645(Entpd4) 101703881(Entpd5) 101708374(Cant1) 101717001(Entpd6) | DME: | Dmel_CG5276 |
| CFA: | 480384(ENTPD5) 485564(ENTPD6) 486117(ENTPD4) | DPO: | Dpse_GA18779 |
| AML: | 100470325(ENTPD5) 100474095 100475785(ENTPD4) 100476810 100477887 | DAN: | Dana_GF14909 Dana_GF16866 |
| FCA: | 101083380(CANT1) 101085117(ENTPD4) 101090270(ENTPD5) 101090852(ENTPD6) | DER: | Dere_GG18156 Dere_GG24477 |
| BTA: | 508097(ENTPD6) 518086(CANT1) 531411(ENTPD4) 533096(ENTPD5) | DPE: | Dper_GL12374 Dper_GL26295 |
| BOM: | 102264690(ENTPD6) 102272160(CANT1) 102278224(ENTPD5) 102283172(ENTPD4) | DSE: | Dsec_GM18184 Dsec_GM23945 |
| PHD: | 102316077(ENTPD6) 102317546(CANT1) 102321161(ENTPD4) 102323649(ENTPD5) | DSI: | Dsim_GD18755 Dsim_GD22791 |

TABLE 5-continued

| Nucleoside diphosphate phosphatases | | | |
|---|---|---|---|
| CHX: | 102174488(ENTPD6) 102177094(CANT1) 102177626(ENTPD4) 102187956(ENTPD5) | DWI: | Dwil_GK11295 Dwil_GK18683 |
| SSC: | 100154506(ENTPD5) 100155254(ENTPD4) 100620107(CANT1) 100626131(ENTPD6) | DYA: | Dyak_GE14979 Dyak_GE26097 |
| ECB: | 100053982(ENTPD4) 100056466(ENTPD5) 100057043(ENTPD6) 100057405(CANT1) | DGR: | Dgri_GH11050 Dgri_GH17322 |
| MYB: | 102243929(ENTPD6) 102251396(CANT1) 102251399(ENTPD4) 102262670(ENTPD5) | DMO: | Dmoj_GI10286 Dmoj_GI17567 |
| MDO: | 100021277(ENTPD4) 100024118 100026552(CANT1) 100033226(ENTPD6) | DVI: | Dvir_GJ11094 Dvir_GJ17910 |
| SHR: | 100914260(ENTPD4) 100934101(CANT1) 100934821(ENTPD5) 100935093(ENTPD6) | AGA: | AgaP_AGAP001217 AgaP_AGAP009265 |
| OAA: | 100075558(ENTPD4) 100088014 100088379 | AAG: | AaeL_AAEL005662 AaeL_AAEL006659 |
| GGA: | 416708(ENTPD6) 419531(ENTPD4) 423343(ENTPD5) 430103(CANT1) | CQU: | CpipJ_CPIJ005468 CpipJ_CPIJ006723 |
| MGP: | 100539042 100541241 100550411(ENTPD4) | AME: | 550987(GB18870) 551373 |
| TGU: | 100219260(CANT1) 100220000(ENTPD5) 100224923(ENTPD6) | NVI: | 100120729 |
| FAB: | 101811604(CANT1) 101814014(ENTPD6) 101820141(ENTPD5) | TCA: | 658576 662718 |
| PHI: | 102101855(ENTPD4) 102106545(ENTPD5) 102108288(CANT1) 102109632(ENTPD6) | BMOR: | 101739670 101746124 |
| APLA: | 101790396(CANT1) 101794207(ENTPD5) 101795352(ENTPD4) 101798772(ENTPD6) | API: | 100162387 100166504 |
| FPG: | 101910519(ENTPD4) 101911075(ENTPD5) 101912651(CANT1) 101920667(ENTPD6) | PHU: | Phum_PHUM421050 Phum_PHUM604210 |
| FCH: | 102047237(ENTPD6) 102056974(ENTPD5) 102057968(CANT1) 102058083(ENTPD4) | ISC: | IscW_ISCW018254 |
| CLV: | 102084705(ENTPD5) 102084729(CANT1) 102092438(ENTPD4) 102095170(ENTPD6) | CEL: | CELE_F08C6.6(apy-1) CELE_K08H10.4(uda-1) CELE_R07E4.4(mig-23) |
| ACS: | 100555642 100561218 100562980(entpd4) 100563392 | CBR: | CBG11542(Cbr-uda-1) CBG14198 CBG14784(Cbr-mig-23) CBG16731 |
| ASN: | 102377226(ENTPD5) 102382407(ENTPD4) 102384786(ENTPD6) 102387737(CANT1) | BMY: | Bm1_34420 |
| XLA: | 379060(cant1) 495422(entpd4) 734187(entpd6) | LOA: | LOAG_01305 |
| PTI: | PHATRDRAFT_14301 | TSP: | Tsp_09215 Tsp_09582 |
| TPS: | THAPSDRAFT_31247 | SMM: | Smp_081450 Smp_166520 |
| PIF: | PITG_20792 | NVE: | NEMVE_v1g175561 |
| EHX: | EMIHUDRAFT_43184 | HMG: | 100202807 100204155 |
| TBR: | Tb927.7.1930(Tb07.43M14.370) | TAD: | TRIADDRAFT_21256 TRIADDRAFT_32564 TRIADDRAFT_61888 |
| LMA: | LMJF_15_0030 | AQU: | 100640578 |
| LIF: | LINJ_15_0030 | CME: | CYME_CMQ456C |
| LDO: | LDBPK_150030 | GSL: | Gasu_48820 |
| LMI: | LMXM_15_0030 | CCP: | CHC_T00001236001 CHC_T00003677001 |
| LBZ: | LBRM_15_0030 | MBR: | MONBRDRAFT_2652 MONBRDRAFT_28836 |
| NGR: | NAEGRDRAFT_79292 | EHI: | EHI_053610(59.t00033) EHI_104590(415.t00008) EHI_112890(17.t00006) |
| CPV: | cgd6_1570 | EDI: | EDI_058390 EDI_125320 EDI_305410 |
| CHO: | Chro.60194 | ACAN: | ACA1_330420 |
| TGO: | TGME49_110810 | PFA: | PF14_0297 |

Figure 7A:
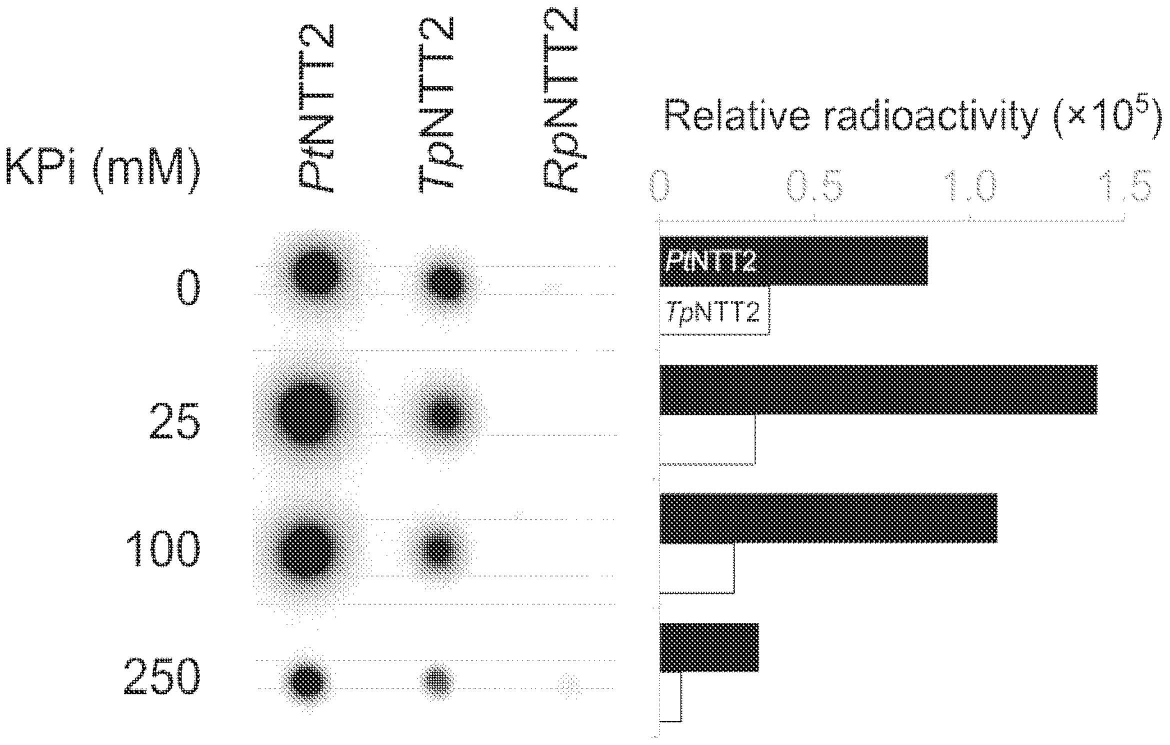
FIG. 7A depicts raw (left) and processed (right) data inhibits the uptake of [α-$^{32}$P]-dATP uptake into cells in the presence of the indicated KPi concentrations. The NTT from *Rickettsia prowazekii* (RpNTT2) was used as a negative control: its background signal was subtracted from those of PtNTT2 (black bars) and TpNTT2 (white bars). Relative radioactivity corresponds to the total number of counts produced by each sample.
Figure 7B:
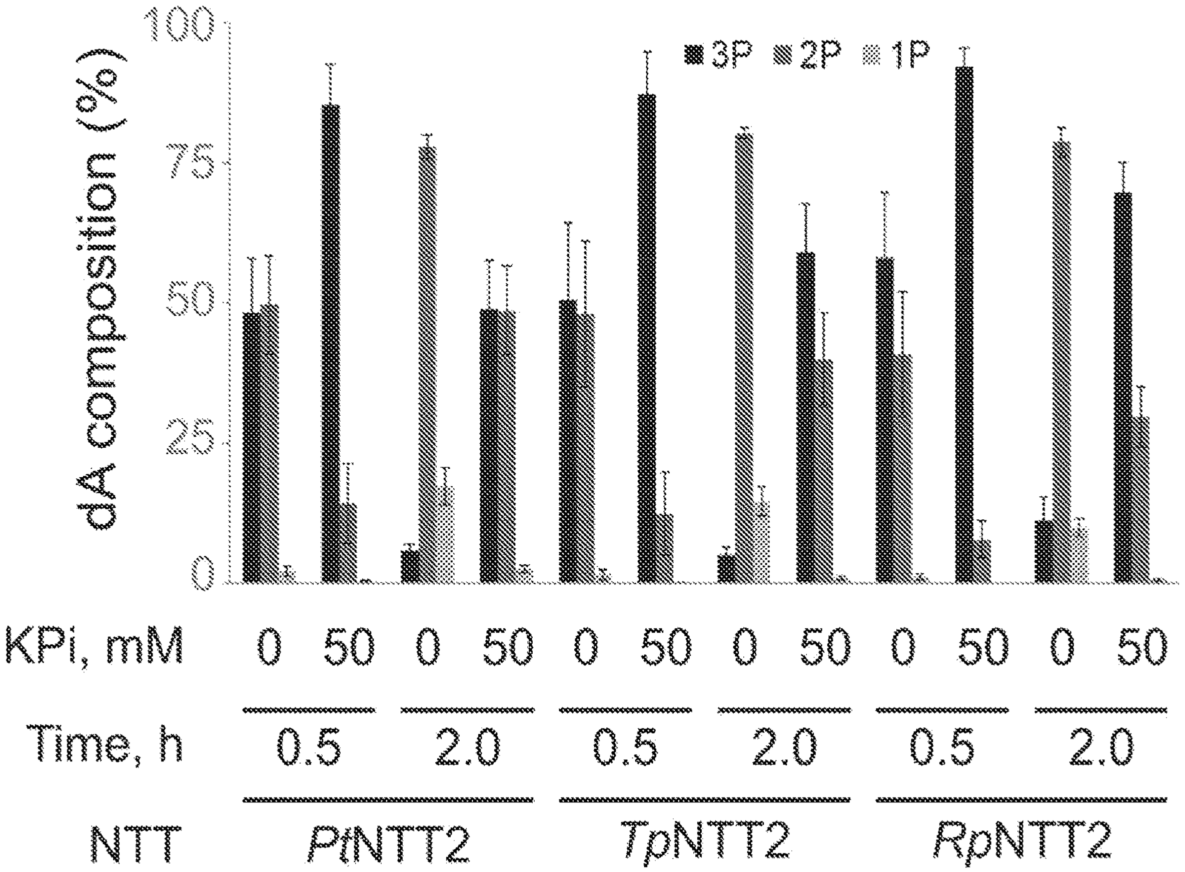
FIG. 7B depicts a graph showing the % composition of [α-$^{32}$P]-dATP in the presence or absence of 50 mM KPi in media from cells expressing the indicated NTTs.
Figure 8A:
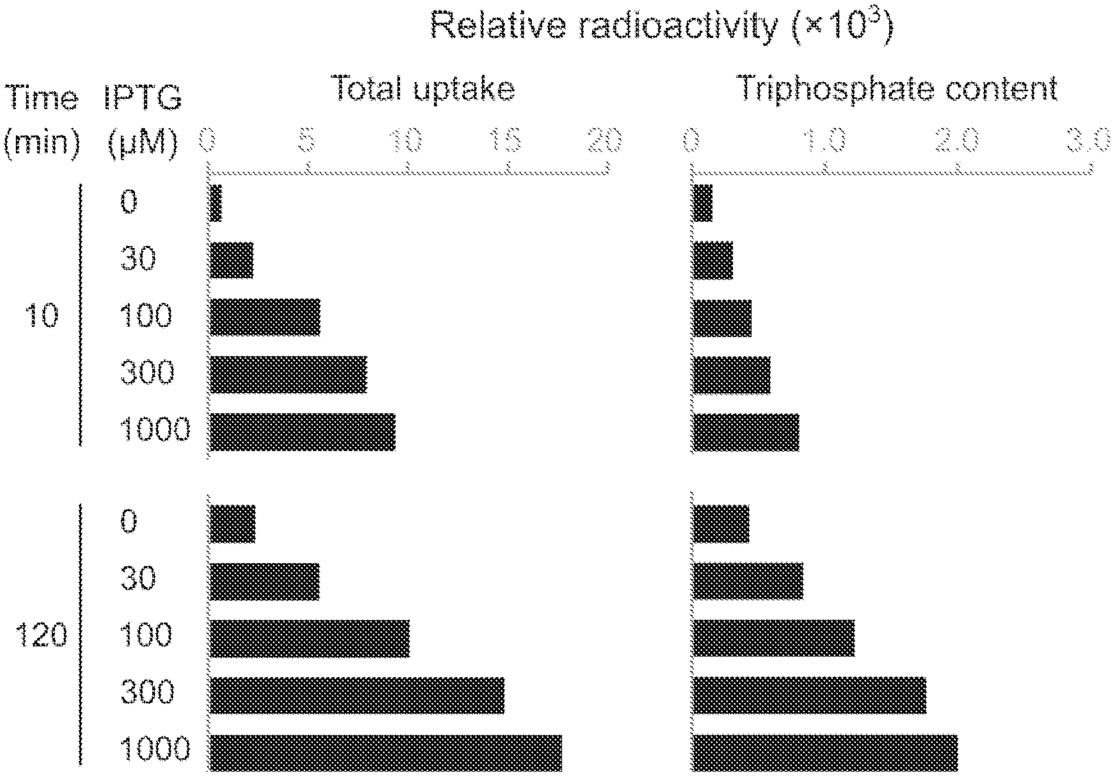
FIG. 8A depicts a graph of the total uptake of radioactive substrate (left) and total intracellular triphosphate content (right) at the indicated time points as a function of IPTG concentration. Relative radioactivity corresponds to the total number of counts produced by each sample.

The extracellular stability of natural nucleic acids, e.g, dATP, was discovered to be significantly increased in the presence of potassium phosphate (KPi) in the growth medium. KPi significantly inhibited the dephosphorylation of unnatural triphosphates (FIG. 6). Such addition of potassium phosphate may suppress phosphatase expression or inhibit phosphatase activity (FIG. 7). As with the natural triphosphate, the addition of potassium phosphate significantly increased the extracellular stability of d5SICSTP and dNaMTP (FIG. 6) by more than 2-fold. The uptake of [$\alpha$-$^{32}$P]-dATP from media containing 50 mM KPi as a function of transporter induction, e.g, with IPTG, can also be determined (FIG. 8). 1 mMv IPTG induction resulted in maximal [$\alpha$-$^{32}$P]-dATP uptake (FIG. 8A).

Figure 8B:
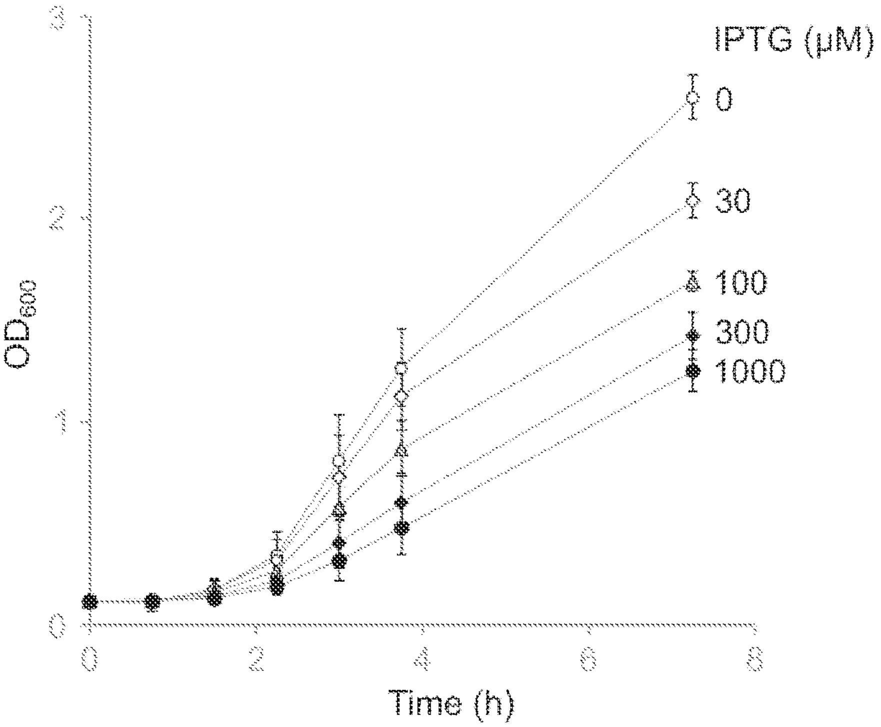
FIG. 8B depicts growth curves and [α-$^{32}$P]-dATP uptake by bacterial cells transformed with pCDF-1b-PtNTT2 (pACS) plasmid as a function of IPTG concentration.
Figure 9A:
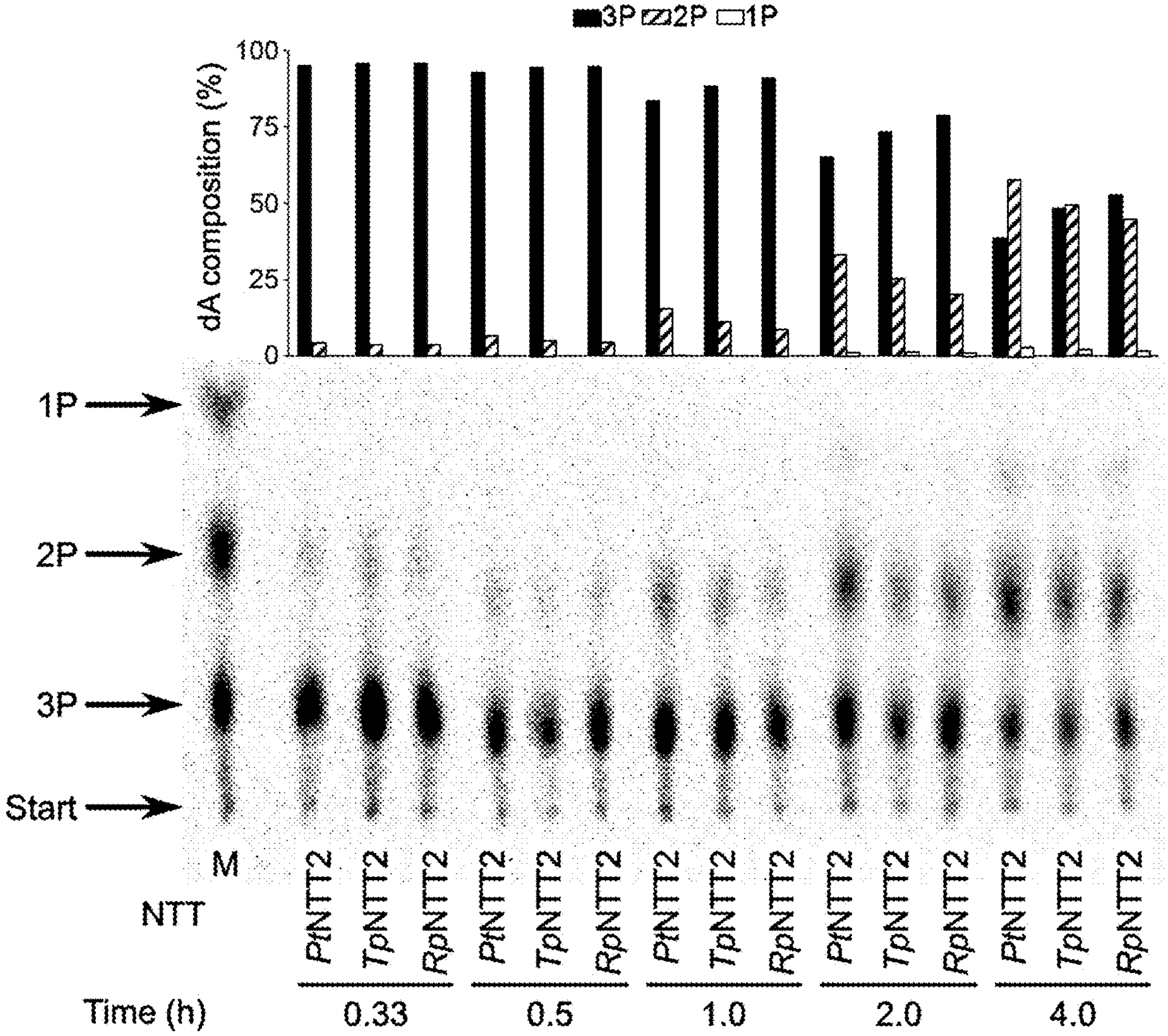
FIG. 9A depicts TLC images (bottom) [α-$^{32}$P]-dATP in the media as a function of time and their quantifications (top). M refers to a mixture of all three compounds [3P, 2P and 1P] that was used as a TLC standard. The position labeled “Start” corresponds to the position of sample spotting on the TLC plate.
Figure 9B:
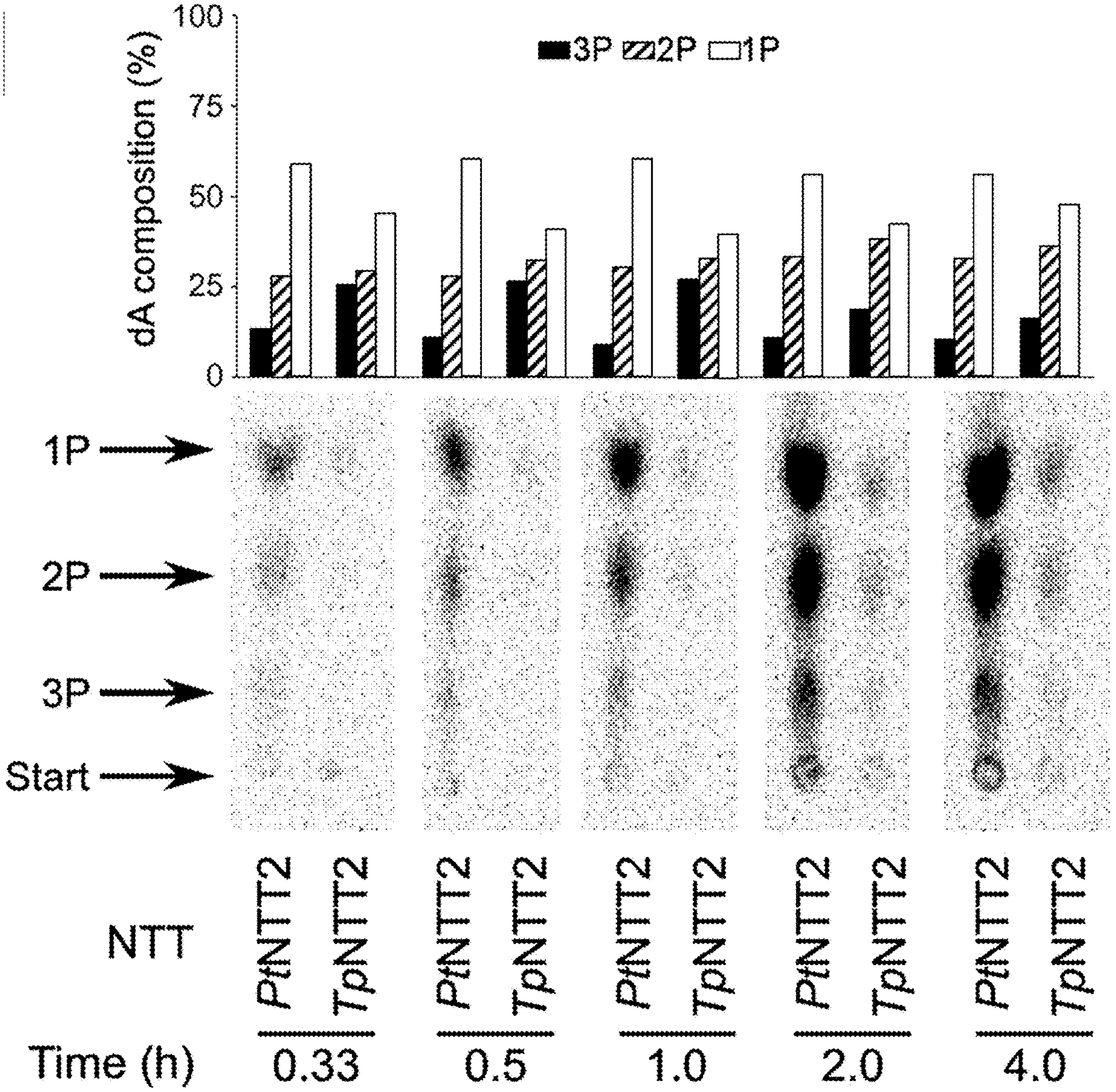
FIG. 9B depicts TLC images (bottom) [α-P]-dATP in cell lysates as a function of time and their quantifications (top). M refers to a mixture of all three compounds [3P, 2P and 1P] that was used as a TLC standard. The position labeled “Start” corresponds to the position of sample spotting on the TLC plate.

Inhibitors of phosphatases can be employed to increase the stability of one or more unnatural and/or natural nucleic acids. In this manner, inhibitors of phosphatases can be employed to facilitate intracellular import and transport of nucleic acids. The uptake of [$\alpha$-$^{32}$P]-dATP from media containing 50 mM KPi as a function of transporter induction, e.g, with IPTG, can be determined (FIG. 8).

Potassium phosphate can facilitate such transport. In some embodiments, a phosphatase inhibitor, e.g., KPi, facilitates intracellular import and transport of nucleic acids at a pH. In some embodiments, a phosphatase inhibitor, e.g., KPi, facilitates intracellular import and transport of nucleic acids at approximately neutral pH. Such a neutral pH can be between about pH 4.5 to pH 8.5, or between about pH 6.8 to about pH 7.6, or about pH 7.0 to about pH 7.4.

In some embodiments, a phosphatase inhibitor, e.g., KPi, facilitates intracellular import and transport of nucleic acids at a concentration. A variety of phosphatase inhibitor, e.g., KPi, concentrations can be employed. For example, the phosphatase inhibitor, e.g., KPi, can be present at a concentration of 0.1 mM to 500 mM, or 0.2 mM to 250 mM, or 0.25 mM to 200 mM, or 1.0 mM to 150 mM, or 2.5 mM to 125 mM, or 5 mM to 100 mM, or 25 mM to 75 mM, or 40 mM to 60 mM potassium phosphate. As illustrated, 50 mM phosphatase inhibitor, e.g., KPi, appears to be sufficient for initial contact of the cells and unnatural nucleotide triphosphates (FIG. 7B). Inhibitors of phosphatases can be employed, either with addition of potassium phosphate or without addition of potassium phosphate.

In some embodiments, disruption of a nucleotidase or phosphatase, or addition of a phosphatase inhibitor, e.g., KPi, can be used to increase the half-life of a natural and unnatural nucleotide triphosphates. For example, disruption of a nucleotidase or phosphatase, or addition of a phosphatase inhibitor can be used to increase the half-life of a natural nucleic acid and/or an unnatural nucleic acid by at least about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11.0, 11.5, 12.0, 12.5, 3.0, 13.5, 14.0, 14.5, 15.0, 15.5, 16.0, 16.5, 17.0, 17.5, 18.0, 18.5, 19.0, 19.5, 20, 25, 30, 35, 40, 45, 50, 55, 60, 65, 70, 75, 80, 85, 90, 95, 100 or more hours.

In some embodiments, disruption of a nucleotidase or phosphatase, or addition of a phosphatase inhibitor, e.g., KPi, can be used to increase the stability of a natural nucleic acid and/or an unnatural nucleic acid such that the natural or unnatural nucleic acid intracellular concentration is at least the $K_M$ value of the natural or unnatural nucleic acid for a polymerase. For example, disruption of a nucleotidase or phosphatase, or addition of a phosphatase inhibitor can be used increase the stability of natural and unnatural nucleotide triphosphates such that their intracellular concentration is at least about 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11.0, 11.5, 12.0, 12.5, 3.0, 13.5, 14.0, 14.5, 15.0, 15.5, 16.0, 16.5, 17.0, 17.5, 18.0, 18.5, 19.0, 19.5, 20, 25, 30, 35, 40, 45, 50, 55, 60, 65, 70, 75, 80, 85, 90, 95, 100 or more times the $K_M$ value of the natural or unnatural nucleic acid for a polymerase.

Kits

Various combinations of the components set forth above in regard to exemplary reaction mixtures and reaction methods can be provided in a kit form. Such a kit can include individual components that are separated from each other, for example, being carried in separate vessels or packages. A kit can include one or more sub-combinations of the components set forth herein, the one or more sub-combinations being separated from other components of the kit. The sub-combinations can be combinable to create a reaction mixture set forth herein (or combined to perform a reaction set forth herein). In particular embodiments, a sub-combination of components that is present in an individual vessel or package is insufficient to perform a reaction set forth herein.

However, the kit as a whole can include a collection of vessels or packages the contents of which can be combined to perform a reaction set forth herein.

A kit can include a suitable packaging material to house the contents of the kit. The packaging material can be constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit. For example, a label can indicate that the kit is useful for a method of synthesizing a polynucleotide or for a method of determining the sequence of a nucleic acid.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

According to an aspect of the present invention, a kit is provided that is useful for stably incorporating an unnatural nucleic acid into a cellular nucleic acid, e.g., using the methods provided by the present invention for preparing genetically engineered cells. In one embodiment, a kit of the invention includes a genetically engineered cell and one or more unnatural nucleic acids.

In another embodiment, a kit of the invention includes a primer that binds to a portion of a nucleic acid molecule containing an unnatural nucleic acid. In another embodiment, the kit includes a microarray that contains primers that binds to a portion of a nucleic acid molecule containing an unnatural nucleic acid and at least a fragment of a target gene of interest. In some embodiments, many reagents may be provided in a kit of the invention, only some of which should be used together in a particular reaction or procedure. For example, multiple primers may be provided, only two of which are needed for a particular application.

In another embodiment, the kit of the invention provides a cell and a nucleic acid molecule containing a heterologous gene for introduction into the cell to thereby provide a genetically engineered cell. For example, the invention provides expression vectors comprising the nucleic acid of any of the embodiments hereinabove described in this paragraph. In one embodiment, the expression vector of the foregoing further comprises a recombinant regulatory sequence operably linked to the polynucleotide sequence.

Nucleic Acid Reagents & Tools

A nucleic acid reagent sometimes comprises one or more ORFs. An ORF may be from any suitable source, sometimes from genomic DNA, mRNA, reverse transcribed RNA or complementary DNA (cDNA) or a nucleic acid library comprising one or more of the foregoing, and is from any organism species that contains a nucleic acid sequence of interest, protein of interest, or activity of interest. Non-limiting examples of organisms from which an ORF can be obtained include bacteria, yeast, fungi, human, insect, nematode, bovine, equine, canine, feline, rat or mouse, for example. In some embodiments, a nucleic acid reagent, protein reagent, protein fragment reagent or other reagent described herein is isolated or purified.

A nucleic acid reagent sometimes comprises a nucleotide sequence adjacent to an ORF that is translated in conjunction with the ORF and encodes an amino acid tag. The tag-encoding nucleotide sequence is located 3' and/or 5' of an ORF in the nucleic acid reagent, thereby encoding a tag at the C-terminus or N-terminus of the protein or peptide encoded by the ORF. Any tag that does not abrogate in vitro transcription and/or translation may be utilized and may be appropriately selected by the artisan. Tags may facilitate isolation and/or purification of the desired ORF product from culture or fermentation media.

A tag sometimes specifically binds a molecule or moiety of a solid phase or a detectable label, for example, thereby having utility for isolating, purifying and/or detecting a protein or peptide encoded by the ORF. In some embodiments, a tag comprises one or more of the following elements: FLAG (e.g., DYKDDDDKG) (SEQ ID NO:42), V5 (e.g., GKPIPNPLLGLDST) (SEQ ID NO:43), c-MYC (e.g., EQKLISEEDL) (SEQ ID NO: 44), HSV (e.g., QPELAPEDPED) (SEQ ID NO: 45), influenza hemaglutinin, HA (e.g., YPYDVPDYA) (SEQ ID NO: 46), VSV-G (e.g., YTDIEMNRLGK) (SEQ ID NO: 47), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC, wherein X is any amino acid and n is 1 to 3, and the cysteine-rich sequence sometimes is CCPGCC. In certain embodiments, the tag comprises a cysteine-rich element and a polyhistidine element (e.g., CCPGCC (SEQ ID NO: 48), and His6).

A tag often conveniently binds to a binding partner. For example, some tags bind to an antibody (e.g., FLAG) and sometimes specifically bind to a small molecule. For example, a polyhistidine tag specifically chelates a bivalent metal, such as nickel, copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents (e.g., U.S. Pat. Nos. 5,932,474; 6,054,271; 6,451,569; and 6,008,378; U.S. Patent Publication No. US2003/0083373; and International Publication No. WO99/21013). Such antibodies and small molecules sometimes are linked to a solid phase for convenient isolation of the target protein or target peptide.

A tag sometimes comprises a signal sequence or localization signal sequence. A signal sequence can be incorporated at the N-terminus of a target protein or target peptide, and sometimes is incorporated at the C-terminus. Examples of signal sequences are known to the artisan, are readily incorporated into a nucleic acid reagent, and often are selected according to the organism in which expression of the nucleic acid reagent is performed. A signal sequence in some embodiments localizes a translated protein or peptide to a cell membrane. Examples of signal sequences include, but are not limited to, a nucleus targeting signal (e.g., steroid receptor sequence and N-terminal sequence of SV40 virus large T antigen); mitochondrial targeting signal (e.g., amino acid sequence that forms an amphipathic helix); peroxisome targeting signal (e.g., C-terminal sequence in YFG from *S. cerevisiae*); and a secretion signal (e.g., N-terminal sequences from invertase, mating factor alpha, PHO5 and SUC2 in *S. cerevisiae*; multiple N-terminal sequences of *B. subtilis* proteins (e.g., Tjalsma et al., Microbiol. Molec. Biol. Rev. 64: 515-547 (2000)); alpha amylase signal sequence (e.g., U.S. Pat. No. 6,288,302); pectate lyase signal sequence (e.g., U.S. Pat. No. 5,846,818); precollagen signal sequence (e.g., U.S. Pat. No. 5,712,114); OmpA signal sequence (e.g., U.S. Pat. No. 5,470,719); lam beta signal sequence (e.g., U.S. Pat. No. 5,389,529); *B. brevis* signal sequence (e.g., U.S. Pat. No. 5,232,841); and *P. pastoris* signal sequence (e.g., U.S. Pat. No. 5,268,273).

A tag sometimes is directly adjacent to the amino acid sequence encoded by an ORF (i.e., there is no intervening sequence) and sometimes a tag is substantially adjacent to an ORF encoded amino acid sequence (e.g., an intervening sequence is present). An intervening sequence sometimes includes a recognition site for a protease, which is useful for cleaving a tag from a target protein or peptide. In some embodiments, the intervening sequence is cleaved by Factor Xa (e.g., recognition site I (E/D)GR), thrombin (e.g., recognition site LVPRGS), enterokinase (e.g., recognition site DDDDK), TEV protease (e.g., recognition site ENLYFQG) or PreScission™ protease (e.g., recognition site LEVLFQGP), for example.

An intervening sequence sometimes is referred to herein as a "linker sequence," and may be of any suitable length selected by the artisan. A linker sequence sometimes is about 1 to about 20 amino acids in length, and sometimes about 5 to about 10 amino acids in length. The artisan may select the linker length to substantially preserve target protein or peptide function (e.g., a tag may reduce target protein or peptide function unless separated by a linker), to enhance disassociation of a tag from a target protein or peptide when a protease cleavage site is present (e.g., cleavage may be enhanced when a linker is present), and to enhance interaction of a tag/target protein product with a solid phase. A linker can be of any suitable amino acid content, and often comprises a higher proportion of amino acids having relatively short side chains (e.g., glycine, alanine, serine and threonine).

A nucleic acid reagent sometimes includes a stop codon between a tag element and an insertion element or ORF, which can be useful for translating an ORF with or without the tag. Mutant tRNA molecules that recognize stop codons (described above) suppress translation termination and thereby are designated "suppressor tRNAs." Suppressor tRNAs can result in the insertion of amino acids and continuation of translation past stop codons (e.g., U.S. Patent Application No. 60/587,583; Eggertsson, et al., (1988) Microbiological Review 52(3):354-374, and Engleerg-Kukla, et al. (1996) in *Escherichia coli* and *Sal-*

*monella* Cellular and Molecular Biology, Chapter 60, pps 909-921, Neidhardt, et al. eds., ASM Press, Washington, D.C.). A number of suppressor tRNAs are known, including but not limited to, supE, supP, supD, supF and supZ suppressors, which suppress the termination of translation of the amber stop codon; supB, glT, supL, supN, supC and supM suppressors, which suppress the function of the ochre stop codon and glyT, trpT and Su-9 suppressors, which suppress the function of the opal stop codon. In general, suppressor tRNAs contain one or more mutations in the anti-codon loop of the tRNA that allows the tRNA to base pair with a codon that ordinarily functions as a stop codon. The mutant tRNA is charged with its cognate amino acid residue and the cognate amino acid residue is inserted into the translating polypeptide when the stop codon is encountered. Mutations that enhance the efficiency of termination suppressors (i.e., increase stop codon read-through) have been identified. These include, but are not limited to, mutations in the uar gene (also known as the prfA gene), mutations in the ups gene, mutations in the sueA, sueB and sueC genes, mutations in the rpsD (ramA) and rpsE (spcA) genes and mutations in the rplL gene.

Thus, a nucleic acid reagent comprising a stop codon located between an ORF and a tag can yield a translated ORF alone when no suppressor tRNA is present in the translation system, and can yield a translated ORF-tag fusion when a suppressor tRNA is present in the system. Suppressor tRNA can be generated in cells transfected with a nucleic acid encoding the tRNA (e.g., a replication incompetent adenovirus containing the human tRNA-Ser suppressor gene can be transfected into cells, or a YAC containing a yeast or bacterial tRNA suppressor gene can be transfected into yeast cells, for example). Vectors for synthesizing suppressor tRNA and for translating ORFs with or without a tag are available to the artisan (e.g., Tag-On-Demand™ kit (Invitrogen Corporation, California); Tag-On-Demand™ Suppressor Supernatant Instruction Manual, Version B, 6 Jun. 2003; Tag-On-Demand™ Gateway® Vector Instruction Manual, Version B, 20 June, 2003; and Capone et al., EMBO J., 4:213, 1985).

A nucleic acid or nucleic acid reagent can comprise certain elements, e.g., regulatory elements, often selected according to the intended use of the nucleic acid. Any of the following elements can be included in or excluded from a nucleic acid reagent. A nucleic acid reagent, for example, may include one or more or all of the following nucleotide elements: one or more promoter elements, one or more 5' untranslated regions (5'UTRs), one or more regions into which a target nucleotide sequence may be inserted (an "insertion element"), one or more target nucleotide sequences, one or more 3' untranslated regions (3'UTRs), and one or more selection elements. A nucleic acid reagent can be provided with one or more of such elements and other elements may be inserted into the nucleic acid before the nucleic acid is introduced into the desired organism. In some embodiments, a provided nucleic acid reagent comprises a promoter, 5'UTR, optional 3'UTR and insertion element(s) by which a target nucleotide sequence is inserted (i.e., cloned) into the nucleotide acid reagent. In certain embodiments, a provided nucleic acid reagent comprises a promoter, insertion element(s) and optional 3'UTR, and a 5' UTR/target nucleotide sequence is inserted with an optional 3'UTR. The elements can be arranged in any order suitable for expression in the chosen expression system (e.g., expression in a chosen organism, or expression in a cell free system, for example), and in some embodiments a nucleic acid reagent comprises the following elements in the 5' to 3' direction: (1) promoter element, 5'UTR, and insertion element(s); (2) promoter element, 5'UTR, and target nucleotide sequence; (3) promoter element, 5'UTR, insertion element (s) and 3'UTR; and (4) promoter element, 5'UTR, target nucleotide sequence and 3'UTR.

Nucleic acid reagents, e.g., expression cassettes and/or expression vectors, can include a variety of regulatory elements, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleotide triphosphate transporter nucleic acid segment. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3" to the transcription unit. Furthermore, enhancers can be within an intron as well as within the coding sequence itself. They are usually between 10 and 300 by in length, and they function in cis. Enhancers function to increase transcription from nearby promoters. Enhancers, like promoters, also often contain response elements that mediate the regulation of transcription. Enhancers often determine the regulation of expression.

As noted above, nucleic acid reagents may also comprise one or more 5' UTR's, and one or more 3'UTR's. For example, expression vectors used in eukaryotic host cells (e.g., yeast, fungi, insect, plant, animal, human or nucleated cells) and prokaryotic host cells (e.g., virus, bacterium) can contain sequences that signal for the termination of transcription which can affect mRNA expression. These regions can be transcribed as polyadenylated segments in the untranslated portion of the mRNA encoding tissue factor protein. The 3" untranslated regions also include transcription termination sites. In some preferred embodiments, a transcription unit comprises a polyadenylation region. One benefit of this region is that it increases the likelihood that the transcribed unit will be processed and transported like mRNA. The identification and use of polyadenylation signals in expression constructs is well established. In some preferred embodiments, homologous polyadenylation signals can be used in the transgene constructs.

A 5' UTR may comprise one or more elements endogenous to the nucleotide sequence from which it originates, and sometimes includes one or more exogenous elements. A 5' UTR can originate from any suitable nucleic acid, such as genomic DNA, plasmid DNA, RNA or mRNA, for example, from any suitable organism (e.g., virus, bacterium, yeast, fungi, plant, insect or mammal). The artisan may select appropriate elements for the 5' UTR based upon the chosen expression system (e.g., expression in a chosen organism, or expression in a cell free system, for example). A 5' UTR sometimes comprises one or more of the following elements known to the artisan: enhancer sequences (e.g., transcriptional or translational), transcription initiation site, transcription factor binding site, translation regulation site, translation initiation site, translation factor binding site, accessory protein binding site, feedback regulation agent binding sites, Pribnow box, TATA box, −35 element, E-box (helix-loop-helix binding element), ribosome binding site, replicon, internal ribosome entry site (IRES), silencer element and the like. In some embodiments, a promoter element may be isolated such that all 5' UTR elements necessary for proper conditional regulation are contained in the promoter element fragment, or within a functional subsequence of a promoter element fragment.

A 5'UTR in the nucleic acid reagent can comprise a translational enhancer nucleotide sequence. A translational enhancer nucleotide sequence often is located between the promoter and the target nucleotide sequence in a nucleic acid reagent. A translational enhancer sequence often binds to a ribosome, sometimes is an 18S rRNA-binding ribonucleotide sequence (i.e., a 40S ribosome binding sequence) and sometimes is an internal ribosome entry sequence (IRES). An IRES generally forms an RNA scaffold with precisely placed RNA tertiary structures that contact a 40S ribosomal subunit via a number of specific intermolecular interactions. Examples of ribosomal enhancer sequences are known and can be identified by the artisan (e.g., Mignone et al., Nucleic Acids Research 33: D141-D146 (2005); Paulous et al., Nucleic Acids Research 31: 722-733 (2003); Akbergenov et al., Nucleic Acids Research 32: 239-247 (2004); Mignone et al., Genome Biology 3(3): reviews0004.1-0001.10 (2002); Gallie, Nucleic Acids Research 30: 3401-3411 (2002); Shaloiko et al., DOI: 10.1002/bit.20267; and Gallie et al., Nucleic Acids Research 15: 3257-3273 (1987)).

A translational enhancer sequence sometimes is a eukaryotic sequence, such as a Kozak consensus sequence or other sequence (e.g., hydroid polyp sequence, GenBank accession no. U07128). A translational enhancer sequence sometimes is a prokaryotic sequence, such as a Shine-Dalgarno consensus sequence. In certain embodiments, the translational enhancer sequence is a viral nucleotide sequence. A translational enhancer sequence sometimes is from a 5' UTR of a plant virus, such as Tobacco Mosaic Virus (TMV), Alfalfa Mosaic Virus (AMV); Tobacco Etch Virus (ETV); Potato Virus Y (PVY); Turnip Mosaic (poty) Virus and Pea Seed Borne Mosaic Virus, for example. In certain embodiments, an omega sequence about 67 bases in length from TMV is included in the nucleic acid reagent as a translational enhancer sequence (e.g., devoid of guanosine nucleotides and includes a 25 nucleotide long poly (CAA) central region).

A 3' UTR may comprise one or more elements endogenous to the nucleotide sequence from which it originates and sometimes includes one or more exogenous elements. A 3' UTR may originate from any suitable nucleic acid, such as genomic DNA, plasmid DNA, RNA or mRNA, for example, from any suitable organism (e.g., a virus, bacterium, yeast, fungi, plant, insect or mammal). The artisan can select appropriate elements for the 3' UTR based upon the chosen expression system (e.g., expression in a chosen organism, for example). A 3' UTR sometimes comprises one or more of the following elements known to the artisan: transcription regulation site, transcription initiation site, transcription termination site, transcription factor binding site, translation regulation site, translation termination site, translation initiation site, translation factor binding site, ribosome binding site, replicon, enhancer element, silencer element and polyadenosine tail. A 3' UTR often includes a polyadenosine tail and sometimes does not, and if a polyadenosine tail is present, one or more adenosine moieties may be added or deleted from it (e.g., about 5, about 10, about 15, about 20, about 25, about 30, about 35, about 40, about 45 or about 50 adenosine moieties may be added or subtracted).

In some embodiments, modification of a 5' UTR and/or a 3' UTR can be used to alter (e.g., increase, add, decrease or substantially eliminate) the activity of a promoter. Alteration of the promoter activity can in turn alter the activity of a peptide, polypeptide or protein (e.g., enzyme activity for example), by a change in transcription of the nucleotide sequence(s) of interest from an operably linked promoter element comprising the modified 5' or 3' UTR. For example, a microorganism can be engineered by genetic modification to express a nucleic acid reagent comprising a modified 5' or 3' UTR that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent comprising a modified 5' or 3' UTR that can decrease the expression of an activity by decreasing or substantially eliminating transcription from a homologous or heterologous promoter operably linked to a nucleotide sequence of interest, in certain embodiments.

Expression of a nucleotide triphosphate transporter from an expression cassette or expression vector can be controlled by any promoter capable of expression in prokaryotic cells or eukaryotic cells. A promoter element typically is required for DNA synthesis and/or RNA synthesis. A promoter element often comprises a region of DNA that can facilitate the transcription of a particular gene, by providing a start site for the synthesis of RNA corresponding to a gene. Promoters generally are located near the genes they regulate, are located upstream of the gene (e.g., 5' of the gene), and are on the same strand of DNA as the sense strand of the gene, in some embodiments. In some embodiments, a promoter element can be isolated from a gene or organism and inserted in functional connection with a polynucleotide sequence to allow altered and/or regulated expression. A non-native promoter (e.g., promoter not normally associated with a given nucleic acid sequence) used for expression of a nucleic acid often is referred to as a heterologous promoter. In certain embodiments, a heterologous promoter and/or a 5'UTR can be inserted in functional connection with a polynucleotide that encodes a polypeptide having a desired activity as described herein. The terms "operably linked" and "in functional connection with" as used herein with respect to promoters, refer to a relationship between a coding sequence and a promoter element. The promoter is operably linked or in functional connection with the coding sequence when expression from the coding sequence via transcription is regulated, or controlled by, the promoter element. The terms "operably linked" and "in functional connection with" are utilized interchangeably herein with respect to promoter elements.

A promoter often interacts with a RNA polymerase. A polymerase is an enzyme that catalyzes synthesis of nucleic acids using a preexisting nucleic acid reagent. When the template is a DNA template, an RNA molecule is transcribed before protein is synthesized. Enzymes having polymerase activity suitable for use in the present methods include any polymerase that is active in the chosen system with the chosen template to synthesize protein. In some embodiments, a promoter (e.g., a heterologous promoter) also referred to herein as a promoter element, can be operably linked to a nucleotide sequence or an open reading frame (ORF). Transcription from the promoter element can catalyze the synthesis of an RNA corresponding to the nucleotide sequence or ORF sequence operably linked to the promoter, which in turn leads to synthesis of a desired peptide, polypeptide or protein.

Promoter elements sometimes exhibit responsiveness to regulatory control. Promoter elements also sometimes can be regulated by a selective agent. That is, transcription from promoter elements sometimes can be turned on, turned off, up-regulated or down-regulated, in response to a change in environmental, nutritional or internal conditions or signals (e.g., heat inducible promoters, light regulated promoters, feedback regulated promoters, hormone influenced promoters, tissue specific promoters, oxygen and pH influenced promoters, promoters that are responsive to selective agents (e.g., kanamycin) and the like, for example). Promoters influenced by environmental, nutritional or internal signals frequently are influenced by a signal (direct or indirect) that binds at or near the promoter and increases or decreases expression of the target sequence under certain conditions.

Non-limiting examples of selective or regulatory agents that can influence transcription from a promoter element used in embodiments described herein include, without limitation, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like). In some embodiments, the regulatory or selective agent can be added to change the existing growth conditions to which the organism is subjected (e.g., growth in liquid culture, growth in a fermenter, growth on solid nutrient plates and the like for example).

In some embodiments, regulation of a promoter element can be used to alter (e.g., increase, add, decrease or substantially eliminate) the activity of a peptide, polypeptide or protein (e.g., enzyme activity for example). For example, a microorganism can be engineered by genetic modification to express a nucleic acid reagent that can add a novel activity (e.g., an activity not normally found in the host organism) or increase the expression of an existing activity by increasing transcription from a homologous or heterologous promoter operably linked to a nucleotide sequence of interest (e.g., homologous or heterologous nucleotide sequence of interest), in certain embodiments. In some embodiments, a microorganism can be engineered by genetic modification to express a nucleic acid reagent that can decrease expression of an activity by decreasing or substantially eliminating transcription from a homologous or heterologous promoter operably linked to a nucleotide sequence of interest, in certain embodiments.

Nucleic acids encoding heterologous proteins, e.g., nucleotide triphosphate transporters, can be inserted into or employed with any suitable expression system. In some embodiments, a nucleic acid reagent sometimes is stably integrated into the chromosome of the host organism, or a nucleic acid reagent can be a deletion of a portion of the host chromosome, in certain embodiments (e.g., genetically modified organisms, where alteration of the host genome confers the ability to selectively or preferentially maintain the desired organism carrying the genetic modification). Such nucleic acid reagents (e.g., nucleic acids or genetically modified organisms whose altered genome confers a selectable trait to the organism) can be selected for their ability to guide production of a desired protein or nucleic acid molecule. When desired, the nucleic acid reagent can be altered such that codons encode for (i) the same amino acid, using a different tRNA than that specified in the native sequence, or (ii) a different amino acid than is normal, including unconventional or unnatural amino acids (including detectably labeled amino acids).

Recombinant expression is usefully accomplished using an expression cassette that can be part of a vector, such as a plasmid. A vector can include a promoter operably linked to nucleic acid encoding a nucleotide triphosphate transporter. A vector can also include other elements required for transcription and translation as described herein. An expression cassette, expression vector, and sequences in a cassette or vector can be heterologous to the cell to which the unnatural nucleotides are contacted. For example, a nucleotide triphosphate transporter sequence can be heterologous to the cell.

A variety of prokaryotic and eukaryotic expression vectors suitable for carrying, encoding and/or expressing nucleotide triphosphate transporters can be produced. Such expression vectors include, for example, pET, pET3d, pCR2.1, pBAD, pUC, and yeast vectors. The vectors can be used, for example, in a variety of in vivo and in vitro situations. Non-limiting examples of prokaryotic promoters that can be used include SP6, T7, T5, tac, bla, trp, gal, lac, or maltose promoters. Non-limiting examples of eukaryotic promoters that can be used include constitutive promoters, e.g., viral promoters such as CMV, SV40 and RSV promoters, as well as regulatable promoters, e.g., an inducible or repressible promoter such as a tet promoter, a hsp70 promoter, and a synthetic promoter regulated by CRE. Vectors for bacterial expression include pGEX-5X-3, and for eukaryotic expression include pCIneo-CMV. Viral vectors that can be employed include those relating to lentivirus, adenovirus, adeno-associated virus, herpes virus, vaccinia virus, polio virus, AIDS virus, neuronal trophic virus, Sindbis and other viruses. Also useful are any viral families which share the properties of these viruses which make them suitable for use as vectors. Retroviral vectors that can be employed include those described in Verma, American Society for Microbiology, pp. 229-232, Washington, (1985). For example, such retroviral vectors can include Murine Maloney Leukemia virus, MMLV, and other retroviruses that express desirable properties. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral nucleic acid Cloning Any convenient cloning strategy known in the art may be utilized to incorporate an element, such as an ORF, into a nucleic acid reagent. Known methods can be utilized to insert an element into the template independent of an insertion element, such as (1) cleaving the template at one or more existing restriction enzyme sites and ligating an element of interest and (2) adding restriction enzyme sites to the template by hybridizing oligonucleotide primers that include one or more suitable restriction enzyme sites and amplifying by polymerase chain reaction (described in greater detail herein). Other cloning strategies take advantage of one or more insertion sites present or inserted into the nucleic acid reagent, such as an oligonucleotide primer hybridization site for PCR, for example, and others described herein. In some embodiments, a cloning strategy can be combined with genetic manipulation such as recombination (e.g., recombination of a nucleic acid reagent with a nucleic acid sequence of interest into the genome of the organism to be modified, as described further herein). In some embodiments, the cloned ORF(s) can produce (directly or indirectly) modified or wild type nucleotide triphosphate transporters and/or polymerases), by engineering a microorganism with one or more ORFs of interest, which microorganism comprises altered activities of nucleotide triphosphate transporter activity or polymerase activity.

A nucleic acid may be specifically cleaved by contacting the nucleic acid with one or more specific cleavage agents. Specific cleavage agents often will cleave specifically according to a particular nucleotide sequence at a particular site. Examples of enzyme specific cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bln I, Bsm I, BssH II, BstE II, Cfo I, CIa I, Dde I, Dpn I, Dra I, EcIX I, EcoR I, EcoR I, EcoR II, EcoR V, Hae II, Hae II, Hind II, Hind III, Hpa I, Hpa II, Kpn I, Ksp I, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sea I, ScrF I, Sfi I, Sma I, Spe I, Sph I, Ssp I, Stu I, Sty I, Swa I, Taq I, Xba I, Xho I); glycosylases (e.g., uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Sample nucleic acid may be treated with a chemical agent, or synthesized using modified nucleotides, and the modified nucleic acid may be cleaved. In non-limiting examples, sample nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

In some embodiments, the nucleic acid reagent includes one or more recombinase insertion sites. A recombinase insertion site is a recognition sequence on a nucleic acid molecule that participates in an integration/recombination reaction by recombination proteins. For example, the recombination site for Cre recombinase is loxP, which is a 34 base pair sequence comprised of two 13 base pair inverted repeats (serving as the recombinase binding sites) flanking an 8 base pair core sequence (e.g., Sauer, Curr. Opin. Biotech. 5:521-527 (1994)). Other examples of recombination sites include attB, attP, attL, and attR sequences, and mutants, fragments, variants and derivatives thereof, which are recognized by the recombination protein k Int and by the auxiliary proteins integration host factor (IHF), FIS and excisionase (Xis) (e.g., U.S. Pat. Nos. 5,888,732; 6,143,557; 6,171,861; 6,270,969; 6,277,608; and 6,720,140; U.S. patent application Ser. Nos. 09/517,466, and 09/732,914; U.S. Patent Publication No. US2002/0007051; and Landy, Curr. Opin. Biotech. 3:699-707 (1993)).

Examples of recombinase cloning nucleic acids are in Gateway® systems (Invitrogen, California), which include at least one recombination site for cloning desired nucleic acid molecules in vivo or in vitro. In some embodiments, the system utilizes vectors that contain at least two different site-specific recombination sites, often based on the bacteriophage lambda system (e.g., att1 and att2), and are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the Gateway® system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

A nucleic acid reagent sometimes contains one or more origin of replication (ORI) elements. In some embodiments, a template comprises two or more ORIs, where one functions efficiently in one organism (e.g., a bacterium) and another functions efficiently in another organism (e.g., a eukaryote, like yeast for example). In some embodiments, an ORI may function efficiently in one species (e.g., *S. cerevisiae*, for example) and another ORI may function efficiently in a different species (e.g., *S. pombe*, for example). A nucleic acid reagent also sometimes includes one or more transcription regulation sites.

A nucleic acid reagent, e.g., an expression cassette or vector, can include nucleic acid sequence encoding a marker product. A marker product is used to determine if a gene has been delivered to the cell and once delivered is being expressed. Example marker genes include the *E. coli* lacZ gene which encodes β-galactosidase and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin (Southern etal., J. Molec. Appl. Genet. 1: 327 (1982)), mycophenolic acid, (Mulligan et al., Science 209: 1422 (1980)) or hygromycin, (Sugden, et al., Mol. Cell. Biol. 5: 410-413 (1985)).

A nucleic acid reagent can include one or more selection elements (e.g., elements for selection of the presence of the nucleic acid reagent, and not for activation of a promoter element which can be selectively regulated). Selection elements often are utilized using known processes to determine whether a nucleic acid reagent is included in a cell. In some embodiments, a nucleic acid reagent includes two or more selection elements, where one functions efficiently in one organism, and another functions efficiently in another organism. Examples of selection elements include, but are not limited to, (1) nucleic acid segments that encode products that provide resistance against otherwise toxic compounds (e.g., antibiotics); (2) nucleic acid segments that encode products that are otherwise lacking in the recipient cell (e.g., essential products, tRNA genes, auxotrophic markers); (3) nucleic acid segments that encode products that suppress the activity of a gene product; (4) nucleic acid segments that encode products that can be readily identified (e.g., phenotypic markers such as antibiotics (e.g., β-lactamase), β-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; (11) nucleic acid segments that encode products that either are toxic or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, and the like).

A nucleic acid reagent can be of any form useful for in vivo transcription and/or translation. A nucleic acid sometimes is a plasmid, such as a supercoiled plasmid, sometimes is a yeast artificial chromosome (e.g., YAC), sometimes is a linear nucleic acid (e.g., a linear nucleic acid produced by PCR or by restriction digest), sometimes is single-stranded and sometimes is double-stranded. A nucleic acid reagent sometimes is prepared by an amplification process, such as a polymerase chain reaction (PCR) process or transcription-mediated amplification process (TMA). In TMA, two enzymes are used in an isothermal reaction to produce amplification products detected by light emission (e.g., Biochemistry 1996 Jun. 25; 35(25):8429-38). Standard PCR processes are known (e.g., U.S. Pat. Nos. 4,683,202; 4,683,195; 4,965,188; and 5,656,493), and generally are performed in cycles. Each cycle includes heat denaturation, in which hybrid nucleic acids dissociate; cooling, in which primer oligonucleotides hybridize; and extension of the oligonucleotides by a polymerase (i.e., Taq polymerase). An example of a PCR cyclical process is treating the sample at 95° C. for 5 minutes; repeating forty-five cycles of 95° C. for 1 minute, 59° C. for 1 minute, 10 seconds, and 72° C. for 1 minute 30 seconds; and then treating the sample at 72° C. for 5 minutes. Multiple cycles frequently are performed using a commercially available thermal cycler. PCR amplification products sometimes are stored for a time at a lower temperature (e.g., at 4° C.) and sometimes are frozen (e.g., at −20° C.) before analysis.

Nucleic Acid Fragmentation

In certain embodiments a nucleic acid can be from a library or can be obtained from enzymatically digested, sheared or sonicated genomic DNA (e.g., fragmented) from an organism of interest. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000 or 10000 base pairs. Fragments can be generated by any suitable method in the art, and the average, mean or nominal length of nucleic acid fragments can be controlled by selecting an appropriate fragment-generating procedure by the person of ordinary skill. In some embodiments, the fragmented DNA can be size selected to obtain nucleic acid fragments of a particular size range.

Nucleic acid can be fragmented by various methods known to the person of ordinary skill, which include without limitation, physical, chemical and enzymatic processes. Examples of such processes are described in US2005/0112590. Certain processes can be selected by the person of ordinary skill to generate non-specifically cleaved fragments or specifically cleaved fragments. Examples of processes that can generate non-specifically cleaved fragment sample nucleic acid include, without limitation, contacting sample nucleic acid with apparatus that expose nucleic acid to shearing force (e.g., passing nucleic acid through a syringe needle; use of a French press); exposing sample nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

Amplification

A nucleic acid suitable for use in the embodiments described herein sometimes is amplified by any amplification process known in the art (e.g., PCR, RT-PCR and the like). Nucleic acid amplification may be particularly beneficial when using organisms that are typically difficult to culture (e.g., slow growing, require specialize culture conditions and the like).

Exemplary methods for amplifying nucleic acids include the polymerase chain reaction (PCR) (Mullis et al., (1986) Cold Spring Harb. Symp. Quant. Biol. 51 pt. 1:263; Cleary et al., (2004) Nature Methods 1:241; and U.S. Pat. Nos. 4,683,195 and 4,683,202), anchor PCR, RACE PCR, ligation chain reaction (LCR) (Landegran et al., (1988) Science 241:1077-1080; and Nakazawa et al., (1994) Proc. Natl. Acad. Sci. U.S.A. 91:360-364), self-sustained sequence replication (Guatelli et al., (1990) Proc. Natl. Acad. Sci. U.S.A. 87:1874), transcriptional amplification system (Kwoh et al., (1989) Proc. Natl. Acad. Sci. U.S.A. 86:1173), Q-Beta Replicase (Lizardi et al., (1988) BioTechnology 6:1197), recursive PCR (Jaffe et al., (2000) J. Biol. Chem. 275:2619; and Williams et al., (2002) I Biol. Chem. 277:7790), the amplification methods described in U.S. Pat. Nos. 6,391,544; 6,365,375; 6,294,323; 6,261,797; 6,124,090; and 5,612,199, isothermal amplification (e.g., rolling circle amplification (RCA), hyperbranched rolling circle amplification (HRCA), strand displacement amplification (SDA), helicase-dependent amplification (HDA), PWGA, polymerase and/or ligase chain reactions, thermal cycling (PCR) or isothermally (e.g. RCA, hRCA, SDA, HDA, PWGA), or any other nucleic acid amplification method using techniques well known to those of skill in the art.

In some embodiments, a limited amplification reaction, also known as pre-amplification, can be performed. Pre-amplification is a method in which a limited amount of amplification occurs due to a small number of cycles, for example 10 cycles, being performed. Pre-amplification can allow some amplification, but stops amplification prior to the exponential phase, and typically produces about 500 copies of the desired nucleotide sequence(s). Use of pre-amplification may also limit inaccuracies associated with depleted reactants in standard PCR reactions.

Sequencing

Sequencing can be accomplished through classic Sanger sequencing methods, which are known in the art. In some embodiments sequencing can be performed using high-throughput sequencing methods some of which allow detection of a sequenced nucleotide immediately after or upon its incorporation into a growing strand, for example, detection of sequence in substantially real time or real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read (or 500-1,000 bases per read).

High-throughput sequencing methods can include but are not limited to, Massively Parallel Signature Sequencing (MPSS, Lynx Therapeutics), Polony sequencing, 454 pyrosequencing, Illumina (Solexa) sequencing, SOLiD sequencing, on semiconductor sequencing, DNA nanoball sequencing, Helioscope™ single molecule sequencing, Single Molecule SMRT™ sequencing, Single Molecule real time (RNAP) sequencing, Nanopore DNA sequencing, and/or sequencing by hybridization, for example, a non-enzymatic method that uses a DNA microarray, or microfluidic Sanger sequencing.

Homology and Identity

In addition to the regulated promoter sequences, regulatory sequences, and coding polynucleotides provided herein, a nucleic acid reagent may include a polynucleotide sequence 80% or more identical to the foregoing (or to the complementary sequences). That is, a nucleotide sequence that is at least 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, or 99% or more identical to a nucleotide sequence described herein can be utilized. The term "identical" as used herein refers to two or more nucleotide sequences having substantially the same nucleotide sequence when compared to each other. One test for determining whether two nucleotide sequences or amino acids sequences are substantially identical is to determine the percent of identical nucleotide sequences or amino acid sequences shared.

Calculations of sequence identity can be performed as follows. Sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is sometimes 30% or more, 40% or more, 50% or more, often 60% or more, and more often 70% or more, 80% or more, 90% or more, or 100% of the length of the reference sequence. The nucleotides or amino acids at corresponding nucleotide or polypeptide positions, respectively, are then compared among the two sequences. When a position in the first sequence is occupied by the same nucleotide or amino acid as the corresponding position in the second sequence, the nucleotides or amino acids are deemed to be identical at that position. The percent identity between the two sequences is a function of the number of identical positions shared by the sequences, taking into account the number of gaps, and the length of each gap, introduced for optimal alignment of the two sequences.

Comparison of sequences and determination of percent identity between two sequences can be accomplished using a mathematical algorithm. Percent identity between two amino acid or nucleotide sequences can be determined using the algorithm of Meyers & Miller, CABIOS 4: 11-17 (1989), which has been incorporated into the ALIGN program (version 2.0), using a PAM120 weight residue table, a gap length penalty of 12 and a gap penalty of 4. Also, percent identity between two amino acid sequences can be determined using the Needleman & Wunsch, J. Mol. Biol. 48: 444-453 (1970) algorithm which has been incorporated into the GAP program in the GCG software package (available at the http address www.gcg.com), using either a Blossum 62 matrix or a PAM250 matrix, and a gap weight of 16, 14, 12, 10, 8, 6, or 4 and a length weight of 1, 2, 3, 4, 5, or 6. Percent identity between two nucleotide sequences can be determined using the GAP program in the GCG software package (available at http address www.gcg.com), using a NWSgapdna.CMP matrix and a gap weight of 40, 50, 60, 70, or 80 and a length weight of 1, 2, 3, 4, 5, or 6. A set of parameters often used is a Blossum 62 scoring matrix with a gap open penalty of 12, a gap extend penalty of 4, and a frameshift gap penalty of 5.

Sequence identity can also be determined by hybridization assays conducted under stringent conditions. An example of stringent hybridization conditions is hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions is hybridization in 6×sodium chloride/sodium citrate (SSC) at about 45° C., followed by one or more washes in 0.2×SSC, 0.1% SDS at 60° C. Often, stringent hybridization conditions are hybridization in 6×sodium chloride/sodium citrate (SSC) at about 45° C., followed by one or more washes in 0.2×SSC, 0.1% SDS at 65° C. More often, stringency conditions are 0.5M sodium phosphate, 7% SDS at 65° C., followed by one or more washes at 0.2×SSC, 1% SDS at 65° C.

Definitions

As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment. As used herein, unless otherwise indicated, some inventive embodiments herein contemplate numerical ranges. When ranges are present, the ranges include the range endpoints. Additionally, every sub-range and value within the range is present as if explicitly written out.

The terms "amplify", "amplification", "amplification reaction", or "amplifying" as used herein refer to any in vitro processes for multiplying the copies of a target sequence of nucleic acid. Amplification sometimes refers to an "exponential" increase in target nucleic acid. However, "amplifying" as used herein can also refer to linear increases in the numbers of a select target sequence of nucleic acid, but is different than a one-time, single primer extension step.

As used herein, "bicyclic nucleoside" refers to a nucleoside having a sugar moiety comprising a sugar-ring (including, but not limited to, furanose) comprising a bridge connecting two carbon atoms of the sugar ring to form a second ring. In certain embodiments, the bridge connects the 4' carbon to the 2' carbon of a 5-membered sugar ring group at the position of the sugar ring.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acids of interest may be treated with one or more specific cleavage agents (e.g., 1, 2, 3, 4, 5, 6, 7, 8, 9, 10 or more specific cleavage agents) in one or more reaction vessels (e.g., nucleic acid of interest is treated with each specific cleavage agent in a separate vessel).

The term "DNA polymerase" as used herein includes DNA polymerases that have been modified by e.g. natural process such as posttranslational processing, or non-natural process such as chemical modification. Such modifications can occur on the peptide backbone, amino acid side chains, or the N- or C-terminus. Modifications include e.g. acetylations, acylations, ADP-ribosylations, amidations, covalent attachment of flavines, haem-groups, nucleotides or nucleotide derivatives, lipids or lipid derivatives, cyclizations, disulfide bridges, methylations and demethylations, cystine linkages, formylations, γ-carboxylations, glycosylations, hydroxylations, phosphorylations and the tRNA-mediated addition of amino acids.

The term "engineered" as used herein, when referring to a microorganism or cell, refers to a modified organism or cell that includes one or more activities distinct from an activity present in a microorganism or cell utilized as a starting point for modification (e.g., host microorganism/cell or unmodified organism/cell). Engineered microorganisms typically arise as a result of a genetic modification, usually introduced or selected for, by one of skill in the art using readily available techniques. Non-limiting examples of methods useful for generating an altered activity include, introducing a heterologous polynucleotide (e.g., nucleic acid or gene integration, also referred to as "knock in"), removing an endogenous polynucleotide, altering the sequence of an existing endogenous nucleic acid sequence (e.g., site-directed mutagenesis), disruption of an existing endogenous nucleic acid sequence (e.g., knock outs and transposon or insertion element mediated mutagenesis), selection for an altered activity where the selection causes a change in a naturally occurring activity that can be stably inherited (e.g., causes a change in a nucleic acid sequence in the genome of the organism or in an epigenetic nucleic acid that is replicated and passed on to daughter cells), PCR-based mutagenesis, and the like.

The term "genetic modification" as used herein refers to any suitable nucleic acid addition, removal or alteration that facilitates transport, e.g., import, of a target nucleic acid in an engineered microorganism. Genetic modifications include, without limitation, insertion of one or more nucleotides in a native nucleic acid of a host organism in one or more locations, deletion of one or more nucleotides in a native nucleic acid of a host organism in one or more locations, modification or substitution of one or more nucleotides in a native nucleic acid of a host organism in one or more locations, insertion of a non-native nucleic acid into a host organism (e.g., insertion of an autonomously replicating vector), and removal of a non-native nucleic acid in a host organism (e.g., removal of a vector).

The term "heterologous" nucleic acid, as used herein, refers to a nucleic acid sequence not present in a host microorganism in some embodiments. In certain embodiments, a heterologous polynucleotide is present in a different amount (e.g., different copy number) than in a host microorganism, which can be accomplished, for example, by introducing more copies of a particular nucleotide sequence to a host microorganism (e.g., the particular nucleotide sequence may be in a nucleic acid autonomous of the host chromosome or may be inserted into a chromosome). A heterologous nucleic acid is from a different organism in some embodiments, and in certain embodiments, is from the same type of organism but from an outside source (e.g., a recombinant source). As used herein, the term "heterologous" when used in reference to a protein, promoter, or nucleic acid refers to a protein, promoter, or nucleic acid that has been manipulated in some way. For example, a heterologous nucleic acid, heterologous coding region, or a heterologous promoter includes a nucleic acid, coding region, or promoter that is not normally in the species to which it has been introduced or that is not normally linked to the nucleic acids to which it is linked. A heterologous nucleic acid or protein therefore includes a nucleic acid or protein that is native to one type of organism but that has been altered in some way (e.g., placed in a different chromosomal location, mutated, added in multiple copies, linked to a non-native promoter, or enhancer element, etc.). Heterologous genes include gene sequences that comprise cDNA forms of a gene. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that are linked to a coding region to which they are not linked in nature.

The term “isolated” as used herein refers to material removed from its original environment (e.g., the natural environment if it is naturally occurring, or a host cell if expressed exogenously), and thus is altered “by the hand of man” from its original environment.

As used herein, “modified nucleoside” refers to a nucleoside comprising at least one modification compared to naturally occurring RNA or DNA nucleosides. Such modification may be at the sugar moiety and/or at the nucleobases.

The term “mutagenesis” as used herein refers to any modification to a nucleic acid (e.g., nucleic acid reagent, or host chromosome, for example) that is subsequently used to generate a product in a host or modified organism. Non-limiting examples of mutagenesis include deletion, insertion, substitution, rearrangement, point mutations, suppressor mutations and the like. Mutagenesis methods are known in the art and are readily available to the artisan. Non-limiting examples of mutagenesis methods are described herein and can also be found in Maniatis et al., (1982) Molecular Cloning: a Laboratory Manual; Cold Spring Harbor Laboratory, Cold Spring Harbor, N.Y. Another non-limiting example of mutagenesis can be conducted using a Stratagene (San Diego, Calif.) “QuickChange” kit according to the manufacturer’s instructions.

The term “native sequence” as used herein refers to an unmodified nucleotide sequence as found in its natural setting (e.g., a nucleotide sequence as found in an organism).

A “nucleic acid modification” as used herein refers to an alteration, typically a chemical alteration, which is present in the modified nucleic acid molecule compared to the commonly or naturally occurring nucleic acid molecule. A modification may have been made to any component of the nucleic acid, for example, to the backbone, sugar component, or base. By way of example, a modified nucleic acid may have a phosphorothioate backbone, instead of the naturally occurring phosphodiester backbone. Modifications of this kind are often made to nucleic acids which are to be used in therapy. Modifications and modified nucleic acids are described further herein.

As used herein, “nucleobase” refers to the heterocyclic base portion of a nucleoside. Nucleobases may be naturally occurring, may be modified, may bear no similarity to natural bases, and may be synthetized, e.g., by organic synthesis. In certain embodiments, a nucleobase may comprise any atom or group of atoms capable of hydrogen bonding to a base of another nucleic acid or lacking hydrogen bonds altogether. In certain embodiments, an unnatural nucleobase may not be derived from a natural nucleobase. In certain embodiments, an unnatural nucleobase may be a synthetic nucleobase. It should be noted that unnatural nucleobases do not necessarily possess basic properties, however, are referred to as nucleobases for simplicity. When referring to a nucleobase, a “(d)” indicates that the nucleobase can be attached to a deoxyribose or a ribose.

As used herein, “nucleoside” refers to a compound comprising a nucleobase moiety and a sugar moiety. Nucleosides include, but are not limited to, naturally occurring nucleosides (as found in DNA and RNA), abasic nucleosides, modified nucleosides, and nucleosides having mimetic bases and/or sugar groups. Nucleosides may be modified with any of a variety of substituents. A nucleoside can be a glycoside compound formed through glycosidic linking between a nucleic acid base and a reducing group of a sugar. It should be noted that the term “nucleic acid base” is intended to encompass adenine, guanine, cytosine, thymine, uracil, and also derivatives thereof. The type of the above derivative is not limited in any way.

The term “nucleotide” refers to a compound in which the sugar moiety of the above nucleoside forms an ester with phosphoric acid, more preferably a mono-, di- or tri-phosphate ester. The sugar moiety of such a nucleoside or nucleotide may be ribofuranosyl, 2'-deoxyribofuranosyl, or 2'-substituted ribofuranosyl having a substituent at the 2'-position. Likewise, the phosphoric acid moiety may be thiophosphoric acid. Namely, the sugar and phosphoric acid moieties may be in the same form as found in known nucleosides, nucleotides, or derivatives thereof. A ribonucleotide whose sugar moiety is ribofuranosyl can be used as a member constituting RNA. A deoxyribonucleotide whose sugar moiety is deoxyribofuranosyl can be used as a member constituting DNA. A nucleotide can be a nucleoside further comprising a phosphate linking group. Nucleotides may include nucleosides containing a phosphate moiety. As used herein, “linked nucleosides” may or may not be linked by phosphate linkages and thus includes “linked nucleotides.”

The term “probes” or “primers” as used herein refer to oligonucleotides that hybridize in a base-specific manner to a complementary strand of a nucleic acid molecule. Probes can include primers, which can be a single-stranded oligonucleotide probe that can act as a point of initiation of template-directed DNA synthesis or amplification using methods including but not limited to, polymerase chain reaction (PCR) and ligase chain reaction (LCR) for amplification of a target sequence. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen et al., Science 254: 1497-1500 (1991). A probe or primer can comprise a region of nucleotide sequence that hybridizes to at least about 15, typically about 20-25, and in certain embodiments about 40, 50, 60 or 75, consecutive nucleotides of a nucleic acid molecule.

The term “protein” as used herein refers to a molecule having a sequence of amino acids linked by peptide bonds. This term includes fusion proteins, oligopeptides, peptides, cyclic peptides, polypeptides and polypeptide derivatives, whether native or recombinant, and also includes fragments, derivatives, homologs, and variants thereof.

The term “purified” as used herein with reference to molecules does not refer to absolute purity. Rather, “purified” refers to a substance in a composition that contains fewer substance species in the same class (e.g., nucleic acid or protein species) other than the substance of interest in comparison to the sample from which it originated. "Purified," if a nucleic acid or protein for example, refers to a substance in a composition that contains fewer nucleic acid species or protein species other than the nucleic acid or protein of interest in comparison to the sample from which it originated. Sometimes, a protein or nucleic acid is "substantially pure," indicating that the protein or nucleic acid represents at least 50% of protein or nucleic acid on a mass basis of the composition. Often, a substantially pure protein or nucleic acid is at least 75% on a mass basis of the composition, and sometimes at least 95% on a mass basis of the composition.

As used herein, a "signal sequence" or "localization signal sequence" refers to as sequence that localizes a translated protein or peptide to a component in a system.

The term "specific cleavage agent" as used herein refers to an agent, sometimes a chemical or an enzyme that can cleave a nucleic acid at one or more specific sites.

As used herein, the term "stringent conditions" refers to conditions for hybridization and washing. Stringent conditions are known to those skilled in the art and can be found in Current Protocols in Molecular Biology, John Wiley & Sons, N.Y., 6.3.1-6.3.6 (1989). Aqueous and non-aqueous methods are described in that reference and either can be used.

As used herein, "sugar moiety" means a natural or modified sugar ring. As used herein, "vector" refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes.

EXAMPLES

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

Example 1

Preparation of Electrocompetent C41(DE3)-pACS

A single clone of freshly transformed *E. coli* C41(DE3)-pACS was grown overnight in 2×YT medium (3 ml) supplemented with streptomycin (50 μg/ml) and KPi (50 mM). After 100-fold dilution into the same medium (300 ml) and outgrowth at 37° C. to an $OD_{600}$ of 0.20, IPTG was added to a final concentration of 1 mM to induce the expression of PtNTT2. After 40 min, the cultures were rapidly cooled to 0° C., washed with sterile water (3×150 ml), and resuspended in 10% glycerol (1.5 ml).

Electroporation and Recovery

An aliquot of electrocompetent C41(DE3)-pACS cells (50 μL) was mixed with pINF (2 μL, 400 ng), and electroporated in a 0.2 cm gap cuvette. Pre-warmed 2×YT medium (0.95 ml, 50 μg/ml streptomycin, 1 mM IPTG, 50 mM KPi) was added, and after mixing, 45 μL was removed and combined with 105 μl of the same media (3.3×dilution) supplemented with 0.25 mM of dNaMTP and d5SICSTP. The resulting mixture was allowed to recover for 1 h at 37° C. with shaking (210 rpm).

Growth and Analysis

Figure 12A:
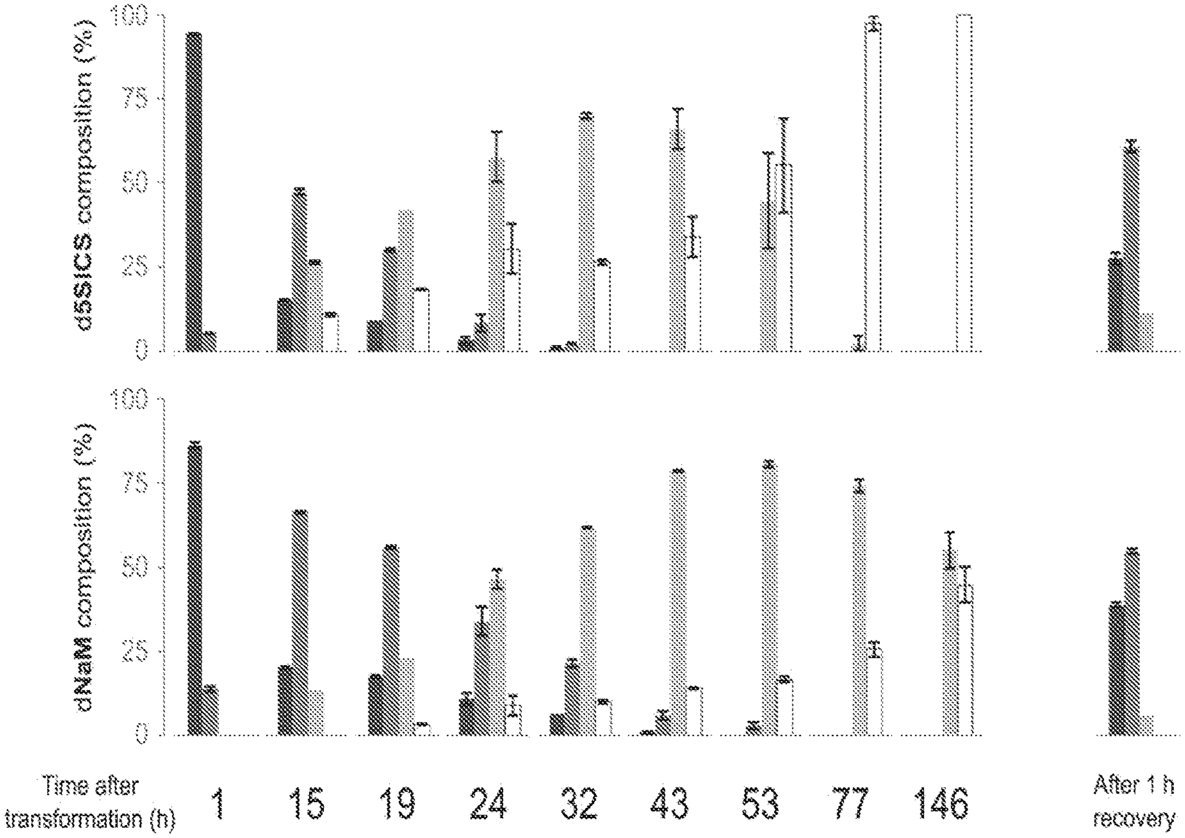
FIG. 12A depicts graphs of the % of the 3P (black), 2P (dark grey), 1P (light grey), and 0P (white) phosphorylation states of the indicated unnatural nucleoside triphosphates in the composition. The composition at the end of the 1 h recovery is shown at the right of each graph.
Figure 12B:
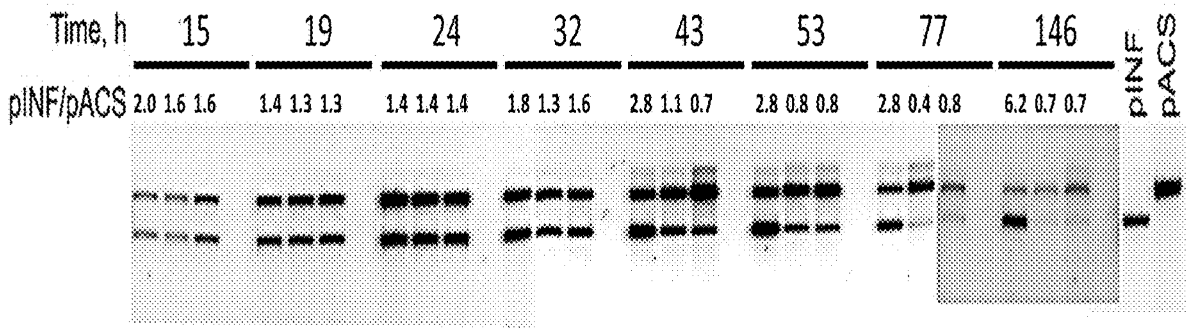
FIG. 12B depicts a restriction analysis of pINF and pACS plasmids purified from *E. coli*, linearized with NdeI restriction endonuclease, and separated on a 1% agarose gel. For each time point, triplicate data are shown in three lanes with untransformed control shown in the fourth, rightmost lane. Molar ratios of pINF/pACS plasmids are shown at the top of each lane.
Figure 12C:
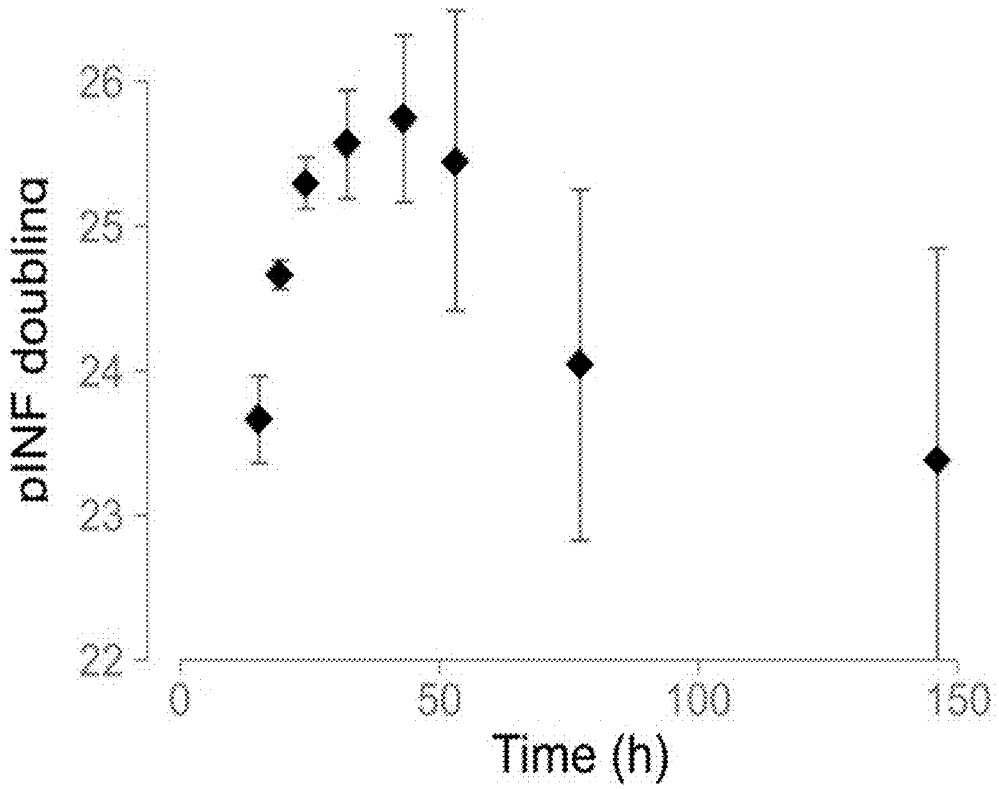
FIG. 12C depicts a graph showing the number of pINF doublings as a function of time. The decrease starting at ~50 h is due to the loss of the pINF plasmid that also results in increased error.
Figure 13A:
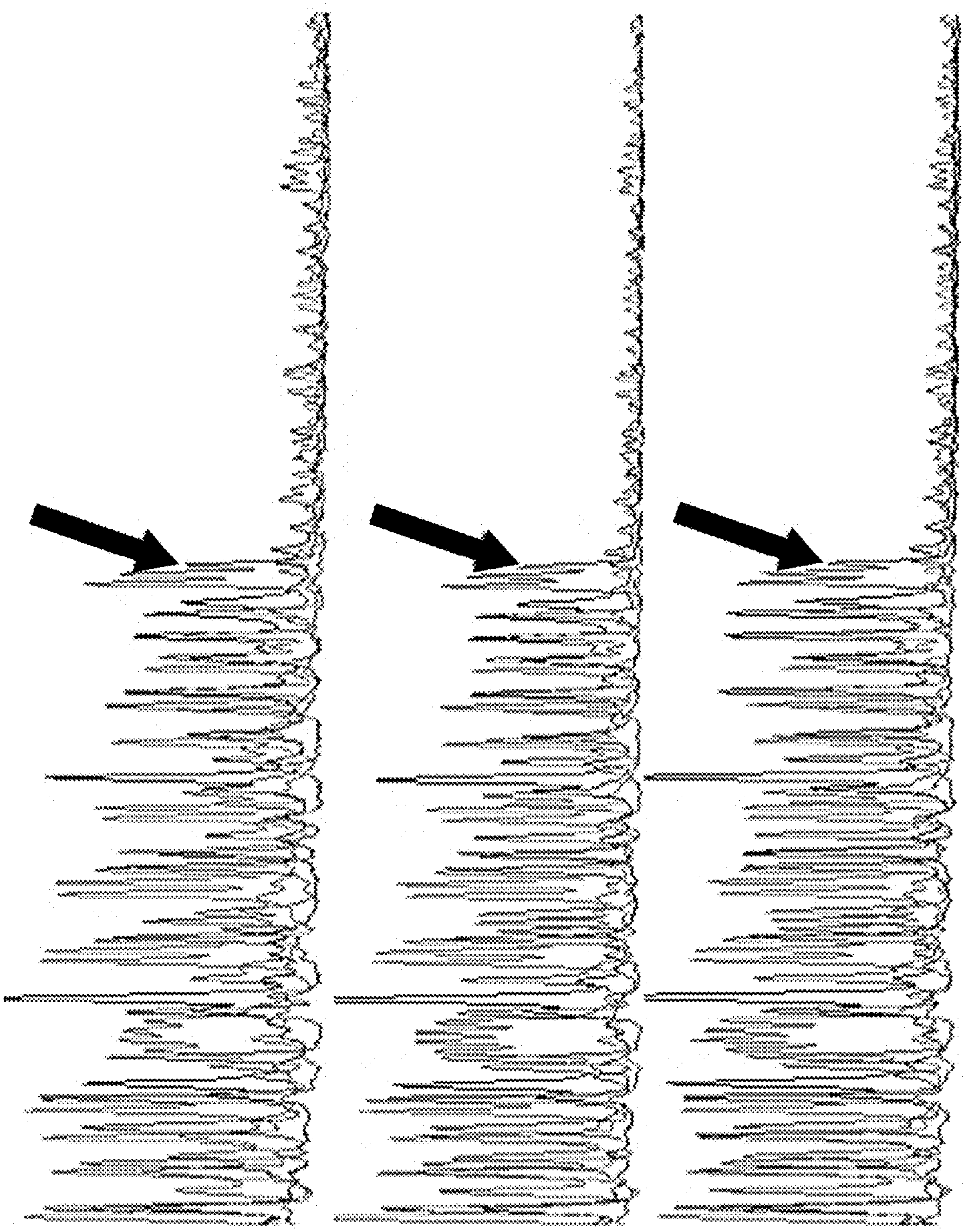
FIGS. 13A-H depict raw sequencing traces for PCR fragments generated from pINF plasmid propagated in *E. coli* at different time points. Triplicate data are shown. The position of the unnatural nucleotide is indicated with an arrow.
Figure 13B:
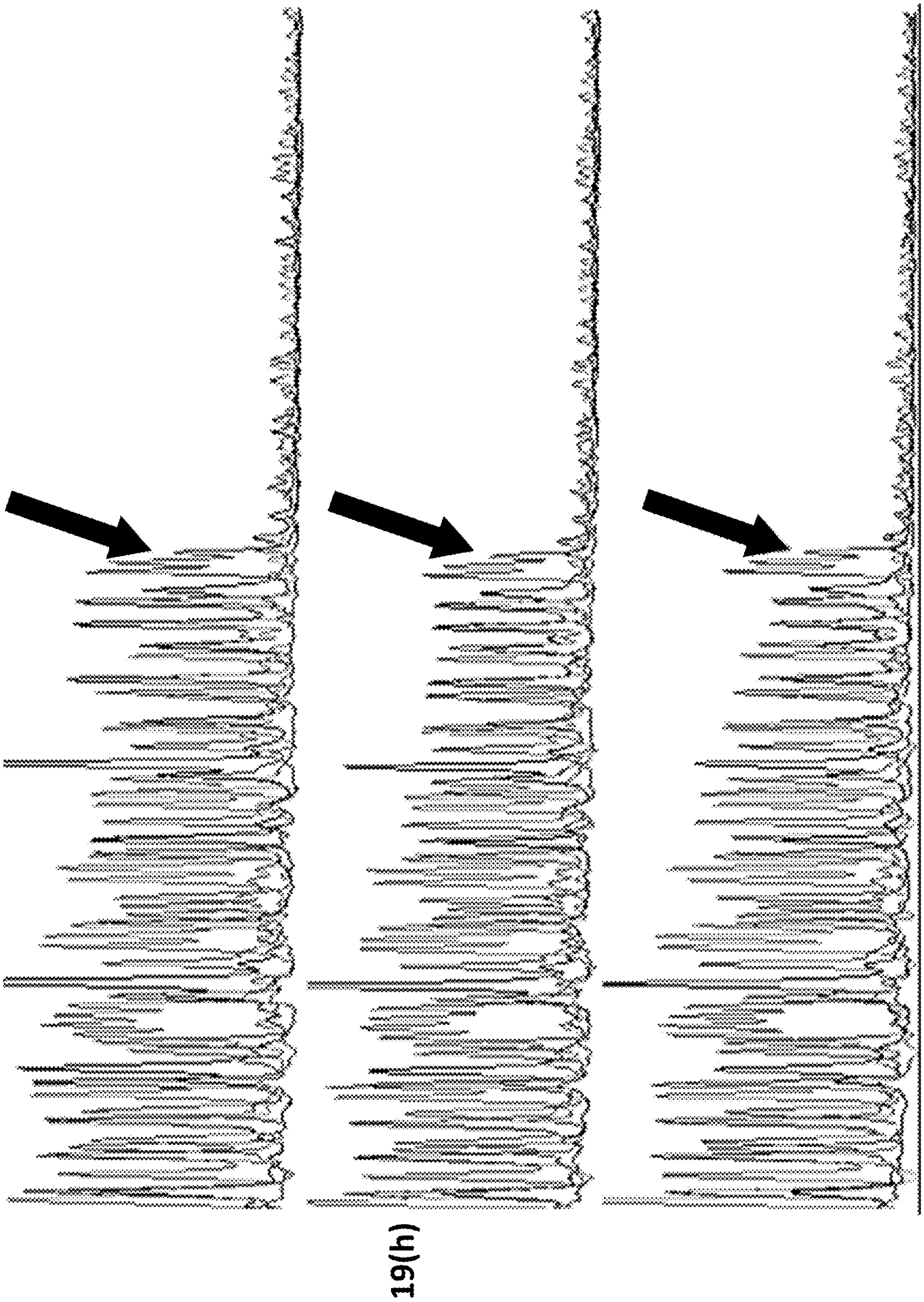
Figure 13C:
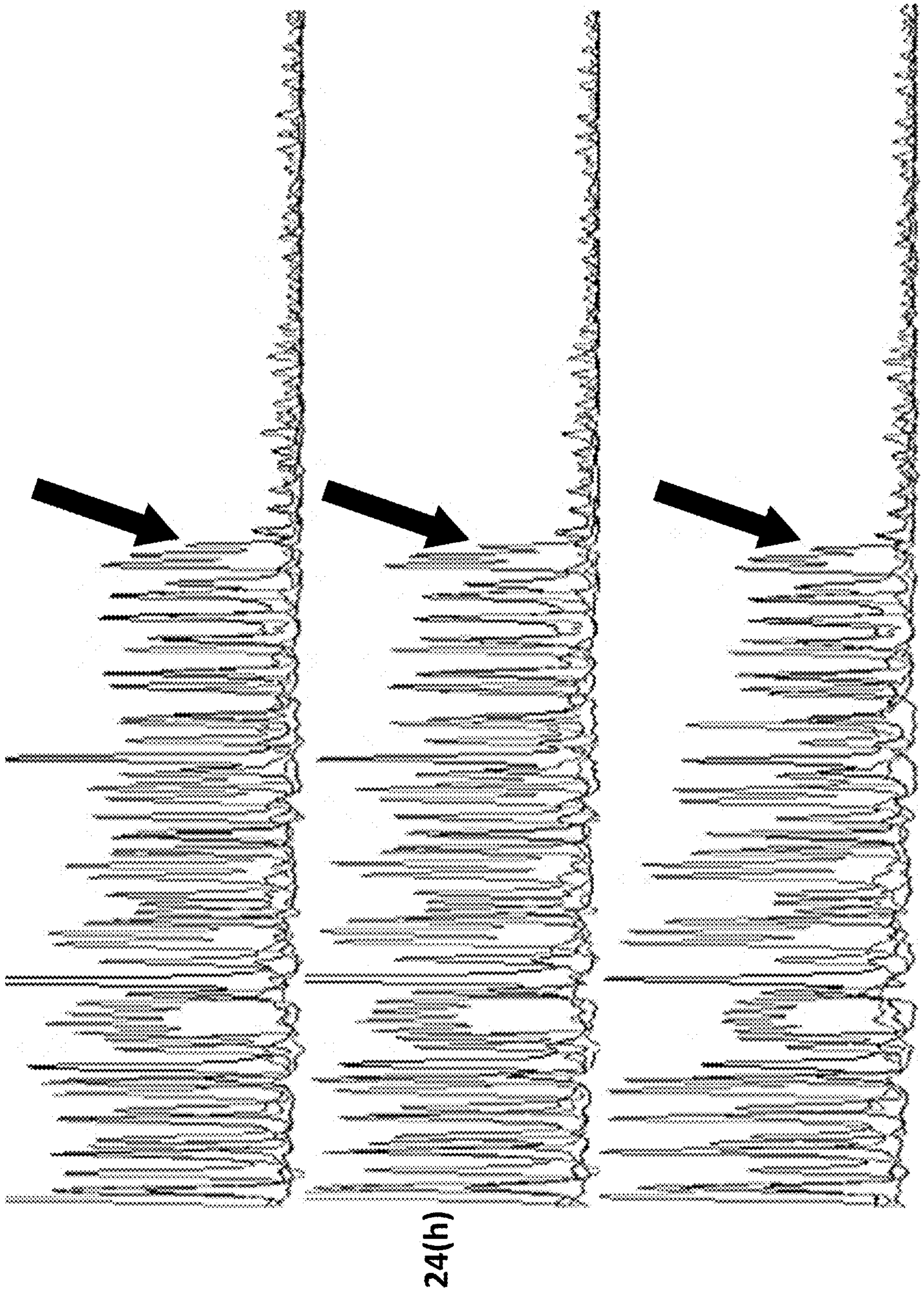
Figure 13D:
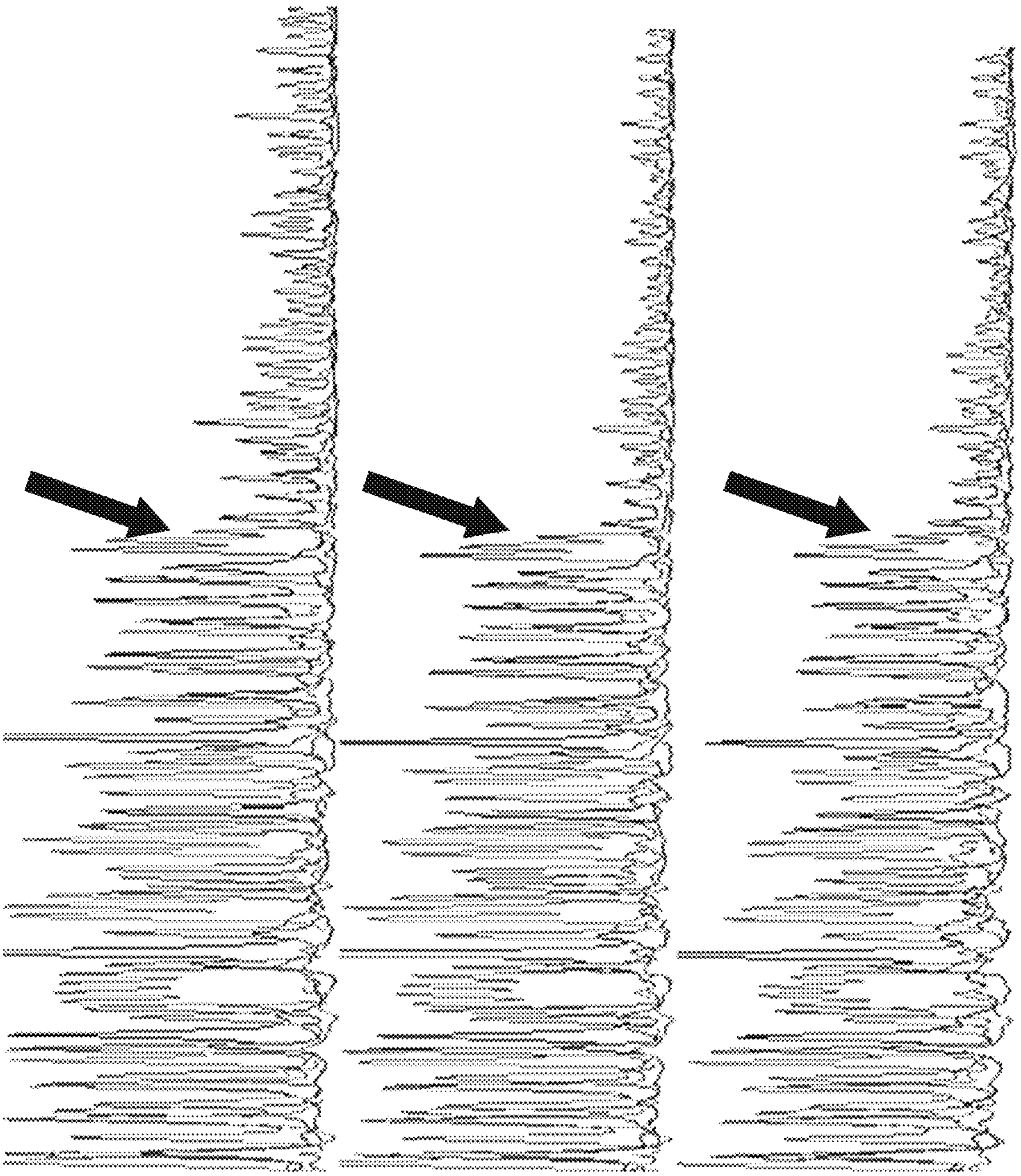
Figure 13E:
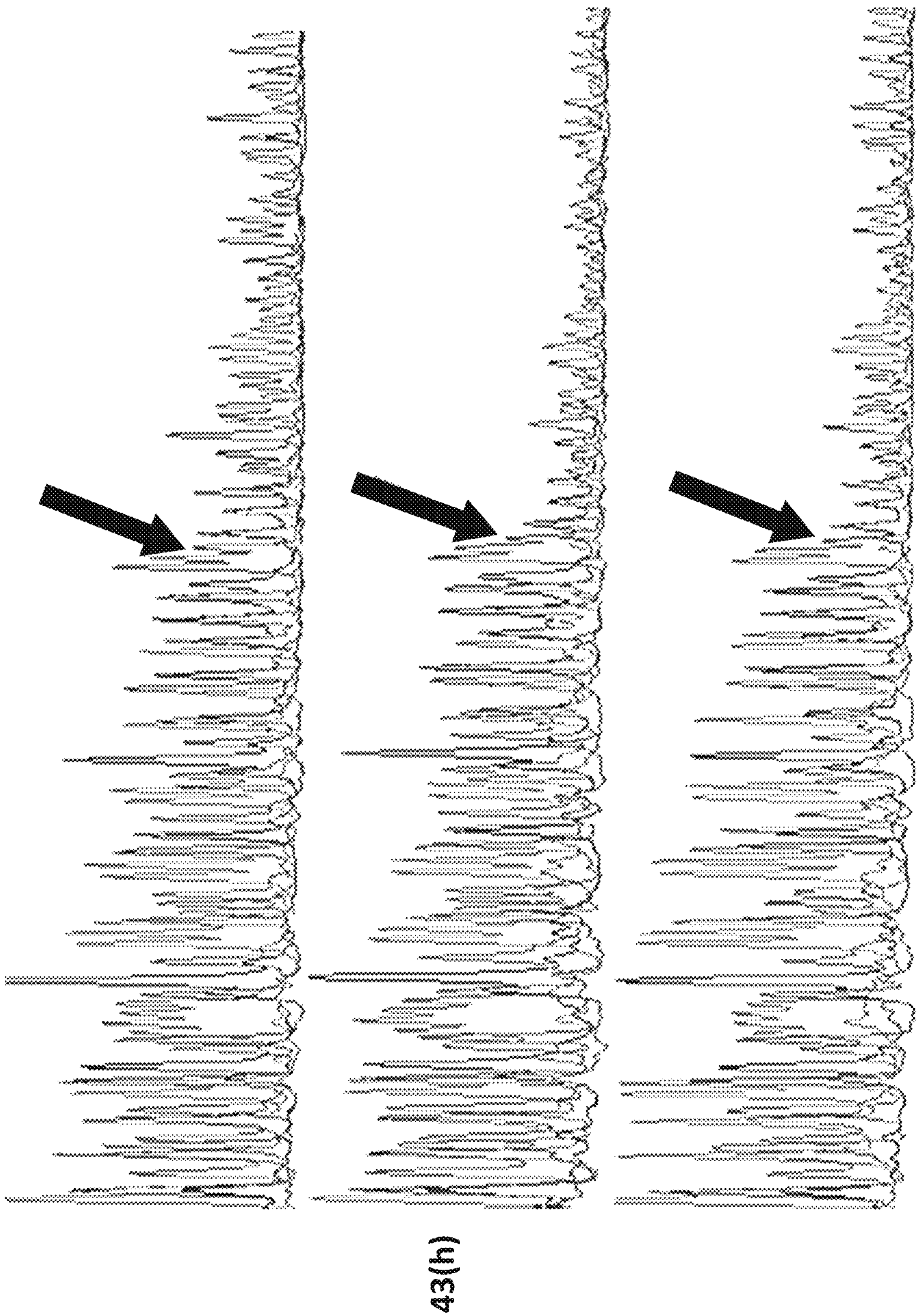
Figure 13F:
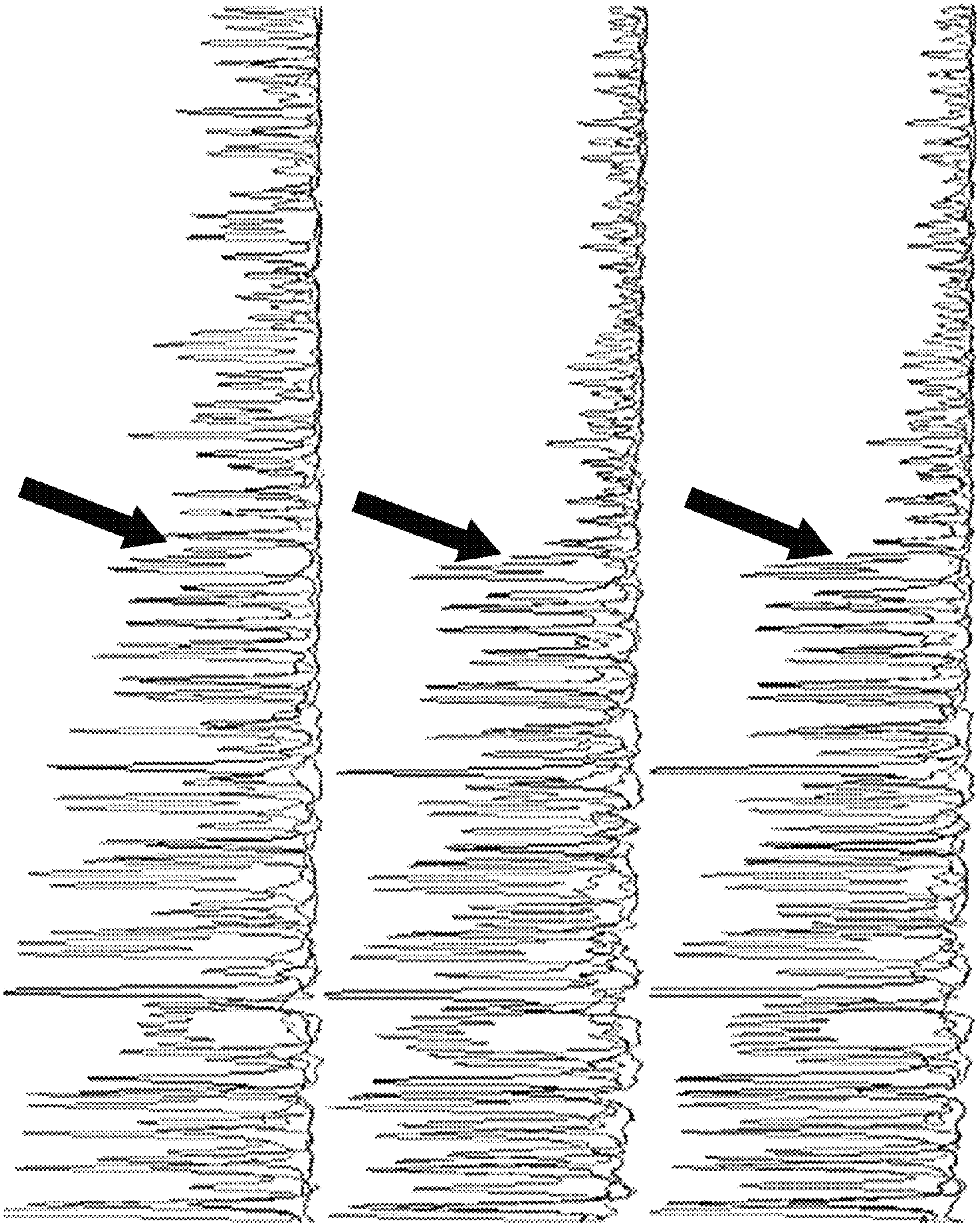
Figure 13G:
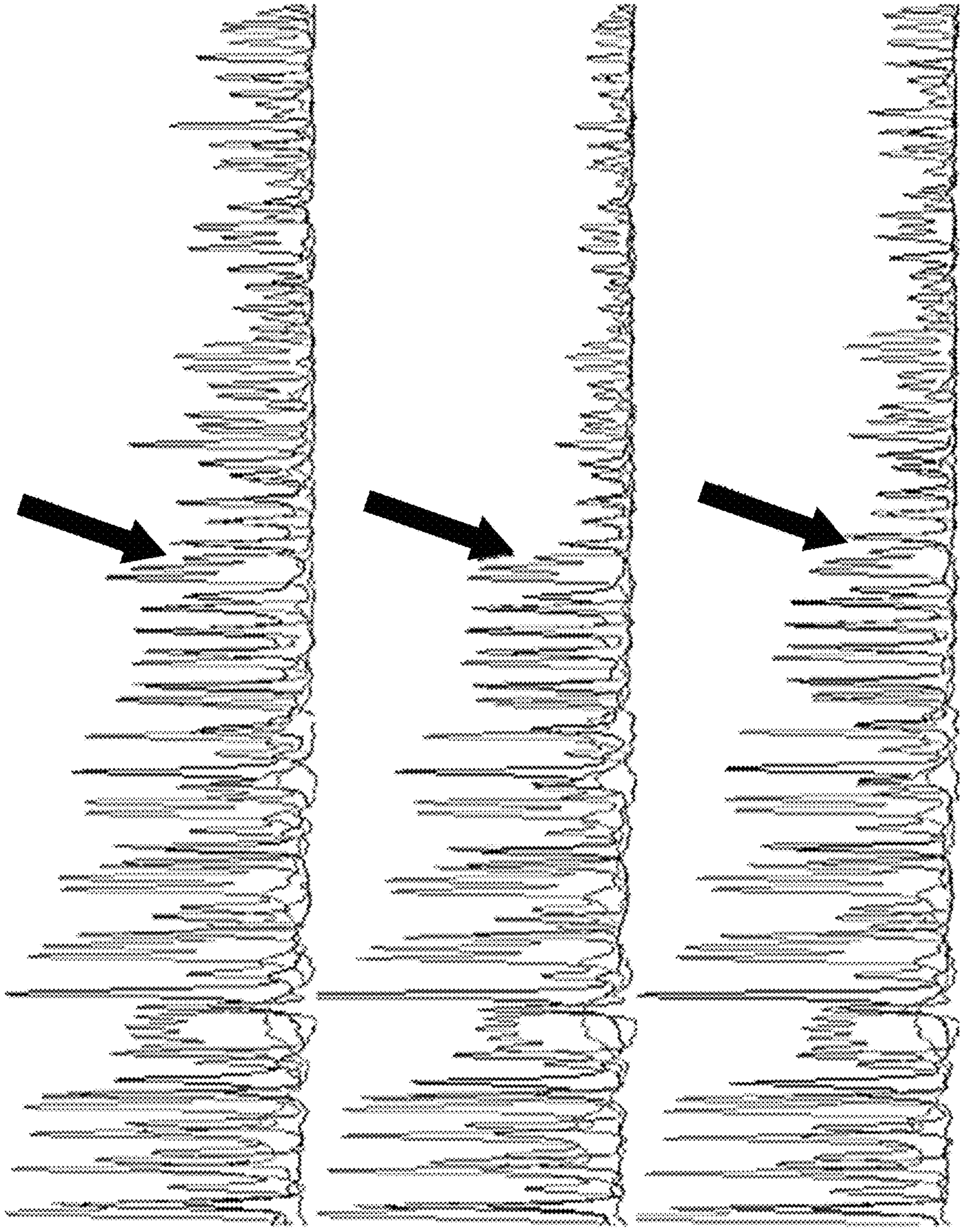
Figure 13H:
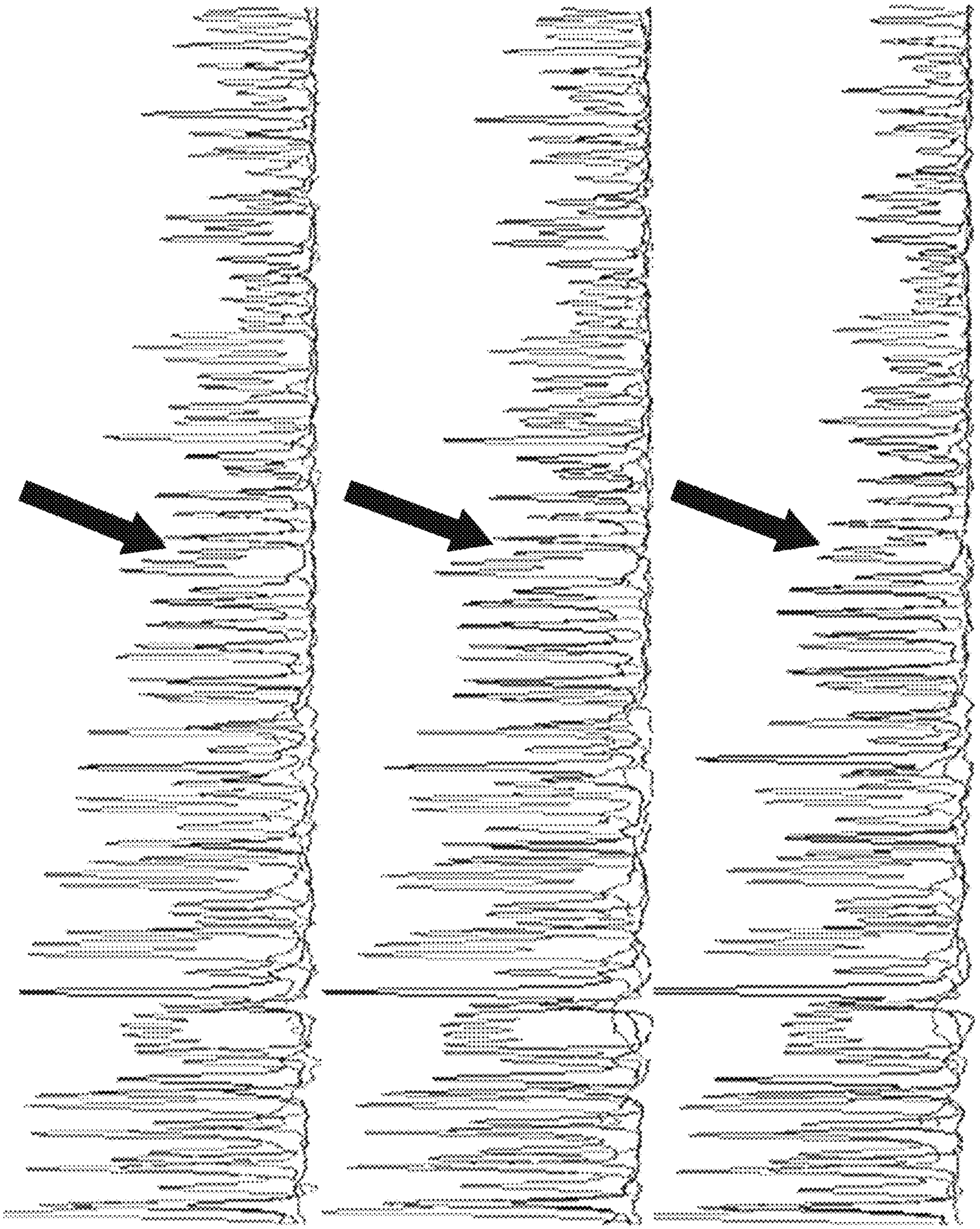

After recovery, cells were centrifuged and spent media (0.15 ml) was removed and analyzed for nucleotide composition by HPLC (FIG. 12A). The cells were resuspended in fresh 2×YT medium (1.5 ml, 50 μg/ml streptomycin, 100 μg/ml ampicillin, 1 mM IPTG, 50 mM KPi, 0.25 mM dNaMTP, 0.25 mM d5SICSTP) and grown at 37° C. with shaking (250 rpm). At defined time points, $OD_{600}$ was determined and aliquots (100 μl) were removed and centrifuged (8000 rfu for 5 min, 4° C.). Spent media was analyzed for nucleotide composition by HPLC and pINF was recovered by spin column purification (Zymo Research Corp.). Retention of the UBP was characterized by PCR amplification and gel electrophoresis or sequencing as described below. The data represents the average of three independent experiments. No PCR product was observed when pINF was added without electroporation, eliminating unamplified plasmid as a source of the PCR product (FIG. 12B).

Materials

2×YT, 2×YT-agar, IPTG, ampicillin and streptomycin were obtained from Fisher Scientific. Ampicillin and streptomycin were used at 100 μg/ml and 50 μg/ml, respectively. pET-16b constructs containing the nucleotide transporters, pET16b-RpNTT2, C41(DE3) *E. coli* strain. Plasmids pUC19 Thermo Scientific and pCDF-1b EMD Millipore. Plasmids were purified using the PureLink Quick Plasmid DNA Miniprep Kit (Life Technologies). OneTaq, DeepVent, Q5 Hot Start High-Fidelity DNA Polymerases, and all restriction endonucleases were obtained from New England Biolabs. In general, PCR reactions were divided into multiple aliquots with one followed in real time using 0.5×Sybr Green I (Life Technologies); following PCR, the aliquots were recombined, purified by spin column (DNA Clean and Concentrator-5; Zymo Research, Irvine, Calif.) with elution in 20 μl of water, then separated on an agarose gel, followed by band excision and recovery (Zymoclean Gel DNA Recovery Kit), eluting with 20 μl of water unless stated otherwise. PAGE gels were stained with 1×Sybr Gold (Life Technologies) for 30 min, agarose gels were cast with 1×Sybr Gold. Gels were visualized using a Molecular Imager Gel Doc XR+ equipped with 520DF30 filter (Bio-Rad) and quantified with Quantity One software (Bio-Rad). The sequences of exemplary DNA oligonucleotides used are shown in Table 8. Natural oligonucleotides were purchased from a commercial source. The concentration of dsDNA was measured by fluorescent dye binding (Quant-iT dsDNA HS Assay kit, Life Technologies) unless stated otherwise. The concentration of ssDNA was determined by UV absorption at 260 nm using a NanoDrop 1000 (Thermo Scientific). [α-$^{32}$P]-dATP (25 μCi). Polyethyleneiminecellulose precoated Bakerflex® TLC plates (0.5 mm). dNaM phosphoramidite, dNaM and d5SICS nucleosides. Free nucleosides of dNaM and d5SICS were converted to the corresponding triphosphates under Ludwig conditions. After purification by anion exchange chromatography (DEAE Sephadex A-25) followed by reverse phase (C18) HPLC and elution through a Dowex 50WX2-sodium column, both triphosphates were lyophilized and kept at −20° C. until use. The d5SICSTP analog dTPT3TP and the biotinylated dNaMTP analog $dMMO2^{SSBIO}$ $TP^4$ were made as reported previously. MALDI-TOF mass spectrometry was performed.

Construction of NTT Expression Plasmids

The PtNTT2 gene was amplified from plasmid pET-16b-PtNTT2 using primers PtNTT2-fwd and PtNTT2-rev; the TpNTT2 gene was amplified from plasmid pET-16b-TpNTT2 using primers TpNTT2-fwd and TpNTT2-rev. A linear fragment of pCDF-1b was generated using primers pCDF-1b-fwd and pCDF-1b-rev. Fragments were purified. The pCDF-1b fragment (100 ng, $4.4\times10^{-14}$ mol) and either the PtNTT2 (78 ng, $4.4\times10^{-14}$ mol) or TpNTT2 (85 ng, $4.4\times10^{-14}$ mol) fragment were then assembled together using restriction-free circular polymerase extension cloning in 1×OneTaq reaction buffer, $MgSO_4$ adjusted to 3.0 mM, 0.2 mM of dNTP, and 0.02 U/μl of OneTaq DNA under the following thermal cycling conditions: Initial denaturation (96° C., 1 min); 10 cycles of denaturation (96° C., 30 s), touchdown annealing (54° C. to 49.5° C. for 30 s (−0.5° C. per cycles)), extension of 68° C. for 5 min, and final extension (68° C., 5 min). Upon completion, the samples were purified and used for heat-shock transformation of *E. coli* XL10. Individual colonies were selected on LB-agar containing streptomycin, and assayed by colony PCR with primers PtNTT2-fwd/rev or TpNTT2-fwd/rev. The presence of the NTT genes was confirmed by sequencing and double digestion with ApaI/EcoO109I restriction endonucleases with the following expected pattern: pCDF-1b-PtNTT2 (2546/2605 bp), pCDF-1b-TpNTT2 (2717/2605 bp), pCDF-1b (1016/2605 bp). The complete nucleotide sequence of the pCDF-1b PtNTT2 plasmid (i.e. pACS) is provided as SEQ ID NO:1.

Example 2: General Protocol to Quantify Nucleoside Triphosphate Uptake

Growth Conditions

*E. coli* C41(DE3) freshly transformed with pCDF-1b-PtNTT2 was grown in 2×YT with streptomycin overnight, then diluted (1:100) into fresh 2×YT medium (1 ml of culture per uptake with [α-$^{32}$P]-dATP; 2 ml of culture per uptake with d5SICSTP or dNaMTP) supplemented with 50 mM potassium phosphate (KPi) and streptomycin. A negative control with the inactive transporter pET-16b-RpNTT2, was treated identically except ampicillin was used instead of streptomycin. Cells were grown to an $OD_{600}$ of ~0.6 and expression was induced by the addition of IPTG (1 mM). The culture was allowed to grow for another hour (final $OD_{600}$ ~1.2) and then assayed directly for uptake as described below using a method adapted from Haferkamp, et al.

Preparation of Media Fraction dNaMTP or d5SICSTP (10 mM each) were added to media to a final concentration of 0.25 mM. Cells were incubated with the substrate with shaking at 37° C. for 30 min and then pelleted (8,000 rfu for 5 min, 4° C.). An aliquot of the media fraction (40 μl) was mixed with acetonitrile (80 μl) to precipitate proteins, and then incubated at RT for 30 min. Samples were either analyzed immediately by HPLC or stored at −80° C. until analysis. Analysis began with centrifugation (12,000 rfu for 10 min, RT), then the pellet was discarded, and the supernatant was reduced to ~20 μl, resuspended in 95% 0.1 M TEAB, pH 7.5; 5% acetonitrile, to a final volume of 50 μl, and analyzed by HPLC.

Preparation of Cytoplasmic Fraction

To analyze the intracellular dephosphorylation of unnatural nucleoside triphosphates, cell pellets were subjected to 3×100 μl washes of ice cold KPi (50 mM). Pellets were then resuspended in 250 μl of ice cold KPi (50 mM) and lysed with 250 μl of Lysis buffer L7 of the PureLink Quick Plasmid DNA Miniprep Kit (200 mM NaOH, 1% w/v SDS), after which the resulting solution was incubated at RT for 5 min. Precipitation buffer $N_4$ (350 μl, 3.1 M potassium acetate, pH 5.5) was added, and the sample was mixed to homogeneity. Following centrifugation (>12,000 rfu for 10 min, RT) the supernatant containing the unnatural nucleotides was applied to a C18 solid phase extraction column prewashed with acetonitrile (1 ml) and 95% 0.1 M TEAB, pH 7.5; 5% acetonitrile (1 ml). The column was then washed with 95% 0.1 M TEAB, pH 7.5; 5% acetonitrile and nucleotides were eluted with 1 ml of 50% acetonitrile:50% triethylammonium bicarbonate (TEAB) 0.1 M (pH 7.5). The eluent was reduced to ~50 μl and its volume was adjusted to 100 μl with 95% 0.1 M TEAB, pH 7.5; 5% acetonitrile before HPLC analysis.

HPLC

Samples were applied to a LC column (3 μm C18 300 Å, 250×4.6 mm) and subjected to a linear gradient of 0-40% with 20% 0.1 M TEAB, pH 7.5; 80% acetonitrile over 40 min at a flow rate of 1 ml/min. Quantification Injection series included two extra control samples containing 5 nmol of dNaMTP or d5SICSTP. The areas under the peaks that corresponded to triphosphate, diphosphate, monophosphate and free nucleoside (confirmed by MALDI-TOF) were integrated for both the control and the unknown samples. After peak integration, the ratio of the unknown peak to the control peak adjusted for the loss from the extraction step (62% and 70% loss for dNaM and d5SICS, respectively), provided a measure of the amount of each of the moieties in a sample. To determine the relative concentrations of unnatural nucleotide inside a cell, the amount of imported unnatural nucleotide was then divided by the volume of cells, which was calculated from the volume of a single *E. coli* cell of (1 μm$^3$) multiplied by the number of cells in each culture ($OD_{600}$ of 1.0 equal to $1\times10^9$ cells per ml). An RpNTT2 sample was used as a negative control and its signal was subtracted to account for any incomplete washing of nucleotide species from the media.

$$[dXTP] = \frac{dXTP(\mu\text{mol})}{\text{cell volume}(1\times10^{-9}\mu l\ \text{cell}^{-1})\times\text{numberof cells}(2.4\times10^{9})}$$

dATP Uptake

To analyze the intracellular dephosphorylation of dATP, after induction of an NTT, an uptake reaction was initiated by the addition of dATP (spiked with [α-$^{32}$P]-dATP) to a final concentration of 0.25 mM, followed by incubation at 37° C. with shaking for 30 min. A culture was then centrifuged (8,000 rfu for 5 min, RT). Supernatant was analyzed by thin layer chromatography (TLC), while cell pellets were washed 3 times with ice cold KPi (50 mM, 100 μL) to remove excess radioactive substrate, lysed with NaOH (0.2 M, 100 μl) and centrifuged (10,000 rfu for 5 min RT) to pellet the cell debris, before the supernatant (1.5 μl) was analyzed by TLC.

TLC Analysis

Samples (1 μl) were applied on a 0.5 mm polyethyleneimine cellulose TLC plate and eluted first by sodium formate (0.5 M, pH 3.0) for 30 sec, then by sodium formate (2.5 M, pH 3.0) for 2.5 m, and finally by sodium formate (4.0 M, pH 3.0) for 40 m. Plates were dried using a heat gun and quantified by phosphorimaging and imaging software.

Example 3: Methods Developed for Nucleotide Extraction from Cells for HPLC Analysis To minimize the effect of the lysis and triphosphate extraction protocols on the decomposition of nucleoside triphosphate within the cell, the following extraction procedure was discovered that led to an unexpectedly highest recovery with and low extent of decomposition (Table 9). Cells were grown, washed, and then 5 nmol of either dNaMTP or d5SICSTP was added to the pellets, which were then subjected to various types of extractions including boiling water, hot ethanol, cold methanol, freeze and thaw, lysozyme, glass beads, NaOH, trichloroacetic acid (TCA) with Freon, and perchloric acid (PCA) with KOH. The recovery and composition of the control was quantified by HPLC. Method 3, i.e. cell lysis with NaOH (Table 6), was found to be unexpectedly effective and reproducible. Pellets were resuspended in ice cold KPi (50 mM, 250 μl) before addition of NaOH to decrease dephosphorylation after cell lysis (Method 4).

under the following thermal cycling conditions: Initial denaturation (96° C., 1 min) followed by 12 cycles of denaturation (96° C., 10 s), annealing (60° C., 15 s), and extension (68° C., 2 min). A similar PCR without unnatural triphosphates was run to obtain fully natural insert under similar conditions for construction of natural control plasmid. Reactions were subjected to spin column purification and then the target PCR product (122 bp) was purified by a 4% agarose gel.

pUC19 Linearization pUC19 (20 ng) was amplified by PCR under the following conditions: 1×Q5 reaction buffer, $MgSO_4$ adjusted to 3.0 mM, 0.2 mM of dNTP, 1 μM of each primers pUC19-lin-fwd and pUC19-lin-rev, and 0.02 U/μl of Q5 Hot Start High-Fidelity DNA Polymerase (in a total of 4×50 μl reactions with one reaction containing 0.5×Sybr Green I) under the following thermal cycling conditions: Initial denaturation (98° C., 30 s); 20 cycles of denaturation (98° C., 10s), annealing (60° C., 15 s), and extension (72° C., 2 min); and final extension (72° C., 5 min). The desired PCR product (2611 bp) was purified by a 4% agarose gel.

TABLE 6

| Extraction methods | | | | | | |
|---|---|---|---|---|---|---|
| | | | Total recovery, %[a] | | Triphosphate stability, %[b] | |
| | Method | Protocol summary | dNaM | d5SICS | dNaM | d5SICS |
| 1 | TCA with Freon | Lyse with cold TCA Extract aqueous phase using Freon with trioctylaminesolution. | 38 | 23 | 92 | 99 |
| 2 | PCA w/KOH | Lyse with cold PCA Precipitate proteins with KOH and KPi | 36 | 21 | 98 | 77 |
| 3 | NaOH w/KOAc | Lyse with NaOH and SDS Precipitate proteins with potassium acetate. | 21 | 26 | 86 | 100 |
| 4 | NaOH w/KOAc supplemented w/ KPi (50 mM) | Suspend cells in KPi Lyse with NaOH and SDS Precipitate proteins with potassium acetate. | 38 | 30 | 99 | 100 |

[a]Recovery of all nucleotides (3P, 2P, 1P and nucleoside).

[b]Calculated as a ratio of 3P composition (%) before and after the extraction.

Example 4: Construction of pINF

Preparation of the Unnatural Insert

The TK-1-dNaM oligonucleotide containing dNaM was prepared using solid phase DNA synthesis with ultra-mild DNA synthesis phosphoramidites on CPG ultramild supports (1 μmol) and a nucleic acid synthesizer. After the synthesis, the DMT-ON oligonucleotide was deprotected by treatment with concentrated ammonia hydroxide at 50° C. overnight, purified, and then subjected to 8 M urea 8% PAGE. The gel was visualized by UV shadowing, the band corresponding to a 75mer was excised, and DNA was recovered by crush and soak extraction, filtration (0.45 μm), and final desalting over Sephadex G-25. The concentration of single stranded oligonucleotide was determined by UV absorption at 260 nm (where extinction coefficient of dNaM at 260 nm assumed equal to that of dA). TK-1-dNaM (4 ng) was next amplified by PCR under the following conditions: 1×OneTaq reaction buffer, $MgSO_4$ adjusted to 3.0 mM, 0.2 mM of dNTP, 0.1 mM of dNaMTP, 0.1 mM of the d5SICSTP analog dTPT3TP, 1 μM of each of the primers pUC19-fusion-fwd and pUC19-fusion-rev, and 0.02 U/μl of OneTaq DNA Polymerase (in a total of 4×50 μl reactions)

PCR Assembly of pINF and the Natural Control Plasmid

A linear fragment was amplified from pUC19 using primers pUC19-lin-fwd and pUC19-lin-rev. The resulting product (800 ng, $4.6\times10^{-13}$ mol) was combined with either the natural or unnatural insert (see above) (56 ng, $7.0\times10^{-13}$ mol) and assembled by circular overlap extension PCR under the following conditions: 1×OneTaq reaction buffer, $MgSO_4$ adjusted to 3.0 mM, 0.2 mM of dNTP, 0.1 mM of dNaMTP, 0.1 mM of the d5SICSTP analog dTPT3TP, and 0.02 U/μl of OneTaq DNA Polymerase (in a total of 4×50 μl reactions with one reaction containing 0.5×Sybr Green I) using the following thermal cycling conditions: Initial denaturation (96° C., 1 min); 12 cycles of denaturation (96° C., 30 s), annealing 62° C., 1 min), and extension (68° C., 5 min); final extension (68° C., 5 min); and slow cooling (68° C. to 10° C. at a rate of −0.1° C./s). The PCR product was analyzed by restriction digestion on 1% agarose and used directly for *E. coli* transformation. The d5SICS analog dTPT3 pairs with dNaM and dTPT3TP was used in place of d5SICSTP as DNA containing dTPT3-dNaM is better PCR amplified than DNA containing d5SICS-dNaM, and this facilitated the construction of high-quality pINF (UBP content >99%).

Example 5: pINF Replication in *E. coli*

Preparation of Electrocompetent Cells

C41(DE3) cells were transformed by heat shock with 200 ng of pACS plasmid, and the transformants were selected overnight on 2×YT-agar supplemented with streptomycin. A single clone of freshly transformed C41(DE3)-pACS was grown overnight in 2×YT medium (3 ml) supplemented with streptomycin and KPi (50 mM). After 100-fold dilution into the same fresh 2×YT media (300 ml), the cells were grown at 37° C. until they reached an $OD_{600}$ of 0.20 at which time IPTG was added to a final concentration of 1 mM to induce the expression of PtNTT2. Cells were grown for another 40 min and then growth was stopped by rapid cooling in ice water with intensive shaking. After centrifugation in a prechilled centrifuge (2400 rfu for 10 min, 4° C.), the spent media was removed, and the cells were prepared for electroporation by washing with ice-cold sterile water (3×150 ml). After washing, the cells were resuspended in ice cold 10% glycerol (1.5 ml) and split into 50 μl aliquots. Cells were frozen if to store for later use. Freshly prepared cells were used and frozen cells can be used.

Electroporation and Recovery

The aliquot of cells was mixed with 2 μl of plasmid (400 ng), transferred to 0.2 cm gap electroporation cuvette and electroporated using a Bio-Rad Gene Pulser according to the manufacturer's recommendations (voltage 25 kV, capacitor 2.5 ρF, resistor 200Ω, time constant 4.8 ms). Pre-warmed 2×YT media (0.95 ml, streptomycin, 1 mM IPTG, 50 mM KPi) was added, and after mixing, 45 μl was taken and combined with 105 μl of the same media (3.33×dilution) supplemented with 0.25 mM of dNaMTP and d5SICSTP.

Growth and Analysis

After recovery, the cells were centrifuged (4000 rfu for 5 min, 4° C.), spent media (0.15 ml) was removed and analyzed for nucleotide composition by HPLC. The cells were resuspended in fresh 2×YT media (1.5 ml, streptomycin, ampicillin, 1 mM IPTG, 50 mM KPi, 0.25 mM dNaMTP, 0.25 mM d5SICSTP) and grown overnight at 37° C. while shaking (250 rpm), resulting in 10×dilution compared to recovery media or 33.3×dilution compared to the originally transformed cells. Aliquots (100 μl) were taken after 15, 19, 24, 32, 43, 53, 77, 146 h, $OD_{600}$ was determined, and the cells were centrifuged (8000 rfu for 5 min, 4° C.). Spent media was analyzed for nucleotide composition by HPLC and the pINF and pACS plasmid mixtures were purified by recovered by spin column, eluted in 30 μl of water and analyzed by restriction digestion. The retention of the UBP on the pINF plasmid was quantified by biotin gel shift mobility assay and sequencing.

Figure 11A:
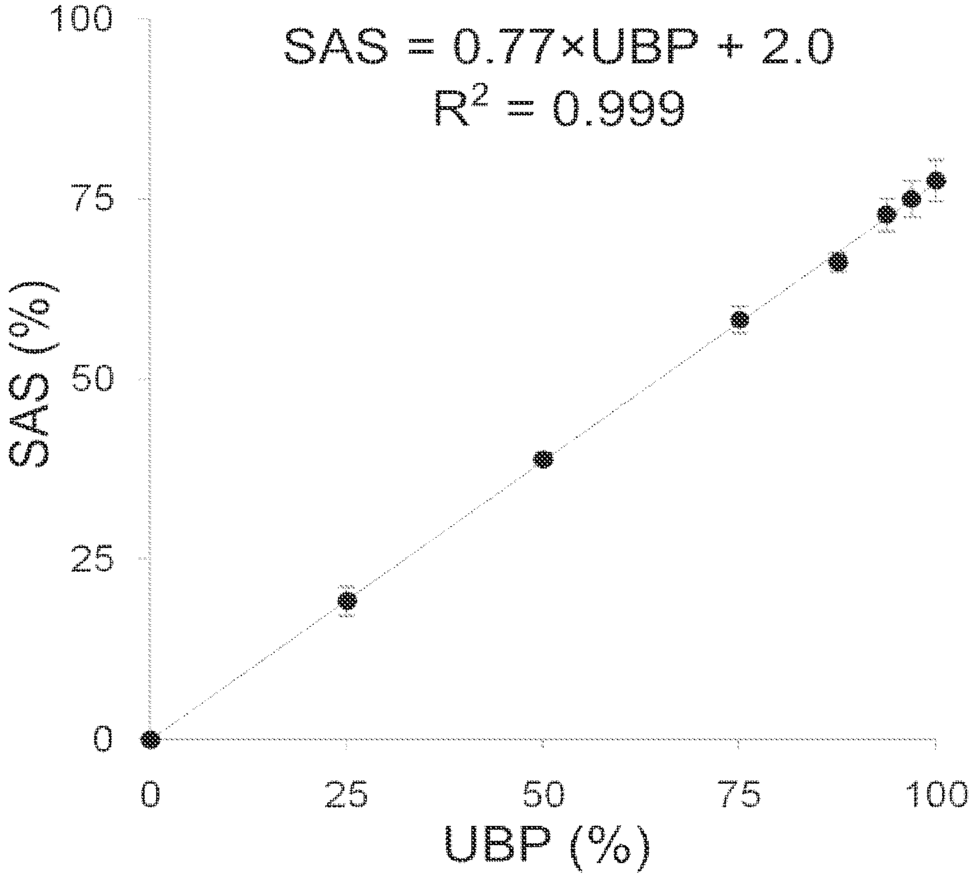
FIG. 11A illustrates a calibration graph of the streptavidin shift (SAS) as a function of the fraction of template containing the UBP.
Figure 11B:
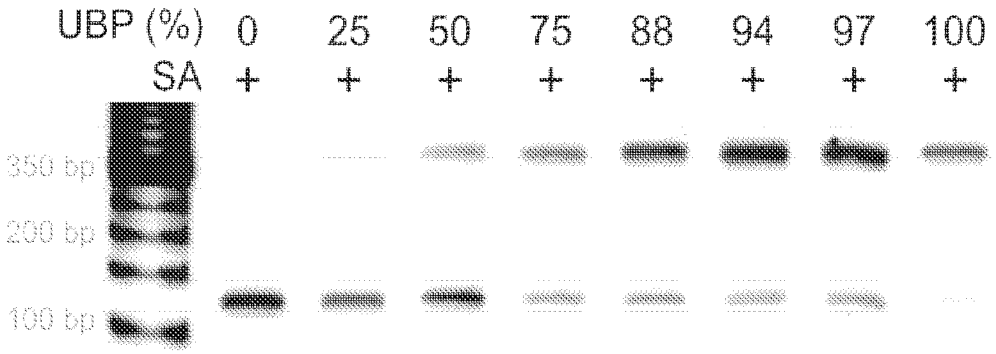
FIG. 11B illustrates and representative raw data from SAS samples run in triplicate. SA=streptavidin.

Transformation media (10 μl) was spread onto 2×YT-agar containing streptomycin with 10×and 50×dilutions to determine viable colony forming units after overnight growth at 37° C. to calculate the number of the transformed pINF molecules. Transformation, recovery, and growth were carried out similarly for the natural control plasmid. Additionally, a negative control was run and treated similarly to pINF transformation except that it was not subjected to electroporation (FIG. 11). No growth in the negative control samples was observed after at least 6 days. No PCR amplification of the negative control was detected. Thus, unamplified pINF plasmid was carried through cell growth and later detected erroneously as the propagated plasmid.

Example 6: Fidelity Measurement

DNA Biotinylation by PCR

Purified mixtures of pINF and pACS plasmids (1 ng) from growth experiments (FIGS. 3 and 4) were amplified by PCR under the following conditions: 1×OneTaq reaction buffer, $MgSO_4$ adjusted to 3.0 mM, 0.3 mM of dNTP, 0.1 mM of the biotinylated dNaMTP analog dMMO2$^{SSBIO}$TP, 0.1 mM of d5SICSTP, 1 μM of each of the primers pUC19-seq-fwd and pUC19-seq-rev, 0.02 U/μl of OneTaq DNA Polymerase, and 0.0025 U/μl of DeepVent DNA Polymerase in a total volume of 25 μl in an CFX Connect Real-Time PCR Detection System (Bio-Rad) under the following thermal cycling conditions: Initial denaturation (96° C., 1 min); 10 cycles of denaturation (96° C., 30 s), annealing (64° C., 30 s), and extension (68° C., 4 min).

PCR products were purified as described in Materials, and the resulting biotinylated DNA duplexes (5 μl, 25-50 ng) were mixed with streptavidin (1 μl, 1 μg/μl, Promega) in phosphate buffer (50 mM sodium phosphate, pH 7.5, 150 mM NaCl, 1 mM EDTA), incubated for 30 min at 37° C., mixed with 5× non-denaturing loading buffer, and loaded onto 6% non-denaturing PAGE. After running at 110 V for 30 min, the gel was visualized and quantified. The resulting fragment (194 bp) with primer regions underlined and the unnatural nucleotide in bold (X=dNaM or its biotinylated analog dMMO2$^{SSBIO}$) is shown below (SEQ ID NO:26).

```
5'-GCAGGCATGCAAGCTTGGCGTAATCATGGTCATAGCTGTTTCCTGTG
TGAAATTGTTATCCGCTCACAXTTCCACACAACATACGAGCCGGAAGCAT
AAAGTGTAAAGCCTGGGGTGCCTAATGAGTGAGCTAACTCACATTAATTG
CGTTGCGCTCACTGCCCGCTTTCCAGTCGGGAAACCTGTCGTGCCAG
```

Streptavidin Shift Calibration

To build a calibration curve between streptavidin (SA) shift and the fraction of sequences with UBP in the population (UBP), a PCR method was developed where the reaction was spiked with DeepVent. The method improved the fidelity with which DNA containing d5SICS-dMMO2$^{SSBIO}$ was amplified. Calibration was conducted under similar conditions. To quantify the net retention of the UBP, nine mixtures of the TK-1-dNaM template and its natural counterpart with a known ratio of unnatural and natural were prepared, subjected to biotinylation by PCR, and analyzed by a mobility-shift assay on 6% non-denaturing PAGE. For calibration, the mixtures TK-1-dNaM template and its natural counterpart with a known ratio of unnatural and natural templates (0.04 ng) were amplified under similar conditions over nine cycles of PCR with pUC19-fusion primers and analyzed similar to samples from growth experiments described herein. Experiments were run in triplicate and the streptavidin shift (SAS, %) was plotted as function of the UBP content (UBP, %) and the data fit to a linear equation:

$$SAS=0.77\times UBP+2.0 R^2=0.999. \quad \text{Equation 1:}$$

where UBP corresponds to the retention of the UBP (%) in the analyzed samples after cellular replication and was calculated from the SAS shift using Equation 1.

Calculation of Plasmid Amplification

Cells were plated on 2×YT-agar containing ampicillin and streptavidin after transformation with pINF, and colonies were counted after overnight growth at 37° C. Transformed cells were assumed to contain one molecule of plasmid. Colony counts corresponded to the original amount of plasmid that was taken up by the cells. After overnight growth (FIG. 4), the plasmids were purified from a volume of the cell culture and quantified. Since purified plasmid DNA represent a mixture of pINF and pACS plasmid, digestion restriction analysis with NdeI exonuclease was performed that linearized both plasmids followed by 1% agarose gel. An example of calculations for the 19 h time point with one out of three triplicates is provided below.

Example of Calculation of Plasmid Amplification after 19 h

Known (or Measured) Parameters:

| | |
|---|---|
| Number of colonies after transformation (10 µl of culture plated) | 1750 ± 200 |
| Dilution for growth experiment, fold | 33.3 |
| Volume of culture purified for plasmid extraction, µl | 100 |
| Elution volume, µl | 30 |
| pINF fraction in total plasmid mixture, % | 43 |
| Total plasmid concentration, ng µl−1 | 2.97 |
| Biotin shift, % | 74.2 |

Calculation of Plasmid Concentration Before Growth:

$$\frac{175 \text{ molecules } \mu l^{-1}}{33.3} = 5.3 \text{ molecules } \mu l^{-1}$$

Calculation of Plasmid Amount in 100 µl of Media after Growth (19 h):

pINF amount:

$2.97 \text{ ng } 1\ \mu l^{-1} \times 43\% \times 30\ \mu l = 38 \text{ ng}$

Number of pINF Molecules:

$$\frac{38\times 10^{-9} \text{ g}}{2686 \text{ bp}\times 660 \text{ g mol}^{-1}\text{bp}^{-1}} \times 6.02\times 10^{23} \text{ molecules mol}^{-1} = 1.3\times 10^{10} \text{ molecules}$$

Plasmid Concentration:

$$\frac{1.3\times 10^{10} \text{ molecules}}{100\ \mu l} = 1.3\times 10^{8} \text{ molecules } \mu l^{-1}$$

Calculation of Amplification (A), the Number of Doubling (n), Retention (F), and Fidelity (f)

$$A = \frac{1.3\times 10^{8} \text{ molecules } \mu l^{-1}}{5.3 \text{ molecules } \mu l^{-1}} = 2.4\times 10^{7}$$

$$n = \log_2(2.4\times 10^{7}) = 24.5$$

$$F = \frac{0.742 - 0.020}{0.772} = 93.5\%$$

$$f = 0.935^{\frac{1}{24.5}} = 99.7\%$$

Since plasmid recovery during purification is below 100%, our calculations underestimate the amplification level (A) and thus the number of doubling (n).

The fidelity (retention per doubling) is related to retention of the UBP (F) as $$f^n = F$$

and, since $n=\log_2(A)$, fidelity was calculated as $$f = F^{\frac{1}{n}}.$$

Figure 3A:
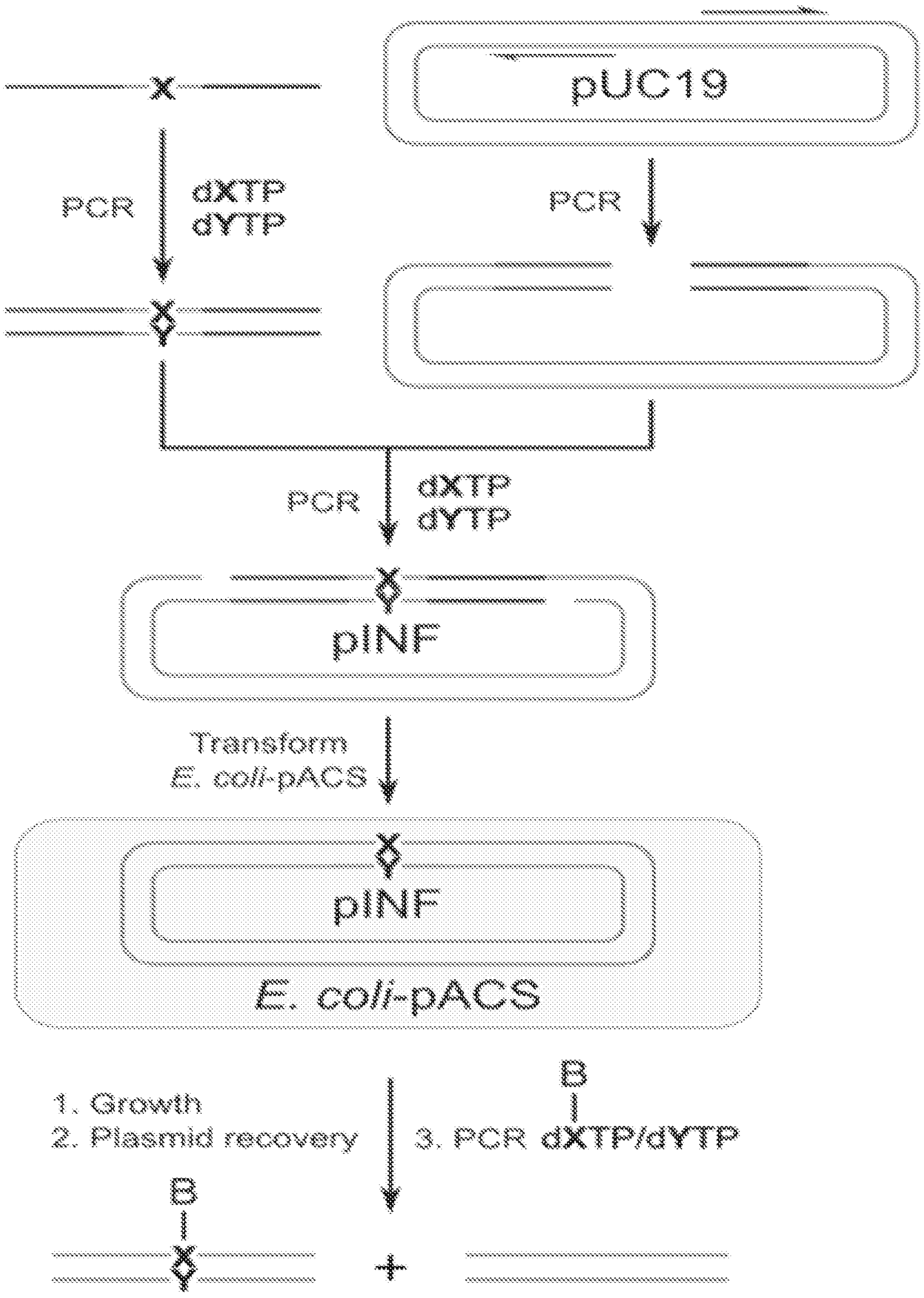
FIG. 3A depicts an exemplary pINF construction and scheme of an in vivo replication experiment. Regions of homology are depicted by shading. (Y=5SICS and X=NaM). B=biotin.
Figure 3B:
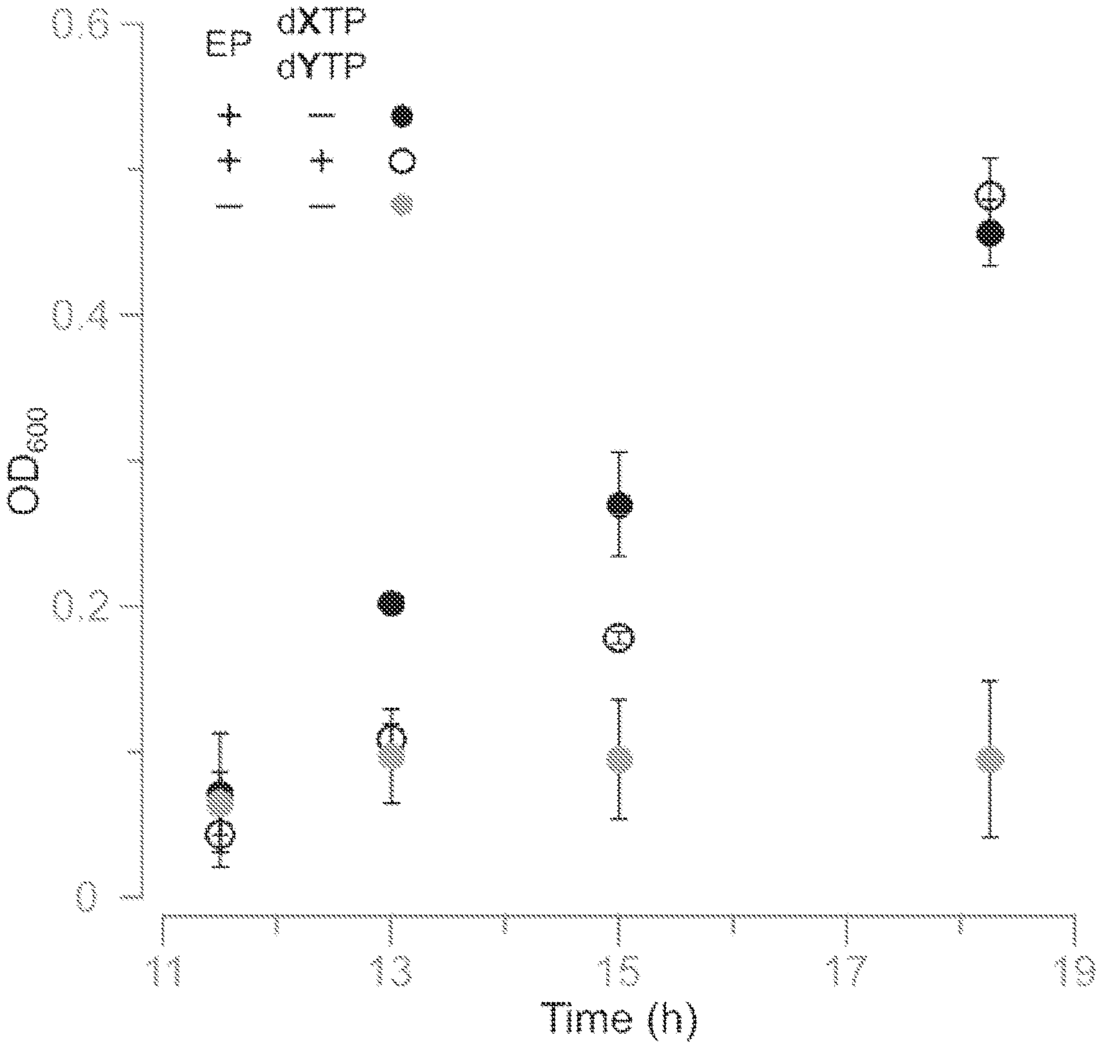
FIG. 3B depicts a growth curve of cells harboring pINF to which d5SICSTP and dNaMTP have been added. EP=electroporation.
Figure 3C:
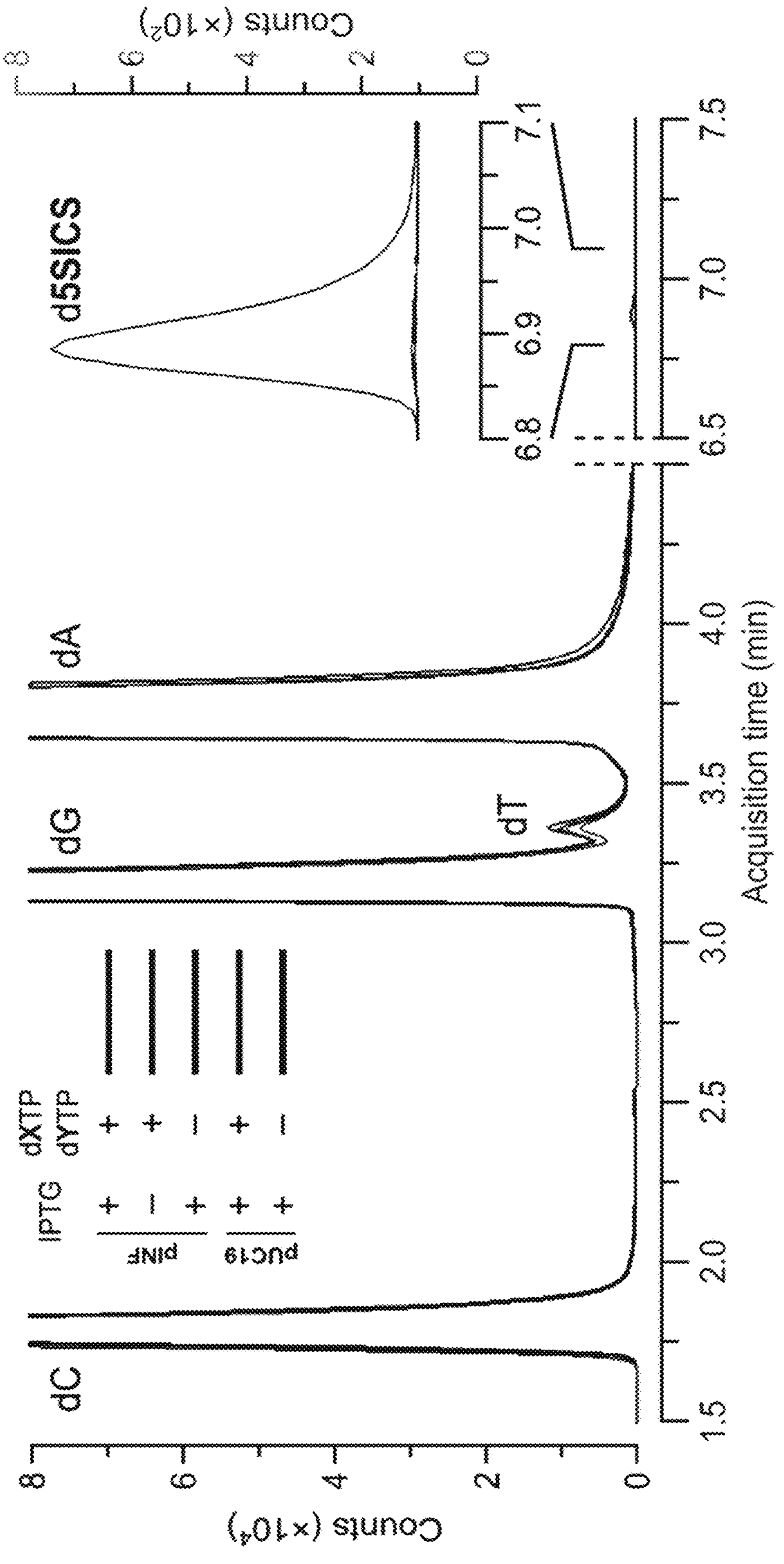
FIG. 3C depicts an LC-MS/MS total ion chromatogram of global nucleoside content in pINF and pUC19 recorded in Dynamic Multiple Reaction Monitoring (DMRM) mode. pINF and pUC19 (control) were propagated in *E. coli* in the presence or absence of unnatural triphosphates, and with or without PtNTT2 induction. The inset shows a 100×expansion of the mass count axis in the d5SICS region.
Figure 3D:
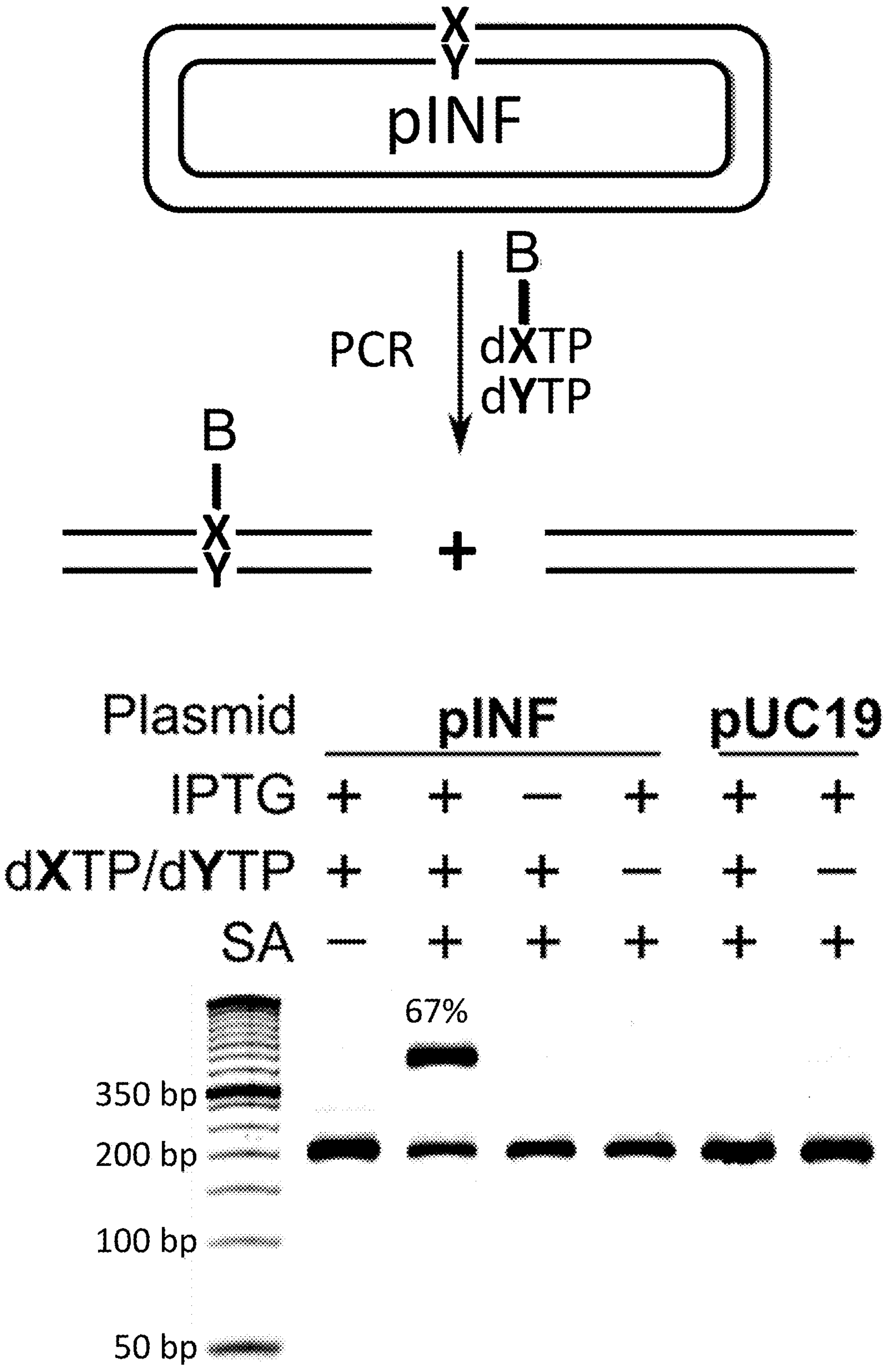
FIG. 3D depicts a gel shift analysis of PCR fragments demonstrating biotinylation in the presence of the UBP, unnatural triphosphates, and transporter induction. B=biotin. SA=streptavidin. A 50 bp DNA ladder is shown to the left.
Figure 3E:
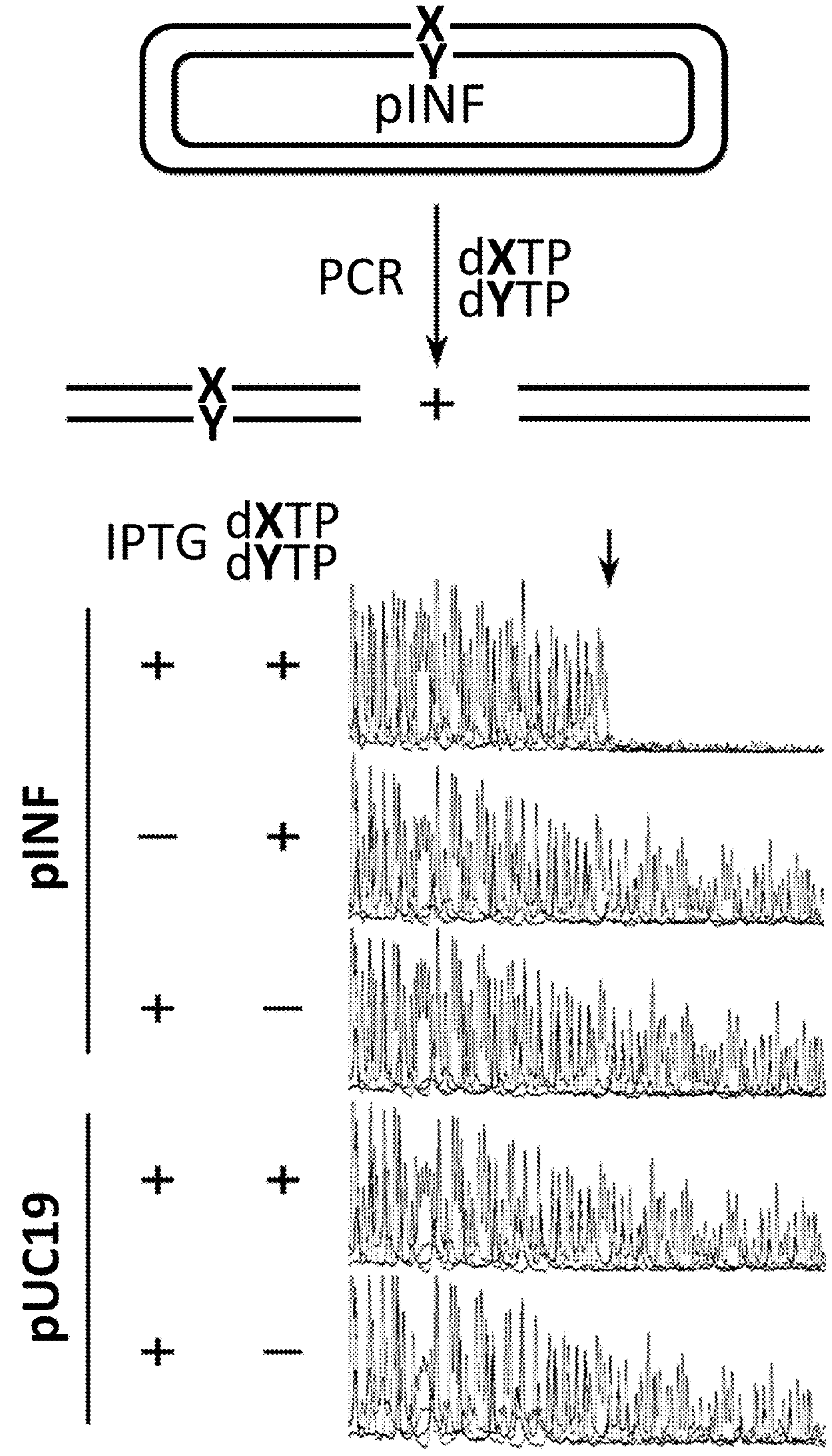
FIG. 3E depicts a Sanger sequencing analysis demonstrating retention of the UBP, as evidenced by an abrupt termination in the sequencing reaction at the position of UBP incorporation (indicated with arrow).

Example 7: Fidelity Measurement by Sequencing (FIG. 3E)

Fragment Generation for Sequencing

Purified mixtures of pINF and pACS plasmids (1 ng) after the overnight growth were amplified by PCR under the following conditions: 1×OneTaq reaction buffer, $MgSO_4$ adjusted to 3.0 mM, 0.2 mM of dNTP, 0.1 mM of dNaMTP, 0.1 mM of the d5SICSTP analog dTPT3TP, 1 µM of each of the primers pUC19-seq2-fwd and pUC19-seq-rev (see below), and 0.02 U/µl of OneTaq DNA Polymerase in a total volume of 25 µl under the following thermal cycling conditions: denaturation (96° C., 1 min); and 10 cycles of denaturation (96° C., 30 s), annealing 64° C., 30 s), and extension 68° C., 2 min. Products were purified by spin column, quantified to measure DNA concentration and then sequenced as described below. Sequencing fragment (304 bp) with primer regions are underlined and the unnatural nucleotide in bold (X=dNaM) is shown below.

(SEQ ID NO: 27)

```
5'-GCTGCAAGGCGATTAAGTTGGGTAACGCCAGGGTTTTCCCAGTCACG

ACGTTGTAAAACGACGGCCAGTGAATTCGAGCTCGGTACCCGGGGATCCT

CTAGAGTCGACCTGCAGGCATGCAAGCTTGGCGTAATCATGGTCATAGCT

GTTTCCTGTGTGAAATTGTTATCCGCTCACAXTTCCACACAACATACGAG

CCGGAAGCATAAAGTGTAAAGCCTGGGGTGCCTAATGAGTGAGCTAACTC

ACATTAATTGCGTTGCGCTCACTGCCCGCTTTCCAGTCGGGAAACCTGTC

GTGCCAG.
```

Sanger Sequencing

The cycle sequencing reactions (10 µl) were performed on a 9800 Fast Thermal Cycler (Applied Biosystems) with the Cycle Sequencing Mix (0.5 µl) of the BigDye Terminator v3.1 Cycle Sequencing Kit (Applied Biosystems) containing 1 ng template and 6 pmol of sequencing primer pUC19-seq-rev under the following thermal cycling conditions: initial denaturation (98° C., 1 min); and 25 cycles of denaturation (96° C., 10 s), annealing (60° C., 15 s), and extension (68° C., 2.5 min). Upon completion, residual dye terminators were removed from the reaction. Products were eluted off the beads with deionized water and sequenced directly. Sequencing traces were collected and analyzed with imaging software.

Analysis of Sanger Sequencing Traces

Sanger Sequencing traces were analyzed to determine the retention of the UBP. Briefly, the presence of an unnatural nucleotide leads to a sharp termination of the sequencing profile, while mutation to a natural nucleotide results in "read-through". The extent of this read-through after normalization is inversely correlated with the retention of an UBP. Raw sequencing traces were analyzed by first adjusting the start and stop points for the sequencing analysis software and then determining the average signal intensity individually for each channel (A, C, G and T) for peaks within the defined points. This was done separately for the parts of the sequencing trace before (section L) and after (section R) the unnatural nucleotide. The R/L ratio after normalization $(R/L)_{norm}$ for sequencing decay and read-through in the control unamplified sample (R/L=

$0.55(R/L)_{norm}+7.2$, corresponds to the percentage of the natural sequences in the pool (Malyshev et al.). Therefore, an overall retention (F) of the incorporation of the UBP during PCR was calculated as:

$$1-\left(\frac{R}{L}\right)_{norm}.$$

Over 20% read-through occurred in the direction of pUC19-seq2-fwd primer using a control plasmid pINF. Sequencing of the opposite direction (pUC19-seq-rev) was performed and used to gauge fidelity and UDP retention as a function of growth (Table 7). Raw sequencing traces are shown in FIG. 3F.

TABLE 7

UBP retention (%) as a function of growth

| Time (h) | Sequencing Analysis | Gel Shift Analysis |
|---|---|---|
| 15 | >95 | 97 ± 5 |
| 19 | >95 | 91 ± 3 |
| 24 | >95 | 83 ± 1 |
| 32 | 85 ± 5 | 64 ± 10 |
| 43 | 71 ± 10 | 55 ± 13 |
| 53 | 68 ± 21 | 51 ± 18 |
| 77 | 60 ± 16 | 42 ± 18 |
| 146 | 30 ± 12 | 12 ± 8 |

Example 8: Polymerase Incorporation of Unnatural Nucleic Acids

Test reaction mixtures are added to the wells of a multi-well plate, where each well contains primed DNA templates attached to the bottoms of the wells. The test reaction mixtures contain a polymerase variant and an unnatural nucleic acid, an unnatural nucleic acid having (1) a base moiety that complements the appropriate position of the template for accurate extension to occur and (2) a biotinylated moiety attached to the sugar moiety. Following sufficient incubation time for extension to occur (e.g. for a control reaction having a polymerase of known reactivity with the unnatural nucleic acid), the reaction mixture is removed, the wells of the plate are washed to remove residual unnatural nucleic acids, and a development reagent is added to the wells. The development reagent includes a labeled streptavidin molecule that is capable of binding to nucleic acid molecules attached to well bottoms that have incorporated the unnatural nucleic acid. The label on the streptavidin molecule is any of a variety known in the art. The plate is washed again to remove unbound labeled streptavidin molecules. The label is then detected using a multiwell plate reader. The presence of signal from the labeled streptavidin indicates a polymerase having the ability to incorporate an unnatural nucleic acid. The same assay is used to determine kinetics or other quantitative parameters by varying the reaction time and or concentration of liquid-

TABLE 8

Exemplary oligonucleotide sequences

| Name | Sequence (5' to 3') | Purpose |
|---|---|---|
| pCDF-1b-fwd | GGTATATCTCCTTATTAAAGTTAAACAAAATTATT TCTACAGGGG (SEQ ID NO: 29) | Primers for pCDF-1b linearization |
| pCDF-1b-rev | TTAACCTAGGCTGCTGCCACCG (SEQ ID NO: 49) | |
| PtNTT2-fwd | GTTTAACTTTAATAAGGAGATATACCATGAGACCA TTTCCGAC (SEQ ID NO: 30) | Primers for PtNTT2 cloning |
| PtNTT2-rev | GCAGCAGCCTAGGTTAACTACTTTTCTTTGTTGGTC TTTG (SEQ ID NO: 31) | |
| TpNTT2-fwd | GTTTAACTTTAATAAGGAGATATACCATGAAAAAA TCTTGTACAATCC (SEQ ID NO: 32) | Primers for TpNTT2 cloning |
| TpNTT2-rev | GCAGCAGCCTAGGTTAACTACTTCTGGTGCTCTTT TG (SEQ ID NO: 33) | |
| pUC19-lin-fwd | TGGGGTGCCTAATGAGTGAGC (SEQ ID NO: 50) | Primers for pUC19 linearization |
| pUC19-lin-rev | CTATGACCATGATTACGCCAAGCTTG (SEQ ID NO: 34) | |
| TK-1-dNaM | CTGTTTCCTGTGTGAAATTGTTATCCGCTCACA**Na** **M**TTCCACACAACATACGAGCCGGAAGCATAAAGT GTAAAGCC (SEQ ID NO: 35) | Unnatural fragment with dNaM |
| TK-1-dT | CTGTTTCCTGTGTGAAATTGTTATCCGCTCACA**T** TTCCACACAACATACGAGCCGGAAGCATAAAGTG TAAAGCC (SEQ ID NO: 36) | Natural fragment with dT |
| pUC19-fusion-fwd | CAAGCTTGGCGTAATCATGGTCATAGCTGTTTCCT GTGTGAAATTGTTATCCGC (SEQ ID NO: 37) | Primers for unnatural fragment cloning |
| pUC19-fusion-rev | GCTCACTCATTAGGCACCCCAGGCTTTACACTTTA TGCTTCCGGC (SEQ ID NO: 38) | |
| pUC19-seq-fwd | GCAGGCATGCAAGCTTGGCGTAATCATGG (SEQ ID NO: 39) | Primers for pINF analysis by gel shift and Sanger sequencing |
| pUC19-seq2-fwd | GCTGCAAGGCGATTAAGTTGGGTAACGCC (SEQ ID NO: 40) | |
| pUC19-seq-rev | CTGGCACGACAGGTTTCCCGACTGG (SEQ ID NO: 41) | |

phase reagents. Similar screens are carried out for other unnatural nucleic acid by minor modification of the reagents exemplified above.

Example 9: Polymerase Incorporation of TPT3, (d)FTPT3, (d)NaM, (d)5SICS, (d)FEMO, (d)FIMO, and/or (d)MMO2 into DNA Polymerase (15 μg/ml) is incubated at 30° C. in buffer (50 mM TRIS pH 7.5, 0.05% Tween 20, 6 mM $MgSO_4$, 1 mM EDTA, 50 mM NaCl) with 20 nM DNA. A time zero aliquot is taken for each concentration and then TPT3, (d)FTPT3, (d)NaM, (d)5SICS, (d)FEMO, (d)FIMO, and/or (d)MMO2 is added at 10, 5, 2 or 1 μM final concentration to start the reaction. Tubes are incubated at 30° C. and aliquots are taken at 0.33, 0.66, 1, 2, 5, and 15 mins from the 4 reaction tubes for quenching and 15% urea acrylamide gel analysis. 1 mM dNTPs are added to the remaining reaction tubes and after a further 10 mins an aliquot is taken for gel analysis (chase).

A photograph of the gel resulting from the above polymerase extension reaction is then taken. The results show the primer changing into larger band over the time course, with an increase in the amount of the larger band over time. The larger band demonstrates the addition of the (d)TPT3, (d)FTPT3, (d)NaM, (d)5SICS, (d)FEMO, (d)FIMO, and/or (d)MMO2 to the DNA (i.e. extension by one base). Following the addition of natural dNTPs the polymerase is able to extend the primer to the end of the template demonstrating that addition of the (d)TPT3, (d)FTPT3, (d)NaM, (d)5SICS, (d)FEMO, (d)FIMO, and/or (d)MMO2 does not create a 3' blocked primer and that the polymerase is able to extend the primer with natural and unnatural nucleic acids. The incorporation is more rapid at higher concentrations (10 μM) than at lower ones (1 μM) and shows time dependence indicative of genuine enzyme incorporation.

The results demonstrate the surprising finding that the polymerase can have selective primer extension reactivity for (d)TPT3, (d)FTPT3, (d)NaM, (d)5SICS, (d)FEMO, (d)FIMO, and/or (d)MMO2 and natural nucleic acids.

Example 10: Creation of a Cell with an Expanded Genetic Alphabet

Figure 5:
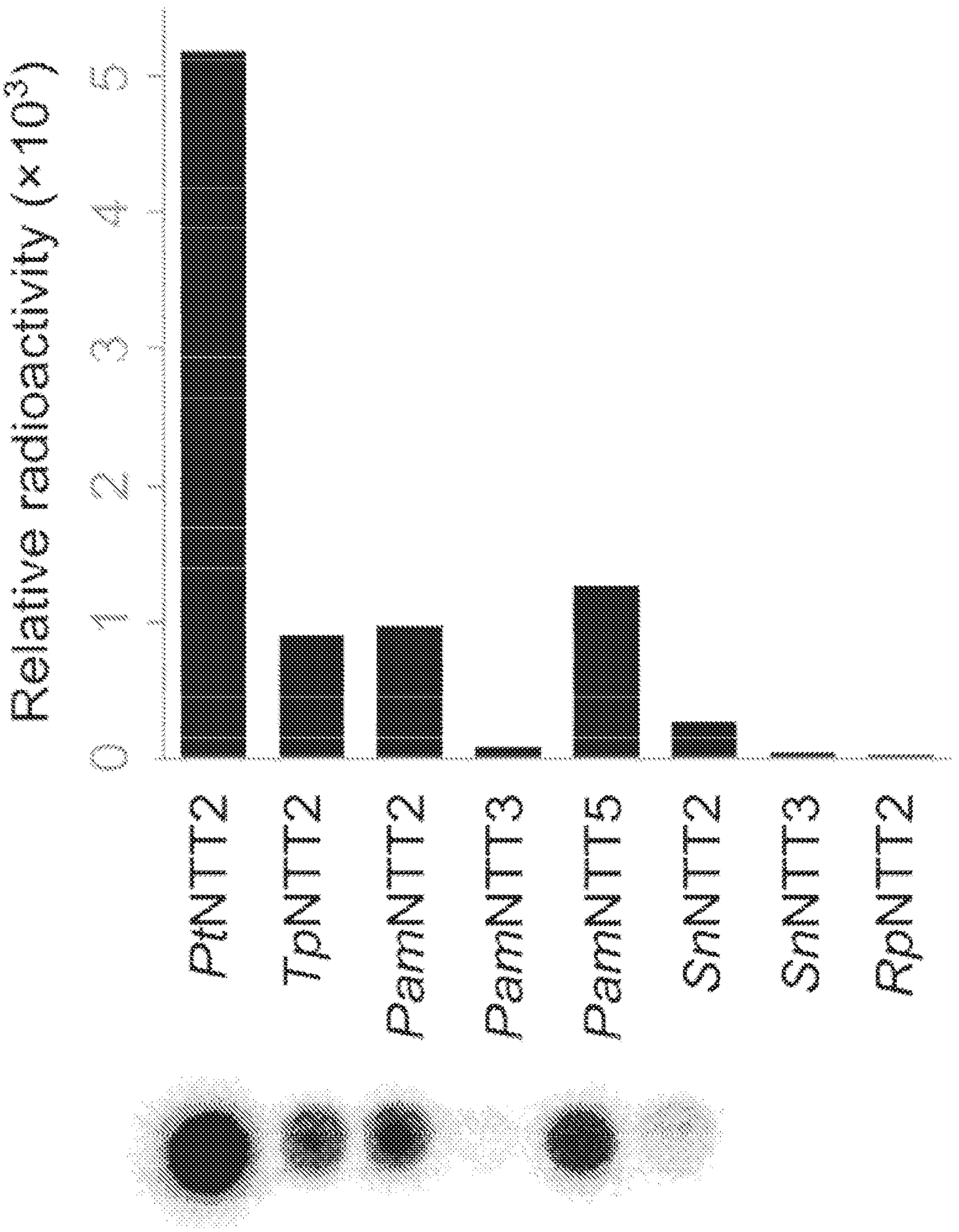
FIG. 5 depicts that PtNTT2 is significantly more active in the uptake of [α-$^{32}$P]-dATP compared to other nucleotide transporters. Raw (left) and processed (right) data are shown. Relative radioactivity corresponds to the total number of counts produced by each sample.

The experiments described herein illustrate the plasmid-based expression of eight different NTTs in *E. coli* C41 (DE3) (Table 9A). The uptake of [α-$^{32}$P]-dATP was examined as a surrogate for the unnatural triphosphates (FIG. 5). The dATP was efficiently transported into cells by the NTTs from *Phaeodactylum tricornutum* (PtNTT2) and *Thalassiosira pseudonana* (TpNTT2). Unexpectedly, the NTTs from *Protochlamydia amoebophila* (PamNTT2 and PamNTT5) were found to also import dATP. Both PamNTT2 and PamNTT5 exhibited a measurable uptake of dATP (FIG. 5). PtNTT2 showed the most activity, and both it and TpNTT2 are demonstrated broad specificity, making them putative NTTs for importing nucleotide triphosphates.

Figure 10:
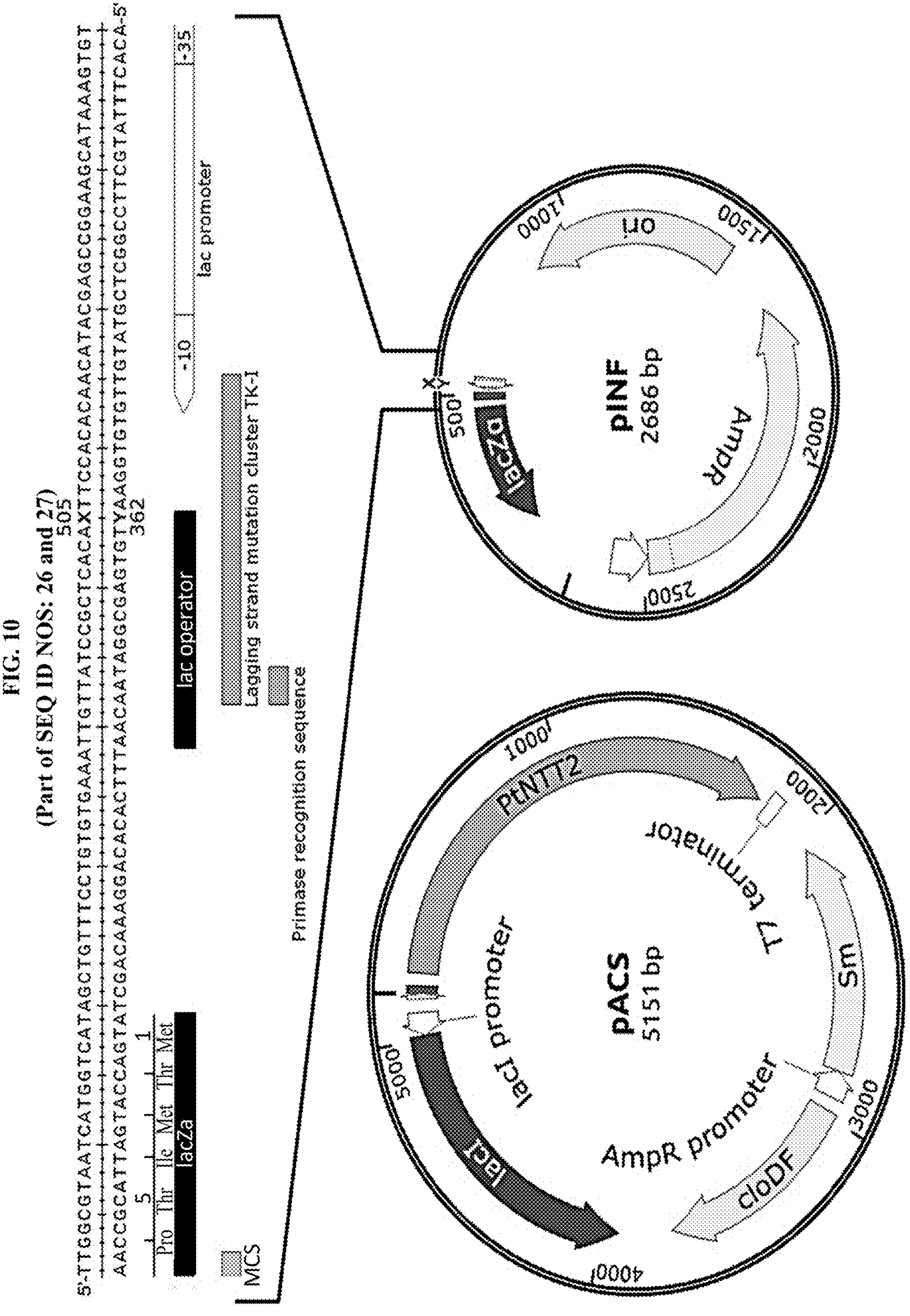
FIG. 10 shows schematic representations of the plasmid pINF, constructed from pUC19 by replacing $dT_{505}$ with dNaM, and of the pCDF-1b plasmid encodingPPtNTT2 (pACS). dX and dY correspond to dNaM and a d5SICS analog. cloDF=origin of replication of pCDF-1b plasmid; Sm=streptomycin resistance gene; AmpR=ampicillin resistance gene; ori=ColE1 origin of replication; MCS=multiple cloning site; lacZα=β-galactosidase fragment gene.

The replication of DNA containing d5SICS-dNaM has been validated in vitro with different polymerases, but most so with the family A polymerases, such as the Klenow fragment of *E. coli* DNA Polymerase I (Pol I). While the majority of the *E. coli* genome is replicated by Pol III, an plasmid was engineered that focused on replication of the UBP by Pol I. The accessory plasmid (pACS) was derived from pCDF-1b by inserting the PtNTT2 gene (FIG. 10). The information plasmid (pINF) was derived from pUC19 by replacing $dT_{505}$ (standard numbering of the pUC19 map available for download at http://www.thermoscientificbio-.com/uploadedFiles/Resources/pUC18-pUC19-map.pdf) with dNaM. This places the UBP 362 nts downstream of the ColE1 origin (FIG. 10). Plasmid pINF (i.e. the information plasmid) was constructed from pUC19 by replacing $dT_{505}$ with dNaM using solid phase synthesis and circular extension PCR (FIG. 3A and FIG. 10). The dA-dT pair at position 505 was replaced with dNaM paired opposite an analog of d5SICS (dTPT3). This positions the UBP downstream of the ColE1 origin of replication where leading strand replication is mediated by Pol I, and within the TK-1 Okazaki processing site, where lagging strand synthesis is also expected to be mediated by Pol I. Synthetic pINF was constructed using the d5SICS analog because it should be efficiently replaced by d5SICS if replication occurs in vivo and thus makes it possible to differentiate in vivo replicated pINF from synthetic pINF.

To determine whether *E. coli* can use the imported unnatural triphosphates to stably propagate pINF, C41(DE3) cells were first transformed with a pCDF-1b plasmid encoding PtNTT2 (hereafter referred to as pACS, for accessory plasmid, FIG. 10, and see Seq ID No. 1, below) and grown in media containing 0.25 mM of both unnatural triphosphates, 50 mM KPi, and 1 mM IPTG to induce transporter production. Cells were then transformed with pINF, and after a 1 h recovery period, cultures were diluted 10-fold with the same media supplemented with ampicillin and growth was monitored via culture turbidity (FIG. 3A and Table 9A and B).

TABLE 9A

| | Deoxyribotriphosphates | | | | Ribotriphosphates | | | |
|---|---|---|---|---|---|---|---|---|
| Transporter | dG | dA | dC | T | G | A | C | U |
| PtNTT2 | 82 | 271 | 31 | 428 | 78 | 197 | 49 | 86 |
| TpNTT2 | 74 | 665 | 60 | 251 | 59 | 49 | 33 | 90 |
| PamNTT2 | | | | | 156 | 437 | 570 | 676 |
| PamNTT3 | | | | | | | | 1320 |
| PamNTT5 | 121 | | | | 22 | 360 | | |
| SnNTT2 | | | | | 179 | 654 | | |
| SnNTT3 | | | 42 | | 407 | 375 | 9 | 34 |
| RpNTT2 | | | Substrate is unknown | | | | | |

Substrate specificity ($K_M$, μM) of depicted NTT

TABLE 9B

| Plasmid | IPTG | dXTP/dYTP | Relative Copy Number | OD600 (15 h) | OD600 (19 h) |
|---|---|---|---|---|---|
| pINF | + | + | 1.8 | 0.34 | 0.75 |
| | + | − | 4.6 | 0.15 | 0.75 |
| | − | + | 8.9 | 3.13 | 3.98 |
| pUC19 | + | + | 2.8 | 0.54 | 1.25 |
| | − | − | 2.6 | 0.73 | 1.30 |

$OD_{600}$ and relative plasmid copy number of pINF as determined by its molar ratio to pACS after 15 and 19 h of growth.
X = NaM and
Y = 5SICS.

As controls, cells were also transformed with pUC19, or grown without either IPTG or the unnatural triphosphates. Growth was slower in the presence of IPTG, likely due to the effects of transporter induction. However, the addition of d5SICSTP and dNaMTP resulted in only a slight decrease in growth in the absence of pINF, and it eliminated a growth lag in the presence of pINF (FIG. 3B). This indicates that the unnatural triphosphates are not toxic and are required for the efficient replication of pINF.

To determine whether pINF is propagated with retention of the UBP, we recovered the plasmid from cells after 15 h of growth. The introduction of the UBP resulted in only a small reduction in plasmid copy number (<2-fold, Table 9B), and based on the amount of recovered plasmid and the transformation efficiency, pINF was amplified $2\times10^7$-fold during growth (~24 doublings).

To determine the level of UBP retention, the recovered plasmid was digested, dephosphorylated to single nucleosides, and analyzed by LC-MS/MS. While the detection and quantification of dNaM were precluded by its poor fragmentation efficiency and low product ion counts over background, signal for d5SICS was clearly observable (FIG. 3C). External calibration curves were constructed using the unnatural nucleoside and validated by determining its ratio to dA in synthetic oligonucleotides (Table 7). Using the resulting calibration curve, we determined the ratio of dA to d5SICS in recovered pINF was 1106 to 1, which when compared to the expected ratio of 1325 to 1, suggests the presence of approximately one UBP per plasmid. No d5SICS was detected in control experiments in which the transporter was not induced, nor when the unnatural triphosphates were not added to the media, nor when pUC19 was used instead of pINF (FIG. 3C), demonstrating that its presence results from the replication of the UBP and not from misinsertion of the unnatural triphosphates opposite a natural nucleotide. Importantly, as the synthetic pINF contained an analog of d5SICS, and d5SICS was only provided as a triphosphate added to the media, its presence in pINF confirms in vivo replication.

The region of pINF surrounding nucleotide 505 was then PCR amplified in the presence of d5SICSTP and a biotinylated dNaMTP analog. Analysis by streptavidin gel shift showed that 67% of the amplified DNA contained biotin (FIG. 3D). No shift was observed in control experiments in which the transporter was not induced, nor when the unnatural triphosphates were not added to the media, demonstrating that the shift required the import of the unnatural triphosphates. Similarly, no gel shift was observed with DNA isolated from identically treated control cells transformed with pUC19, demonstrating that the shift results from the retention of the UBP and not from misinsertion of the unnatural triphosphates opposite a natural nucleotide. Based on a calibration curve constructed from the shifts observed with the amplification products of controlled mixtures of DNA containing dNaM or its fully natural counterpart (Methods), the observed gel shift corresponds to a UBP retention of 86%, which in turn corresponds to a fidelity (retention per doubling) of 99.4% (0.994=0.86).

To confirm the high retention of the UBP, the same region of pINF was PCR amplified in the presence of d5SICSTP and dNaMTP, and the products were analyzed by Sanger sequencing (FIG. 3E). The presence of the UBP caused an abrupt termination in the sequencing reaction, and thus the level of UBP retention may be quantified from the ratio of the amplitudes of the peaks in the chromatogram before and after the site of UPB incorporation. Sequencing chromatograms of pINF isolated from cultures grown either without PtNTT2 induction or without addition of the unnatural triphosphates showed no termination. In contrast, chromatograms from the amplification products of pINF isolated from cells grown with PtNTT2 induction and with added unnatural triphosphates showed an abrupt termination at the expected position. With a lower limit of read-through detection estimated to be 5% (corresponding to 95% retention), this places a lower limit of 99.7% on the fidelity of UBP replication. The estimates of fidelity from both sets of experiments correspond to an error rate of $\sim10^3$, which is comparable to the intrinsic error-rate of some polymerases with natural DNA.

Figure 4:
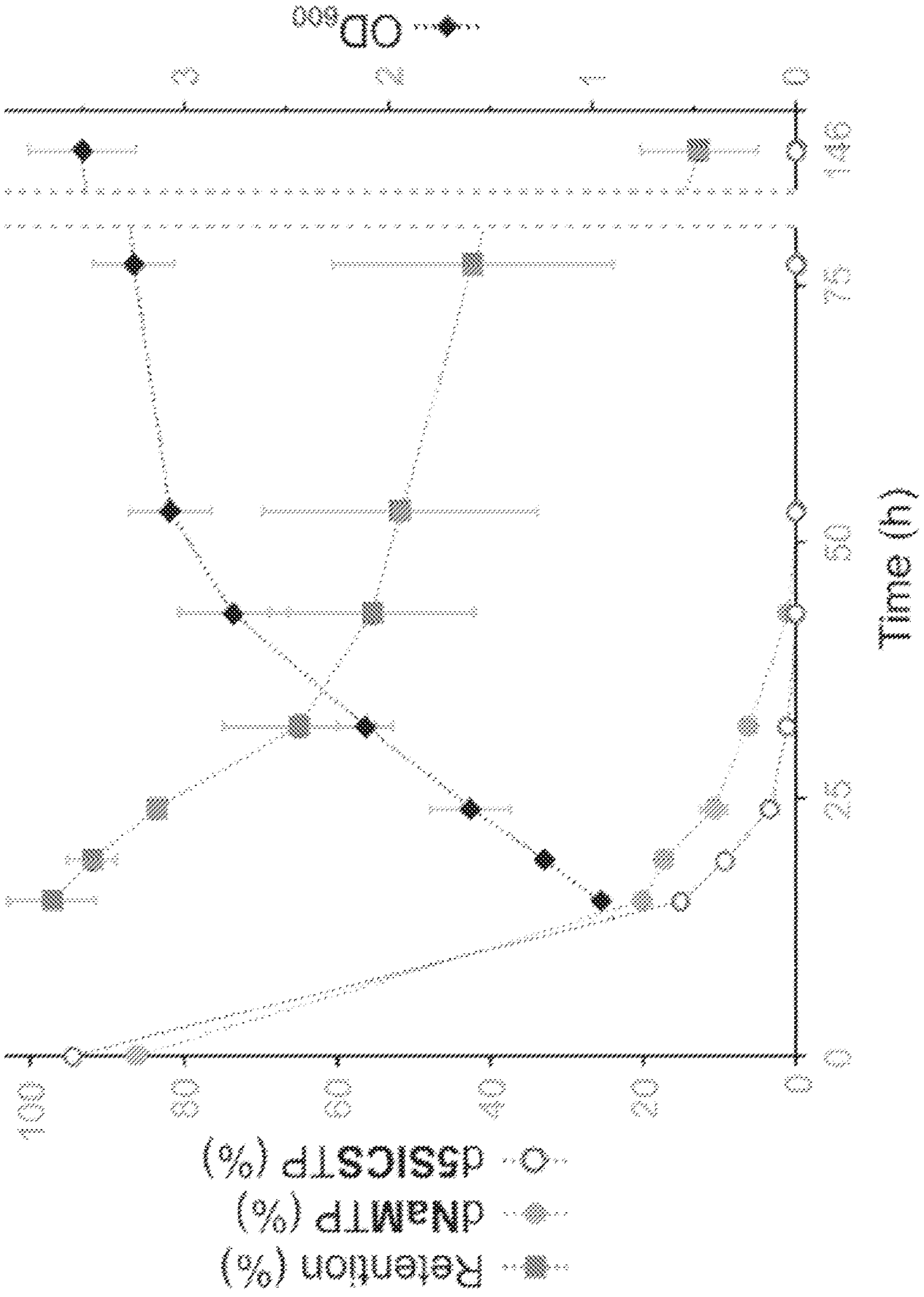
FIG. 4 depicts data relating to the intracellular stability of the UBP. *E. coli* C41(DE3)-pACS was transformed with pINF and grown after a single dose of d5SICSTP and dNaMTP was provided in the media. UBP retention (squares), $OD_{600}$ (diamonds), and relative amount of d5SICSTP and dNaMTP in the media (open and closed circles, respectively; 100%=0.25 mM), were determined as a function of time.

The high retention of the UBP over a 15 h period of growth indicates that it is not efficiently excised by DNA repair pathways. To further support this conclusion, we repeated the experiments, but monitored UBP retention, cell growth, and unnatural triphosphate decomposition for up to 6 days (FIG. 4).

At 15 and 19 h of growth, the cultures reached an $OD_{600}$ of ~0.9 and ~1.2, respectively, and both d5SICSTP and dNaMTP decomposed to only 17-20% and 10-16% of their initial 0.25 mM concentrations (FIG. 12A). In agreement with the above described experiments, retention of the UBP after 15 h was 97±5% and >95%, as determined by gel shift and sequencing, respectively, and after 19 h it was 91±3% and >95%. As the cultures entered stationary phase and the triphosphates decomposed completely, plasmid loss began to compete with replication (FIGS. 12B and C), but even then, retention of the UBP remained at ~45% and ~15%, at 3 and 6 days respectively. Moreover, when d5SICS-dNaM was lost, it was replaced by dA-dT, which is consistent with the mutational spectrum of Kf. Finally, the shape of the retention vs. time curve mirrors that of the growth vs. time curve. Taken together, these data strongly support the conclusion that loss of the UBP results from replication-mediated mispairing (which is unavoidable after unnatural triphosphate decomposition), and not from the activity of DNA repair pathways.

Example 11: Directed Evolution of Cells with Increased NTT Activity

Cells harboring endogenous NTTs are incubated in the presence of natural dNTPs and one or more unnatural nucleic acids. The concentration of one or more of the natural dNTPs in contact with the cells is decreased slowly over time and with growth. The concentration of one or more of the unnatural nucleic acids in contact with the cells is increased slowly over time and with growth. Surviving cells are subjected to further rounds of exposure to increasing concentrations of the unnatural nucleic acids and decreasing concentrations of the natural dNTPs. Surviving cells, lysates, or purified NTTs are assayed for binding kinetics, import, replication, and/or incorporation of the unnatural nucleic acids. Cell pools demonstrating increased import, replication, and/or incorporation of the unnatural nucleic acids compared to the initial cells harboring endogenous NTTs are further assayed for the NTT variants using PCR and sequencing methods. The cells and/or information of the NTT variant sequences are used to generate recombinant proteins and nucleic acid reagents for expression in host cells as described above. Further, genetically engineered cells are engineered that contain increased import activity, replication activity, and/or incorporation of the unnatural nucleic acids compared to the initial cells harboring endogenous NTTs.

Example 12: Directed Evolution of Cells with Polymerase Activity for Unnatural Nucleic Acids Cells harboring endogenous polymerases are incubated in the presence of natural dNTPs and one or more unnatural nucleic acids. The concentration of one or more of the natural dNTPs in contact with the cells is decreased slowly over time and with growth. The concentration of one or more of the unnatural nucleic acids in contact with the cells is increased slowly over time and with growth. Surviving cells are subjected to further rounds of exposure to increasing concentrations of the unnatural nucleic acids and decreasing concentrations of the natural dNTPs. Surviving cells, lysates, or purified polymerases are assayed for replication and/or incorporation of the unnatural nucleic acids. Cell pools demonstrating increased import, replication, and/or incorporation of the unnatural nucleic acids compared to the initial cells harboring endogenous polymerases are further assayed for the polymerase variants using PCR and sequencing methods. The cells and/or information of the polymerase variant sequences are used to generate recombinant proteins and nucleic acid reagents for expression in host cells as described above. Further, genetically engineered cells are engineered that contain increased polymerase activity, replication activity, and/or incorporation of the unnatural nucleic acids compared to the initial cells harboring endogenous polymerases.

Other Embodiments

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-911910-18-2); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. coligan, et. al., ed., John Wiley and Sons, Inc.), Current Protocols in Immunology (CPI) (John E. coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998), which are all incorporated by reference herein in their entireties.

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed molecules and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

All publications, patents, and patent applications mentioned in the above specification are hereby incorporated by reference. Various modifications and variations of the described methods, compositions, and kits of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

What is claimed is:

1. An isolated prokaryotic cell comprising:

(a) a heterologous nucleoside triphosphate transporter comprising an amino acid sequence that is at least about 85% identical to SEQ ID NO: 1; and (b) a first unnatural nucleotide comprising a base selected from:

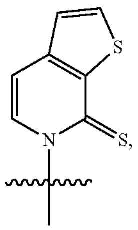
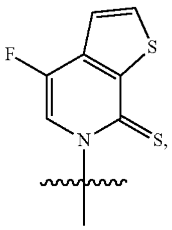
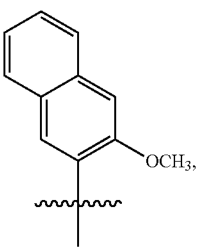
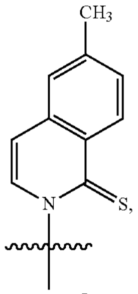
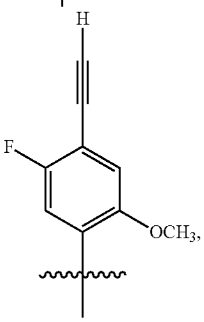
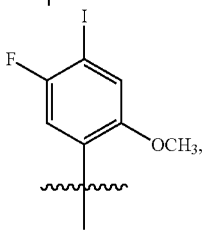
and
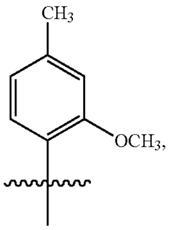

wherein the heterologous nucleoside triphosphate transporter is capable of transporting triphosphates of the first unnatural nucleotide into the cell.

2. The isolated cell of claim 1, wherein the heterologous nucleoside triphosphate transporter comprises an amino acid sequence that is at least about 90% identical to SEQ ID NO: 1.

3. The isolated cell of claim 1, further comprising a second unnatural nucleotide comprising a base selected from:

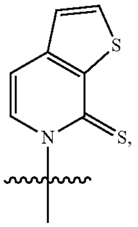 [SMILES: *n1ccc2ccsc2c1=S]
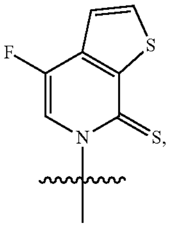
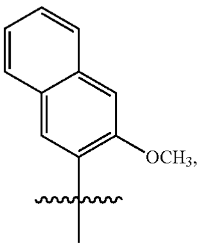
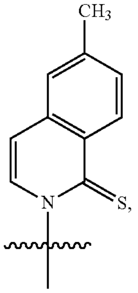
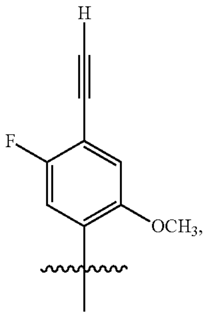
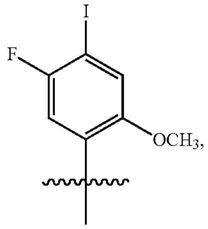
and
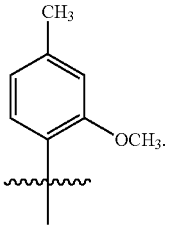

4. The isolated cell of claim 3, wherein the first unnatural nucleotide and the second unnatural nucleotide each independently comprise a base selected from:

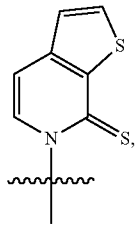
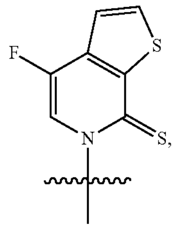

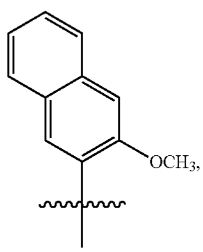 [SMILES: *c1cc2ccccc2cc1OC]
and
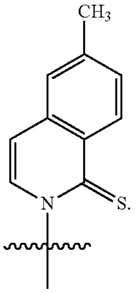

5. The isolated cell of claim 4, wherein the first unnatural nucleotide and the second unnatural nucleotide each independently comprise a base selected from:

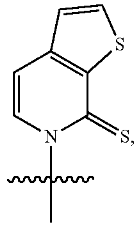
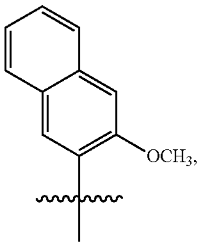
and
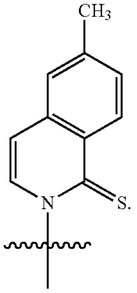

6. The isolated cell of claim 5, wherein the first unnatural nucleotide and the second unnatural nucleotide each independently comprise a base selected from

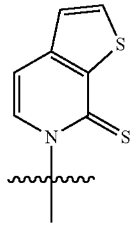
and
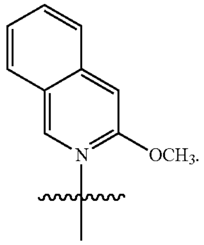

7. The isolated cell of claim 3, wherein:

(a) the first unnatural nucleotide comprises a base selected from

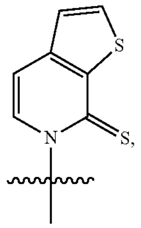
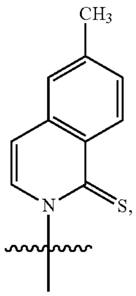
and
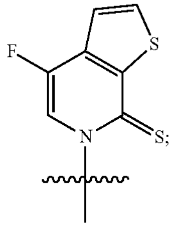

and;

(b) the second unnatural nucleotide comprises a base selected from

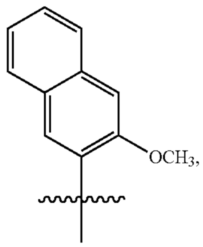
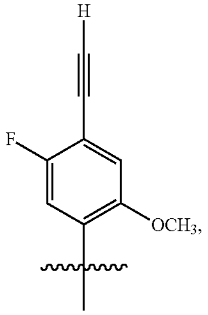
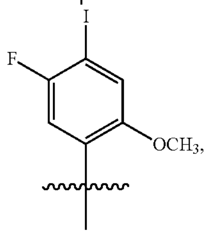
and
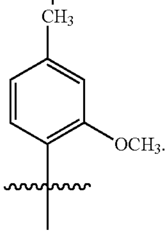

8. The isolated cell of claim 7, wherein the second unnatural nucleotide comprises a base selected from

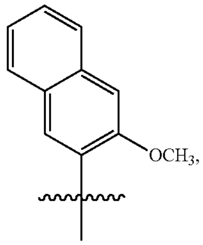
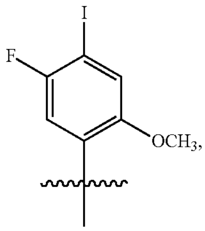
and
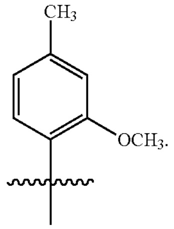

9. The isolated cell of claim 8, wherein the second unnatural nucleotide comprises a base selected from

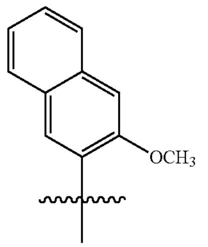
and
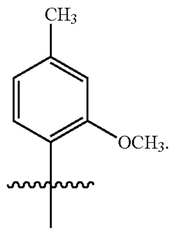

10. The isolated cell of claim 9, wherein:

(a) the first unnatural nucleotide comprises a base which is

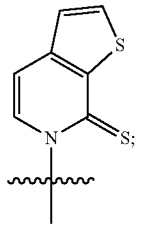

and (b) the second unnatural nucleotide comprises a base selected from

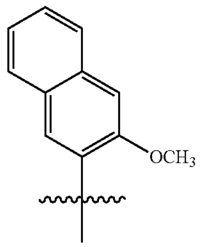
and
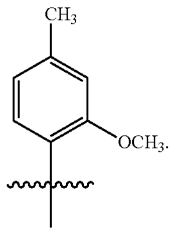

11. The isolated cell of claim 9, wherein the second unnatural nucleotide comprises a base which is

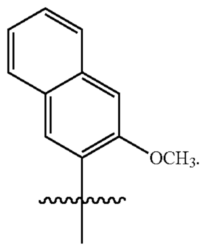 [SMILES: *c1cc2ccccc2cc1OC]

12. An isolated prokaryotic cell comprising:

(a) a heterologous nucleoside triphosphate transporter comprising an amino acid sequence that is at least about 85% identical to SEQ ID NO: 1; and (b) a first unnatural nucleotide, wherein the heterologous nucleoside triphosphate transporter is capable of transporting triphosphates of the first unnatural nucleotide into the cell.

13. The isolated cell of claim 12, wherein the first unnatural nucleotide comprises a base or is selected from: 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifiuoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, fluorinated nucleic acids, tricyclic pyrimidines, phenoxazine cytidine ([5,4-b][1,4] benzoxazin-2 (3H)-one), phenothiazine cytidine (1H-pyrimido [5,4-b][1,4] benzothiazin-2 (3H)-one), G-clamps, phenoxazine cytidine (9-(2-aminoethoxy)-H-pyrimido [5,4-b] [1,4] benzoxazin-2 (3H)-one), carbazole cytidine (2H-pyrimido [4,5-b] indol-2-one), pyridoindole cytidine (H-pyrido [3',2': 4,5] pyrrolo [2,3-d] pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, and 2,6-diaminopurine and those in which the purine or pyrimidine base is replaced with a heterocycle.

14. The isolated cell of claim 12, wherein the heterologous nucleoside triphosphate transporter comprises an amino acid sequence that is at least about 90% identical to SEQ ID NO: 1.

15. The isolated cell of claim 14, further comprising a second unnatural nucleotide, wherein the first unnatural nucleotide and the second unnatural nucleotide each independently comprise a base or are selected from: 2-aminoadenin-9-yl, 2-aminoadenine, 2-F-adenine, 2-thiouracil, 2-thio-thymine, 2-thiocytosine, 2-propyl and alkyl derivatives of adenine and guanine, 2-amino-adenine, 2-amino-propyl-adenine, 2-aminopyridine, 2-pyridone, 2'-deoxyuridine, 2-amino-2'-deoxyadenosine 3-deazaguanine, 3-deazaadenine, 4-thio-uracil, 4-thio-thymine, uracil-5-yl, hypoxanthin-9-yl (I), 5-methyl-cytosine, 5-hydroxymethyl cytosine, xanthine, hypoxanthine, 5-bromo, and 5-trifiuoromethyl uracils and cytosines; 5-halouracil, 5-halocytosine, 5-propynyl-uracil, 5-propynyl cytosine, 5-uracil, 5-substituted, 5-halo, 5-substituted pyrimidines, 5-hydroxycytosine, 5-bromocytosine, 5-bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 6-alkyl derivatives of adenine and guanine, 6-azapyrimidines, 6-azo-uracil, 6-azo cytosine, azacytosine, 6-azo-thymine, 6-thio-guanine, 7-methylguanine, 7-methyladenine, 7-deazaguanine, 7-deazaguanosine, 7-deaza-adenine, 7-deaza-8-azaguanine, 8-azaguanine, 8-azaadenine, 8-halo, 8-amino, 8-thiol, 8-thioalkyl, and 8-hydroxyl substituted adenines and guanines; N4-ethylcytosine, N-2 substituted purines, N-6 substituted purines, O-6 substituted purines, fluorinated nucleic acids, tricyclic pyrimidines, phenoxazine cytidine ([5,4-b][1,4] benzoxazin-2 (3H)-one), phenothiazine cytidine (1H-pyrimido [5,4-b][1,4] benzothiazin-2 (3H)-one), G-clamps, phenoxazine cytidine (9-(2-aminoethoxy)-H-pyrimido [5,4-b] [1,4] benzoxazin-2 (3H)-one), carbazole cytidine (2H-pyrimido [4,5-b] indol-2-one), pyridoindole cytidine (H-pyrido [3',2': 4,5] pyrrolo [2,3-d] pyrimidin-2-one), 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methythio-N6-isopentenyladeninje, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N-2-carboxypropyl) uracil, and 2,6-diaminopurine and those in which the purine or pyrimidine base is replaced with a heterocycle.

16. The isolated cell of claim 1, wherein the cell is an *Escherichia coli* cell.

17. The isolated cell of claim 12, wherein the cell is an *Escherichia coli* cell.

18. The isolated cell of claim 1, wherein the first unnatural nucleotide is present in deoxyribonucleic acid (DNA).

19. The isolated cell of claim 18, wherein the DNA comprises at least one unnatural base pair (UBP), wherein the at least one UBP comprises the first unnatural nucleotide and a second unnatural nucleotide, wherein the second unnatural nucleotide comprises a base independently selected from:

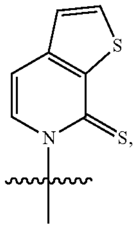
,
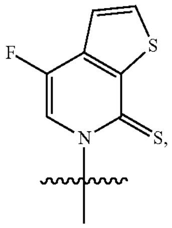
,

-continued

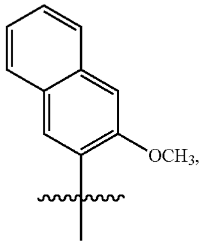
,
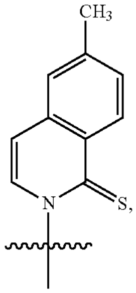
,
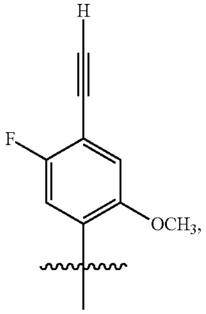
,
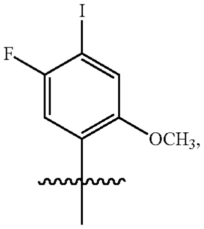
, and
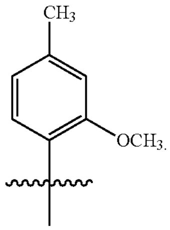
.

20. The isolated cell of claim 19, wherein the first unnatural nucleotide and the second unnatural nucleotide each independently comprise a base selected from:

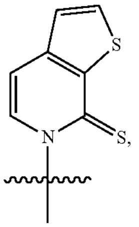 [SMILES: *n1ccc2ccsc2c1=S]
,
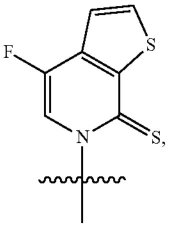
,
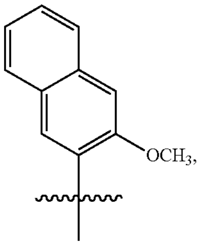
,
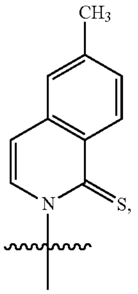
, and
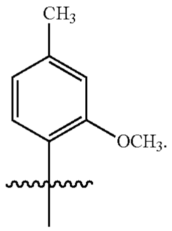
.

21. The isolated cell of claim 1, wherein the heterologous nucleoside triphosphate transporter comprises an amino acid sequence that is at least about 95% identical to SEQ ID NO: 1.

22. The isolated cell of claim 12, wherein the heterologous nucleoside triphosphate transporter comprises an amino acid sequence that is at least about 95% identical to SEQ ID NO: 1.

23. The isolated cell of claim 1, wherein the cell is a bacterial cell.

24. The isolated cell of claim 12, wherein the cell is a bacterial cell.

25. An isolated bacterial cell comprising a heterologous nucleoside triphosphate transporter comprising an amino acid sequence that is at least about 85% identical to SEQ ID NO: 1, wherein the heterologous nucleoside triphosphate transporter is capable of transporting a triphosphate of an unnatural nucleotide into the isolated bacterial cell.

26. The isolated bacterial cell of claim 25, wherein the unnatural nucleotide comprises a base selected from:

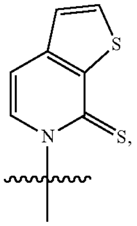
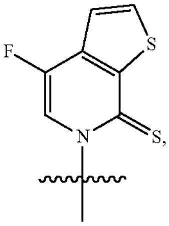
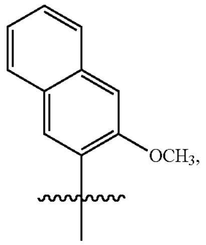

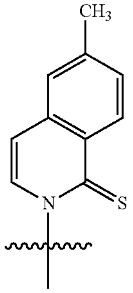
,
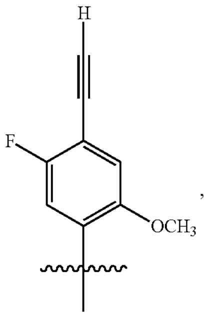

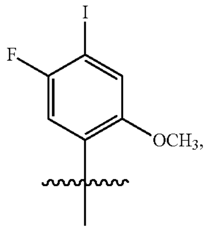
and
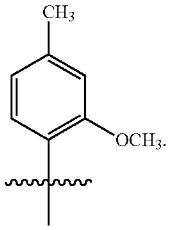

27. The isolated bacterial cell of claim 25, wherein the unnatural nucleotide is an unnatural deoxyribonucleotide.

28. The isolated bacterial cell of claim 27, wherein the unnatural deoxyribonucleotide comprises a base

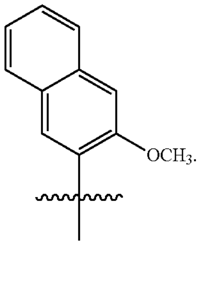

29. The isolated bacterial cell of claim 25, wherein the unnatural nucleotide is an unnatural ribonucleotide.

30. The isolated bacterial cell of claim 29, wherein the unnatural ribonucleotide comprises a base

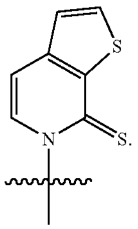

31. The isolated bacterial cell of claim 25, wherein the heterologous nucleoside triphosphate transporter comprises an amino acid sequence that is at least about 90% identical to SEQ ID NO: 1.

32. The isolated bacterial cell of claim 25, wherein the heterologous nucleoside triphosphate transporter comprises an amino acid sequence that is at least about 95% identical to SEQ ID NO: 1.

33. The isolated bacterial cell of claim 25, wherein the isolated bacterial cell is an *Escherichia* bacterium.

34. The isolated bacterial cell of claim 33, wherein the Escherichia bacterium is *Escherichia coli.*

35. The isolated bacterial cell of claim 25, comprising a nucleotide sequence that encodes the heterologous nucleoside triphosphate transporter, wherein the nucleotide sequence comprises a nucleotide sequence that is at least about 85% identical to SEQ ID NO: 2.

36. The isolated bacterial cell of claim 31, comprising a nucleotide sequence that encodes the heterologous nucleoside triphosphate transporter, wherein the nucleotide sequence comprises a nucleotide sequence that is at least about 90% identical to SEQ ID NO: 2.

37. The isolated bacterial cell of claim 32, comprising a nucleotide sequence that encodes the heterologous nucleoside triphosphate transporter, wherein the nucleotide sequence comprises a nucleotide sequence that is at least about 90% identical to SEQ ID NO: 2.

38. The isolated cell of claim 1, wherein the heterologous nucleoside triphosphate transporter comprises an amino acid sequence that is 100% identical to SEQ ID NO: 1.

39. The isolated cell of claim 12, wherein the heterologous nucleoside triphosphate transporter comprises an amino acid sequence that is 100% identical to SEQ ID NO: 1.

40. The isolated bacterial cell of claim 25, wherein the heterologous nucleoside triphosphate transporter comprises an amino acid sequence that is 100% identical to SEQ ID NO: 1.

* * * * *

SEQUENCE LISTING

```
Sequence total quantity: 50
SEQ ID NO: 1            moltype = AA  length = 575
FEATURE                 Location/Qualifiers
source                  1..575
                        mol_type = protein
                        organism = Phaeodactylum tricornutum
SEQUENCE: 1
MRPYPTIALI SVFLSAATRI SATSSHQASA LPVKKGTHVP DSPKLSKLYI MAKTKSVSSS  60
FDPPRGGSTV APTTPLATGG ALRKVRQAVF PIYGNQEVTK FLLIGSIKFF IILALTLTRD  120
TKDTLIVTQC GAEAIAFLKI YGVLPAATAF IALYSKMSNA MGKKMLFYST CIPFFTFFGL  180
FDVFIYPNAE RLHPSLEAVQ AILPGGAASG GMAVLAKIAT HWTSALFYVM AEIYSSVSVG  240
LLFWQFANDV VNVDQAKRFY PLFAQMSGLA PVLAGQYVVR FASKAVNFEA SMHRLTAAVT  300
FAGIMICIFY QLSSSYVERT ESAKPAADNE QSIKPKKKKP KMSMVESGKF LASSQYLRLI  360
AMLVLGYGLS INFTEIMWKS LVKKQYPDPL DYQRFMGNFS SAVGLSTCIV IFFGVHVIRL  420
LGWKVGALAT PGIMAILALP FFACILLGLD SPARLEIAVI FGTIQSLLSK TSKYALFDPT  480
```

-continued

```
TQMAYIPLDD ESKVKGKAAI DVLGSRIGKS GGSLIQQGLV FVFGNIINAA PVVGVVYYSV  540
LVAWMSAAGR LSGLFQAQTE MDKADKMEAK TNKEK                            575

SEQ ID NO: 2            moltype = DNA  length = 1728
FEATURE                 Location/Qualifiers
source                  1..1728
                        mol_type = genomic DNA
                        organism = Phaeodactylum tricornutum
SEQUENCE: 2
atgagaccat atccgacgat tgccttgatt tcggtttttc tttcggcggc gactcgtatt  60
tcggccactt cctctcatca agcaagtgca cttcctgtca aaaagggaac gcatgtcccg  120
gactctccga agttgtcaaa gctatatatc atggccaaaa ccaagagtgt atcctcgtcc  180
ttcgaccccc ctcggggagg cagtactgtt gcgccaacta caccgttggc aaccggcggt  240
gcgctccgca aagtgcgaca agccgtcttt cccatctacg gaaaccaaga agtcaccaaa  300
tttctgctca tcggatccat taaattcttt ataatcttgg cactcacgct cacgcgtgat  360
accaaggaca cgttgattgt cacgcaatgt ggtgccgaag cgattgcctt tctcaaaata  420
tacggggtgc tacccgcagc gaccgcattt atcgcgctct attccaaaat gtccaacgcc  480
atgggcaaaa aaatgctatt ttattccact tgcattcctt tctttacctt tttcgggctg  540
tttgatgttt tcatttaccc gaacgcggag cgactgcacc ctagtttgga agccgtgcag  600
gcaattctcc cgggcggtgc cgcatctggc ggcatggcgg ttctggccaa gattgcgaca  660
cactggacat ccgccttatt ttacgtcatg gcggaaatat attcttccgt atcggtgggg  720
ctattgtttt ggcagtttgc gaacgacgtc gtcaacgtgg atcaggccaa gcgcttttat  780
ccattatttg ctcaaatgag tggcctcgct ccagttttag cgggccagta tgtggtacgg  840
tttgccagca aagcggtcaa ctttgaggca tccatgcatc gactcacggc ggccgtaaca  900
tttgctggta ttatgatttg catcttttac caactcagtt cgtcatatgt ggagcgaacg  960
gaatcagcaa agccagcggc agataacgag cagtctatca aaccgaaaaa gaagaaaccc  1020
aaaatgtcca tggttgaatc ggggaaattt ctcgcgtcaa gtcagtacct gcgtctaatt  1080
gccatgctgg tgctgggata cggcctcagt attaacttta ccgaaatcat gtggaaaagc  1140
ttggtgaaga aacaatatcc agacccgcta gattatcaac gatttatggg taacttctcg  1200
tcagcggttg gtttgagcac atgcattgtt attttcttcg gtgtgcacgt gatccgtttg  1260
ttggggtgga aagtcggagc gttggctaca cctgggatca tggccattct agcgttaccc  1320
tttttgcttc gcattttgtt gggtttggat agtccagcac gattggagat cgccgtaatc  1380
tttggaacaa ttcagagttt gctgagcaaa acctccaagt atgccctttt cgaccctacc  1440
acacaaatgg cttatattcc tctggacgac gaatcaaagg tcaaaggaaa agcggcaatt  1500
gatgttttgg gatcgcggat tggaaagagt ggaggctcac tgatccagca gggcttggtc  1560
tttgtttttg gaaatatcat taatgccgca cctgtagtag gggttgtcta ctacagtgtc  1620
cttgttgcgt ggatgagcgc agctggccga ctaagtgggc tttttcaagc acaaacagaa  1680
atggataagg ccgacaaaat ggaggcaaag accaacaaag aaaagtag               1728

SEQ ID NO: 3            moltype = AA  length = 515
FEATURE                 Location/Qualifiers
source                  1..515
                        mol_type = protein
                        organism = Protochlamydia amoebophila
SEQUENCE: 3
MSQQESEFGK LRAFFWPIHG HEVKKVLPMM LMLFLICFNY SILRNVKDAI VVTAKASGAE  60
VIPFIKVWVL LPTAVLFTLI FTKLSNRFSQ EKVFYIVIST FLLFFGSFTY IFYPLRDVLH  120
PHQLCDYLET ILPAGFKGLI AMFRNWSFTL FYVICELWGS IVLTVLFWGF ANEITKMTEA  180
RRFYSMLGVI ASFAATIAGI IANLLSNDQS WEQTLNILMV AVIVSGTIAM VIFRWMNKNV  240
NGPEFQEFHE AKRIQKMKKR LSIRESFTYL ANSKYLICIA VLVISYNLVI NLVEIVWKDQ  300
LRQLYSSALD YNRYMNNMTS AVGIIATITS LFMSTMITRF GWTRTALVTP TIMLVTSVGF  360
FAFMLFRNDL ADPVYILTGT TPLTIAVFFG AAQVCMSKAC KYSVFDSTKE MAFIPLDYES  420
KLKGKAAIDG VGSRLGKSGG SLIHQSLLMI FATVSSSAPY VAVILIGVII VWMLCVRSLG  480
KQFAAIIGEK AREDIGESTP RTSEEQVLHP LKAAS                            515

SEQ ID NO: 4            moltype = DNA  length = 1551
FEATURE                 Location/Qualifiers
source                  1..1551
                        mol_type = genomic DNA
                        organism = Protochlamydia amoebophila
SEQUENCE: 4
atgtctcaac aagaatcaga gtttggtaaa ttgagggcat ttttttggcc tattcacggc  60
catgaagtca aaaaagtgct gccgatgatg ttgatgctat ttttgatttg tttcaactat  120
agtattttac gcaatgttaa agatgctatt gttgtgactg ctaaggcttc aggggctgaa  180
gttattccat ttattaaagt atgggtgctg ttacccacgg cagtcttatt tactttaatt  240
tttactaagt tgtctaaccg ttttagccaa gaaaaagttt tttatattgt catttctaca  300
tttttgctat tttttggttc gtttacttat atttttttatc ctttacgtga cgtactacat  360
cctcatcaac tatgcgatta cttagaaacg attttaccag cgggatttaa aggattaatt  420
gccatgttcc gtaattggtc atttactttg ttttatgtaa tttgtgaact ttggggcagt  480
attgttttaa ctgtcctttt ttggggattt gcgaatgaaa tcacaaaaat gactgaagct  540
cgtcgttttt atagtatgct tggtgtcatt gcaagttttg ccgcgacgat agcaggaatc  600
atagccaatc ttctttctaa tgatcaaagt tgggaacaga ctttaaatat tctcatggtt  660
gctgtaattg taagtggaac gatagccatg gttatttttc gttggatgaa taaaaatgta  720
ctcaatggcc cagaattcca agaattccat gaagcaaaac gcattcaaaa aatgaaaaaa  780
agattatcga tccgagaaag ttttacctat ctcgctaatt ctaaatatct tatttgtatt  840
gcagttttag ttatttctta taatcttgtc attaacttag ttgaaattgt atggaaagac  900
cagcttcgcc aactttattc gtcagccctt gattataatc gctatatgaa taacatgaca  960
tcagcagtcg gaattattgc cacaatcaca tccttattta tgtctacaat gattactcgg  1020
tttggatgga cacggacagc tctagtaaca ccgactatta tgcttgtcac aagtgtggga  1080
```

```
tttttgctt ttatgctatt tcgaaatgat ttggctgatc ctgtttatat attaacagga  1140
acgacacctt taactatagc cgtctttttt ggtgcagctc aagtctgcat gagtaaagcc  1200
tgtaagtatt ctgtttttga ttctacaaaa gaaatggctt ttatccctct ggattatgaa  1260
agtaaattga aaggaaaagc tgcgattgat ggtgtgggtt ctcgtcttgg taaatcgggc  1320
ggttccttaa ttcatcaaag tttattgatg atttttgcaa ctgttagctc cagcgctcct  1380
tatgtagctg tgatcttaat tggcgttatc attgtttgga tgctctgcgt acgttcatta  1440
ggtaagcaat ttgctgctat tattggggaa aaggctcgag aagatattgg tgaatctact  1500
ccaagaacga gtgaagagca agttttacat cccttaaaag ctgcatctta a           1551

SEQ ID NO: 5            moltype = AA  length = 536
FEATURE                 Location/Qualifiers
source                  1..536
                        mol_type = protein
                        organism = Protochlamydia amoebophila
SEQUENCE: 5
MSQTPTGSRE FSPWRSNLWP VHRYELKKLI PMLLIFFFIS FDYNILRTLK DSLLITAKSS  60
GAEVIPFVKV WAMFPGAILM TLLFTWLSNR LSREIVFYLI TSLFLSYFFI FTFILYPIRD  120
IIHPHATADY LETILPIGFK GLVAMFRYWT FTIFYVMSEL WGSTVLFVLF WGFANQVTKI  180
SEAKRFYGLF GVGANLSGIF AGQASVYCCQ FNKQNDLGIL GSDPWYQSLV MMVSLILLSG  240
ALVLALFRWM NVEVLTDKRF YDPSSVKTEG EAKGKLSLKQ SFSYLLRSNY LLCIALIVIS  300
YNLVINLTEV LWKHQVRELY PDPNDYTLYM NHIVSIIGVV ATLSSLFVSG NAIRKFGWTT  360
TALITPIILA VTSLGFFSFF FLKKASPEIF LSFSGVTPLV LVVFFGTAQN ILSRGAKYSV  420
FDATKEMSFV PLNPESKLVG KAAIDGVCSR LGKSGGSVVH QSLLLLFSTI NASAPYVAIV  480
LFAVILVWAM AIRVLGKQFN ELTSQVENNE TSGTLMTPIR AVNILSDTIL KEQKAV      536

SEQ ID NO: 6            moltype = DNA  length = 1611
FEATURE                 Location/Qualifiers
source                  1..1611
                        mol_type = genomic DNA
                        organism = Protochlamydia amoebophila
SEQUENCE: 6
atgtcacaga caccaacagg gtcccgtgaa tttagtccat ggcggagcaa tctttggccc  60
gttcatcgct atgagcttaa aaaactcatc ccaatgttgt taatattctt ttttatttct  120
tttgattaca acatattacg tactttaaaa gactcactac ttataactgc aaaatcttca  180
ggtgctgagg tcattccttt tgtaaaggtt tgggctatgt tccctggagc tattttaatg  240
acccttttgt tcacttggtt gtctaatcgc ctgtcaagag aaatcgtttt ttaccttatc  300
acttctcttt ttttatctta ttttttttatt ttcactttta ttctctatcc tattcgagat  360
attatccatc ctcacgcaac tgctgactat cttgaaacaa ttttaccgat tggatttaaa  420
gggctagttg cgatgtttcg ttactggact tttactattt tctatgtgat gtcagaactt  480
tggggaagta ctgttttatt tgtcttattt tggggtttg ctaatcaagt gactaaaatt  540
agtgaggcaa aaagatttta cggtctgttt ggggtaggtg ctaatctttc gggtattttc  600
gcaggacaag cttctgtgta ctgttgtcaa tttaataagc agaacgattt gggaatcctt  660
ggtagtgatc catggtatca atcattagtg atgatggttt ctttaatttt attatcgggt  720
gctttagttt tagctttatt tcgttggatg aatgtagaag tcttaaccga taaacgtttt  780
tatgatcctt cttcggttaa aacagaagga gaagctaaag gtaagctttc tctaaagcaa  840
agcttttcct atcttcttcg ctctaattac ttactttgta ttgctcttat tgttatttct  900
tataacctag ttattaacct cacagaagtt ttatggaaac atcaagtccg agagctatat  960
cctgatccta atgattatac tttatatatg aatcatatcg tatccattat tggggtagta  1020
gcgaccttaa gttccctttt cgtatcagga aatgcgattc gcaaatttgg gtggaccact  1080
actgctttaa ttacacctat cattttagct gtaacaagtt tgggcttttt ctccttttc  1140
ttccttaaaa aggcatctcc cgaaattttc ttatcttttt ccggagtaac tcctttggtt  1200
ttagtggttt tctttggaac tgctcaaaac atattgagtc gaggagctaa atactctgta  1260
tttgatgcca ctaaagaaat gagttttgtt cctttaaatc ctgaatccaa actcgttgga  1320
aaagcggcga ttgatggagt ttgttctcgc ctcggaaaat cgggtggatc tgtggttcat  1380
cagagccttc tacttttgtt ttctacaatt aatgcaagtg ccccttatgt agctatcgtc  1440
ttgttcgccg taattctagt ctgggcaatg gcaattcgcg ttttaggtaa acaatttaat  1500
gaattgacaa gtcaggtaga aaacaatgaa acttctggga cattgatgac tcctattcga  1560
gctgttaata ttctttcaga cacaattttg aaagaacaga aagctgtata a           1611

SEQ ID NO: 7            moltype = AA  length = 489
FEATURE                 Location/Qualifiers
source                  1..489
                        mol_type = protein
                        organism = Protochlamydia amoebophila
SEQUENCE: 7
MKNQQNSVSS TLLILKKRSL ILFQFFLIII VYHTLKDLKD TIVITASDAG AEIIPFIKIW  60
GMLPLAICAS YFFAKFYNKF GREKTFYIFS SFLLVNYLFF AFVLYPFRKF FYLENVADYL  120
HMILPVGAKG FVAMVSYWHY TLFYLTAELW SMLILSILFW GYVSDTTSLV EAKKFYPLCM  180
FVGNMAGIIS GQLSHFLCQH LSDFMSWERT LQWMIGIVCV CGLLIMIINR RLALTTDFSA  240
IKQKVKKQIA PSSFKDNVMD VLRTGPLLCI AVLVVGFGLT TNLIEVIWKE NIRQLHPTPQ  300
AYNAYINQLT SLIGTGAVCI ALLSSWIFRK FTWTQIALTT PLCLLITSSA FFSSLLMPKE  360
LLAEIASFFQ FSPTQLIVTL GSICYVFSMS AKYTIFDTSK EIAFLSIETE KRTYAKSVID  420
SIGSRLGKSG ASCFYQFLLI AFGIASEHIL LIGVVSIIMI GISIFATKKL GGQLSGKNEN  480
HRFIEASHG                                                        489

SEQ ID NO: 8            moltype = DNA  length = 1470
FEATURE                 Location/Qualifiers
source                  1..1470
                        mol_type = genomic DNA
```

```
                         organism = Protochlamydia amoebophila
SEQUENCE: 8
atgaaaaatc aacaaaattc tgtatcttct accttactaa tcttaaaaaa gcgtagcttg  60
atcctatttc aattttttct aattatcatt gtttatcata cattaaaaga cctcaaagat  120
acgattgtta tcacagcaag tgatgcaggt gcagagatca ttccttttat taaaatttgg  180
ggaatgcttc ctcttgccat ttgtgctagt tatttttttg ctaaatttta taataaattt  240
ggaagagaaa aaacatttta tattttttagc tctttcttac tagttaacta tcttttcttt  300
gcttttgtat tatatccatt ccgcaagttt ttttatttag aaaatgttgc agattattta  360
catatgattt tacctgttgg agcgaaaggg tttgttgcca tggtaagcta ttggcattac  420
actctatttt atttaacggc agaattatgg tcgatgctca ttctatctat ccttttttgg  480
ggttatgtga gtgatacgac ttctttagta gaagccaaaa aattttaccc cctctgtatg  540
ttcgttggaa atatggcagg aattatttct ggtcagctct ctcatttctt atgtcaacat  600
ttgtctgatt tcatgtcatg ggaaagaacc ctgcaatgga tgattggtat tgtctgtgtt  660
tgcggccttt taattatgat tattaataga cggctggctc ttacaactga tttttcggca  720
attaaacaaa aagtaaaaaa acaaatagct ccctcttctt tcaaagataa tgttatggat  780
gttttaagaa caggtccctt actttgtata gctgtattgg tagtggggtt tggactgaca  840
acgaatctaa ttgaagttat ttggaaagaa aatattaggc aactacaccc gacacctcaa  900
gcctacaatg cttatattaa tcaattgact tctttaattg ggactggtgc tgtttgtata  960
gccttgttat caagctggat ttttagaaag tttacttgga cgcaaattgc cctcacaacc  1020
cctttatgtt tattaatcac aagctctgct ttttttttcat cgcttcttat gcctaaagag  1080
ctgttagcgg aaattgcttc ttttttttcag ttttccccaa ctcaattgat agtgacacta  1140
ggatctattt gctatgtttt tagcatgtct gcgaagtaca caatttttga tactagtaaa  1200
gaaatagctt ttctttctat tgaaacagaa aaaagaacgt atgctaaatc tgtaattgat  1260
agcattggct ctcgtttggg aaaatctggc gcttcttgtt tttatcaatt tcttcttatt  1320
gcctttggaa ttgcttccga acatatttta ttaattggag ttgtatccat tataatgatt  1380
ggaatttcga tttttgctac gaaaaaattg ggtgggcagc tgtctggtaa aaatgaaaac  1440
catcgcttta tagaagcttc ccatggataa                                    1470

SEQ ID NO: 9             moltype = AA  length = 632
FEATURE                  Location/Qualifiers
source                   1..632
                         mol_type = protein
                         organism = Thalassiosira pseudonana
SEQUENCE: 9
MKTSCTIQRR VKSISSKHSI IDTHHSTSRR LSVILLFFLL HSSAEMLFAS ATGNHNANTS  60
PPPANIPMIS TNNKSCMMRR TRSQSRRDSS RSPDSVASAN VVGRGGDGGT IMGAKSVFQT  120
ASKALPPNTV SSTASGSVSK ASRLRTVLFP IQNDEMKKFL LIGSIKFFVI LALTLTRDNK  180
DTMVVTECGA EAIAFLKIYG VLPSATLFIA LYSKMATIFD KKTLFYATCI PFFAFFFLFD  240
AIIYPNRNVI QPSLESVQRV MRITADSSGA MSIFAKLFAN WTSALFYIVA EVYSSVSVGI  300
LFWQYANDVV SVSQAKRFYP LFAQMSGLAP IVAGQYVVRY ASRANDFEES LHRLTWMVSF  360
SGVMICLFYK WSNEYNDQTS GGLNGGIEDG VKETKVVKKK KAKMSMRDSA KFLASSEYLR  420
LIAALVVGYG LSINFTDIMW KSIVKRQYPD PLDYQRFMGN FSSVVGLSTC IVIFLGVHAI  480
RILGWRMGAL ATPAVMAILA FPYFSSILVG LDSPGSLRIA VIFGTIQCLL SKTAKYALFD  540
PTTQMAYIPL DDESKIKGKA AIEVLGSRIG KSGGSLIQQG LVLVFGNIIN AAPALVVLYY  600
SVLAWWVYSA NRLGSLFLAK TAMQEETKEH QK                                632

SEQ ID NO: 10            moltype = DNA  length = 1899
FEATURE                  Location/Qualifiers
source                   1..1899
                         mol_type = genomic DNA
                         organism = Thalassiosira pseudonana
SEQUENCE: 10
atgaaaacat cttgtacaat ccaacgtcgt gtcaaatcca tctcatccaa acacagtatc  60
atcgacacac accactctac ttctcgccgt ttaagtgtca tcctactctt ctttctacta  120
cactcctcgg cagagatgct atttgcttcc gccacgggca atcacaacgc caatacatca  180
ccaccacctg cgaatattcc catgattagc actaacaaca aatcatgtat gatgcgacga  240
accaggagtc aatcacgacg agatagcagc cgttcgcctg attcggtggc ctcggccaat  300
gttgttggga ggggcggcga tgggggtacc attatgggtg ccaagagtgt cttccagact  360
gcttcgaaag cattacctcc caacactgtg tcgtccacag caagcggcag tgtatccaaa  420
gcatcgcgcc tacgaacggt cctcttcccc attcaaaatg acgagatgaa gaagtttctc  480
ttgattggaa gtatcaagtt ctttgtaatt ctagcgttga cactcacgag agataataag  540
gatacaatgg tggttaccga gtgtggagct gaggccatcg cttttctaaa gatctacgga  600
gtactaccat ccgccacact cttcatagca ctctactcga aaatggccac tatctttgac  660
aaaaagacct tattctacgc cacgtgcatt ccattctttg cattcttctt cttattcgat  720
gcaatcatct atcctaaccg gaatgtcatt cagccttcct tagagagtgt tcagcgtgtc  780
atgagaatca cagccgattc atcgggtgcc atgtccatct ttgcaaagtt gttcgccaat  840
tggacgtcgg ccttgtttta tattgtagca gaggtatact cgtctgtttc agtggggata  900
ttgttctggc agtatgccaa tgatgtggtg tctgtctcgc aagcaaaacg attttaccca  960
ctctttgcac agatgagtgg acttgcccca attgtggctg gacagtatgt ggtacgatat  1020
gctagtagag ccaatgactt tgaagaatca ttgcataggt tgacgtggat ggtatccttt  1080
tcgggagtga tgatttgtct gttttacaag tggagcaatg agtacaatga tcagacgtct  1140
ggagggttaa atgggggaat tgaggatgga gtaaaagaga cgaaggtggt gaagaaaaag  1200
aaagccaaaa tgtcaatgag ggattcagcc aagtttttgg cttcatccga gtatttgaga  1260
ctgattgctg ctttggttgt gggatatggt ctgtcgatca actttacaga tataatgtgg  1320
aaatcaatcg tcaagagaca atatcccgat cctctcgact atcaacgttt catggggaac  1380
ttttcatcag tagttggatt gtctacgtgc atcgttatct ttctcggtgt acatgctatt  1440
cgtatactag gctggcgaat gggtgcccta gcgactccag ccgtcatggc aatcttggca  1500
ttcccttact tctcgagcat tctcgttggg ttggacagtc caggtagttt acgaattgca  1560
gtgatctttg gtactattca atgcctgctt agtaagacag caaagtatgc cctgttcgat  1620
```

-continued

```
ccgacaactc aaatggccta cattcctttg gatgacgaat caaagatcaa gggaaaggca  1680
gcaatagaag tacttggttc tcggattgga aaaagtggtg gttcgttgat acaacaaggt  1740
cttgtgttgg tgtttgggaa cattatcaat gctgctcccg cgttggttgt tctttactac  1800
tcagtgttgg cgtggtgggt gtactcagca aatcggctcg gatcattgtt cttggcaaag  1860
acagctatgc aagaggaaac aaaagagcac cagaagtag                         1899

SEQ ID NO: 11          moltype = AA  length = 517
FEATURE                Location/Qualifiers
source                 1..517
                       mol_type = protein
                       organism = Simkania negevensis
SEQUENCE: 11
MSSTEYEKST WTQKIWPIRR FELKKVLPLL ILKFLVSMVY ATLTLIKDPL VVTAKHSGAE  60
VIPVLKGWIV FPLSILCAIG YSKLSNHFKR STLFYGIITA FLAIVLIYGF VLYPNMGILT  120
PSDSANLLTA KFGEKYTHWI AVYRNWIHSL FFVTTELWGQ VVIFLLYWGF ANHICQVKEA  180
KRSYTLFIAA GDLATILAGP LTYYYGKKFL GQSYALTLQS LLGYVLVCGL LIMAVYWWMN  240
RYVLTDKRYY DPSVTKQTVN QKTKLSLRDS IRHIFSSKYL LAIAVLVVGC ALTINMVEVT  300
WKAHLKMQYP TTADYQMFMG RVTTIVGVVA LITVFFLGGN FLRRFGWHFS AQITPWAIGI  360
TGGVFFLLCL LKPYLGSFAH YVGLTPLMMI VIFGAFQNIT SKVVKYSFFD STKEMAYIPL  420
DPESKVKGKA AIDMVGSRLG KSSSSWLQIG LIELVGTGSV ISITPYLLPI VLGAALYWSY  480
SVRYLNKELS VREETLLEEE EAKKRAGELQ PEPEPAT                           517

SEQ ID NO: 12          moltype = DNA  length = 1554
FEATURE                Location/Qualifiers
source                 1..1554
                       mol_type = genomic DNA
                       organism = Simkania negevensis
SEQUENCE: 12
atgagtagta ccgaatatga gaagtccaca tggactcaaa aaatctggcc aataaggcgc  60
tttgaactta agaaagtcct tcctctttta atccttaaat ttctagtctc tatggtttat  120
gccactctca ccttaatcaa ggatcccctt gtggtgacgg caaaacattc tggagcagaa  180
gtcattccag ttctaaaagg ttggattgtt ttccccttat cgattctttg tgctattggt  240
tactcaaagt taagcaacca cttcaaacgt tccaccctct tttacggaat cattacagct  300
ttcctagcta ttgttcttat ctacggcttc gttttgtatc ccaatatggg aattctcaca  360
ccaagcgact ctgcaaactt gttaacagct aaatttgggg aaaaatacac acactggatt  420
gcagtttatc ggaattggat ccattctctc tttttcgtca ccacagagct ttgggggcaa  480
gttgtcattt tcctcctcta ctggggattt gccaaccaca tttgccaagt gaaagaagct  540
aaaagatctt acactctttt catcgctgca ggcgatttag caacgatctt ggctggtcca  600
cttacctatt actacggaaa aaagtttcta ggacaaagct atgctctcac tcttcaatcc  660
ctactaggat atgtcttagt ctgcgggcta ctcatcatgg cagtctattg gtggatgaat  720
cgatatgtcc taacagacaa acggtactac gatccatcag tgacgaagca aacagtcaac  780
caaaagacca aactctctct gcgtgatagt atccggcata tcttttcatc aaagtatctc  840
cttgctattg cggtcctcgt tgtcggttgc gctctcacca tcaacatggt agaagtcacc  900
tggaaagctc acttaaagat gcaataccca acaactgctg attaccaaat gttcatgggg  960
cgagtcacaa ctattgttgg agttgttgcc ctcatcactg tattcttctt aggaggaaac  1020
ttcctgagac ggtttggatg gcacttcagt gctcaaatca ccccatgggc gattggaatc  1080
acaggtggtg ttttcttttt actctgcctt ttgaagccct atctcgggtc tttcgctcat  1140
tatgttggac tcacccctct tatgatgatt gtcatctttg gagccttcca aaatatcact  1200
agtaaagtcg tcaaatactc gttctttgat tcgacgaaag aaatggctta tattccacta  1260
gaccctgaat ctaaagtgaa aggaaaagca gccatcgaca tggtcggttc aagattgggt  1320
aagtcgagct cctcctggct acaaattggc ttgattgaac tagttgggac tggttcggtg  1380
atctcaatca ctccttatct actgcctatc gttctaggtg ccgccctcta ttggagctac  1440
tctgtacgct acctcaataa agagctttct gtgcgtgaag aaacactcct cgaggaagaa  1500
gaagctaaga aaagagcggg agagcttcag cctgaacctg agcctgccac ttga        1554

SEQ ID NO: 13          moltype = AA  length = 517
FEATURE                Location/Qualifiers
source                 1..517
                       mol_type = protein
                       organism = Simkania negevensis
SEQUENCE: 13
MSSTEYEKST WTQKIWPIRR FELKKVLPLL ILKFLVSMVY ATLTLIKDPL VVTAKHSGAE  60
VIPVLKGWIV FPLSILCAIG YSKLSNHFKR STLFYGIITA FLAIVLIYGF VLYPNMGILT  120
PSDSANLLTA KFGEKYTHWI AVYRNWIHSL FFVTTELWGQ VVIFLLYWGF ANHICQVKEA  180
KRSYTLFIAA GDLATILAGP LTYYYGKKFL GQSYALTLQS LLGYVLVCGL LIMAVYWWMN  240
RYVLTDKWYY DPSVTKQTVN QKTKLSLRDS IRHIFSSKYL LAIAVLVVGC ALTINMVEVT  300
WKAHLKMQYP TTADYQMFMG RVTTIVGVVA LITVFFLGGN FLRRFGWHFS AQITPWAIGI  360
TGGVFFLLCL LKPYLGSFAH YVGLTPLMMI VIFGAFQNIT SKVVKYSFFD STKEMAYIPL  420
DPESKVKGKA AIDMVGSRLG KSSSSWLQIG LIELVGTGSV ISITPYLLPI VLGAALYWSY  480
SVRYLNKELS VREETLLEEE EAKKRAGELQ PEPEPAT                           517

SEQ ID NO: 14          moltype = AA  length = 526
FEATURE                Location/Qualifiers
source                 1..526
                       mol_type = protein
                       organism = Simkania negevensis
SEQUENCE: 14
MSTQTDVSFS KWRSFLWPIQ GREIKKFLPL LLIYALICLN YSVLKVAKDT LVITAPGSGA  60
EAIPFIKVWV ILPMALLVTY LFTRLFNRFS QEQVFYIMIG SFISFFALFA FVLYPLRDFL  120
```

-continued

```
HPHDTADKLQ AMLPQGFQGL IAIFRNWSYT LFYVMSELWG TAIMSVLFWG FTNEIISVGE  180
AKRYYGILSV GANIATIFSG YITTFLSLQV IDMSFIFGPD RWGQSLGLVT CVVVAAGLLI  240
MALFRWYNKR VINRDAVLLK MKQDHTETKK TMKMGMRKNF AYLAKSKYLI CIAVLVVAFN  300
VGINMVEIIW KDQIKELYPN PNDFIVYMGK VMSAIGWVAT FVGLFLSSNL IRRLGWTVSA  360
LITPVALLVT GVFFFGFILF KNNPTLVGWT AAIGFTPLAL GVLFGTIQNV MSRACKYTLF  420
DSTKEIAFIP LSPESKLKGK AAIDGVGSRV GKSGGSIVHG GLLMLFGSVS LSAPYVGLIL  480
LAVVFGWIGA ARSLGRQFNL LTTHHEKLEI NEEAQPSEKK PLLESV                526

SEQ ID NO: 15          moltype = DNA  length = 1581
FEATURE                Location/Qualifiers
source                 1..1581
                       mol_type = genomic DNA
                       organism = Simkania negevensis
SEQUENCE: 15
atgtcaacac agactgatgt gagtttcagt aaatggcgct catttttgtg gccaattcaa  60
ggaagagaaa ttaaaaaatt tcttcctctt ctcctgattt acgctctcat ttgtcttaac  120
tatagcgtct taaaagtcgc aaaagacaca cttgtcatta cagcccctgg atcaggcgca  180
gaagcaatcc cgtttatcaa ggtctgggtc attctcccca tggcactcct cgtaacttat  240
ctctttactc gcctcttcaa tcgatttagc caagaacaag tgttttacat catgatcggg  300
agcttcattt cgtttttcgc tctatttgca tttgtcctct accccttgcg agattttctt  360
catcctcatg acacagctga taaattacaa gccatgcttc cacagggatt ccaagggctc  420
atagccattt tccgtaactg gtcctatacc ctcttttatg tgatgtctga gctatgggga  480
accgctatta tgtctgtcct cttttgggga ttcacaaatg aaattatttc tgtaggtgag  540
gccaaaaggt attatggaat tctcagtgta ggggccaata ttgcaactat tttttcaggg  600
tacatcacca cctttctctc tttgcaagtg attgacatgt cattcatttt tggacctgac  660
cgctggggac aatcattagg tcttgtgaca tgtgttgttg ttgcagcagg tctccttatt  720
atggcccttt tcagatggta caacaagcga gtcattaatc gtgatgcagt actattaaaa  780
atgaaacaag accacacaga aacgaagaag accatgaaaa tgggaatgcg taagaatttt  840
gcttaccttg caaaatcaaa gtatttaatt tgcattgcag ttctggttgt tgcattcaat  900
gttggaatca acatggtcga aattatctgg aaagatcaaa tcaaagaact gtatcccaat  960
cccaacgatt ttattgttta tatggggaag gtcatgagtg caattggttg ggttgcaaca  1020
tttgtcggac tatttctcag tagtaattta atcaggcgct taggatggac tgtcagcgcc  1080
ttaatcactc ctgttgctct cctcgtaaca ggtgtttttct ttttcggatt cattctcttt  1140
aaaaacaacc ctacattagt gggttggaca gccgccatag gatttacacc tcttgcacta  1200
ggggttctct ttgggacaat ccaaaatgtg atgtctcgag catgtaaata caccttattt  1260
gactctacaa aagaaatagc gtttatcccc cttagccctg agtccaagct aaaaggaaaa  1320
gctgcaattg atggagtagg ctctcgcgtt ggaaagtccg gagggtcgat tgttcatggt  1380
ggactactga tgctcttcgg ctccgtttct ctcagcgcac cttacgtcgg cttgatctta  1440
ctcgccgttg ttttcggttg gattggtgca gctcgttcac tcgggagaca atttaatctc  1500
cttacgacgc atcatgaaaa actcgagatt aacgaggagg cacagccctc cgaaaaaaag  1560
cccttacttg aatccgttta a                                           1581

SEQ ID NO: 16          moltype = AA  length = 498
FEATURE                Location/Qualifiers
source                 1..498
                       mol_type = protein
                       organism = Rickettsia prowazekii
SEQUENCE: 16
MSTSKSENYL SELRKIIWPI EQYENKKFLP LAFMMFCILL NYSTLRSIKD GFVVTDIGTE  60
SISFLKTYIV LPSAVIAMII YVKLCDILKQ ENVFYVITSF FLGYFALFAF VLYPYPDLVH  120
PDHKTIESLS LAYPNFKWFI KIVGKWSFAS FYTIAELWGT MMLSLLFWQF ANQITKIAEA  180
KRFYSMFGLL ANLALPVTSV VIGYFLHEKT QIVAEHLKFV PLFVIMITSS FLIILTYRWM  240
NKNVLTDPRL YDPALVKEKK TKAKLSFIES LKMIFTSKYV GYIALLIIAY GVSVNLVEGV  300
WKSKVKELYP TKEAYTIYMG QFQFYQGWVA IAFMLIGSNI LRKVSWLTAA MITPLMMFIT  360
GAAFFSFIFF DSVIAMNLTG ILASSPLTLA VMIGMIQNVL SKGVKYSLFD ATKNMAYIPL  420
DKDLRVKGQA AVEVIGGRLG KSGGAIIQST FFILFPVFGF IEATPYFASI FFIIVILWIF  480
AVKGLNKEYQ VLVNKNEK                                               498

SEQ ID NO: 17          moltype = DNA  length = 1497
FEATURE                Location/Qualifiers
source                 1..1497
                       mol_type = genomic DNA
                       organism = Rickettsia prowazekii
SEQUENCE: 17
atgagtactt ccaaaagtga aaattatctt tcagaactaa gaaagataat ttggcctata  60
gaacaatatg aaaataagaa gtttttgcca cttgcattta tgatgttctg tattttatta  120
aactactcaa ctcttcgttc aattaaagac ggttttgtag taacagatat aggtacagaa  180
tcgataagtt ttttaaaaac atatatagta ctaccttctg ctgtaattgc tatgataatt  240
tatgttaagc tatgtgatat tttaaagcaa gaaaacgtat tttatgttat tacttcattt  300
tttttagggt attttgcatt atttgccttt gttctttacc catatcctga tttagtccac  360
cctgatcata aaactataga atctttaagt ttagcttatc ctaatttcaa atggtttata  420
aaaatagttg gtaaatggag ttttgcatct ttttatacta ttgccgagct ttggggaaca  480
atgatgctta gtttattatt ttggcaattt gctaatcaaa ttactaaaat cgctgaagct  540
aaacgtttct actcaatgtt tggtttactt gcgaatttag cattgcctgt aacatcagtg  600
gttattggat attttctaca cgaaaaaact caaatagttg cagaacattt aaaatttgta  660
cctttatttg ttataatgat aacaagtagt ttcttaataa tattaacata tagatggatg  720
aataaaaatg ttctaactga tcctagacta tatgatccag cattagtaaa agaaaaaaaa  780
actaaagcta aattgtcgtt catagaaagt ttaaaaatga tctttacttc gaaatatgta  840
ggttatattg cattattaat tattgcttat ggtgtttcag taaatttagt tgaaggtgtt  900
```

-continued

```
tggaaatcca aagtaaaaga attatatccg acaaaggagg cttataccat atatatgggt  960
cagttccaat tttatcaggg ttgggttgca attgctttta tgctgatagg tagtaatatt  1020
ttaagaaaag tatcatggct aactgcagct atgatcactc cattaatgat gttcataaca  1080
ggtgcggcat ttttttcatt tatatttttt gatagcgtta ttgcaatgaa tttaaccggc  1140
atccttgctt caagtccttt aacacttgct gttatgatcg gtatgattca aaatgtttta  1200
agtaaaggtg tgaaatattc tttatttgat gcaactaaaa atatggcgta tattccactt  1260
gataaggatt tacgagtcaa agggcaagct gccgttgaag ttatcggagg aaggctcggt  1320
aaatcaggcg gtgctattat tcaatctaca ttctttattt tatttcctgt atttggtttt  1380
atagaggcga ctccttattt tgcttctata ttctttataa tagtaatatt atggatattt  1440
gcagttaaag gtttaaataa agagtatcaa gttttggtaa ataaaaatga aaaatag     1497

SEQ ID NO: 18          moltype = AA  length = 507
FEATURE                Location/Qualifiers
source                 1..507
                       mol_type = protein
                       organism = Rickettsia prowazekii
SEQUENCE: 18
MNIVDSNCTI WHKARNSKFR HIVWPIRSYE LTKFIPMTLL MFFILLNQNL VRSIKDSFVV  60
TLISSEVLSF IKLWGEMPMG VLFVILYSKL CNIMTTEQVF RIITSTFLFF FAIFGFILFP  120
YKEFFHPNPE LINQYIIVLP HLKWFLIIWG QWSLVLFYIM GELWPVIVFT LLYWQLANKI  180
TKVEEAPRFY SFFTLFGQTN LLFSGTVIIY FAKSEHFLLP LFAHLNDTNE ILLKSFITVI  240
LISGLICLAL HKLIDKSVVE ADKNIKFKNQ RTDILKLSLL ESAKIILTSR YLGFICLLVM  300
SYSMSINLIE GLWMSKVKQL YPATKDFISY HGEVLFWTGV LTLVSAFLGS SLIRIYGWFW  360
GAIITPIMMF VAGVMFFSFT IFEQHLGNIV NTLGYSSPLV IIVFIGGLWH VFAKSVKYSL  420
FDATKEMVYI PLDNEIKTKG KAAVDVMGAK IGKSIGAIIQ FISFSIFPNA VHNDIAGLLM  480
VTFIIVCILW LYGVKVLSQN YNKMIKR                                      507

SEQ ID NO: 19          moltype = DNA  length = 1524
FEATURE                Location/Qualifiers
source                 1..1524
                       mol_type = genomic DNA
                       organism = Rickettsia prowazekii
SEQUENCE: 19
atgaatatag tagattctaa ctgtacaatt tggcataaag caagaaatag taaatttagg  60
catatagtat ggccaattag atcgtatgaa ttaacaaaat tcatcccgat gactttatta  120
atgtttttta ttttacttaa tcaaaattta gtgcgtagta ttaaagatag ttttgttgtt  180
acattaatta gttcagaagt attaagtttt ataaaacttt ggggtgaaat gccgatgggg  240
gttttatttg ttattcttta ttctaaactc tgtaatatta tgaccacaga gcaagttttt  300
aggataatta ccagtacctt tttatttttc tttgcaattt ttggttttat ttttattccca  360
tacaaagagt tttttcatcc taaccctgaa ttaattaatc aatatatcat tgttctgcct  420
cacttaaagt ggtttttaat aatttgggga caatggagtt tagtattatt ttatataatg  480
ggtgagttat ggcctgttat agtttttact cttttatatt ggcagcttgc aaataaaatc  540
accaaagtcg aagaagcacc aagattttac tcattttta ctttatttgg acaaactaat  600
ttgctcttct caggcactgt aattatttat tttgctaaga gcgaacattt tttattacct  660
ttatttgctc atttaaatga cacaaatgaa attcttttaa aatcattcat cacagttatt  720
ttaatatcag gattaatttg tttagctctc cataagctaa ttgataaatc agttgtagaa  780
gctgataaaa atataaaatt taaaaaccaa agaacagata tattaaaatt aagcttgctc  840
gaaagtgcaa aaataatctt aacgtctaga tatcttggtt ttatttgtct tctcgtaatg  900
tcttattcta tgagtattaa cctaatagaa ggattgtgga tgtcaaaagt aaaacaactc  960
tatcctgcta caaaggattt tatatcatat cacggtgaag tattgttttg gactggagtg  1020
ttaactttag ttagtgcatt tttaggcagt agtttaatta gaatttatgg ctggttttgg  1080
ggggctatta taacaccgat tatgatgttt gtagcagggg ttatgttttt ttcattcaca  1140
atttttgaac aacacttagg aaatatagta aatactcttg gctatagttc tccacttgtc  1200
attatagttt ttattggtgg actttggcat gtatttgcta aatctgtaaa gtattccctt  1260
ttcgatgcta ctaaagaaat ggtgtatatt ccactagata atgaaattaa gactaaaggt  1320
aaagcagcag ttgatgttat gggtgctaaa attggtaagt caataggtgc tattattcaa  1380
ttcatatcct ttagtatctt tccaaatgct gtacataacg acatagcagg cttattgatg  1440
gttactttta ttatcgtatg tatattatgg ctatatggag tgaaagtttt atcacaaaat  1500
tataataaaa tgataaaacg ttaa                                         1524

SEQ ID NO: 20          moltype = AA  length = 501
FEATURE                Location/Qualifiers
source                 1..501
                       mol_type = protein
                       organism = Rickettsia prowazekii
SEQUENCE: 20
MLPPKIFFEK VKEIIWPIER KELKLFIPMA LMMLCILFNF GALRSIKDSL VVPSMGAEII  60
SFLKLWLVLP SCVIFTILYV KLSNKLNFEY IFYSIVGTFL LFFLLFAYII YPNQDIYHPN  120
DAMINNLIAS YPNLKWFIKI GSKWSYALMY IFSELWSAVV INLMFWQFAN HIFDTAKAKR  180
FYPVLGMVGN IGLIIAGSVL VFFSSGQYII DSELLTDSYN SSSNNSIMLQ PIISIIVTAG  240
IIAMFLFRII NKFILTNSIN VLDVKKVAAK TKTKLALIES IKLIIHSKYI GRIALLIICY  300
GLLINIVEGP WKAKIKELHP NTVDYVNFMG MFNIWMGISC VTFMIIGSNI LRRLGWLISA  360
LLTPIMLSIT GFMFFIFIIF IEEIGTCFGD FNLLYVAIIV GAIQNILSKS SKYSLFDSTK  420
EMAYIPLSLE LRTKGKAAVE VIGTKFGKSL GAFIQSLIFI IIPTATFDSI IIYLLVIFIV  480
MMNLWIWNII KLNKEYIKLC Q                                            501

SEQ ID NO: 21          moltype = DNA  length = 1506
FEATURE                Location/Qualifiers
source                 1..1506
```

```
                       mol_type = genomic DNA
                       organism = Rickettsia prowazekii
SEQUENCE: 21
atgttaccgc ctaaaatttt ctttgaaaaa gttaaagaaa taatttggcc tatagaaagg  60
aaagaattaa agctatttat accaatggct ttaatgatgt tatgtatcct gtttaatttt  120
ggggctttaa gatctattaa agatagttta gtagtaccct ctatgggggc tgaaattatt  180
agtttcttaa aattatggtt agtgctaccc tcgtgcgtaa tttttacgat actttacgtt  240
aaacttagta ataaattaaa ttttgaatat attttctata gtatagtcgg tacttttttta  300
ctatttttct tattatttgc ctatattatt tatccaaatc aagatattta tcatcctaat  360
gatgcaatga taaataattt aattgcttca taccctaatt taaagtggtt tattaaaata  420
ggtagtaaat ggagttatgc gctaatgtat attttctcag aattatggag tgcagtagtt  480
ataaacttaa tgttttggca atttgctaat cacatttttg atactgctaa agctaaacga  540
ttttatcctg ttcttgggat ggttggtaat atcggtctta taatagcagg cagcgtactt  600
gtttttttttt caagtgggca gtacatcatt gattcagaat tattaacgga ttcttataat  660
tcatcttcta acaattctat catgcttcag ccaatcatat caattattgt tactgcagga  720
ataattgcta tgtttttatt tagaataata aataaattta ttttaactaa ttctataaat  780
gttttagatg taaaaaaagt tgctgctaaa acaaaaacaa aacttgcatt aattgaaagt  840
ataaaattaa taattcattc aaaatatata ggtcgtattg cattattaat aatctgttat  900
ggattactaa taaatatagt tgaaggacct tggaaagcga aaataaaaga attacatcca  960
aatactgtag attatgttaa ttttatgggc atgtttaata tttggatggg gatctcatgt  1020
gttactttca tgataatagg tagtaatatt cttagaaggc ttggttggct catttctgca  1080
ttattaactc ctattatgtt atctattaca ggcttcatgt tttttatctt tataattttt  1140
attgaagaaa taggtacatg ttttggtgat tttaatcttc tatatgtagc gattattgtc  1200
ggagcaattc agaatatact tagtaaatcg tctaaatatt cattattcga ttcaacaaaa  1260
gaaatggcat atattccttt atctttagaa ctgagaacta agggaaaagc cgctgtagag  1320
gtaataggaa cgaaatttgg taaatcactt ggagcattta tccagtcttt gatatttatt  1380
attattccaa cggctacctt tgattctatt ataatatatt tactagtaat ttttatagtg  1440
atgatgaatt tatggatttg gaatattata aaattaaata aggaatatat aaagctgtgt  1500
caataa                                                           1506

SEQ ID NO: 22          moltype = AA  length = 512
FEATURE                Location/Qualifiers
source                 1..512
                       mol_type = protein
                       organism = Rickettsia prowazekii
SEQUENCE: 22
MTINASNIEN SFSKINSHFS KLTDYIWPIK RHEISKFLFI TLLMFCILFI QNLIRALKDS  60
IVTTMIGAET ISFLKFWGVM PSAFLITVIY VKLVNRMKAE NIFYLIISIF LTFFALFAYV  120
IFPNHEMLHL RPVTVHNLTA SLPNLKWFIL LLSKWSFSLF YIIAELWPNV VFALLFWQFV  180
NNITTVEESK RFYPLFGLLS QTGIYLAGHF LENLSNINYY VTNKFALQSS FHTLSIQIIL  240
TIVLILGIVS IKTFWLLNHK VLDKKHMALL RFKTKNKSIT IAKSFQMILS SRHIRLIATL  300
LICYGIAINL VEGPWKAAAT KIYKTPTEYA AFIGSYLSYT GVFTIFFVLL GSNIVRRMGW  360
FTSAVITPSI VFITGILFFA VNNFEGFAGL IIANFILTDP ALVAITIGAI QNVLSKSSKY  420
TLFDSTKEMA YVPLEPEIKI SGKAAADVIG TKLGKSGSAF LQSLIFIILP SASYQSISIC  480
LMIIFILTCV TWIWATKELN KEYKNSIKFS QK                               512

SEQ ID NO: 23          moltype = DNA  length = 1539
FEATURE                Location/Qualifiers
source                 1..1539
                       mol_type = genomic DNA
                       organism = Rickettsia prowazekii
SEQUENCE: 23
atgacgatta acgccagtaa tatagaaaat tctttttcta aaatcaatag ccatttttct  60
aagcttacag attatatctg gcctataaaa cgccacgaaa tttctaagtt tttattcatt  120
acattattaa tgttctgtat tttatttatt caaaatctca tcagagcttt aaaagatagt  180
attgttacta ctatgatagg tgctgagact atatcatttt tgaaattttg gggcgtgatg  240
ccgtcagcat tcttaataac tgttatatat gttaaacttg tcaataggat gaaagcagaa  300
aatatatttt atcttattat atcaattttt ttaacattct ttgctttgtt tgcatacgtt  360
attttcccaa atcatgaaat gctgcattta aggcctgtaa ccgtgcataa tttaacggca  420
agtttaccga atttaaaatg gtttatactt cttttatcaa aatggagttt ttcactattt  480
tatataatag ccgaattatg gccaaatgta gtttttgcat tactgttttg gcagtttgtg  540
aataatatta ctacagtaga agaatcgaaa agattttatc cattatttgg tttacttagt  600
caaacaggta tttatttagc aggacatttt ttagaaaatc taagtaatat aaattattat  660
gtcactaata aatttgcatt gcaatcgtct tttcatacac tttctataca aattatacta  720
actatagtat taattttagg catagtatcg ataaaaactt tttggttact taatcataaa  780
gtactagaca aaaagcatat ggcattactc aggttcaaaa caaaaaataa atctattact  840
attgctaaaa gttttcagat gattctatcg tcaagacaca ttagattaat tgcaactttg  900
cttatctgct atggcattgc aattaattta gtagaaggcc cttggaaagc agcagcaact  960
aaaatttata aaactccaac cgaatatgca gcttttatag gaagttattt aagctacact  1020
ggagtattta ctattttctt tgttctactt ggttccaata tagttagaag aatgggctgg  1080
tttacttcag ctgtgatcac accttcaata gtttttatta ccggtatatt attttttgct  1140
gttaataatt ttgaaggctt tgctggctta ataatagcaa attttatttt gaccgatcct  1200
gctttagttg ctataacaat aggtgctatt caaaatgtac ttagtaaatc aagcaaatat  1260
actttatttg attctacaaa agaaatggct tatgttcctt tagaaccaga aatcaaaata  1320
agtggtaagg ctgctgccga cgttataggt acaaaactcg gtaaatccgg tagtgcattt  1380
ttacaatcat taatatttat aatattacct tctgctagtt atcaatctat ttcaatctgt  1440
ttaatgatta tatttatcct cacttgcgta acttggattt gggctactaa agaactaaat  1500
aaagaatata aaaattctat taaattttct caaaaataa                       1539
```

-continued

```
SEQ ID NO: 24          moltype = AA  length = 500
FEATURE                Location/Qualifiers
source                 1..500
                       mol_type = protein
                       organism = Rickettsia prowazekii
SEQUENCE: 24
MLSTSPSRSF KNKFRAAFWP VHNYELGKFI PISALMFCIL FNQNILRILK DSILISEISA  60
EIAGFAKVYC VTPVAALFVI IYAKMINHLT FEKIFYYLSA FFISCFILFA FVIYPNIHIF  120
HVHPDTLSDW MNKYPHFKWY ISLVGNWGYI VYYSLAELWP NIFYVLLFWQ FTNELTTTEE  180
AKRFYTLFSL FGNSSLILVG FLMMNLSSED TIIKKFISIS DSKITLVQVS TTIIAIVAII  240
CCLLVRFISK YIFTNPLFYH KTKSSRSTAQ RMGLIKSFKY IVKSKYLWLL LICSAAFGFA  300
INLVEAVWKA KIKELYPTVN TYAEFNSLYI LWTGVAIIVM TIIGNNVMRM HNWFVAAVIS  360
PVIIMVTGVL FFGLIVFDQQ ILSLFDGAIL MSPLALAVSI GGIQNILAKG TKYSIWDTSR  420
EMLYIPLDDE LKTKGKAAVD VISAKVGKSS SGLVQSIIFT LVPNATFTSI SPILMVVFTF  480
VCFAWIYAVR KIYFEYQKIA                                           500

SEQ ID NO: 25          moltype = DNA  length = 1503
FEATURE                Location/Qualifiers
source                 1..1503
                       mol_type = genomic DNA
                       organism = Rickettsia prowazekii
SEQUENCE: 25
atgctaagta cctcaccgtc acgatcgttt aaaaacaaat ttagagcagc attttggcct  60
gtgcataatt atgaacttgg gaaatttatt ccgatcagcg ccttaatgtt ttgtatttta  120
tttaatcaaa atattttgcg aatcttaaag gatagtattt taatctctga gattagtgca  180
gaaatagcag gatttgctaa agtttactgc gttacacctg tagctgcttt gtttgttatt  240
atttatgcta aaatgatcaa tcatttgaca tttgaaaaaa tcttttatta tttaagtgca  300
ttttttataa gctgttttat tttatttgcc tttgtgattt atcctaatat tcatattttt  360
catgtacatc ctgatacact atcagactgg atgaacaaat atcctcattt taagtggtat  420
atctcattag taggtaattg ggttatata gtatattata gtcttgccga gctttggcct  480
aatattttt acgtattatt attttggcag tttactaatg aacttactac taccgaagaa  540
gcaaaaagat tttatactct cttttcgcta ttcggtaatt cttccttaat attagtcggc  600
tttttaatga tgaatttatc atcggaagat actattatta agaaatttat aagtatttca  660
gatagtaaaa tcactttagt tcaagtatca acgacgatta tagcaattgt tgcaatcatt  720
tgttgtttgt tagttaggtt tattagcaag tacattttta ctaatccatt attttatcat  780
aaaacaaaaa gcagtagatc aactgcacaa cggatgggac taattaaaag ctttaaatat  840
attgtgaaat caaaatattt atggctactt ttaatttgtt ctgcagcttt cggatttgct  900
ataaacttag tcgaagcagt atggaaagca aaaattaagg aattatatcc gactgtaaat  960
acctacgctg aattcaatag tctgtatata ctttggacag gcgttgcgat aattgttatg  1020
acaattatcg gtaataacgt catgcgtatg cataattggt ttgtagccgc agttatttcc  1080
ccagtgataa taatggtgac aggtgttttg ttctttggac taattgtatt tgatcaacaa  1140
attttatcat tatttgatgg cgcgatttta atgtcacctc ttgcacttgc tgtttctatt  1200
ggcggtattc agaatatttt agccaaaggc actaaatatt ctatatggga tacttcaaga  1260
gaaatgttat atataccact tgatgatgaa cttaaaacaa agggtaaagc agcagttgat  1320
gttataagtg caaaagttgg aaaatcctct agtggtcttg tacaatccat tatttttact  1380
ttagtgccaa atgcgacctt tacctcaatc tcgccgattt taatggtagt atttacgttc  1440
gtatgctttg cttggattta tgcagtaaga aaaatatatt ttgaatatca aaaaatagcc  1500
tga                                                             1503

SEQ ID NO: 26          moltype = DNA  length = 194
FEATURE                Location/Qualifiers
misc_feature           1..194
                       note = Synthetic polynucleotide
misc_feature           69
                       note = dNaM or its biotinylated analog dMMO2^SSBIO
source                 1..194
                       mol_type = other DNA
                       organism = synthetic construct
SEQUENCE: 26
gcaggcatgc aagcttggcg taatcatggt catagctgtt tcctgtgtga aattgttatc  60
cgctcacant tccacacaac atacgagccg gaagcataaa gtgtaaagcc tggggtgcct  120
aatgagtgag ctaactcaca ttaattgcgt tgcgctcact gcccgctttc cagtcgggaa  180
acctgtcgtg ccag                                                 194

SEQ ID NO: 27          moltype = DNA  length = 304
FEATURE                Location/Qualifiers
misc_feature           1..304
                       note = Synthetic polynucleotide
misc_feature           179
                       note = dNaM
source                 1..304
                       mol_type = other DNA
                       organism = synthetic construct
SEQUENCE: 27
gctgcaaggc gattaagttg ggtaacgcca gggttttccc agtcacgacg ttgtaaaacg  60
acggccagtg aattcgagct cggtacccgg ggatcctcta gagtcgacct gcaggcatgc  120
aagcttggcg taatcatggt catagctgtt tcctgtgtga aattgttatc cgctcacant  180
tccacacaac atacgagccg gaagcataaa gtgtaaagcc tggggtgcct aatgagtgag  240
ctaactcaca ttaattgcgt tgcgctcact gcccgctttc cagtcgggaa acctgtcgtg  300
```

```
ccag                                                                    304

SEQ ID NO: 28          moltype = DNA  length = 5151
FEATURE                Location/Qualifiers
misc_feature           1..5151
                       note = Synthetic polynucleotide; sequence of the pACS
                        plasmid
source                 1..5151
                       mol_type = other DNA
                       organism = synthetic construct
SEQUENCE: 28
ggggaattgt gagcggataa caattcccct gtagaaataa ttttgtttaa ctttaataag  60
gagatatacc atgagaccat ttccgacgat tgccttgatt tcggtttttc tttcggcggc  120
gactcgcatt tcggcaactt cctctcatca agcaagtgca cttcctctca aaaagggaac  180
gcatgtcccg gactctccga agttgtcaaa gctatatatc atggccaaaa ccaagagtgt  240
atcctcgtcc ttcgaccccc ctcggggagg cagtactgtt gcaccaacta caccgttggc  300
aaccggcggt gcgctccgca aagtgcgaca agccgtcttt cccatctacg gaaaccaaga  360
agtcaccaaa tttctgctca tcggatccat taaattcttt ataatcttgg cactcacgct  420
cacgcgtgat accaaggaca cgttgattgt cacgcaatgt ggtgccgaag cgattgcctt  480
tctcaaaata tacggggtgc tacccgcagc gaccgcattt atcgcgctct attccaaaat  540
gtccaacgcc atgggcaaaa aaatgctatt ttattccact tgcattcctt tctttacctt  600
tttcgggctg tttgatgttt tcatttaccc gaacgcggag cgactgcacc ctagtttgga  660
agccgtgcag gcaattctcc cgggcggtgc cgcatctggc ggcatggcgg ttctggccaa  720
gattgcgaca cactggacat cggccttatt ttacgtcatg gcggaaatat attcttccgt  780
atcggtgggg ctattgtttt ggcagtttgc gaacgacgtc gtcaacgtgg atcaggccaa  840
gcgcttttat ccattatttg ctcaaatgag tggcctcgct ccagttttag cgggccagta  900
tgtggtacgg tttgccagca aagcggtcaa ctttgaggca tccatgcatc gactcacggc  960
ggccgtaaca tttgctggta ttatgatttg catcttttac caactcagtt cgtcatatgt  1020
ggagcgaacg gaatcagcaa agccagcggc agataacgag cagtctatca aaccgaaaaa  1080
gaagaaaccc aaaatgtcca tggttgaatc ggggaaattt ctcgcgtcaa gtcagtacct  1140
gcgtctaatt gccatgctgg tgctgggata cggcctcagt attaacttta ccgaaatcat  1200
gtggaaaagc ttggtgaaga aacaatatcc agacccgcta gattatcaac gatttatggg  1260
taacttctcg tcagcggttg gtttgagcac atgcattgtt attttcttcg gtgtgcacgt  1320
gatccgtttg ttggggtgga aagtcggagc gttggctaca cctgggatca tggccattct  1380
agcgttaccc ttttttgctt gcattttgtt gggtttggat agtccagcac gattggagat  1440
cgcccgtaatc tttggaacaa ttcagagttt gctgagcaaa acctccaagt atgccctttt  1500
cgaccctacc acacaaatgg cttatattcc tctggacgac gaatcaaagg tcaaaggaaa  1560
agcggcaatt gatgttttgg gatcgcggat tggcaagagt ggaggctcac tgatccagca  1620
gggcttggtc tttgtttttg gaaatatcat taatgccgca cctgtagtag gggttgtcta  1680
ctacagtgtc cttgttgcgt ggatgagcgc agctggccga ctaagtgggc tttttcaagc  1740
acaaacagaa atggataagg ccgacaaaat ggaggcaaag accaacaaag aaaagtagtt  1800
aacctaggct gctgccaccg ctgagcaata actagcataa ccccttgggg cctctaaacg  1860
ggtcttgagg ggttttttgc tgaaacctca ggcatttgag aagcacacgg tcacactgct  1920
tccggtagtc aataaaccgg taaaccagca atagacataa gcggctattt aacgaccctg  1980
ccctgaaccg acgaccgggt catcgtggcc ggatcttgcg gcccctcggc ttgaacgaat  2040
tgttagacat tatttgccga ctaccttggt gatctcgcct ttcacgtagt ggacaaattc  2100
ttccaactga tctgcgcgcg aggccaagcg atcttcttct tgtccaagat aagcctgtct  2160
agcttcaagt atgacgggct gatactgggc cggcaggcgc tccattgccc agtcggcagc  2220
gacatccttc ggcgcgattt tgccggttac tgcgctgtac caaatgcggg acaacgtaag  2280
cactacattt cgctcatcgc cagcccagtc gggcggcgag ttccatagcg ttaaggtttc  2340
atttagcgcc tcaaatagat cctgttcagg aaccggatca aagagttcct ccgccgctgg  2400
acctaccaag gcaacgctat gttctcttgc ttttgtcagc aagatagcca gatcaatgtc  2460
gatcgtggct ggctcgaaga tacctgcaag aatgtcattg cgctgccatt ctccaaattg  2520
cagttcgcgc ttagctggat aacgccacgg aatgatgtcg tcgtgcacaa caatggtgac  2580
ttctacagcg cggagaatct cgctctctcc aggggaagcc gaagtttcca aaaggtcgtt  2640
gatcaaagct cgccgcgttg tttcatcaag ccttacggtc accgtaacca gcaaatcaat  2700
atcactgtgt ggcttcaggc cgccatccac tgcggagccg tacaaatgta cggccagcaa  2760
cgtcggttcg agatggcgct cgatgacgcc aactacctct gatagttgag tcgatacttc  2820
ggcgatcacc gcttccctca tactcttcct ttttcaatat tattgaagca tttatcaggg  2880
ttattgtctc atgagcggat acatatttga atgtatttag aaaaataaac aaatagctag  2940
ctcactcggt cgctacgctc cgggcgtgag actgcggcgg gcgctgcgga cacatacaaa  3000
gttacccaca gattccgtgg ataagcaggg gactaacatg tgaggcaaaa cagcagggcc  3060
gcgccggtgg cgtttttcca taggctccgc ccctcctgcca gagttcacat aaacagacgc  3120
ttttccggtg catctgtggg agccgtgagg ctcaaccatg aatctgacag tacgggcgaa  3180
acccgacagg acttaaagat ccccaccgtt tccggcgggt cgctccctct tgcgctctcc  3240
tgttccgacc ctgccgttta ccggatacct gttccgcctt tctcccttac gggaagtgtg  3300
gcgctttctc atagctcaca cactggtatc tcggctcggt gtaggtcgtt cgctccaagc  3360
tgggctgtaa gcaagaactc cccgttcagc ccgactgctg cgccttatcc ggtaactgtt  3420
cacttgagtc caacccggaa aagcacggta aaacgccact ggcagcagcc attggtaact  3480
gggagttcgc agaggatttg tttagctaaa cacgcggttg ctcttgaagt gtgcgccaaa  3540
gtccggctac actggaagga cagatttggt tgctgtgctc tgcgaaagcc agttaccacg  3600
gttaagcagt tccccaactg acttaacctt cgatcaaacc acctccccag gtggtttttt  3660
cgtttacagg gcaaaagatt acgcgcagaa aaaaaggatc tcaagaagat cctttgatct  3720
tttctactga accgctctag atttcagtgc aatttatctc ttcaaatgta gcacctgaag  3780
tcagccccat acgatataag ttgtaattct catgttagtc atgccccgcg cccaccggaa  3840
ggagctgact gggttgaagg ctctcaaggg catcggtcga gatcccggtg cctaatgagt  3900
gagctaactt acattaattg cgttgcgctc actgcccgct ttccagtcgg gaaacctgtc  3960
gtgccagctg cattaatgaa tcggccaacg cgcggggaga ggcggtttgc gtattgggcg  4020
ccagggtggt ttttcttttc accagtgaga cgggcaacag ctgattgccc ttcaccgcct  4080
```

-continued

```
ggccctgaga gagttgcagc aagcggtcca cgctggtttg ccccagcagg cgaaaatcct  4140
gtttgatggt ggttaacggc gggatataac atgagctgtc ttcggtatcg tcgtatccca  4200
ctaccgagat gtccgcacca acgcgcagcc cggactcggt aatggcgcgc attgcgccca  4260
gcgccatctg atcgttggca accagcatcg cagtgggaac gatgccctca ttcagcattt  4320
gcatggtttg ttgaaaaccg gacatggcac tccagtcgcc ttcccgttcc gctatcggct  4380
gaatttgatt gcgagtgaga tatttatgcc agccagccag acgcagacgc gccgagacag  4440
aacttaatgg gcccgctaac agcgcgattt gctggtgacc caatgcgacc agatgctcca  4500
cgcccagtcg cgtaccgtct tcatgggaga aaataatact gttgatgggt gtctggtcag  4560
agacatcaag aaataacgcc ggaacattag tgcaggcagc ttccacagca atggcatcct  4620
ggtcatccag cggatagtta atgatcagcc cactgacgcg ttgcgcgaga agattgtgca  4680
ccgccgcttt acaggcttcg acgccgcttc gttctaccat cgacaccacc acgctggcac  4740
ccagttgatc ggcgcgagat ttaatcgccg cgacaatttg cgacggcgcg tgcagggcca  4800
gactggaggt ggcaacgcca atcagcaacg actgtttgcc cgccagttgt tgtgccacgc  4860
ggttgggaat gtaattcagc tccgccatcg ccgcttccac tttttcccgc gttttcgcag  4920
aaacgtggct ggcctggttc accacgcggg aaacggtctg ataagagaca ccggcatact  4980
ctgcgacatc gtataacgtt actggtttca cattcaccac cctgaattga ctctcttccg  5040
ggcgctatca tgccataccg cgaaaggttt tgcgccattc gatggtgtcc gggatctcga  5100
cgctctccct tatgcgactc ctgcattagg aaattaatac gactcactat a           5151

SEQ ID NO: 29          moltype = DNA  length = 45
FEATURE                Location/Qualifiers
misc_feature           1..45
                       note = Synthetic polynucleotide
source                 1..45
                       mol_type = other DNA
                       organism = synthetic construct
SEQUENCE: 29
ggtatatctc cttattaaag ttaaacaaaa ttatttctac agggg                  45

SEQ ID NO: 30          moltype = DNA  length = 43
FEATURE                Location/Qualifiers
misc_feature           1..43
                       note = Synthetic polynucleotide
source                 1..43
                       mol_type = other DNA
                       organism = synthetic construct
SEQUENCE: 30
gtttaacttt aataaggaga tataccatga gaccatttcc gac                    43

SEQ ID NO: 31          moltype = DNA  length = 40
FEATURE                Location/Qualifiers
misc_feature           1..40
                       note = Synthetic polynucleotide
source                 1..40
                       mol_type = other DNA
                       organism = synthetic construct
SEQUENCE: 31
gcagcagcct aggttaacta cttttctttg ttggtctttg                        40

SEQ ID NO: 32          moltype = DNA  length = 48
FEATURE                Location/Qualifiers
misc_feature           1..48
                       note = Synthetic polynucleotide
source                 1..48
                       mol_type = other DNA
                       organism = synthetic construct
SEQUENCE: 32
gtttaacttt aataaggaga tataccatga aaaaatcttg tacaatcc               48

SEQ ID NO: 33          moltype = DNA  length = 37
FEATURE                Location/Qualifiers
misc_feature           1..37
                       note = Synthetic polynucleotide
source                 1..37
                       mol_type = other DNA
                       organism = synthetic construct
SEQUENCE: 33
gcagcagcct aggttaacta cttctggtgc tcttttg                           37

SEQ ID NO: 34          moltype = DNA  length = 26
FEATURE                Location/Qualifiers
misc_feature           1..26
                       note = Synthetic polynucleotide
source                 1..26
                       mol_type = other DNA
                       organism = synthetic construct
SEQUENCE: 34
ctatgaccat gattacgcca agcttg                                       26
```

-continued

```
SEQ ID NO: 35          moltype = DNA  length = 75
FEATURE                Location/Qualifiers
misc_feature           1..75
                       note = Synthetic polynucleotide
misc_feature           34
                       note = dNaM
source                 1..75
                       mol_type = other DNA
                       organism = synthetic construct
SEQUENCE: 35
ctgtttcctg tgtgaaattg ttatccgctc acanttccac acaacatacg agccggaagc  60
ataaagtgta aagcc                                                   75

SEQ ID NO: 36          moltype = DNA  length = 75
FEATURE                Location/Qualifiers
misc_feature           1..75
                       note = Synthetic polynucleotide
source                 1..75
                       mol_type = other DNA
                       organism = synthetic construct
SEQUENCE: 36
ctgtttcctg tgtgaaattg ttatccgctc acatttccac acaacatacg agccggaagc  60
ataaagtgta aagcc                                                   75

SEQ ID NO: 37          moltype = DNA  length = 54
FEATURE                Location/Qualifiers
misc_feature           1..54
                       note = Synthetic polynucleotide
source                 1..54
                       mol_type = other DNA
                       organism = synthetic construct
SEQUENCE: 37
caagcttggc gtaatcatgg tcatagctgt ttcctgtgtg aaattgttat ccgc        54

SEQ ID NO: 38          moltype = DNA  length = 45
FEATURE                Location/Qualifiers
misc_feature           1..45
                       note = Synthetic polynucleotide
source                 1..45
                       mol_type = other DNA
                       organism = synthetic construct
SEQUENCE: 38
gctcactcat taggcacccc aggctttaca ctttatgctt ccggc                  45

SEQ ID NO: 39          moltype = DNA  length = 29
FEATURE                Location/Qualifiers
misc_feature           1..29
                       note = Synthetic polynucleotide
source                 1..29
                       mol_type = other DNA
                       organism = synthetic construct
SEQUENCE: 39
gcaggcatgc aagcttggcg taatcatgg                                    29

SEQ ID NO: 40          moltype = DNA  length = 29
FEATURE                Location/Qualifiers
misc_feature           1..29
                       note = Synthetic polynucleotide
source                 1..29
                       mol_type = other DNA
                       organism = synthetic construct
SEQUENCE: 40
gctgcaaggc gattaagttg ggtaacgcc                                    29

SEQ ID NO: 41          moltype = DNA  length = 25
FEATURE                Location/Qualifiers
misc_feature           1..25
                       note = Synthetic polynucleotide
source                 1..25
                       mol_type = other DNA
                       organism = synthetic construct
SEQUENCE: 41
ctggcacgac aggtttcccg actgg                                        25

SEQ ID NO: 42          moltype = AA  length = 9
FEATURE                Location/Qualifiers
REGION                 1..9
                       note = Synthetic polypeptide
source                 1..9
```

```
                        mol_type = protein
                        organism = synthetic construct
SEQUENCE: 42
DYKDDDDKG                                                   9

SEQ ID NO: 43           moltype = AA  length = 14
FEATURE                 Location/Qualifiers
REGION                  1..14
                        note = Synthetic polypeptide
source                  1..14
                        mol_type = protein
                        organism = synthetic construct
SEQUENCE: 43
GKPIPNPLLG LDST                                             14

SEQ ID NO: 44           moltype = AA  length = 10
FEATURE                 Location/Qualifiers
REGION                  1..10
                        note = Synthetic polypeptide
source                  1..10
                        mol_type = protein
                        organism = synthetic construct
SEQUENCE: 44
EQKLISEEDL                                                  10

SEQ ID NO: 45           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 45
QPELAPEDPE D                                                11

SEQ ID NO: 46           moltype = AA  length = 9
FEATURE                 Location/Qualifiers
REGION                  1..9
                        note = Synthetic polypeptide
source                  1..9
                        mol_type = protein
                        organism = synthetic construct
SEQUENCE: 46
YPYDVPDYA                                                   9

SEQ ID NO: 47           moltype = AA  length = 11
FEATURE                 Location/Qualifiers
REGION                  1..11
                        note = Synthetic polypeptide
source                  1..11
                        mol_type = protein
                        organism = synthetic construct
SEQUENCE: 47
YTDIEMNRLG K                                                11

SEQ ID NO: 48           moltype = AA  length = 6
FEATURE                 Location/Qualifiers
REGION                  1..6
                        note = Synthetic polypeptide
source                  1..6
                        mol_type = protein
                        organism = synthetic construct
SEQUENCE: 48
CCPGCC                                                      6
```

-continued

```
SEQ ID NO: 49          moltype = DNA  length = 22
FEATURE                Location/Qualifiers
misc_feature           1..22
                       note = Synthetic polynucleotide
source                 1..22
                       mol_type = other DNA
                       organism = synthetic construct
SEQUENCE: 49
ttaacctagg ctgctgccac cg                                        22

SEQ ID NO: 50          moltype = DNA  length = 21
FEATURE                Location/Qualifiers
misc_feature           1..21
                       note = Synthetic polynucleotide
source                 1..21
                       mol_type = other DNA
                       organism = synthetic construct
SEQUENCE: 50
tggggtgcct aatgagtgag c                                         21
```